(12) United States Patent
Van Zandt et al.

(10) Patent No.: US 9,266,908 B2
(45) Date of Patent: *Feb. 23, 2016

(54) INHIBITORS OF ARGINASE AND THEIR THERAPEUTIC APPLICATIONS

(71) Applicant: MARS, INCORPORATED, McLean, VA (US)

(72) Inventors: Michael Van Zandt, McLean, VA (US); Adam Golebiowski, McLean, VA (US); Min Koo Ji, McLean, VA (US); Darren Whitehouse, McLean, VA (US); Todd Ryder, McLean, VA (US); Raymond Paul Beckett, McLean, VA (US)

(73) Assignee: MARS, INCORPORATED, McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/352,554

(22) PCT Filed: Oct. 18, 2012

(86) PCT No.: PCT/US2012/060789
§ 371 (c)(1),
(2) Date: Apr. 17, 2014

(87) PCT Pub. No.: WO2013/059437
PCT Pub. Date: Apr. 25, 2013

(65) Prior Publication Data
US 2014/0343019 A1    Nov. 20, 2014

Related U.S. Application Data

(60) Provisional application No. 61/548,939, filed on Oct. 19, 2011.

(51) Int. Cl.
C07F 5/02    (2006.01)
(52) U.S. Cl.
CPC ...................................... *C07F 5/025* (2013.01)
(58) Field of Classification Search
None
See application file for complete search history.

(56) References Cited

U.S. PATENT DOCUMENTS

| 8,894,970 B2 * | 11/2014 | Tomczuk et al. ............ 424/1.69 |
| 2004/0063666 A1 | 4/2004 | Christianson et al. |
| 2010/0189544 A1 | 7/2010 | Nakamura et al. |

FOREIGN PATENT DOCUMENTS

| WO | WO-99/19295 A1 | 4/1999 |
| WO | WO-2007/005620 A2 | 1/2007 |
| WO | WO-2010/085797 A2 | 7/2010 |
| WO | WO-2011/133653 A1 | 10/2011 |
| WO | WO-2012/091757 A1 | 7/2012 |
| WO | WO-2013/059437 A1 | 4/2013 |

OTHER PUBLICATIONS

Steppan et al., Development of novel arginase inhibitors for therapy of endothelial dysfunction. Frontier in Immunology, 2013, 51, 5905-5908.*

Segal et al., Chronic Oral Administration of the Arginase Inhibitors 2(S)-amino-6-boronohexanoic Acid (ABH) Improves Erectile Function in Aged Rates. Journal of Andrology, 2012, 33, 1169-1175.*

Shafer, S., Kolkhof, P. Failure is an option: learning from unsuccessful proof-of-concept trials. Drug Discovery Today. Nov. 2008, 13, 913-916.*

Horig, H., Pullman, W. From bench to clinic and back: Perspective on the 1st IQPC Translational Research conference. Journal of Translational Medicine. Dec. 2004, 2, 44.*

Baggio, R., et al. "Inhibition of $Mn^{2+}_2$_Arginase by Borate Leads to the Design of a Transition State Analogue Inhibitor, 2(S)-Amino-6-boronohexanoic Acid," J. Am. Chem. Soc., 119: 8107-8108 (1997).

Busnel, O., et al. "Synthesis and evaluation of new ω-borono-α-amino acids as rat liver arginase inhibitors," Bioorganic & Medicinal Chemistry; 13: 2373-2379 (2005).

Lei, Li, et al. "Progress of Boronic Acids as Enzyme Inhibitors," Chinese Journal of Pharmaceuticals; 40(3): 213-219 (2009). (English Abstract Only).

International Search Report and Written Opinion for PCT/US2011/033223 mailed Jul. 14, 2011.

International Search Report and Written Opinion for PCT/US2012/060789 mailed Dec. 19, 2012.

* cited by examiner

*Primary Examiner* — Michael Barker
*Assistant Examiner* — Po-Chih Chen
(74) *Attorney, Agent, or Firm* — David P. Halstead; Foley Hoag LLP

(57) ABSTRACT

The inventive compounds are small molecule therapeutics that are potent inhibitors of Arginase I and II activity. The invention also provides pharmaceutical compositions of the inventive compounds and methods for using the inventive compounds for treating or preventing a disease or a condition associated with arginase activity.

22 Claims, No Drawings

INHIBITORS OF ARGINASE AND THEIR THERAPEUTIC APPLICATIONS

This application claims priority to U.S. Provisional Application No. 61/548,939 filed on Oct. 19, 2011, which is hereby incorporated by reference in its entirety as if fully set forth herein.

BACKGROUND OF THE INVENTION

The present invention relates generally to inhibitors of arginase and their use for the treatment of pathological states. Two isoforms of arginase have been identified to date. arginase I (ARG I), that is expressed in the cytosole and arginase II (ARG II), that is expressed in mitochondria. The arginase enzymes together with the nitric oxide synthase (NOS) enzymes play an important role in regulating the levels of nitric oxide in cells and in the development of pathophysiological disease states.

The arginases are implicated in various pathological states. These include without limitation erectile dysfunction, pulmonary hypertension, hypertension, atherosclerosis, renal disease, asthma, T-cell dysfunction, ischemia reperfusion injury, neurodegenerative diseases, wound healing, and fibrotic diseases. Although the mechanism of action of arginase enzymes in these disease states is still a subject of ongoing research, several studies imply that the arginase enzymes are often upregulated during pathological disease states.

For example, it is postulated that upregulation of arginase activity results in reduced levels of arginine which in turn reduces the level of nitric oxide (NO) a physiologically important signaling molecule that is required for cell division, arterial vasodilation, regulation of blood flow and for controlling muscular and neurological signal transduction.

In addition to its role in regulating nitric oxide (NO) levels, arginase also affects production of critical polyamines such as putrescine, spermidine and spermine. As arginase catabolizes L-arginine it produces ornithine. Ornithine is subsequently converted to putrescine, spermidine and spermine via ornithine decarboxylase, spermidine synthase and spermine synthase respectively. Thus, the arginase enzymes control physiological signaling events by controlling the intracellular levels of polyamine signal transducers. See Wang, J-Y; and Casero, Jr., R. A., Ed; Humana Press, Totowa, N.J., 2006. Ornithine also provides an alternative biosynthetic pathway to proline and thereby supports collagen production (Smith, R. J.; Phang, J. M., The importance of ornithine as a precursor for proline in mammalian cells. J. Cell. Physiol. 1979, 98, 475-482. Albina, J. E.; Abate, J. A.; Mastrofrancesco, B. Role of ornithine as a proline precursor in healing wounds. J. Surg. Res. 1993, 55, 97-102.)

Given the role of arginase in various pathological states, the present invention provides boron-containing compounds as inhibitors of arginase activity, as well as methodologies for using the inventive compounds as therapeutics.

SUMMARY OF THE INVENTION

The present invention provides certain boron-containing compounds that are inhibitors of arginase activity. The invention also provides methods for using the inventive compounds in treatment. In one embodiment, therefore, inventive compounds and their pharmaceutically acceptable formulations are provided as therapeutic agents capable of inhibiting arginase activity. Compounds and pharmaceutical formulations in accordance with this invention are useful for treating a number of diseases and conditions, including but not limited to pulmonary hypertension, erectile dysfunction (ED), hypertension, atherosclerosis, renal disease, asthma, T-cell dysfunction, ischemia reperfusion injury, neurodegenerative diseases, wound healing, and fibrotic diseases.

In one embodiment, the invention provides a compound that is selected from the following table:

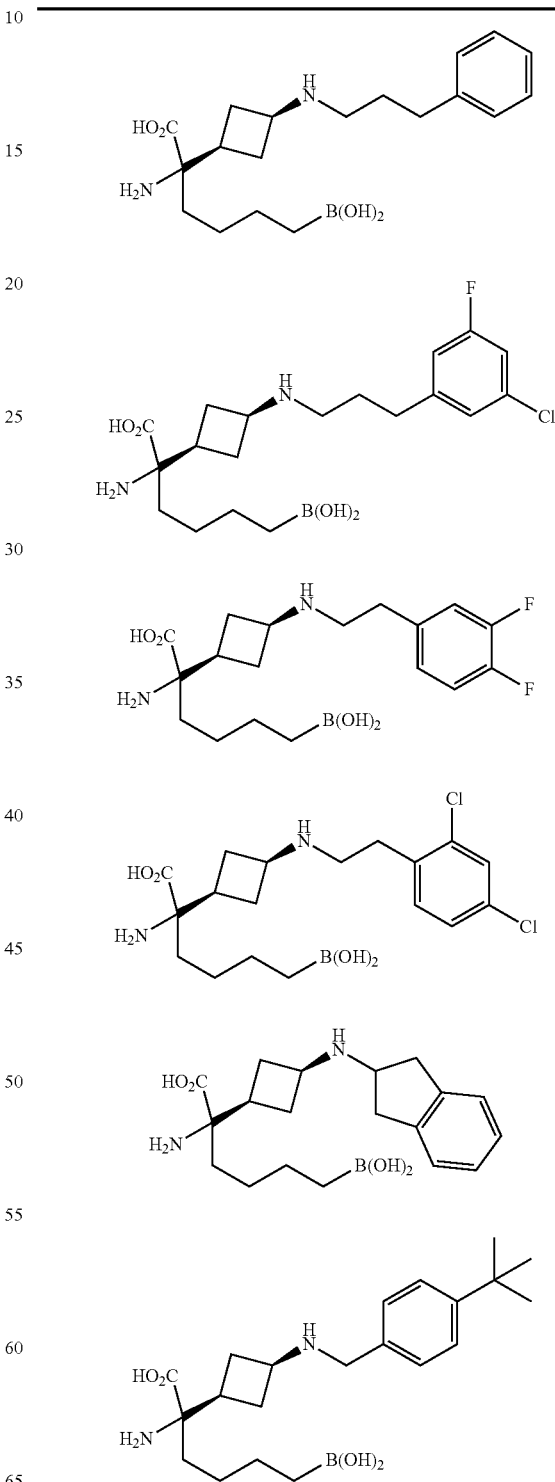

US 9,266,908 B2
3
-continued
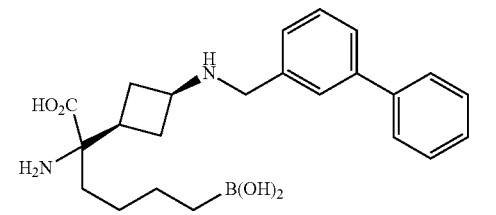 [SMILES: NC(CCCCB(O)O)(C(=O)O)[C@H]1C[C@@H](NCc2cccc(-c3ccccc3)c2)C1]
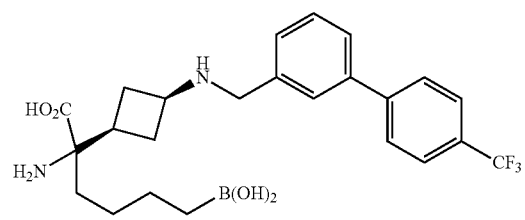
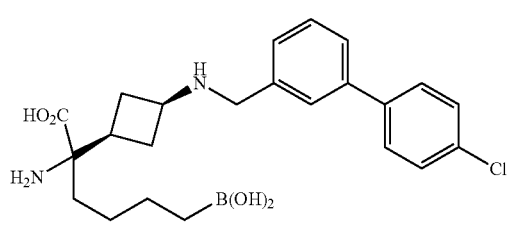
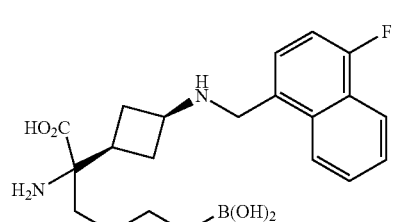
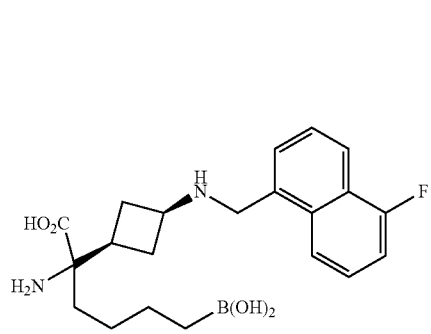 [SMILES: NC(CCCCB(O)O)(C(=O)O)[C@H]1C[C@@H](NCc2cccc3c(F)cccc23)C1]
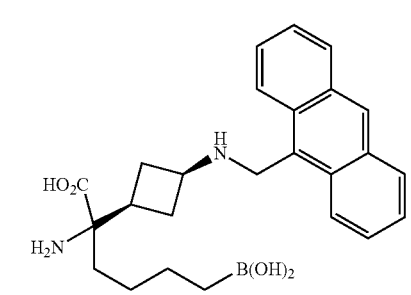 [SMILES: NC(CCCCB(O)O)(C(=O)O)[C@H]1C[C@@H](NCc2c3ccccc3cc3ccccc23)C1]
4
-continued
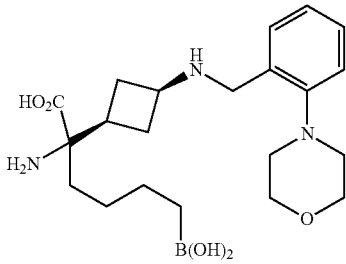 [SMILES: NC(CCCCB(O)O)(C(=O)O)[C@H]1C[C@@H](NCc2ccccc2N2CCOCC2)C1]
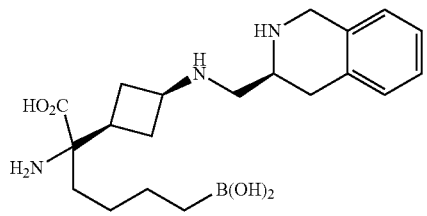 [SMILES: NC(CCCCB(O)O)(C(=O)O)[C@H]1C[C@@H](NC[C@@H]2Cc3ccccc3CN2)C1]
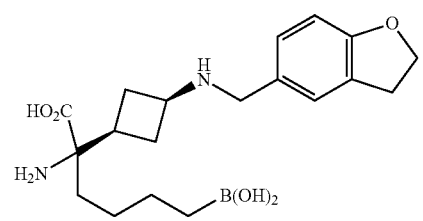 [SMILES: NC(CCCCB(O)O)(C(=O)O)[C@H]1C[C@@H](NCc2ccc3c(c2)CCO3)C1]
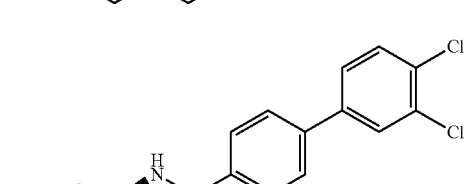
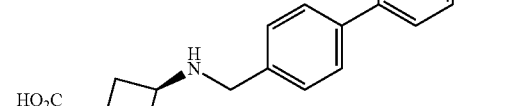
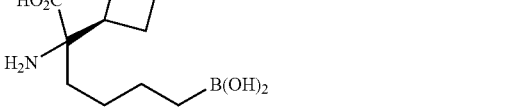

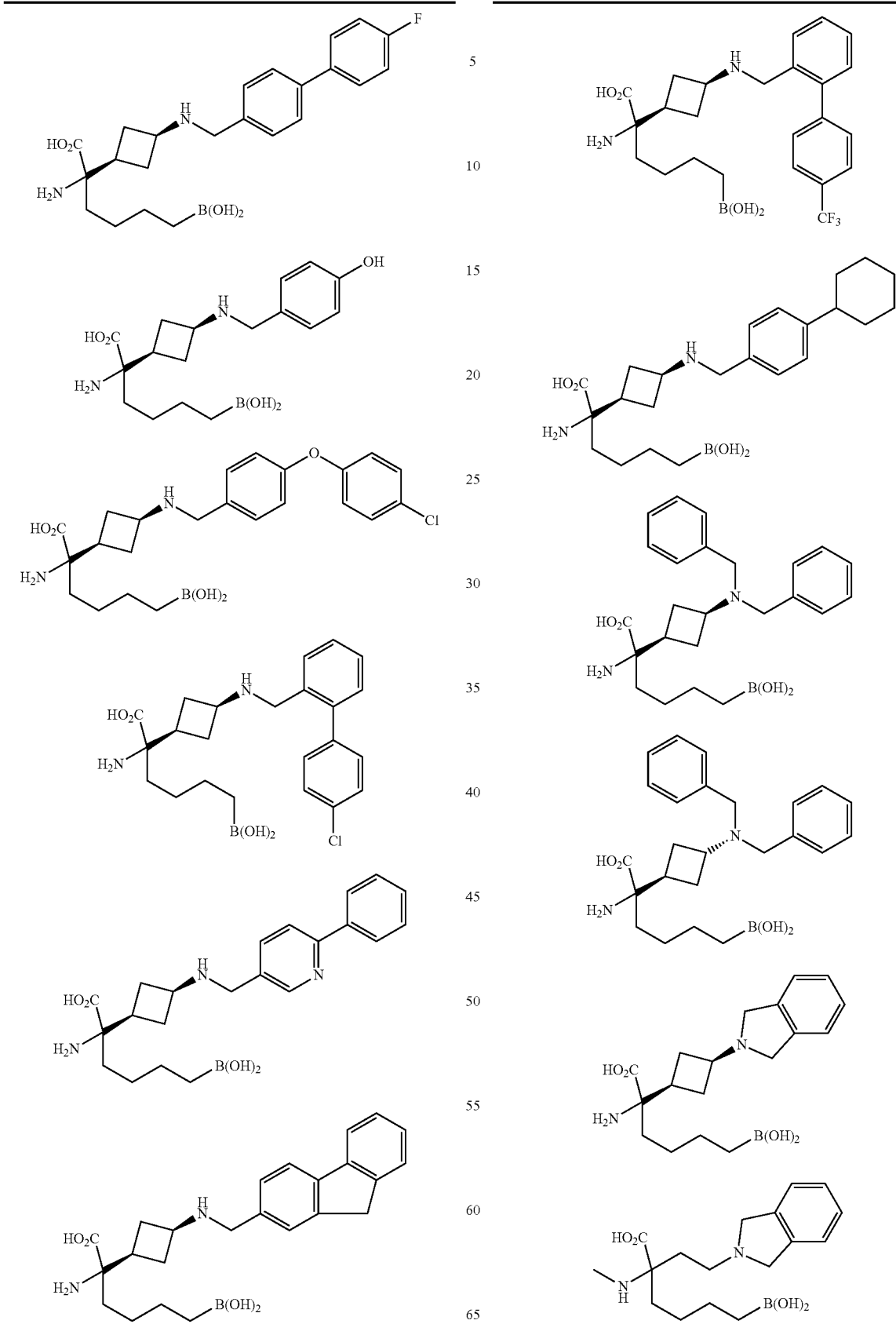

-continued

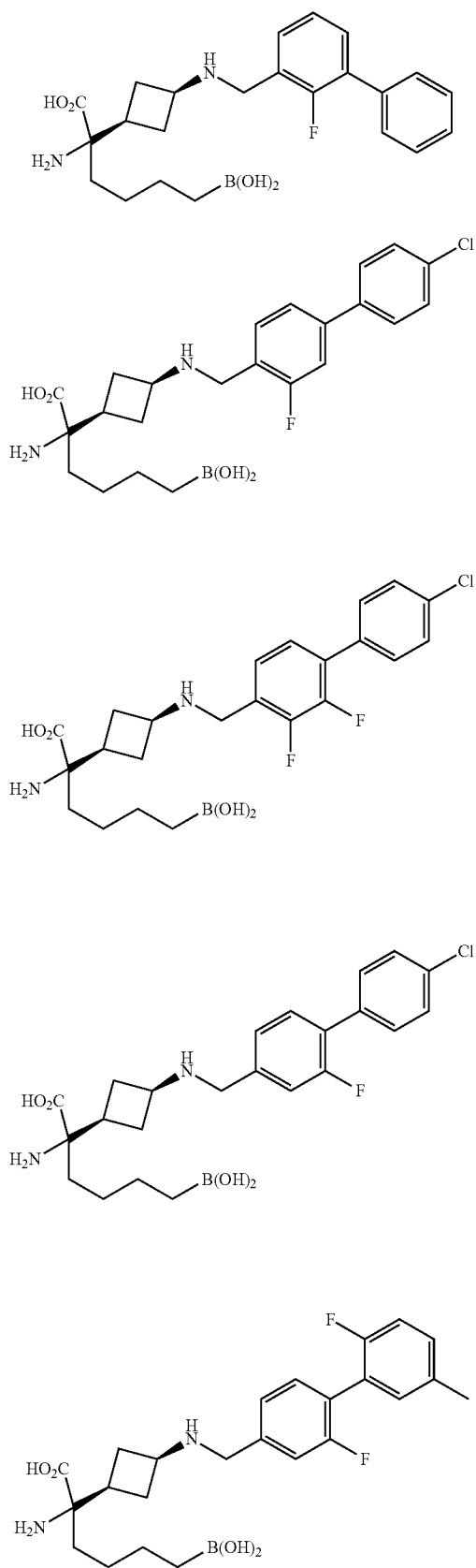
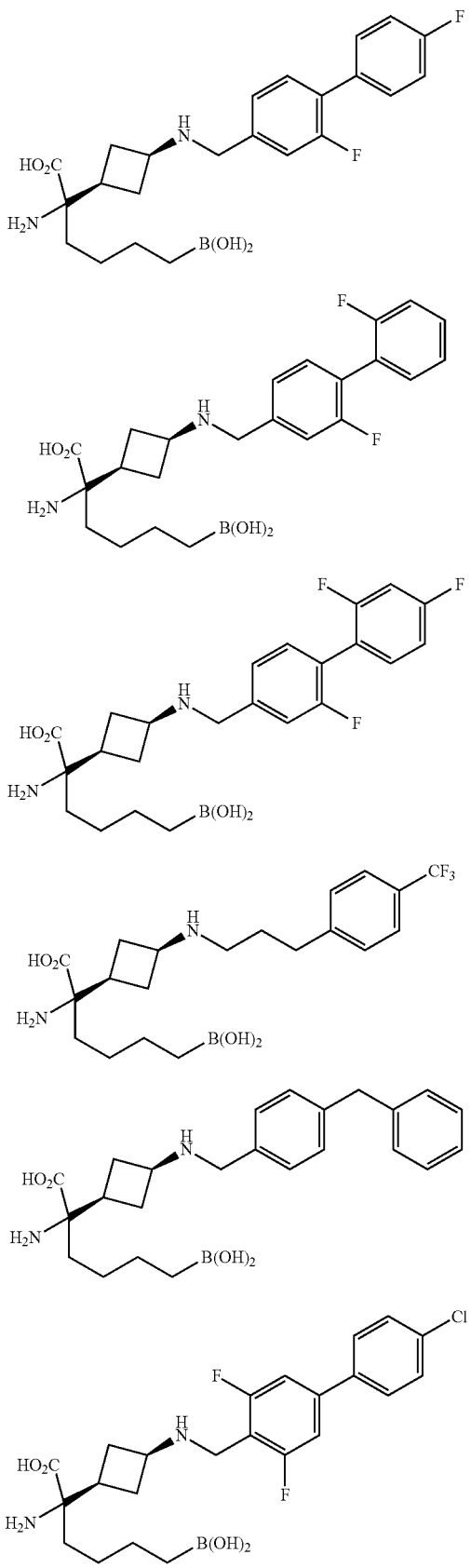

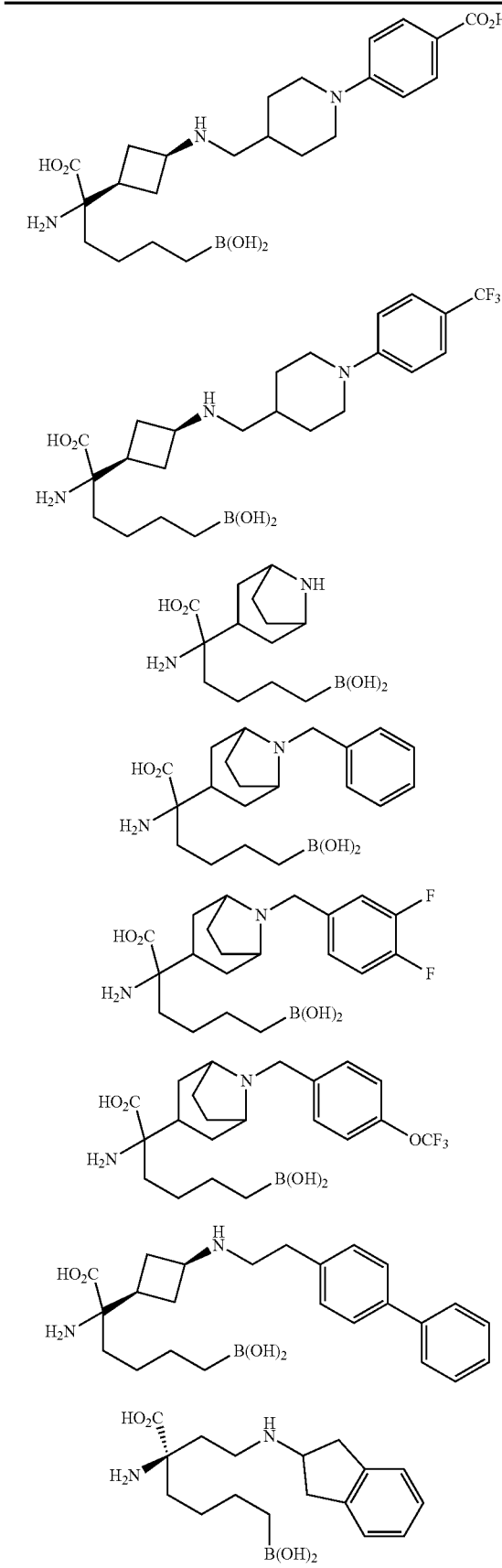
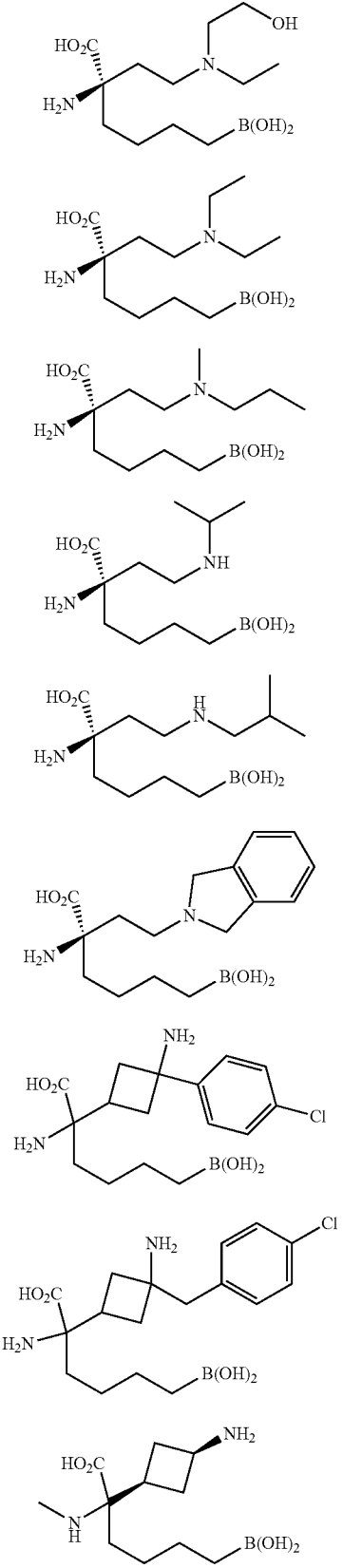

The invention also encompasses pharmaceutically acceptable salts, stereoisomers, tautomers, and prodrugs of such compounds.

In another embodiment invention provides a pharmaceutical composition that comprises a compound that is selected from the above table or pharmaceutically acceptable salts, stereoisomers, tautomers, or a prodrug of the inventive compound and a pharmaceutically acceptable carrier.

Compounds in accordance with the present invention and their pharmaceutical formulations are useful for treating a number of disorders, including but not limited to cardiovascular disorders, sexual disorders, wound healing disorders, -gastrointestinal disorders, autoimmune disorders, immune disorders, infections, pulmonary disorders, fibrotic disorders and hemolytic disorders.

Exemplary cardiovascular disorders are diseases and conditions that selected from the consisting of pulmonary arterial hypertension (PAH), pulmonary arterial hypertension in high altitude, ischemia reperfusion injury and atherosclerosis.

When the disease or condition is a pulmonary disorder, exemplary diseases include chemically-induced lung fibrosis, idiopathic pulmonary fibrosis, cystic fibrosis, chronic obstructive pulmonary disease (COPD), and asthma.

Compounds in accordance with the present invention are also useful at treating autoimmune disorders selected from the group consisting of encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

Other immune diseases or conditions that can be treated using a compound of the invention include without limitation myeloid-derived suppressor cell (MDSC) mediated T-cell dysfunction, human immunodeficiency virus (HIV), autoimmune encephalomyelitis, ABO mismatch transfusion reaction, sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

Exemplary gastrointestinal disorders that can be treated using the inventive compounds include without limitation gastrointestinal motility disorders, gastric cancers, inflammatory bowel disease, Crohn's disease, ulcerative colitis, and gastric ulcers.

The inventive compounds are also useful to protect organs from ischemia reperfusion (IR) injury after organ transplantation. For instance, compounds in accordance with the present invention can be used to prevent liver IR, kidney IR, and myocardial IR.

In one embodiment, the present invention provides a pharmaceutical composition that comprises a therapeutically effective amount of at least one compound selected form the above table, and a pharmaceutically acceptable carrier.

The invention also provides in one embodiment a method for inhibiting arginase I, arginase II, or a combination thereof in a cell comprising contacting the cell with at least one compound selected form the above table. Pursuant to another embodiment, the invention provides a method for treating or preventing a disease or a condition associated with expression or activity of arginase I, arginase II, or a combination thereof in a subject, comprising administering to the subject a therapeutically effective amount of at least one compound selected form the above table.

DETAILED DESCRIPTION

The compounds as described herein are small molecule inhibitors of arginase I activity or arginase II activity. As will be apparent from the description hereinbelow, the inventive compounds and their pharmaceutical compositions are useful in treating or preventing diseases or conditions that are associated with the expression or activity of arginase.

DEFINITIONS

Compounds of the invention can exist in various isomeric forms, including configurational, geometric, and conformational isomers, including, for example, cis- or trans-conformations. Compounds of the present invention may also exist in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention, or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

The terms "modulate", "modulation" and the like refer to the ability of an inventive compound to increase or decrease the function, or activity of, for example, Arginase I or Arginase II. "Modulation", in its various forms, is intended to encompass inhibition, antagonism, partial antagonism, activation, agonism and/or partial agonism of the activity associated with arginase. Arginase inhibitors are compounds that, e.g., bind to, partially or totally block stimulation, decrease, prevent, delay activation, inactivate, desensitize, or down regulate signal transduction. The ability of a compound to modulate arginase activity can be demonstrated in an enzymatic assay or a cell-based assay.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient, must undergo chemical conversion by metabolic processes before becoming an active pharmacological agent. Exemplary prodrugs of compounds in accordance with the present invention are esters, pinenes, dioxaborolanes, and amides.

Inventive Compounds

The present invention provides small molecule therapeutics that are potent inhibitors of arginase I and II activities. Exemplary compounds in accordance with the present invention are shown in Table 1 below. While some exemplary compounds are depicted with stereochemistry, it should be understood that the invention includes all possible stereoisomers, such as diastereomers, of the compounds.

TABLE 1

| Ex# | Structure | Name |
|---|---|---|
| 1 | 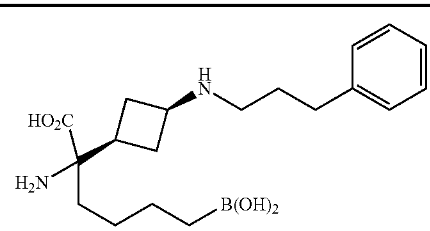 | (S)-2-amino-6-borono-2-((1s,3R)-3-(3-phenylpropylamino)cyclobutyl)hexanoic acid |
| 2 | 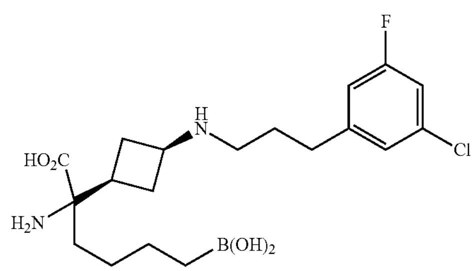 [SMILES: NC(CCCCB(O)O)(C(=O)O)[C@H]1C[C@@H](NCCCc2cc(F)cc(Cl)c2)C1] | (S)-2-amino-6-borono-2-((1s,3R)-3-(3-(3-chloro-5-fluorophenyl)propylamino)cyclobutyl)hexanoic acid |

TABLE 1-continued

| Ex# | Structure | Name |
|---|---|---|
| 3 | 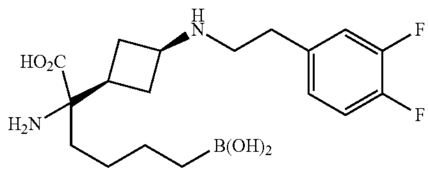 [SMILES: NC(CCCCB(O)O)(C(=O)O)[C@H]1C[C@@H](NCCc2ccc(F)c(F)c2)C1] | (S)-2-amino-6-borono-2-((1s,3R)-3-(3,4-difluorophenethylamino)cyclobutyl)hexanoic acid |
| 4 | 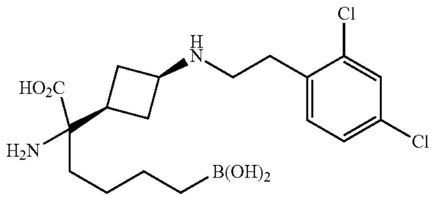 [SMILES: NC(CCCCB(O)O)(C(=O)O)[C@H]1C[C@@H](NCCc2ccc(Cl)cc2Cl)C1] | (S)-2-amino-6-borono-2-((1s,3R)-3-(2,4-dichlorophenethylamino)cyclobutyl)hexanoic acid |
| 5 | 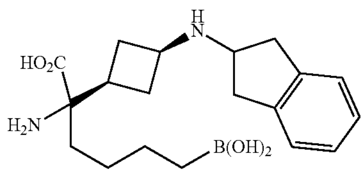 [SMILES: NC(CCCCB(O)O)(C(=O)O)[C@H]1C[C@@H](NC2Cc3ccccc3C2)C1] | (S)-2-amino-6-borono-2-((1s,3R)-3-(2,3-dihydro-1H-inden-2-ylamino)cyclobutyl)hexanoic acid |
| 6 | 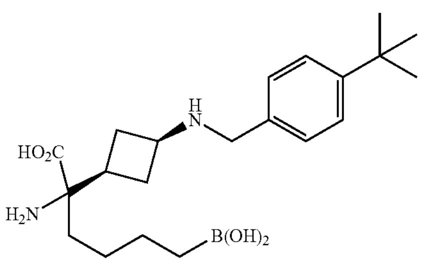 [SMILES: CC(C)(C)c1ccc(CN[C@H]2C[C@@H](C(N)(CCCCB(O)O)C(=O)O)C2)cc1] | (S)-2-amino-6-borono-2-((1s,3R)-3-(4-tert-butylbenzylamino)cyclobutyl)hexanoic acid |
| 7 | 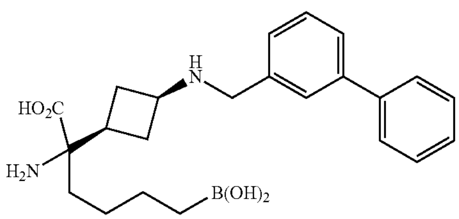 [SMILES: NC(CCCCB(O)O)(C(=O)O)[C@H]1C[C@@H](NCc2cccc(-c3ccccc3)c2)C1] | (S)-2-amino-2-((1s,3R)-3-(biphenyl-3-ylmethylamino)cyclobutyl)-6-boronohexanoic acid |
| 8 | 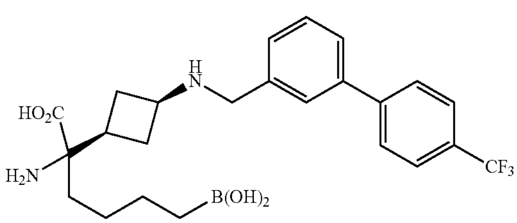 [SMILES: NC(CCCCB(O)O)(C(=O)O)[C@H]1C[C@@H](NCc2cccc(-c3ccc(C(F)(F)F)cc3)c2)C1] | (S)-2-amino-6-borono-2-((1s,3R)-3-((4'-(trifluoromethyl)biphenyl-3-yl)methylamino)cyclobutyl)hexanoic acid |
| 9 | 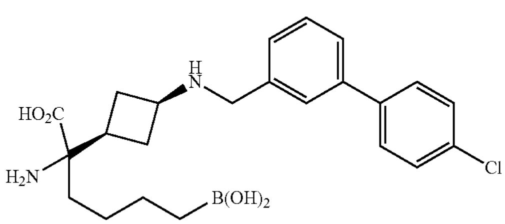 [SMILES: NC(CCCCB(O)O)(C(=O)O)[C@H]1C[C@@H](NCc2cccc(-c3ccc(Cl)cc3)c2)C1] | (S)-2-amino-6-borono-2-((1s,3R)-3-((4'-chlorobiphenyl-3-yl)methylamino)cyclobutyl)hexanoic acid |

TABLE 1-continued

| Ex# | Structure | Name |
| --- | --- | --- |
| 10 | 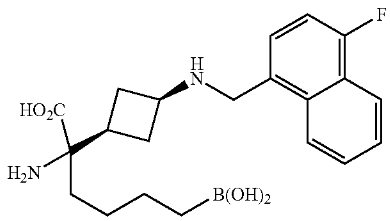 [SMILES: NC(CCCCB(O)O)(C(=O)O)[C@H]1C[C@@H](NCc2ccc(F)c3ccccc23)C1] | (S)-2-amino-6-borono-2-((1s,3R)-3-((4-fluoronaphthalen-1-yl)methylamino)cyclobutyl)hexanoic acid |
| 11 | 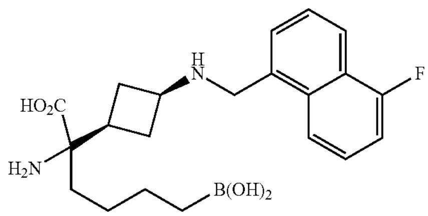 [SMILES: NC(CCCCB(O)O)(C(=O)O)[C@H]1C[C@@H](NCc2cccc3c(F)cccc23)C1] | (S)-2-amino-6-borono-2-((1s,3R)-3-((5-fluoronaphthalen-1-yl)methylamino)cyclobutyl)hexanoic acid |
| 12 | 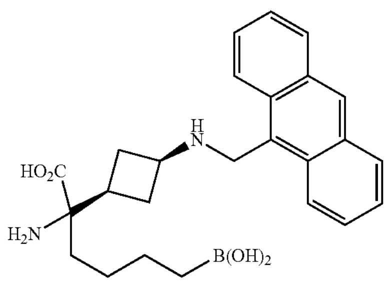 [SMILES: NC(CCCCB(O)O)(C(=O)O)[C@H]1C[C@@H](NCc2c3ccccc3cc3ccccc23)C1] | (S)-2-amino-2-((1s,3R)-3-(anthracen-9-ylmethylamino)cyclobutyl)-6-boronohexanoic acid |
| 13 | 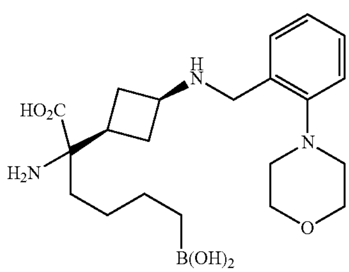 [SMILES: NC(CCCCB(O)O)(C(=O)O)[C@H]1C[C@@H](NCc2ccccc2N2CCOCC2)C1] | (S)-2-amino-6-borono-2-((1s,3R)-3-(2-morpholinobenzylamino)cyclobutyl)hexanoic acid |
| 14 | 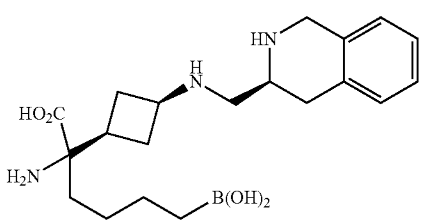 [SMILES: NC(CCCCB(O)O)(C(=O)O)[C@H]1C[C@@H](NC[C@@H]2Cc3ccccc3CN2)C1] | (S)-2-amino-6-borono-2-((1R,3R)-3-(((S)-1,2,3,4-tetrahydroisoquinolin-3-yl)methylamino)cyclobutyl)hexanoic acid |
| 15 | 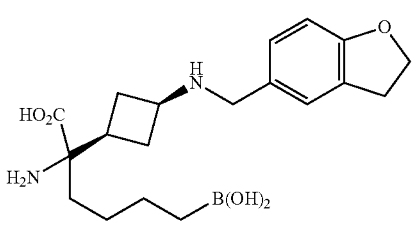 [SMILES: NC(CCCCB(O)O)(C(=O)O)[C@H]1C[C@@H](NCc2ccc3c(c2)CCO3)C1] | (S)-2-amino-6-borono-2-((1s,3R)-3-((2,3-dihydrobenzofuran-5-yl)methylamino)cyclobutyl)hexanoic acid |

TABLE 1-continued

| Ex# | Structure | Name |
|---|---|---|
| 16 | 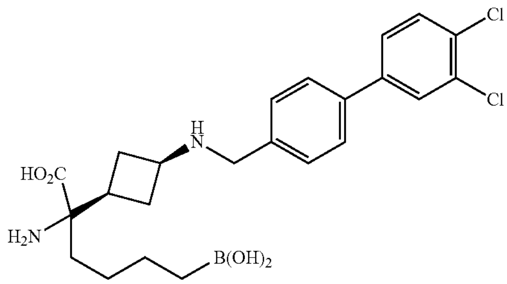 [SMILES: NC(CCCCB(O)O)(C(=O)O)[C@H]1C[C@@H](NCc2ccc(-c3ccc(Cl)c(Cl)c3)cc2)C1] | (S)-2-amino-6-borono-2-((1s,3R)-3-((3',4'-dichlorobiphenyl-4-yl)methylamino)cyclobutyl)hexanoic acid |
| 17 | 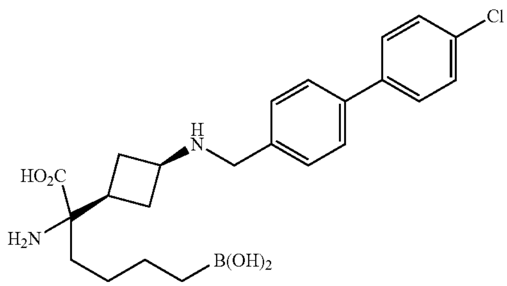 [SMILES: NC(CCCCB(O)O)(C(=O)O)[C@H]1C[C@@H](NCc2ccc(-c3ccc(Cl)cc3)cc2)C1] | (S)-2-amino-6-borono-2-((1s,3R)-3-((4'-chlorobiphenyl-4-yl)methylamino)cyclobutyl)hexanoic acid |
| 18 | 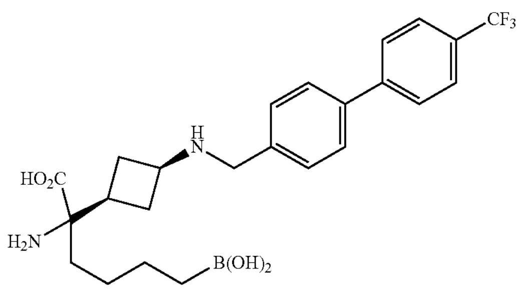 [SMILES: NC(CCCCB(O)O)(C(=O)O)[C@H]1C[C@@H](NCc2ccc(-c3ccc(C(F)(F)F)cc3)cc2)C1] | (S)-2-amino-6-borono-2-((1s,3R)-3-((4'-(trifluoromethyl)biphenyl-4-yl)methylamino)cyclobutyl)hexanoic acid |
| 19 | 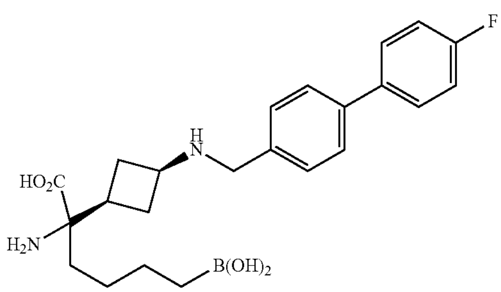 [SMILES: NC(CCCCB(O)O)(C(=O)O)[C@H]1C[C@@H](NCc2ccc(-c3ccc(F)cc3)cc2)C1] | (S)-2-amino-6-borono-2-((1s,3R)-3-((4'-fluorobiphenyl-4-yl)methylamino)cyclobutyl)hexanoic acid |
| 20 | 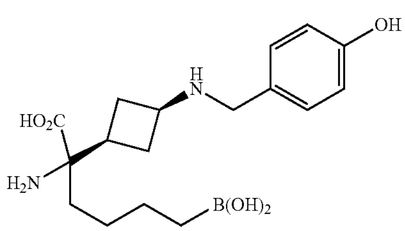 [SMILES: NC(CCCCB(O)O)(C(=O)O)[C@H]1C[C@@H](NCc2ccc(O)cc2)C1] | (S)-2-amino-6-borono-2-((1s,3R)-3-(4-hydroxybenzylamino)cyclobutyl)hexanoic acid |
| 21 | 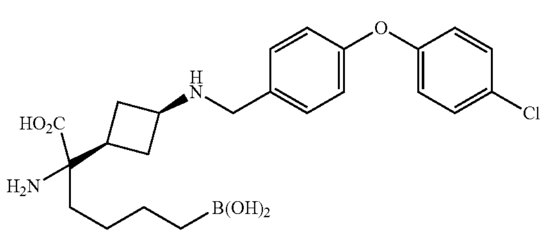 [SMILES: NC(CCCCB(O)O)(C(=O)O)[C@H]1C[C@@H](NCc2ccc(Oc3ccc(Cl)cc3)cc2)C1] | (S)-2-amino-6-borono-2-((1s,3R)-3-(4-(4-chlorophenoxy)benzylamino)cyclobutyl)hexanoic acid |

TABLE 1-continued

| Ex# | Structure | Name |
|---|---|---|
| 22 | 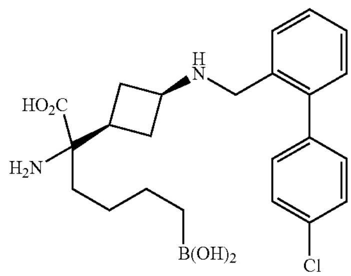 [SMILES: NC(CCCCB(O)O)(C(=O)O)[C@H]1C[C@@H](NCc2ccccc2-c2ccc(Cl)cc2)C1] | (S)-2-amino-6-borono-2-((1s,3R)-3-((4'-chlorobiphenyl-2-yl)methylamino)cyclobutyl)hexanoic acid |
| 23 | 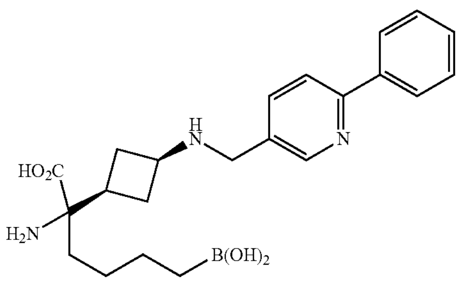 [SMILES: NC(CCCCB(O)O)(C(=O)O)[C@H]1C[C@@H](NCc2ccc(-c3ccccc3)nc2)C1] | (S)-2-amino-6-borono-2-((1s,3R)-3-((6-phenylpyridin-3-yl)methylamino)cyclobutyl)hexanoic acid |
| 24 | 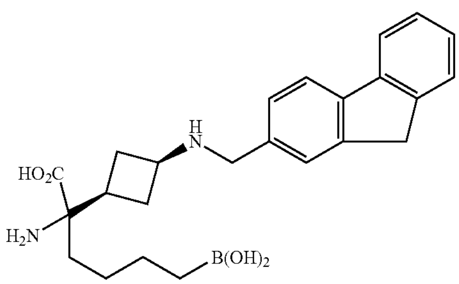 [SMILES: NC(CCCCB(O)O)(C(=O)O)[C@H]1C[C@@H](NCc2ccc3c(c2)Cc2ccccc2-3)C1] | (S)-2-((1s,3R)-3-((9H-fluoren-2-yl)methylamino)cyclobutyl)-2-amino-6-boronohexanoic acid |
| 25 | 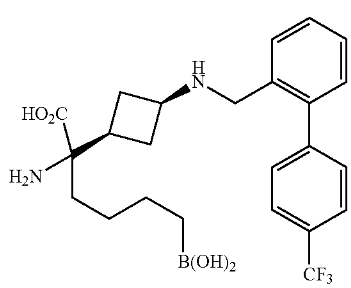 [SMILES: NC(CCCCB(O)O)(C(=O)O)[C@H]1C[C@@H](NCc2ccccc2-c2ccc(C(F)(F)F)cc2)C1] | (S)-2-amino-6-borono-2-((1s,3R)-3-((4'-(trifluoromethyl)biphenyl-2-yl)methylamino)cyclobutyl)hexanoic acid |
| 26 | 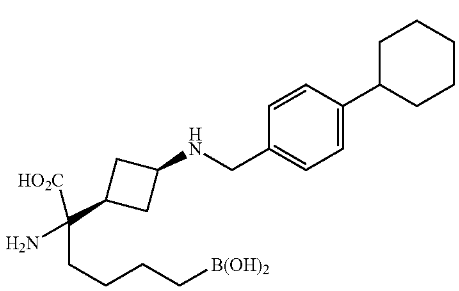 [SMILES: NC(CCCCB(O)O)(C(=O)O)[C@H]1C[C@@H](NCc2ccc(C3CCCCC3)cc2)C1] | (S)-2-amino-6-borono-2-((1s,3R)-3-(4-cyclohexylbenzylamino)cyclobutyl)hexanoic acid |

TABLE 1-continued

| Ex# | Structure | Name |
|---|---|---|
| 27 | 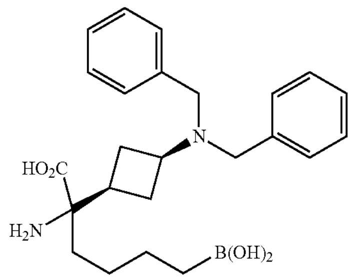 [SMILES: NC(CCCCB(O)O)(C(=O)O)[C@H]1C[C@@H](N(Cc2ccccc2)Cc2ccccc2)C1] | (S)-2-amino-6-borono-2-((1s,3R)-3-(dibenzylamino)cyclobutyl)hexanoic acid |
| 28 | 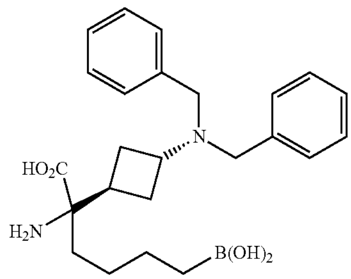 | (S)-2-amino-6-borono-2-((1r,3S)-3-(dibenzylamino)cyclobutyl)hexanoic acid |
| 29 | 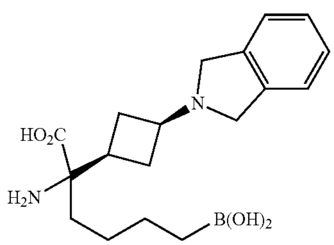 [SMILES: NC(CCCCB(O)O)(C(=O)O)[C@H]1C[C@@H](N2Cc3ccccc3C2)C1] | (S)-2-amino-6-borono-2-((1s,3R)-3-(isoindolin-2-yl)cyclobutyl)hexanoic acid |
| 30 | 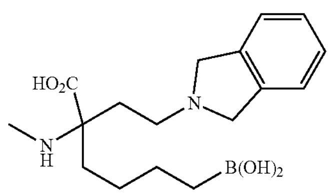 [SMILES: CNC(CCCCB(O)O)(CCN1Cc2ccccc2C1)C(=O)O] | 6-borono-2-(2-(isoindolin-2-yl)ethyl)-2-(methylamino)hexanoic acid |
| 31 | 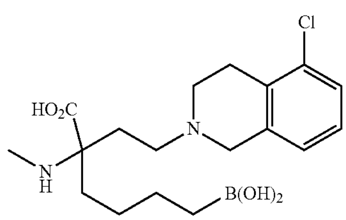 [SMILES: CNC(CCCCB(O)O)(CCN1CCc2c(Cl)cccc2C1)C(=O)O] | 6-borono-2-(2-(5-chloro-3,4-dihydroisoquinolin-2(1H)-yl)ethyl)-2-(methylamino)hexanoic acid |
| 32 | 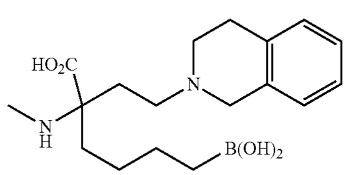 [SMILES: CNC(CCCCB(O)O)(CCN1CCc2ccccc2C1)C(=O)O] | 6-borono-2-(2-(3,4-dihydroisoquinolin-2(1H)-yl)ethyl)-2-(methylamino)hexanoic acid |
| 33 | 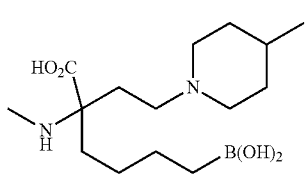 | 6-borono-2-(methylamino)-2-(2-(4-methylpiperidin-1-yl)ethyl)hexanoic acid |

TABLE 1-continued

| Ex# | Structure | Name |
|---|---|---|
| 34 | 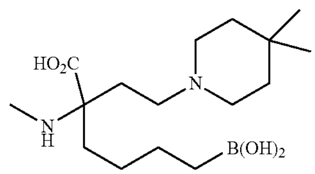 | 6-borono-2-(2-(4,4-dimethylpiperidin-1-yl)ethyl)-2-(methylamino)hexanoic acid |
| 35 | 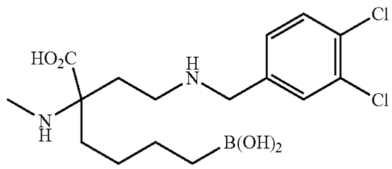 [SMILES: CNC(CCCCB(O)O)(CCNCc1ccc(Cl)c(Cl)c1)C(=O)O] | 6-borono-2-(2-(3,4-dichlorobenzylamino)ethyl)-2-(methylamino)hexanoic acid |
| 36 | 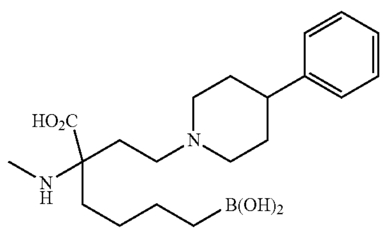 [SMILES: CNC(CCCCB(O)O)(CCN1CCC(c2ccccc2)CC1)C(=O)O] | 6-borono-2-(methylamino)-2-(2-(4-phenylpiperidin-1-yl)ethyl)hexanoic acid |
| 37 | 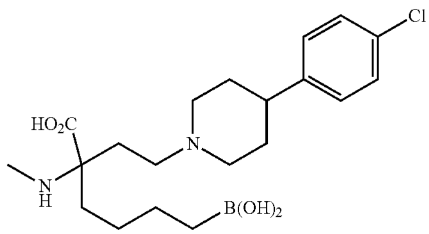 [SMILES: CNC(CCCCB(O)O)(CCN1CCC(c2ccc(Cl)cc2)CC1)C(=O)O] | 6-borono-2-(2-(4-(4-chlorophenyl)piperidin-1-yl)ethyl)-2-(methylamino)hexanoic acid |
| 38 | 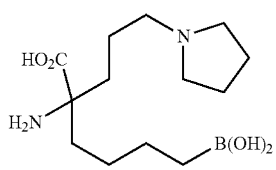 [SMILES: NC(CCCCB(O)O)(CCCN1CCCC1)C(=O)O] | 2-amino-6-borono-2-(3-(pyrrolidin-1-yl)propyl)hexanoic acid |
| 39 | 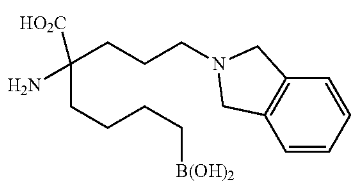 [SMILES: NC(CCCCB(O)O)(CCCN1Cc2ccccc2C1)C(=O)O] | 2-amino-6-borono-2-(3-(isoindolin-2-yl)propyl)hexanoic acid |
| 40 | 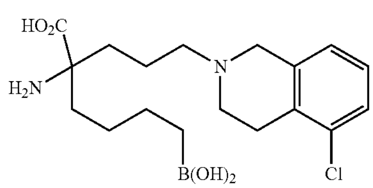 [SMILES: NC(CCCCB(O)O)(CCCN1CCc2c(Cl)cccc2C1)C(=O)O] | 2-amino-6-borono-2-(3-(5-chloro-3,4-dihydro-isoquinolin-2(1H)-yl)propyl)hexanoic acid |
| 41 | 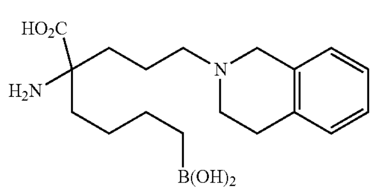 [SMILES: NC(CCCCB(O)O)(CCCN1CCc2ccccc2C1)C(=O)O] | 2-amino-6-borono-2-(3-(3,4-dihydroisoquinolin-2(1H)-yl)propyl)hexanoic acid |

TABLE 1-continued

| Ex# | Structure | Name |
|---|---|---|
| 42 | 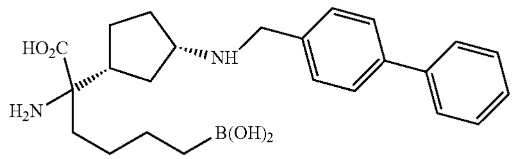 [SMILES: NC(CCCCB(O)O)(C(=O)O)[C@@H]1CC[C@H](NCc2ccc(-c3ccccc3)cc2)C1] | (R)-2-amino-2-((1R,3S)-3-(biphenyl-4-ylmethylamino)cyclopentyl)-6-boronohexanoic acid |
| 43 | 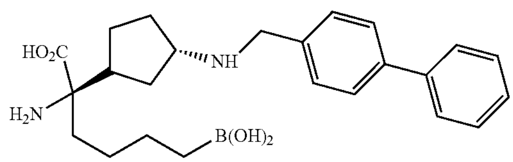 [SMILES: N[C@@](CCCCB(O)O)(C(=O)O)C1CC[C@H](NCc2ccc(-c3ccccc3)cc2)C1] | (S)-2-amino-2-((1S,3S)-3-(biphenyl-4-ylmethylamino)cyclopentyl)-6-boronohexanoic acid |
| 44 | 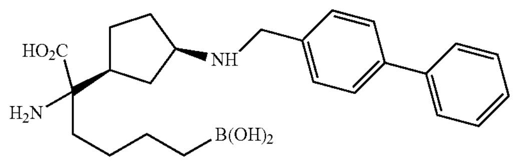 [SMILES: NC(CCCCB(O)O)(C(=O)O)[C@H]1CC[C@@H](NCc2ccc(-c3ccccc3)cc2)C1] | (S)-2-amino-2-((1S,3R)-3-(biphenyl-4-ylmethylamino)cyclopentyl)-6-boronohexanoic acid |
| 45 | 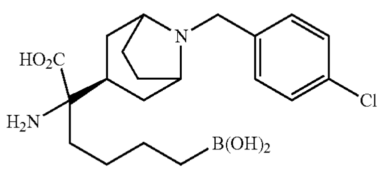 | (2S)-2-amino-6-borono-2-(8-(4-chlorobenzyl)-8-azabicyclo[3.2.1]octan-3-yl)hexanoic acid |
| 46 | 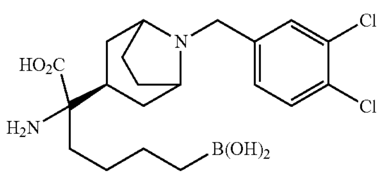 | (2S)-2-amino-6-boron-2-(8-(3,4-dichlorobenzyl)-8-azabicyclo[3.2.1]octan-3-yl)hexanoic acid |
| 47 | 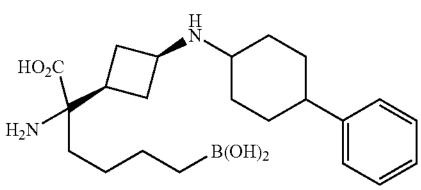 [SMILES: NC(CCCCB(O)O)(C(=O)O)[C@H]1C[C@@H](NC2CCC(c3ccccc3)CC2)C1] | (S)-2-amino-6-borono-2-((1s,3R)-3-(4-phenylcyclohexylamino)cyclobutyl)hexanoic acid |
| 48 | 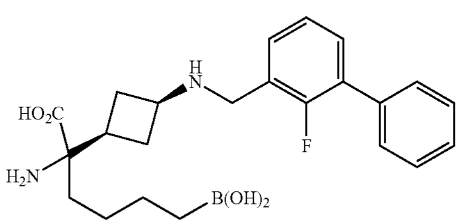 [SMILES: NC(CCCCB(O)O)(C(=O)O)[C@H]1C[C@@H](NCc2cccc(-c3ccccc3)c2F)C1] | (S)-2-amino-6-borono-2-((1s,3R)-3-((2-fluorobiphenyl-3-yl)methylamino)cyclobutyl)hexanoic acid |
| 49 | 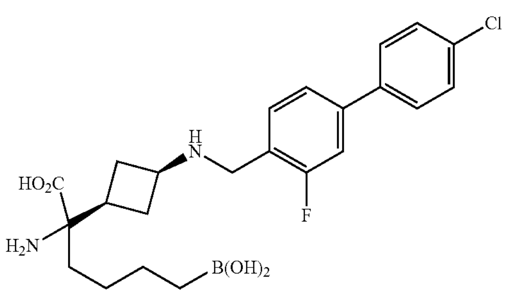 [SMILES: NC(CCCCB(O)O)(C(=O)O)[C@H]1C[C@@H](NCc2ccc(-c3ccc(Cl)cc3)cc2F)C1] | (S)-2-amino-6-borono-2-((1s,3R)-3-((4'-chloro-3-fluorobiphenyl-4-yl)methylamino)cyclobutyl)hexanoic acid |

TABLE 1-continued

| Ex# | Structure | Name |
|---|---|---|
| 50 | 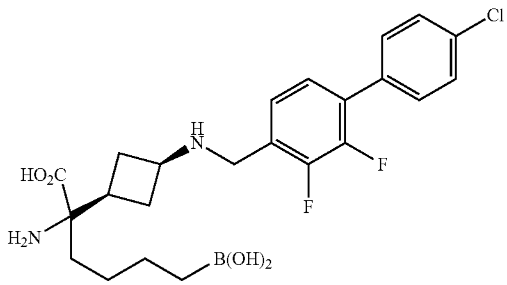 [SMILES: NC(CCCCB(O)O)(C(=O)O)[C@H]1C[C@@H](NCc2ccc(-c3ccc(Cl)cc3)c(F)c2F)C1] | (S)-2-amino-6-borono-2-((1s,3R)-3-((4'-chloro-2,3-difluorobiphenyl-4-yl)methylamino)cyclobutyl)hexanoic acid |
| 51 | 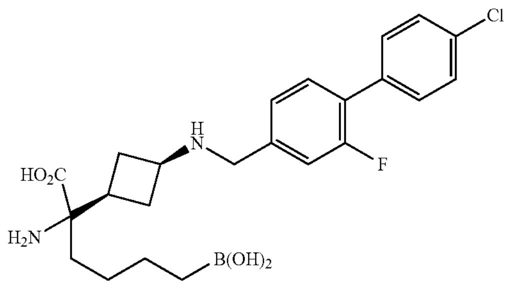 [SMILES: NC(CCCCB(O)O)(C(=O)O)[C@H]1C[C@@H](NCc2ccc(-c3ccc(Cl)cc3)c(F)c2)C1] | (S)-2-amino-6-borono-2-((1s,3R)-3-((4'-chloro-2-fluorobiphenyl-4-yl)methylamino)cyclobutyl)hexanoic acid |
| 52 | 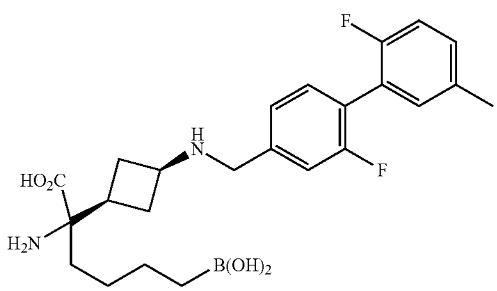 [SMILES: Cc1ccc(F)c(-c2ccc(CN[C@H]3C[C@@H](C(N)(CCCCB(O)O)C(=O)O)C3)cc2F)c1] | (S)-2-amino-6-boron-2-((1s,3R)-3-((2,2'-difluoro-5'-methylbiphenyl-4-yl)methylamino)cyclobutyl)hexanoic acid |
| 53 | 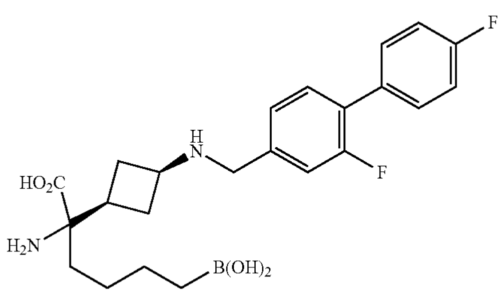 [SMILES: NC(CCCCB(O)O)(C(=O)O)[C@H]1C[C@@H](NCc2ccc(-c3ccc(F)cc3)c(F)c2)C1] | (S)-2-amino-6-borono-2-((1s,3R)-3-((2,4'-difluorobiphenyl-4-yl)methylamino)cyclobutyl)hexanoic acid |
| 54 | 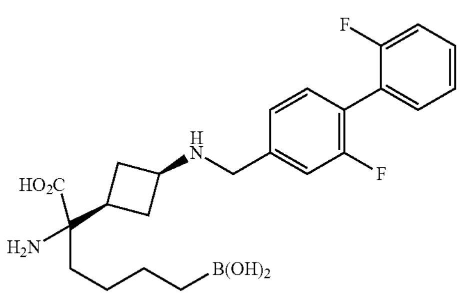 [SMILES: NC(CCCCB(O)O)(C(=O)O)[C@H]1C[C@@H](NCc2ccc(-c3ccccc3F)c(F)c2)C1] | (S)-2-amino-6-borono-2-((1s,3R)-3-((2,2'-difluorobiphenyl-4-yl)methylamino)cyclobutyl)hexanoic acid |

TABLE 1-continued

| Ex# | Structure | Name |
|---|---|---|
| 55 | 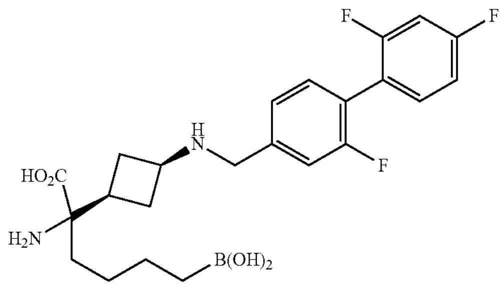 [SMILES: NC(CCCCB(O)O)(C(=O)O)[C@H]1C[C@@H](NCc2ccc(-c3ccc(F)cc3F)c(F)c2)C1] | (S)-2-amino-6-borono-2-((1s,3R)-3-((2,2',4'-trifluorobiphenyl-4-yl)methylamino)cyclobutyl)hexanoic acid |
| 56 | 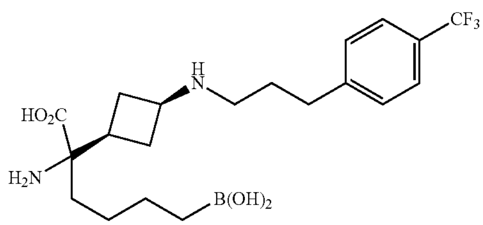 [SMILES: NC(CCCCB(O)O)(C(=O)O)[C@H]1C[C@@H](NCCCc2ccc(C(F)(F)F)cc2)C1] | (S)-2-amino-6-borono-2-((1s,3R)-3-(3-(4-(trifluoromethyl)phenyl)propylamino)cyclobutyl)hexanoic acid |
| 57 | 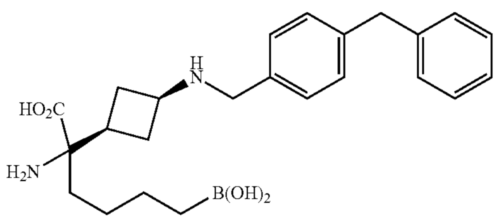 [SMILES: NC(CCCCB(O)O)(C(=O)O)[C@H]1C[C@@H](NCc2ccc(Cc3ccccc3)cc2)C1] | (S)-2-amino-2-((1s,3R)-3-(4-benzylbenzylamino)cyclobutyl)-6-boronohexanoic acid |
| 58 | 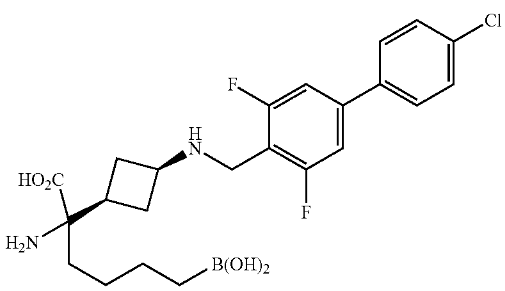 [SMILES: NC(CCCCB(O)O)(C(=O)O)[C@H]1C[C@@H](NCc2c(F)cc(-c3ccc(Cl)cc3)cc2F)C1] | (S)-2-amino-6-borono-2-((1s,3R)-3-((4'-chloro-3,5-difluorobiphenyl-4-yl)methylamino)cyclobutyl)hexanoic acid |
| 59 | 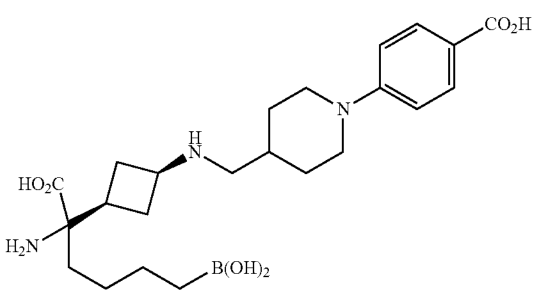 [SMILES: NC(CCCCB(O)O)(C(=O)O)[C@H]1C[C@@H](NCC2CCN(c3ccc(C(=O)O)cc3)CC2)C1] | 4-(4-(((1R,3s)-3-((S)-1-amino-5-borono-1-carboxypentyl)cyclobutylamino)methyl)piperidin-1-yl)benzoic acid |
| 60 | 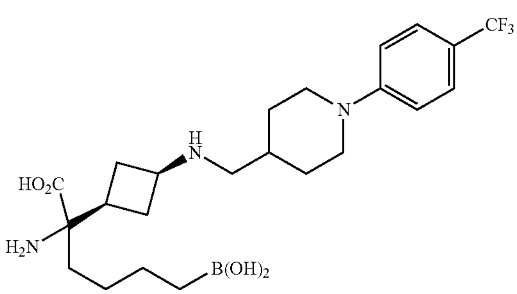 [SMILES: NC(CCCCB(O)O)(C(=O)O)[C@H]1C[C@@H](NCC2CCN(c3ccc(C(F)(F)F)cc3)CC2)C1] | (S)-2-amino-6-borono-2-((1s,3R)-3-((1-(4-(trifluoromethyl)phenyl)piperidin-4-yl)methylamino)cyclobutyl)hexanoic acid |

TABLE 1-continued

| Ex# | Structure | Name |
|---|---|---|
| 61 | 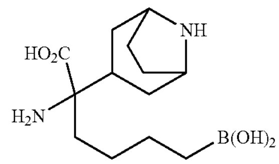 [SMILES: NC(CCCCB(O)O)(C(=O)O)C1CC2CCC(C1)N2] | 2-amino-2-(8-azabicyclo[3.2.1]octan-3-yl)-6-boronohexanoic acid |
| 62 | 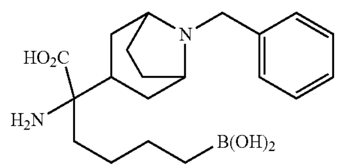 [SMILES: NC(CCCCB(O)O)(C(=O)O)C1CC2CCC(C1)N2Cc1ccccc1] | 2-amino-2-(8-benzyl-8-azabicyclo[3.2.1]octan-3-yl)-6-boronohexanoic acid |
| 63 | 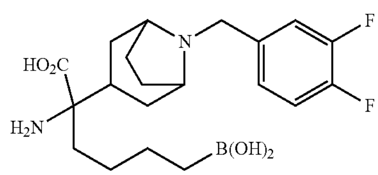 [SMILES: NC(CCCCB(O)O)(C(=O)O)C1CC2CCC(C1)N2Cc1ccc(F)c(F)c1] | 2-amino-6-borono-2-(8-(3,4-difluorobenzyl)-8-azabicyclo[3.2.1]octan-3-yl)hexanoic acid |
| 64 | 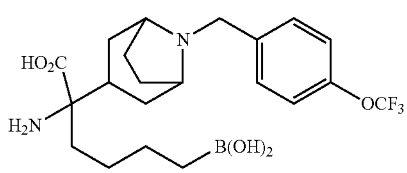 [SMILES: NC(CCCCB(O)O)(C(=O)O)C1CC2CCC(C1)N2Cc1ccc(OC(F)(F)F)cc1] | 2-amino-6-borono-2-(8-(4-(trifluoromethoxy)benzyl)-8-azabicyclo[3.2.1]octan-3-yl)hexanoic acid |
| 65 | 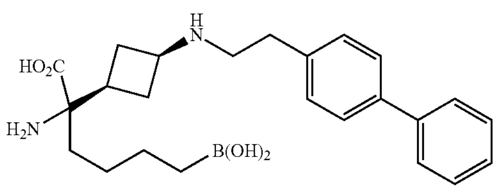 [SMILES: NC(CCCCB(O)O)(C(=O)O)[C@H]1C[C@@H](NCCc2ccc(-c3ccccc3)cc2)C1] | (S)-2-amino-2-((1s,3R)-3-(2-(biphenyl-4-yl)ethylamino)cyclobutyl)-6-boronohexanoic acid |
| 66 | 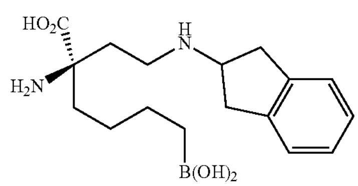 [SMILES: N[C@](CCCCB(O)O)(CCNC1Cc2ccccc2C1)C(=O)O] | (R)-2-amino-6-borono-2-(2-(2,3-dihydro-1H-inden-2-ylamino)ethyl)hexanoic acid |
| 67 | 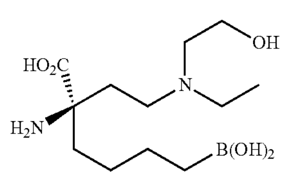 [SMILES: CCN(CCO)CC[C@](N)(CCCCB(O)O)C(=O)O] | (R)-2-amino-6-borono-2-(2-(ethyl(2-hydroxyethyl)amino)ethyl)hexanoic acid |
| 68 | 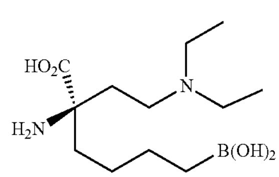 [SMILES: CCN(CC)CC[C@](N)(CCCCB(O)O)C(=O)O] | (R)-2-amino-6-borono-2-(2-(diethylamino)ethyl)hexanoic acid |
| 69 | 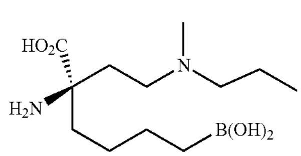 [SMILES: CCCN(C)CC[C@](N)(CCCCB(O)O)C(=O)O] | (R)-2-amino-6-borono-2-(2-(methyl(propyl)amino)ethyl)hexanoic acid |

TABLE 1-continued

| Ex# | Structure | Name |
|---|---|---|
| 70 | 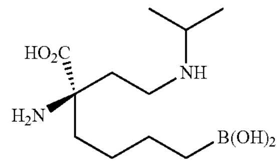 [SMILES: CC(C)NCC[C@](N)(CCCCB(O)O)C(=O)O] | (R)-2-amino-6-borono-2-(2-(isopropylamino)ethyl)hexanoic acid |
| 71 | 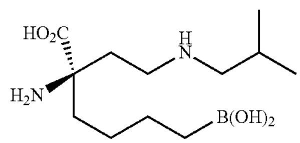 [SMILES: CC(C)CNCC[C@](N)(CCCCB(O)O)C(=O)O] | (R)-2-amino-6-borono-2-(2-(isobutylamino)ethyl)hexanoic acid |
| 72 | 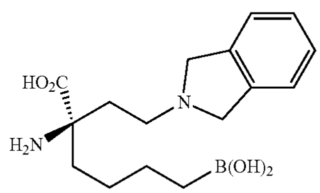 [SMILES: N[C@](CCCCB(O)O)(CCN1Cc2ccccc2C1)C(=O)O] | (R)-2-amino-6-borono-2-(2-(isoindolin-2-yl)ethyl)hexanoic acid |
| 73 | 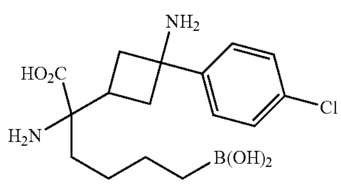 [SMILES: NC1(c2ccc(Cl)cc2)CC(C(N)(CCCCB(O)O)C(=O)O)C1] | 2-amino-2-(3-amino-3-(4-chlorophenyl)cyclobutyl)-6-boronohexanoic acid |
| 74 | 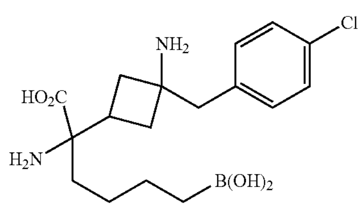 [SMILES: NC1(Cc2ccc(Cl)cc2)CC(C(N)(CCCCB(O)O)C(=O)O)C1] | 2-amino-2-(3-amino-3-(4-chlorobenzyl)cyclobutyl)-6-boronohexanoic acid |
| 75 | 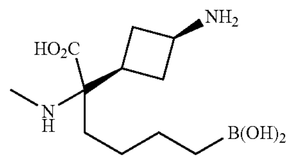 [SMILES: CNC(CCCCB(O)O)(C(=O)O)[C@H]1C[C@@H](N)C1] | (S)-2-(1s,3R)-3-aminocyclobutyl)-6-borono-2-(methylamino)hexanoic acid |

Pharmaceutical Compositions and Dosages

The present invention is directed in part to pharmaceutical formulations of the inventive compounds and the use of the inventive formulations to treat disease conditions associated with an imbalance of arginase activity or the improper function of the arginase enzymes. Accordingly, in one embodiment the invention provides a pharmaceutical composition comprising a compound selected from Table 2 or a salt, solvate, stereoisomer, tautomer or prodrug thereof, and a pharmaceutically acceptable carrier.

TABLE 2

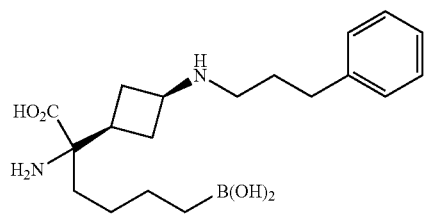 [SMILES: NC(CCCCB(O)O)(C(=O)O)[C@H]1C[C@@H](NCCCc2ccccc2)C1]

TABLE 2-continued
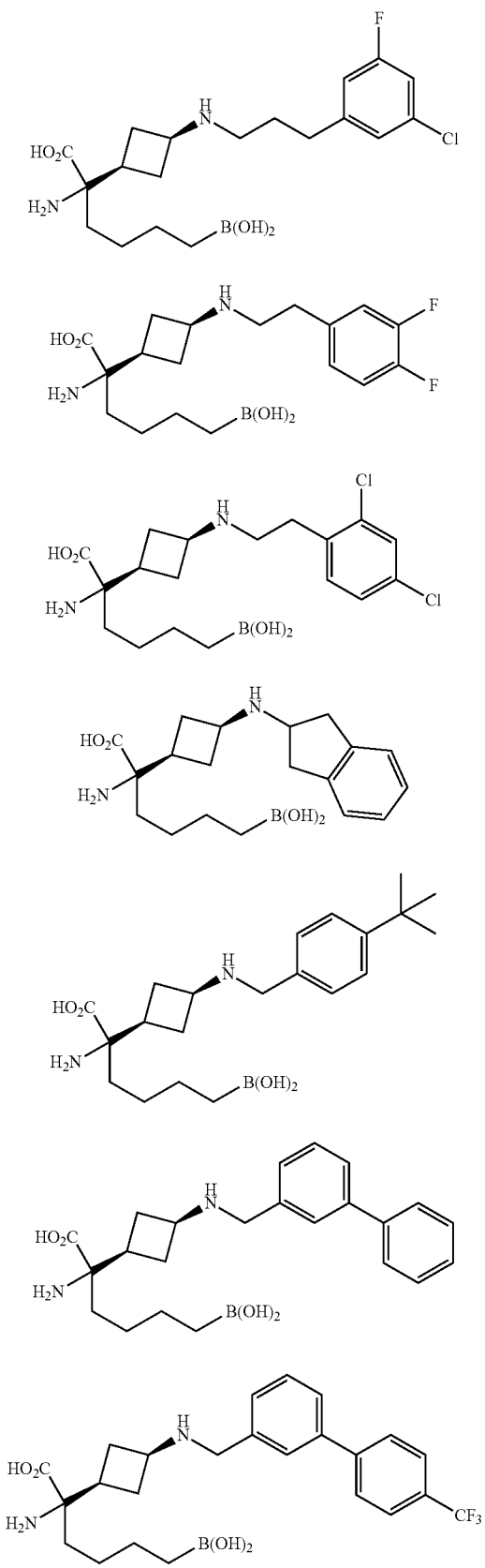
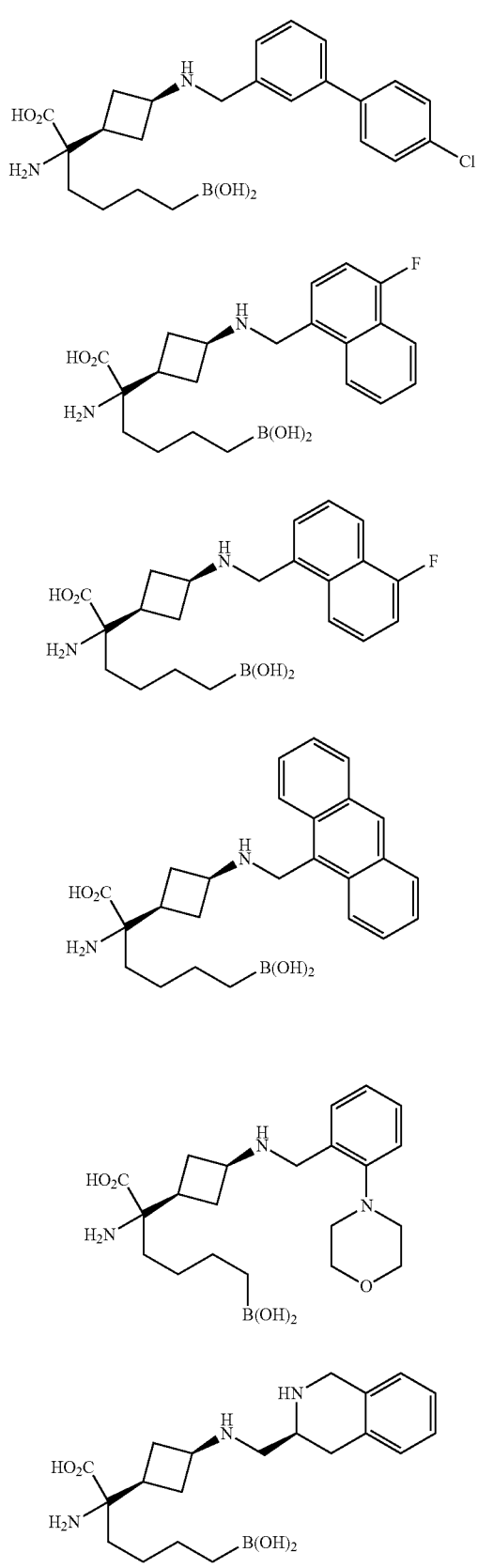

TABLE 2-continued
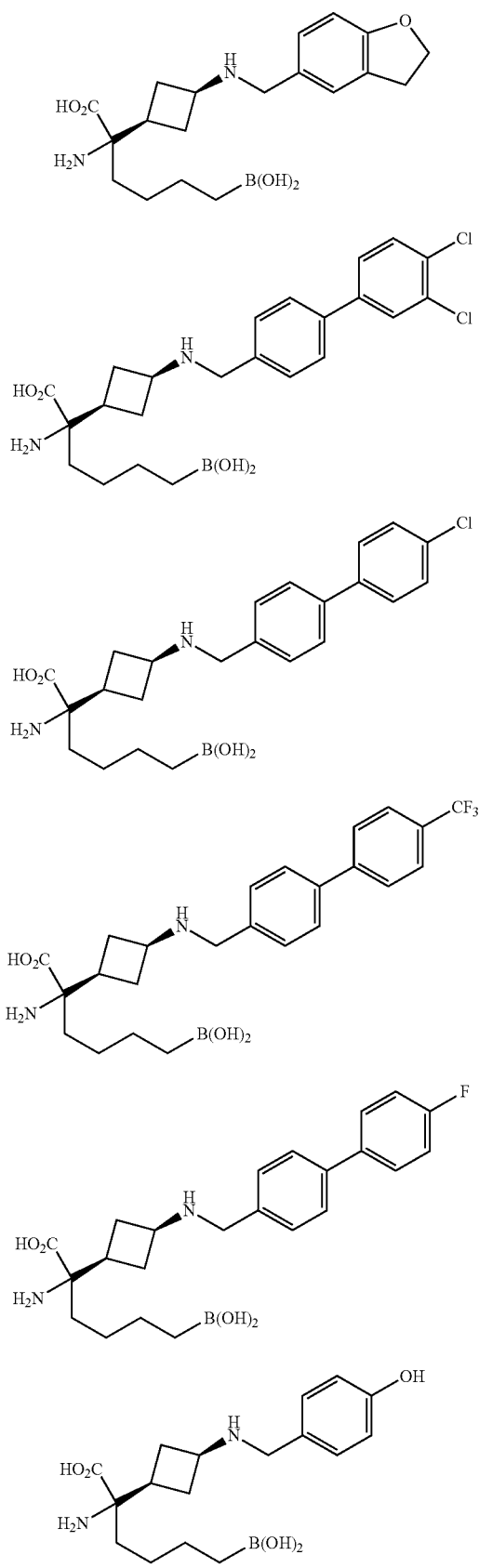
TABLE 2-continued
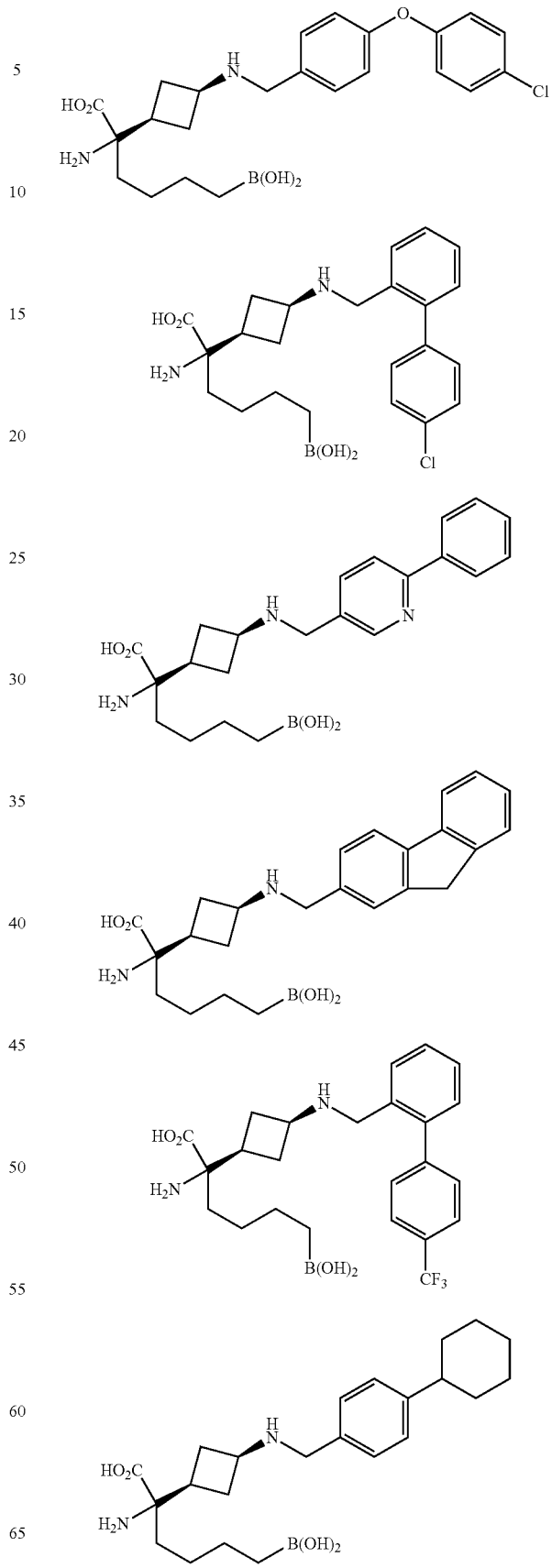

TABLE 2-continued
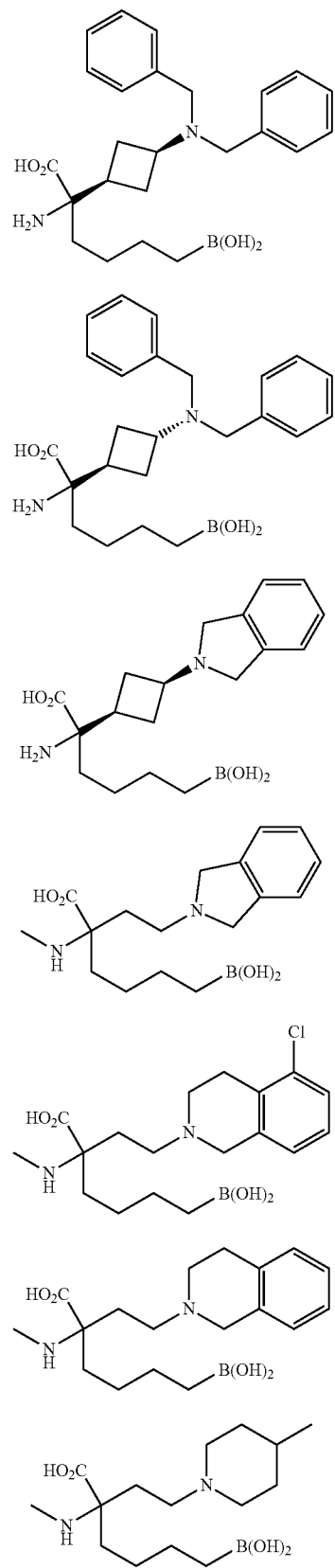
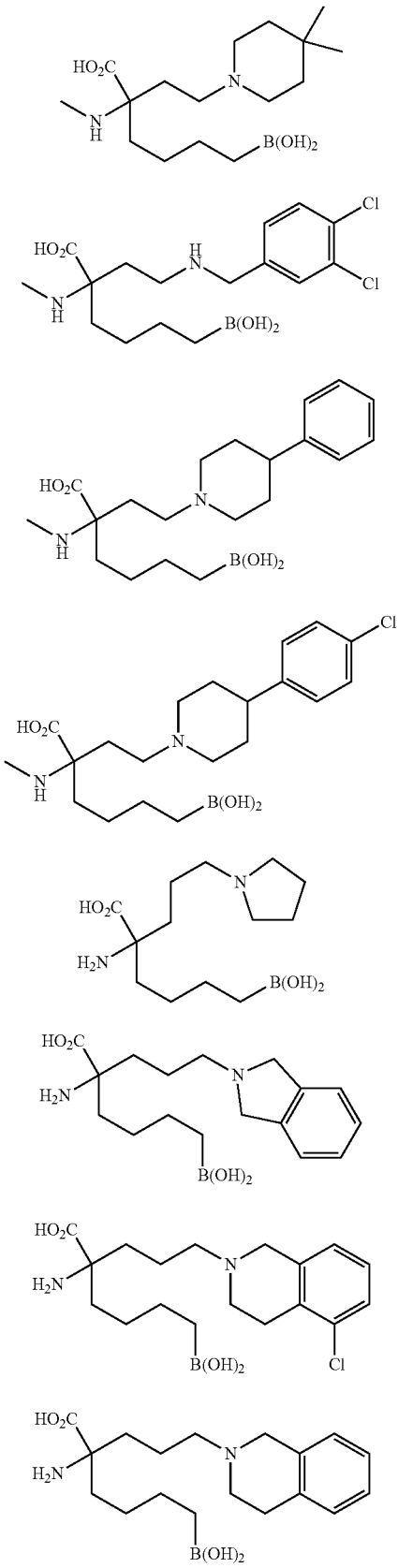

TABLE 2-continued
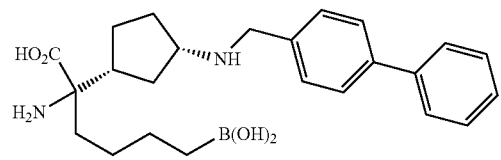 [SMILES: NC(CCCCB(O)O)(C(=O)O)[C@@H]1CC[C@H](NCc2ccc(-c3ccccc3)cc2)C1]
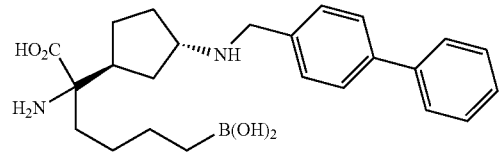 [SMILES: NC(CCCCB(O)O)(C(=O)O)[C@H]1CC[C@H](NCc2ccc(-c3ccccc3)cc2)C1]
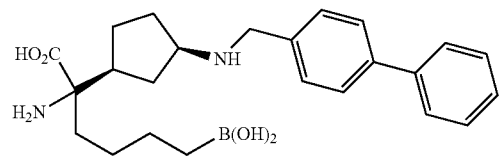 [SMILES: NC(CCCCB(O)O)(C(=O)O)[C@H]1CC[C@@H](NCc2ccc(-c3ccccc3)cc2)C1]
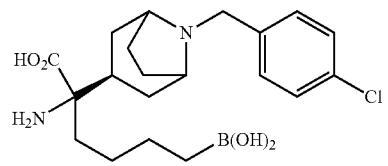
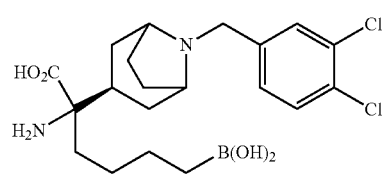
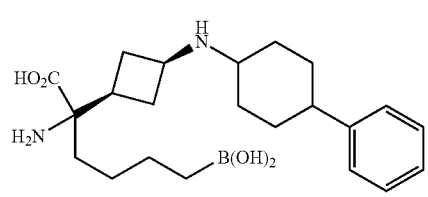 [SMILES: NC(CCCCB(O)O)(C(=O)O)[C@H]1C[C@@H](NC2CCC(c3ccccc3)CC2)C1]
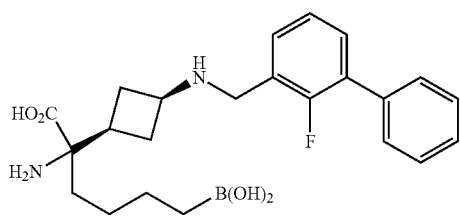 [SMILES: NC(CCCCB(O)O)(C(=O)O)[C@H]1C[C@@H](NCc2cccc(-c3ccccc3)c2F)C1]
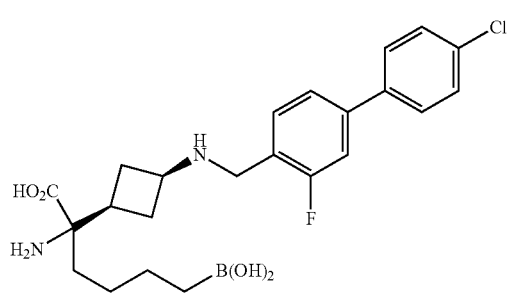
TABLE 2-continued
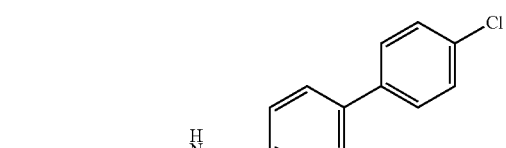
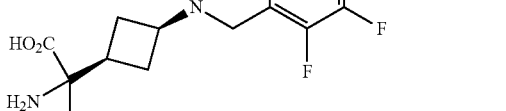
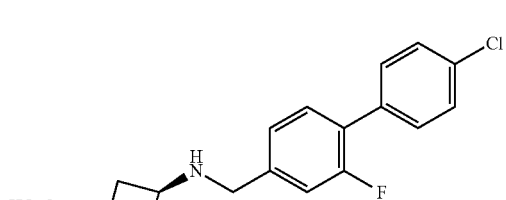
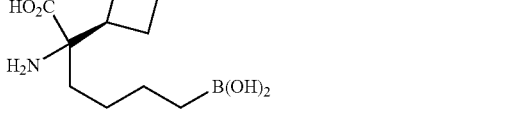
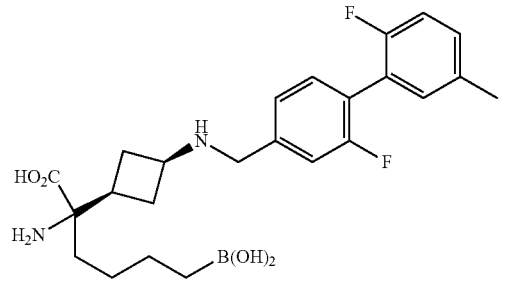 [SMILES: Cc1ccc(F)c(-c2ccc(CN[C@H]3C[C@@H](C(N)(CCCCB(O)O)C(=O)O)C3)cc2F)c1]
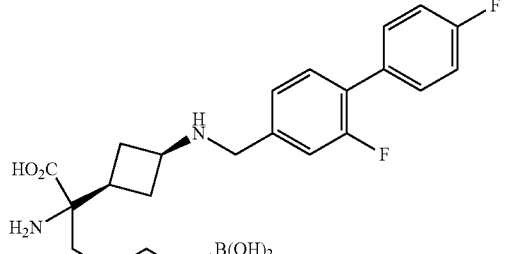
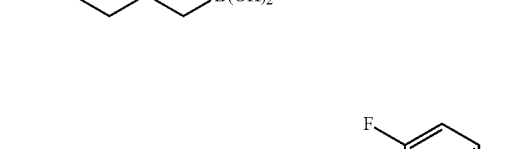
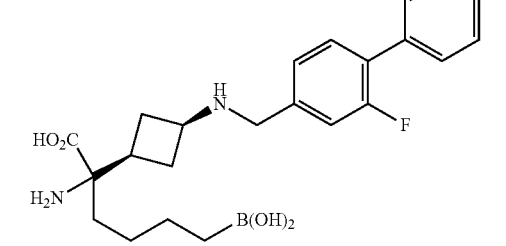

TABLE 2-continued
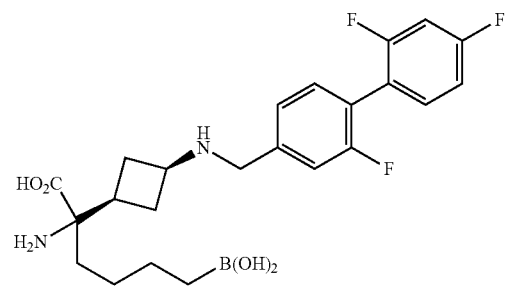 [SMILES: NC(CCCCB(O)O)(C(=O)O)[C@H]1C[C@@H](NCc2ccc(-c3ccc(F)cc3F)c(F)c2)C1]
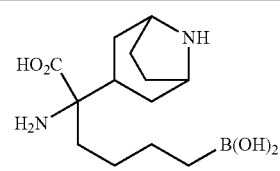
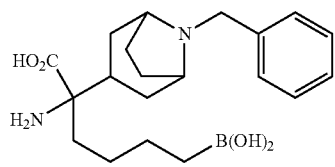 [SMILES: NC(CCCCB(O)O)(C(=O)O)C1CC2CCC(C1)N2Cc1ccccc1]
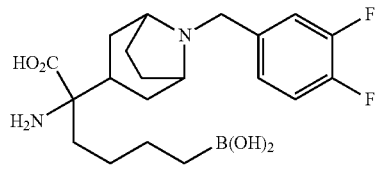 [SMILES: NC(CCCCB(O)O)(C(=O)O)C1CC2CCC(C1)N2Cc1ccc(F)c(F)c1]
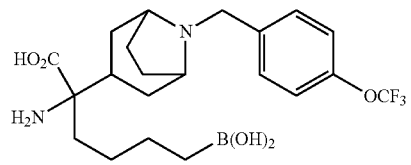 [SMILES: NC(CCCCB(O)O)(C(=O)O)C1CC2CCC(C1)N2Cc1ccc(OC(F)(F)F)cc1]
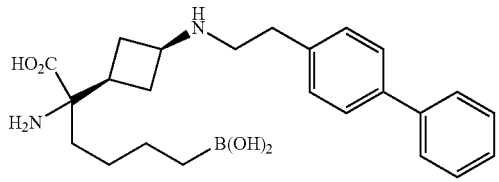 [SMILES: NC(CCCCB(O)O)(C(=O)O)[C@H]1C[C@@H](NCCc2ccc(-c3ccccc3)cc2)C1]
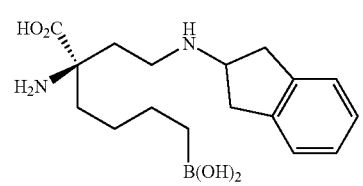 [SMILES: N[C@](CCCCB(O)O)(CCNC1Cc2ccccc2C1)C(=O)O]
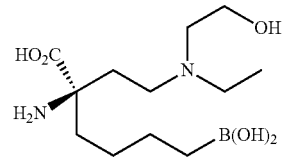 [SMILES: CCN(CCO)CC[C@](N)(CCCCB(O)O)C(=O)O]
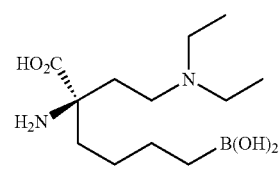
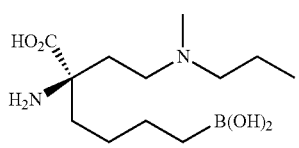 [SMILES: CCCN(C)CC[C@](N)(CCCCB(O)O)C(=O)O]

TABLE 2-continued

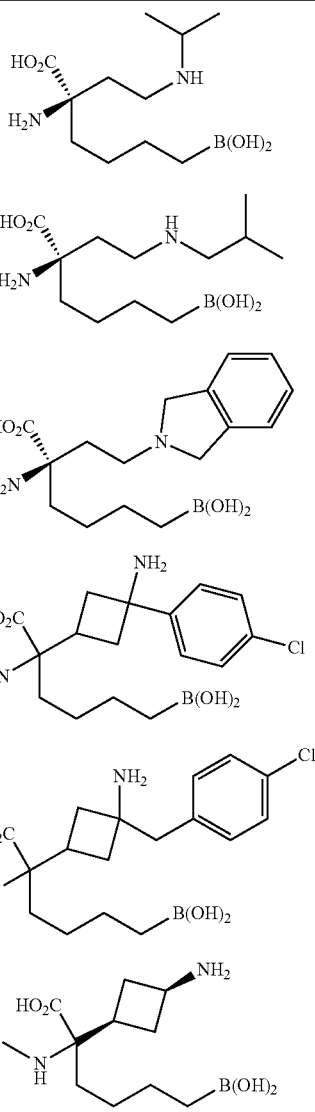

In one aspect, the present invention provides combination therapy in which a patient or subject in need of therapy is administered a formulation of the inventive compound in combination with one or more other compounds having similar or different biological activities.

According to one aspect of the combination therapy routine, a therapeutically effective dose of the inventive compound may be administered separately to a patient or subject in need thereof from a therapeutically effective dose of the combination drug. The person of skill in the art will recognize that the two doses may be administered within hours or days of each other or the two doses may be administered together.

Exemplary disease conditions for which combination therapy in accordance with the present invention may be administered include any of the conditions more specifically described hereinbelow. These include without limitation heart disease, hypertension, sexual disorders, gastric disorders, autoimmune disorders, parasitic infections, pulmonary disorders, smooth muscle relaxation disorders and hemolytic disorders. More specifically, a pharmaceutically acceptable formulation of a compound in accordance with the present invention can be administered independently or in combination with one or more other compounds to treat the following disease conditions: erectile dysfunction, pulmonary hypertension, hypertension, asthma, inflammation, ischaemia reperfusion injury, myocardial infarction, atherosclerosis, immune response, psoriasis and wound healing.

Suitable compounds that may be used in combination with a compound according to the present invention include without limitation:

Erectile Dysfunction: sildenafil, vardenafil, tadalafil and alprostadil.

Pulmonary Hypertension/Hypertension: epoprostenol, iloprost, bosentan, amlodipine, diltiazem, nifedipine, ambrisentan and warfarin.

Asthma: fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn.

Artherosclerosis: atorvastatin, lovastatin, simvastatin, pravastatin, fluvastatin, rosuvastatin, gemfibrozil, fenofibrate, nicotinic acid, clopidogrel.

The invention also provides a pharmaceutical composition comprising one or more compounds selected from Table 2 or pharmaceutically acceptable salts, stereoisomers, tautomers, or prodrugs, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, or flavor imparting agents.

Compounds in accordance with the present invention can be formulated for oral administration, parenteral administration, inhalation, for administration as a spray or as a suppository suitable for rectal use. In the context of the present invention, the term parenteral refers to subcutaneous injections, intravenous injection, intramuscular injection, intrasternal injection or infusion techniques.

Suitable oral compositions in accordance with the invention include without limitation tablets, troches, lozenges, aqueous or oily suspensions, dispersible powders or granules, emulsion, hard or soft capsules, syrups or elixirs.

Encompassed within the scope of the invention are pharmaceutical compositions suitable for single unit dosages that comprise a compound of the invention, its pharmaceutically acceptable stereoisomer, prodrug, salt, solvate, hydrate, or tautomer and a pharmaceutically acceptable carrier.

Inventive compositions suitable for oral use may be prepared according to any method known to the art for the manufacture of pharmaceutical compositions. For instance, liquid formulations of the inventive compounds can contain one or more agents selected from the group consisting of sweetening agents, flavoring agents, coloring agents and preserving agents in order to provide pharmaceutically elegant and palatable preparations of the arginase inhibitor.

For tablet compositions of the inventive compounds, the active ingredient in admixture with non-toxic pharmaceutically acceptable excipients is used for the manufacture of tablets. Examples of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation are sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth naturally-occurring phosphatides, for example soy bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension. This suspension may be formulated according to the known art using those suitable dispersing or wetting agents and suspending agents which have been mentioned above. The sterile injectable preparation may also be sterile injectable solution or suspension in a non-toxic, parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds in accordance with the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Examples of such materials are cocoa butter and polyethylene glycols.

Compositions for parenteral administrations are administered in a sterile medium. Depending on the vehicle used and the concentration of the drug in the formulation, the parenteral formulation can either be a suspension or a solution containing dissolved drug. Adjuvants such as local anesthetics, preservatives and buffering agents can also be added to parenteral compositions.

Synthesis of Compounds

Compounds in accordance with the present invention can be synthesized using a variety of syntheitic methodologies. The choice of an appropriate synthetic methodology is guided by the inventive compound desired and the nature of functional groups present in the intermediate and final products. Thus, selective protection/deprotection protocols may be necessary during synthesis depending on the specific functional groups desired and protecting groups being used. A description of such protecting groups and how to introduce and remove them is found in: *Protective Groups in Organic Synthesis*, Third Edition, T. W. Green and P. G. M. Wuts, John Wiley and Sons, New York, 1999. Illustrative of the general synthetic methodologies used to make the inventive compounds are those set forth below.

According to one embodiment, certain inventive compounds can be conveniently prepared using a glycine benzophenone imine ester as illustrated in Scheme A set forth below. In this method the starting amino acid imine A-1 can be purchased or prepared by reacting benzophenone imine with the desired amino acid ester (O'Donnell, M. J., *Aldrichimica Acta*, 2001, 34, 3-15). Alkylation of A-1 in Scheme A with electrophile A-2 using typical alkylation conditions such as lithium bis(trimethylsilyl)amide, LDA or sodium hydride in a polar aprotic solvent such as THF provides the monoalkylated product A-3. Similar reaction conditions can be used to introduce the second substituent to provide intermediate A-4. Subsequent hydrolysis provides the target compound A-5 (Scheme A).

In some instances it may be preferable or necessary to build one or both amino acid substituents in a multi-step process. An example of this is provided in Scheme A where allyl bromide is used in the second alkylation step giving intermediate A-6 under alkylating conditions described above. Following removal of the benzophenone and subsequent protection of the amine, the terminal olefin is oxidized to give aldehyde intermediate A-8.

The highly versatile aldehyde group can be utilized to prepare a wide variety of target compounds. One convenient use is in reductive amination reactions as shown in Scheme A. Here, treatment with the desired amine and a reducing agent like sodium cyanoborohydride gives amine intermediate A-9, which after hydrolysis, provides compounds that structurally conform to compound A-10. Depending on the specific functional group desired, certain protecting groups may be required.

ment an optically pure ketone is used in place of the achiral benzophenone. See, for example, Tabcheh, et al. *Tetrahedron* 1991, 47, 4611-4618 and Belokon et al. *Angew Chem, Int Ed* 2001, 40, 1948-1951.

Alternatively, asymmetric induction can be achieved in the second alkylation reaction by using a chiral catalyst. See, for example, Ooi, et al. *Tet Lett.* 2004, 45, 1675-1678; Ohshima

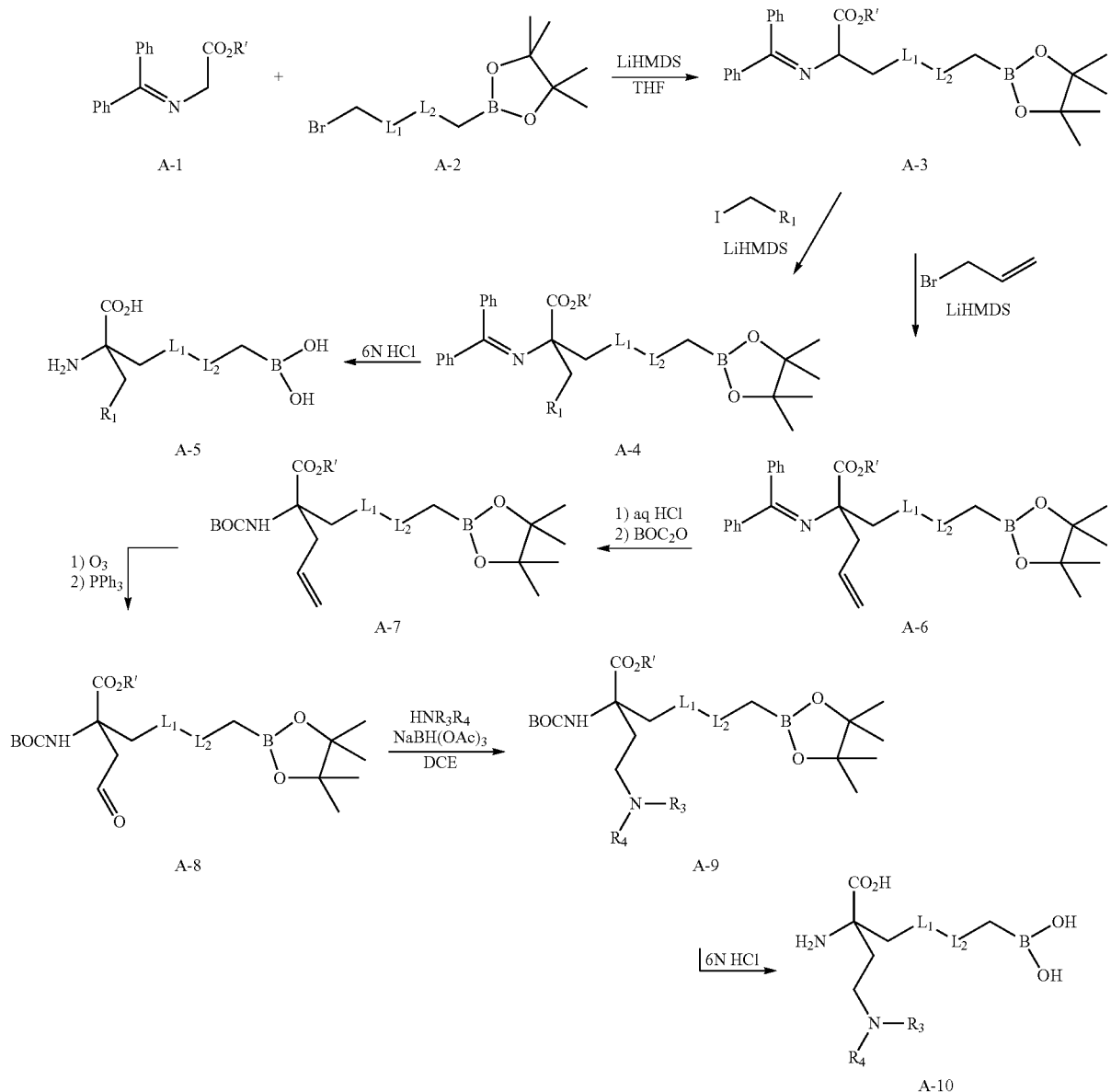

Alternatively, in the case where a protected boronic acid electrophile is not available or is incompatible with synthetic protocol, compounds in accordance with the present invention can be synthesized by replacing electrophile A-2 with a terminal olefin followed by the introduction of boron in a later step following alkylation using hydroboration chemistry.

For enantioselective synthesis, a variety of different synthetic approaches may be used. Accordingly, in one embodiet al. *J. Am. Chem. Soc.* 2009, 125, 11206-11207; and, Belokon et al. *Tetrahedron* 2001, 57, 2491-2498.

In yet another embodiment, enantioselectivity can be introduced by the use of an optically pure oxazinone. See Dastlik, K. A.; Sundermeier, U., Johns, D. M.; Chen, Y.; Williams, R. M. *Synlett* 2005, 4, 693-696. This approach is illustrated in Scheme B.

Scheme B

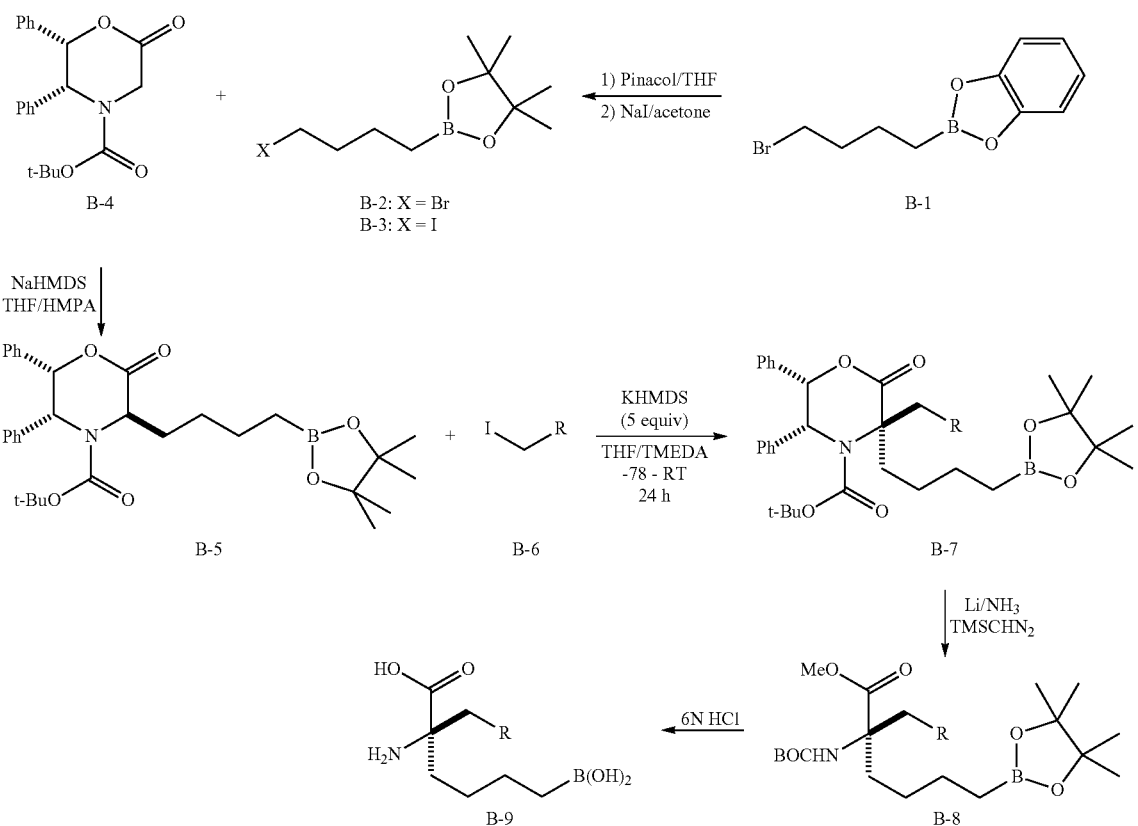

Here, the optically active oxazinone B-4 is used to stereoselectively direct sequential alkylations to form intermediate B-7. These alkylations can be carried out under reaction conditions that are specific for the electrophile being used (e.g. B-2, B-3, and B-6). Alternative approaches to synthesize B-5 and B-7 include the aldol reaction that involves the coupling of an aldehyde with the oxazinone followed by reduction of the resulting double bond. The inventive compounds are obtained by decomposition of the di-substituted oxazinone followed by removal of the protecting groups. Thus, cleaving the oxazinone heterocycle via hydrogenation or using an alkali metal/ammonia reduction followed by treatment of intermediate B-8 with aqueous acid provides the target disubstituted amino acid B-9.

If a butaneboronic acid is desired as one of the substituents in the final product electrophile, B-2 or B-3 can be used as an alkylating agent. B-2 can be easily prepared from B-1 by treatment with pinacol in THF. If iodo-intermediate B-3 is desired, it can be prepared from the corresponding bromide via treatment with sodium iodide in acetone.

Alternatively, one or both substituents may be modified after the alkylation step. This may be required when the desired functionality in the final product is not compatible with the alkylation reaction conditions or if the desired substituent is not conveniently introduced as an electrophile due to limited reactivity. An example is illustrated in Scheme C, wherein allyl iodide is used as an efficient alkylating agent then further modified after cleavage of the oxazinone ring system. In this example, the allyl intermediate C-1 is treated with lithium in ammonia to remove the oxazinone ring. The resulting acid can be protected as ester C-3 and subsequently treated with ozone to give the corresponding aldehyde.

The aldehyde (C-4) is a versatile functional group and can be used in many types of reactions to make a wide variety of different analogs. As an example, it can be used in reductive amination reactions to prepare compounds with amine substituents $R_1$ and $R_2$ as in intermediate C-5. The final target compounds (C-6) can be obtained after deprotection of the ester, amino and boronic acid moieties.

Scheme C

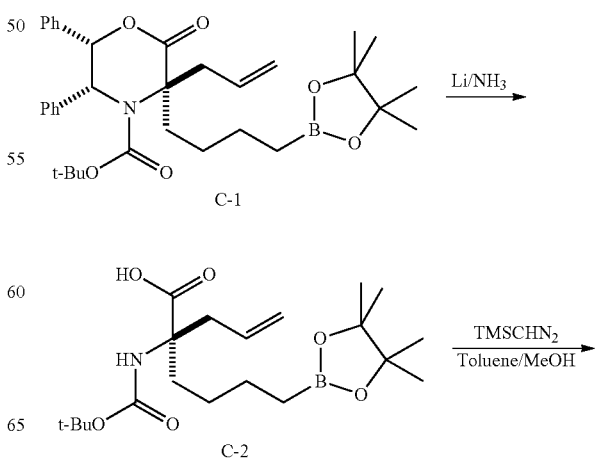

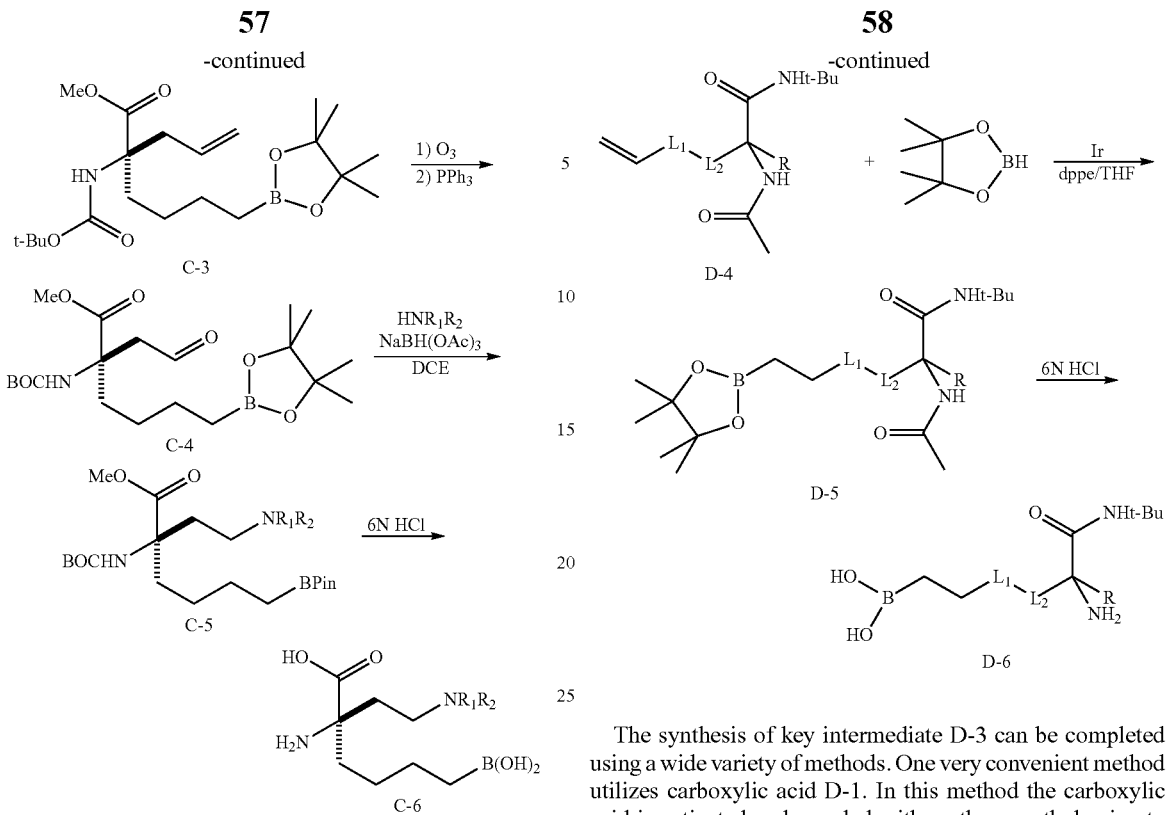

In another embodiment, syntheses of some compounds employs the Ugi reaction (Doemling, A., *Chem. Rev.* 2006, 106, 17-89), as illustrated below in Scheme D. In the Ugi reaction a ketone or aldehyde (D-3) is treated with an isocyanate such as tert-butyl isocyanate and an amine source like ammonium acetate to give directly the amino acid derivative with the carboxylic acid and amine protected as a tert-butylamide and acetamide respectively. In this reaction different isocyanates and amine sources can be used depending on the desired amine and carboxylic acid protecting groups desired. If optically active products are desired chiral optically pure isocyanates and and/or amine sources can be used. The reactions using these reagents may be enantioselective, or at least provide diastereomeric mixtures of products that can be easily separated.

The synthesis of key intermediate D-3 can be completed using a wide variety of methods. One very convenient method utilizes carboxylic acid D-1. In this method the carboxylic acid is activated and coupled with methoxymethylamine to form Weinreb amide D-2. This can be completed using a wide variety of coupling regents such as EDC, DCC or PyBOP, or directly from the acid chloride of D-1. The Weinreb amide can be converted to the desired ketone by reacting it with the appropriate Grignard reagent to give intermediate D-3.

After the Ugi reaction is complete, the terminal olefin can be treated with a borane source such as pinacolborane to introduce the boronic acid moiety. Final deprotection of intermediate D-5 gives target compound D-6.

Those having skill in the art will recognize that the starting materials and reaction conditions may be varied, the sequence of the reactions altered, and additional steps employed to produce compounds encompassed by the present invention, as demonstrated by the following examples. In some cases, protection of certain reactive functionalities may be necessary to achieve some of the above transformations. In general, the need for such protecting groups as well as the conditions necessary to attach and remove such groups will be apparent to those skilled in the art of organic synthesis.

Compounds illustrated in Table 2 above were synthesized using methodologies further described by the following examples, which are not to be construed as limiting the invention in scope or spirit to the specific procedures and compounds described in them.

EXEMPLARY COMPOUNDS

Example 1

Preparation of (S)-2-amino-6-borono-2-(1s,3R)-3-(3-phenylpropylamino)cyclobutyl)hexanoic acid The titled compound was prepared using the following multi-step synthetic protocol.

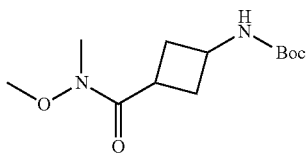 [SMILES: CON(C)C(=O)C1CC(NC(=O)OC(C)(C)C)C1]

Step 1: tert-butyl 3-(methoxy(methyl)carbamoyl)cyclobutylcarbamate (1s,3s)-3-(tert-Butoxycarbonylamino)cyclobutanecarboxylic acid (5.0 g, 23.2 mmol) was dissolved in dichloromethane (77 mL), cooled to 0° C., and treated with N,O-dimethylhydroxylamine hydrochloride (2.95 g, 30.2 mmol) and N-methylmorpholine (3.32 mL, 30.2 mmol) The mixture was stirred for 15 minutes, then EDCI (5.79 g, 30.2 mmol) was added and the reaction was stirred for 18 hours at room temperature. The reaction was cooled to 0° C. and quenched with 1 N HCl (10 mL), then diluted with ethyl acetate, washed successively with aqueous saturated sodium bicarbonate, saturated aqueous sodium chloride, dried over MgSO$_4$, and concentrated in vacuo. The residue was chromatographed on silica gel eluting with 3-40% ethyl acetate in heptane to afford the desired product (4.34 g, 75%). R$_f$ 0.43 (50% ethyl acetate in heptane). $^1$H NMR (CDCl$_3$, 300 MHz) δ 4.80 (br s, 1H), 4.22-4.04 (m, 1H), 3.66 (s, 3H), 3.18 (s, 3H), 3.17-3.06 (m, 1H), 2.61-2.48 (m, 2H), 2.16-2.03 (m, 2H), 1.43 (s, 9H). ESI MS found for C$_{12}$H$_{22}$N$_2$O$_4$ m/z [259.0 (M+1)].

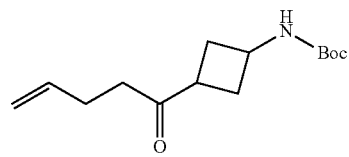 [SMILES: C=CCCC(=O)C1CC(NC(=O)OC(C)(C)C)C1]

Step 2. tert-butyl 3-pent-4-enoylcyclobutylcarbamate tert-Butyl (1s,3s)-3-(methoxy(methyl)carbamoyl)cyclobutylcarbamate (4.34 g, 16.8 mmol) was dissolved in THF (46 mL), cooled to 0° C. and treated dropwise with 3-butenylmagnesium bromide (8.4 mL, 0.5 M/THF, 42 mmol). After stirring for 2 h at room temperature, the reaction was re-cooled to 0° C., quenched with 1 N citric acid (10 mL), diluted with ethyl acetate, washed with a 5% sodium bicarbonate solution, saturated aqueous sodium chloride, dried over MgSO$_4$, and concentrated in vacuo. The residue was chromatographed on silica gel eluting with 3-40% ethyl acetate in heptane to afford the desired product (3.60 g, 85%). R$_f$ 0.69 (50% ethyl acetate in heptane). $^1$H NMR (CDCl$_3$, 300 MHz) δ 5.85-5.70 (m, 1H), 5.06-4.95 (m, 2H), 4.74-4.66 (m, 1H), 4.19-4.06 (m, 1H), 2.97-2.85 (m, 1H), 2.59-2.43 (m, 4H), 2.35-2.25 (m, 2H), 2.06-1.93 (m, 2H), 1.43 (s, 9H). ESI MS found for C$_{14}$H$_{23}$NO$_3$ m/z [254.1 (M+1)].

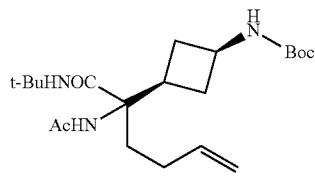

Step 3: tert-butyl (1R,3s)-3-((S)-2-acetamido-1-(tert-butylamino)-1-oxohex-5-en-2-yl)cyclobutylcarbamate tert-Butyl (1s,3s)-3-pent-4-enoylcyclobutylcarbamate (2.0 g, 7.9 mmol) was dissolved in a minimum volume of 2,2,2-trifluoroethanol. Ammonium acetate (2.43 g, 31.6 mmol) and tert-butyl isocyanide (1.78 mL, 15.8 mmol) were added and the reaction was stirred 4 days at room temperature. The reaction was diluted with ethyl acetate, washed successively with water, saturated aqueous sodium chloride, dried over MgSO$_4$, and concentrated in vacuo. The residue was chromatographed on silica gel eluting with 12-100% ethyl acetate in heptane to afford the desired product (2.13 g, 68%) along with a small amount of unreacted starting material. R$_f$ 0.29 (50% ethyl acetate in heptane). $^1$H NMR (CDCl$_3$, 300 MHz) δ 5.83-5.68 (m, 1H), 5.02-4.89 (m, 2H), 4.82-4.73 (m, 1H), 3.73-3.59 (m, 1H), 2.77-2.51 (m, 2H), 2.36-2.17 (m, 3H), 2.10 (s, 3H), 2.01-1.81 (m, 2H), 1.44 (s, 9H), 1.33 (s, 9H). ESI MS found for C$_{21}$H$_{37}$N$_3$O$_4$ m/z [396.0 (M+1)].

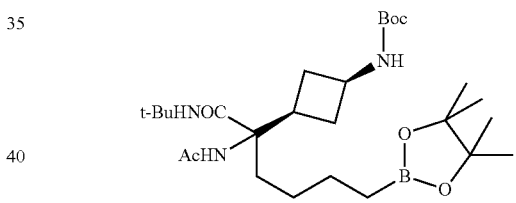

Step 4: tert-butyl (1R,3s)-3-((S)-2-acetamido-1-(tert-butylamino)-1-oxo-6-(4,4,5,5-tetramethyl-1,3,2-dioxaborolan-2-yl)hexan-2-yl)cyclobutylcarbamate tert-Butyl (1S,3s)-3-((R)-2-acetamido-1-(tert-butylamino)-1-oxohex-5-en-2-yl)cyclobutylcarbamate (2.13 g, 5.4 mmol) was dissolved in dichloromethane (30 mL) and treated with [Ir(COD)Cl]$_2$ (109 mg, 0.162 mmol) and dppe (126 mg, 0.324 mmol). The reaction was stirred 15 minutes, cooled to 0° C. and treated with pinacolborane (1.17 mL, 8.08 mmol). After stirring overnight at room temperature, the reaction was diluted with ethyl acetate, washed with saturated aqueous sodium chloride, dried over MgSO$_4$, and concentrated in vacuo. The residue was chromatographed on silica gel eluting with 15-100% ethyl acetate in heptane to afford the desired product (2.32 g, 82%). R$_f$ 0.22 (50% ethyl acetate in heptane). $^1$H NMR (CDCl$_3$, 300 MHz) δ 4.78-4.71 (m, 1H), 3.74-3.58 (m, 1H), 2.65-2.41 (m, 2H), 2.36-2.13 (m, 3H), 2.09 (s, 3H), 1.54-1.03 (m, 38H), 0.73 (t, J=9.0 Hz, 2H). ESI MS found for C$_{27}$H$_{50}$BN$_3$O$_6$ m/z [524.3 (M+1)].

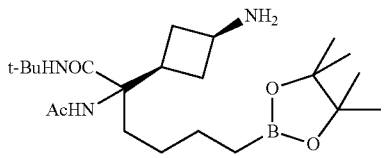

Step 5: (S)-2-acetamido-2-((1s,3R)-3-aminocyclobutyl)-N-tert-butyl-6-(4,4,5,5-tetramethyl-1,3,2-dioxaborolan-2-yl)hexanamide tert-Butyl (1S,3s)-3-((R)-2-acetamido-1-(tert-butylamino)-1-oxo-6-(4,4,5,5-tetramethyl-1,3,2-dioxaborolan-2-yl)hexan-2-yl)cyclobutylcarbamate (1.16 g, 2.22 mmol) was dissolved in dichloromethane (7.5 mL) and treated with 4 N HCl/dioxane. After stirring 3 hours, the reaction mixture was concentrated to give (S)-2-acetamido-2-((1s,3R)-3-aminocyclobutyl)-N-tert-butyl-6-(4,4,5,5-tetramethyl-1,3,2-dioxaborolan-2-yl)hexanamide as the hydrochloride salt (1.03 g) which was used without further purification. ESI MS found for $C_{22}H_{42}BN_3O_4$ m/z [424.2 (M+1)].

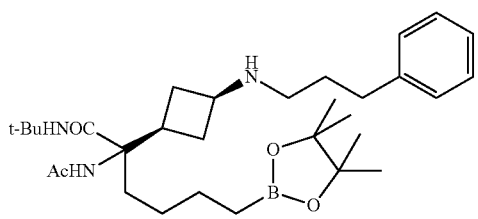

Step 6: (S)-2-acetamido-N-tert-butyl-2-((1s,3R)-3-(3-phenylpropylamino)cyclobutyl)-6-(4,4,5,5-tetramethyl-1,3,2-dioxaborolan-2-yl)hexanamide (R)-2-Acetamido-2-((1s,3S)-3-aminocyclobutyl)-N-tert-butyl-6-(4,4,5,5-tetramethyl-1,3,2-dioxaborolan-2-yl)hexanamide hydrochloride (200 mg, 0.435 mmol) was suspended in 1,2-dichloroethane (2 mL) and treated with 3-phenylpropanal (57 µL, 0.435 mmol). Triethylamine (121 µL, 0.87 mmol) and acetic acid (50 µL, 0.87 mmol) were added and the mixture was stirred for 20 minutes, treated with NaBH(OAc)$_3$ (138 mg, 0.653 mmol) and stirred overnight. The reaction was diluted with ethyl acetate, washed successively with saturated sodium bicarbonate, saturated aqueous sodium chloride, dried over MgSO$_4$, and concentrated in vacuo to afford the crude product (189 mg) which was used without further purification. ESI MS found for $C_{31}H_{52}BN_3O_4$ m/z [542.2 (M+1)].

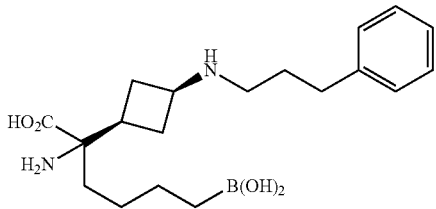 [SMILES: NC(CCCCB(O)O)(C(=O)O)[C@H]1C[C@@H](NCCCc2ccccc2)C1]

Step 7: (S)-2-amino-6-borono-2-((1s,3R)-3-(3-phenylpropylamino)cyclobutyl) hexanoic acid (R)-2-Acetamido-N-tert-butyl-2-((1s,3S)-3-(3-phenylpropylamino)cyclobutyl)-6-(4,4,5,5-tetramethyl-1,3,2-dioxaborolan-2-yl)hexanamide (189 mg) was treated with 6 N HCl (3 mL) and heated to 100° C. overnight. The reaction was cooled to room temperature, diluted with H$_2$O, washed 3× dichloromethane and concentrated in vacuo. The residue was purified by preparative HPLC (10-100% CH$_3$CN/H$_2$O) to afford the desired product. $^1$H NMR (D$_2$O, 400 MHz) δ 7.42-7.38 (m, 2H), 7.33-7.29 (m, 3H), 3.66-3.61 (m, 1H), 2.95 (t, J=8.0 Hz, 2H), 2.73 (t, J=7.6 Hz, 2H), 2.57-2.31 (m, 4H), 2.02-1.83 (m, 4H), 1.69-1.60 (m, 1H), 1.44-1.32 (m, 3H), 1.23-1.19 (m, 1H), 0.80 (t, J=7.6 Hz, 2H). ESI MS found for $C_{19}H_{31}BN_2O_4$ m/z [363.1 (M+1)].

Example 2

Preparation of (S)-2-amino-6-borono-2-((1s,3R)-3-(3-(3-chloro-5-fluorophenyl)propylamino)cyclobutyl)hexanoic acid

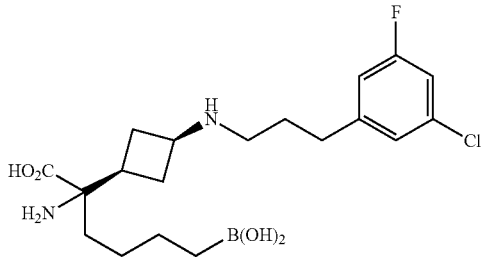 [SMILES: NC(CCCCB(O)O)(C(=O)O)[C@H]1C[C@@H](NCCCc2cc(F)cc(Cl)c2)C1]

2-Amino-6-borono-2-((1s,3s)-3-(3-(3-chloro-5-fluorophenyl)propylamino)cyclobutyl) hexanoic acid was prepared in a manner analogous to that set forth in Example 1, except 3-(3-chloro-5-fluorophenyl)propanal was used instead of 3-phenylpropanal in step 6. $^1$H NMR (D$_2$O, 400 MHz) δ 7.16-7.10 (m, 2H), 6.99 (d, J=9.6 Hz, 1H), 3.68-3.59 (m, 1H), 2.94 (t, J=8.0 Hz, 2H), 2.71 (t, J=7.6 Hz, 2H), 2.57-2.32 (m, 4H), 2.02-1.84 (m, 4H), 1.69-1.61 (m, 1H), 1.44-1.32 (m, 3H), 1.23-1.19 (m, 1H), 0.80 (t, J=7.6 Hz, 2H). ESI MS found for $C_{19}H_{29}BClFN_2O_4$ m/z [415.1 (M+1)].

Example 3

Preparation of (S)-2-amino-6-borono-2-((1s,3R)-3-(3-(3,4-difluorophenyl)propylamino)cyclobutyl)hexanoic acid

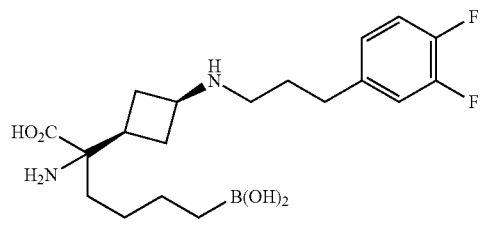 [SMILES: NC(CCCCB(O)O)(C(=O)O)[C@H]1C[C@@H](NCCCc2ccc(F)c(F)c2)C1]

2-Amino-6-borono-2-((1s,3s)-3-(3,4-difluorophenethylamino)cyclobutyl)hexanoic acid was prepared in a manner analogous to that set forth in Example 1, except 2-(3,4-difluorophenyl)acetaldehyde was used instead of 3-phenylpropanal in step 6. $^1$H NMR (D$_2$O, 400 MHz) δ 7.30-7.20 (m, 2H), 7.10-7.07 (m, 1H), 3.70-3.65 (m, 1H), 3.23 (t, J=7.2 Hz, 2H), 2.99 (t, J=7.2 Hz, 2H), 2.57-2.36 (m, 4H), 1.98-1.84 (m, 2H), 1.69-1.62 (m, 1H), 1.45-1.32 (m, 3H), 1.23-1.19 (m, 1H), 0.80 (t, J=8.0 Hz, 2H). ESI MS found for C$_{18}$H$_{27}$BF$_2$N$_2$O$_4$ m/z [385.1 (M+1)].

Example 4

Preparation of (S)-2-amino-6-borono-2-((1s,3R)-3-(3-(2,4-dichlorophenyl)propylamino)cyclobutyl)hexanoic acid

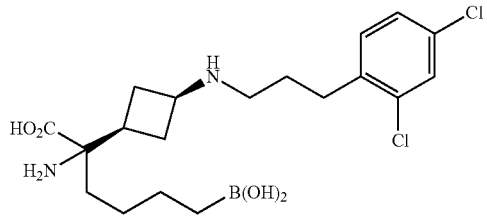 [SMILES: NC(CCCCB(O)O)(C(=O)O)[C@H]1C[C@@H](NCCCc2ccc(Cl)cc2Cl)C1]

2-Amino-6-borono-2-((1s,3s)-3-(2,4-dichlorophenethylamino)cyclobutyl)hexanoic acid was prepared in a manner analogous to that set forth in Example 1, except 2-(2,4-dichlorophenyl)acetaldehyde was used instead of 3-phenylpropanal in step 6. $^1$H NMR (D$_2$O, 400 MHz) δ 7.57-7.32 (m, 3H), 3.72-3.68 (m, 1H), 3.22 (t, J=7.6 Hz, 2H), 3.12 (t, J=7.4 Hz, 2H), 2.56-2.37 (m, 4H), 1.99-1.84 (m, 2H), 1.68-1.62 (m, 1H), 1.45-1.32 (m, 3H), 1.23-1.19 (m, 1H), 0.80 (t, J=7.8 Hz, 2H). ESI MS found for C$_{18}$H$_{27}$BCl$_2$N$_2$O$_4$ m/z [417.2 (M+)].

Example 5

Preparation of (S)-2-amino-6-borono-2-((1s,3R)-3-(2,3-dihydro-1H-inden-2-ylamino)cyclobutyl)hexanoic acid

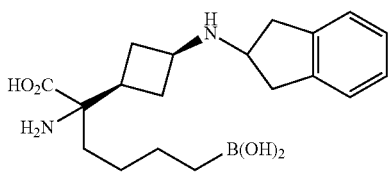 [SMILES: NC(CCCCB(O)O)(C(=O)O)[C@H]1C[C@@H](NC2Cc3ccccc3C2)C1]

2-Amino-6-borono-2-((1s,3s)-3-(2,3-dihydro-1H-inden-2-ylamino)cyclobutyl)hexanoic acid was prepared in a manner analogous to that set forth in Example 1, except 2-indanone was used instead of 3-phenylpropanal in step 6. $^1$H NMR (D$_2$O, 400 MHz) δ 7.24 (br d, J=16 Hz, 4H), 4.71 (s, 4H), 4.01-3.97 (m, 1H), 3.74-3.71 (m, 1H), 3.37-3.28 (m, 2H), 3.02-2.97 (m, 2H), 2.52-2.26 (m, 4H), 1.94-1.91 (m, 1H), 1.84-1.77 (m, 1H), 1.61-1.53 (m, 1H), 1.36-1.20 (m, 3H), 1.19-1.08 (m, 1H), 0.72 (t, J=6.8 Hz, 2H). ESI MS found for C$_{19}$H$_{29}$BN$_2$O$_4$ m/z [361.3 (M+1)].

Example 6

Preparation of (S)-2-amino-6-borono-2-((1s,3R)-3-(4-tert-butylbenzylamino)cyclobutyl)hexanoic acid

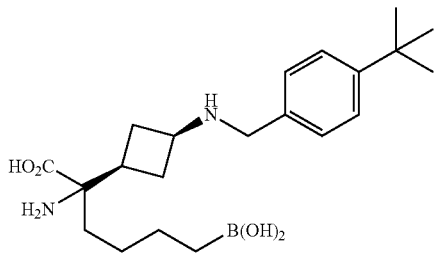 [SMILES: CC(C)(C)c1ccc(CN[C@H]2C[C@@H](C(N)(CCCCB(O)O)C(=O)O)C2)cc1]

2-Amino-6-borono-2-((1s,3s)-3-(4-tert-butylbenzylamino)cyclobutyl)hexanoic acid was prepared in a manner analogous to that set forth in Example 1, except 4-tert-butylbenzaldehyde was used instead of 3-phenylpropanal in step 6. $^1$H NMR (D$_2$O, 400 MHz) δ 7.59 (d, J=7.6 Hz, 2H), 7.42 (d, J=7.2 Hz, 2H), 4.14 (s, 2H), 3.69-3.64 (m, 1H), 2.59-2.37 (m, 4H), 2.05-1.70 (m, 2H), 1.65 (br t, J=10.6 Hz, 1H), 1.49-1.38 (m, 3H), 1.33 (s, 9H), 1.28-1.15 (m, 1H), 0.79 (t, J=7.4 Hz, 2H). ESI MS found for C$_{21}$H$_{35}$BN$_2$O$_4$ m/z [391.3 (M+1)].

Example 7

Preparation of (S)-2-amino-2-((1s,3R)-3-(biphenyl-3-ylmethylamino)cyclobutyl)-6-boronohexanoic acid

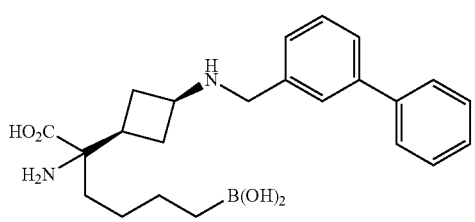 [SMILES: NC(CCCCB(O)O)(C(=O)O)[C@H]1C[C@@H](NCc2cccc(-c3ccccc3)c2)C1]

(S)-2-Amino-2-((1s,3R)-3-(biphenyl-3-ylmethylamino)cyclobutyl)-6-boronohexanoic acid was prepared in a manner analogous to that set forth in Example 1, except biphenyl-3-carbaldehyde was used instead of 3-phenylpropanal in step 6. $^1$H NMR (CD$_3$OD) δ 7.84 (m, 1H), 7.74-7.65 (m, 3H), 7.58-7.33 (m, 5H), 4.21 (s, 2H), 3.84-3.69 (m, 1H), 2.77-2.60 (m, 1H), 2.60-2.21 (m, 4H), 2.05-1.90 (m, 1H), 1.88-1.73 (m, 1H), 1.53-1.10 (m, 4H), 0.83 (t, J=7.1 Hz, 2H). MS found for $C_{23}H_{31}BN_2O_4$ m/z [411 (M+1)].

Example 8

Preparation of (S)-2-amino-6-borono-2-((1s,3R)-3-((4'-(trifluoromethyl)biphenyl-3-yl)methylamino)cyclobutyl)hexanoic acid

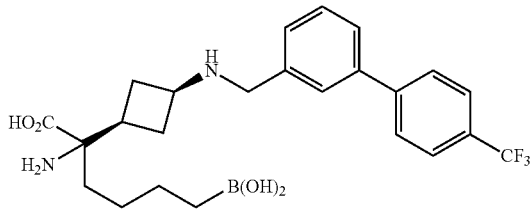 [SMILES: NC(CCCCB(O)O)(C(=O)O)[C@H]1C[C@@H](NCc2cccc(-c3ccc(C(F)(F)F)cc3)c2)C1]

(S)-2-Amino-6-borono-2-((1s,3R)-3-((4'-(trifluoromethyl)biphenyl-3-yl)methylamino)cyclobutyl)hexanoic acid was prepared in a manner analogous to that set forth in Example 1, except 4'-(trifluoromethyl)biphenyl-3-carbaldehyde was used instead of 3-phenylpropanal in step 6. $^1$H NMR (D$_2$O) δ 7.85 (s, 4H), 7.84-7.79 (m, 1H), 7.77 (m, 1H), 7.62 (t, J=8.0 Hz, 1H), 7.52 (m, 1H), 4.25 (s, 2H), 3.80-3.68 (m, 1H), 2.60-2.37 (m, 4H), 2.08-1.94 (m, 1H), 1.94-1.79 (m, 1H), 1.70-1.58 (m, 1H), 1.53-1.12 (m, 4H), 0.78 (t, J=7.6 Hz, 2H). MS found for $C_{24}H_{30}BF_3N_2O_4$ m/z[479 (M+1)].

Example 9

Preparation of (S)-2-amino-6-borono-2-((1s,3R)-3-((4'-chlorobiphenyl-3-yl)methylamino)cyclobutyl)hexanoic acid

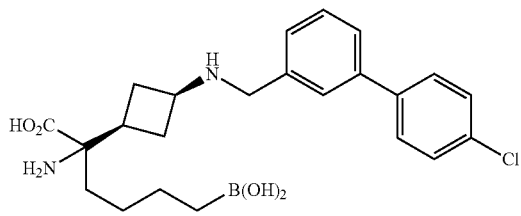 [SMILES: NC(CCCCB(O)O)(C(=O)O)[C@H]1C[C@@H](NCc2cccc(-c3ccc(Cl)cc3)c2)C1]

(S)-2-Amino-6-borono-2-((1s,3R)-3-((4'-chlorobiphenyl-3-yl)methylamino)cyclobutyl)hexanoic acid was prepared in a manner analogous to that set forth in Example 1, except 4'-chlorobiphenyl-3-carbaldehyde was used instead of 3-phenylpropanal in step 6. $^1$H NMR (D$_2$O) δ 7.76 (dt, J=8.0, 1.2 Hz, 1H), 7.71 (t, J=1.6 Hz, 1H), 7.67 (dt, J=8.4, 2.4 Hz, 2H), 7.59 (t, J=7.6 Hz, 1H), 7.54 (dt, J=8.4, 2.4 Hz, 2H), 7.47 (dm, J=7.6 Hz, 1H), 4.23 (s, 2H), 3.77-3.67 (m, 1H), 2.60-2.35 (m, 4H), 2.09-1.94 (m, 1H), 1.93-1.80 (m, 1H), 1.69-1.58 (m, 1H), 1.45-1.13 (m, 4H), 0.78 (t, J=7.8 Hz, 2H). MS found for $C_{23}H_{30}BClN_2O_4$ m/z[445 (M+1)].

Example 10

Preparation of (S)-2-amino-6-borono-2-((1s,3R)-3-((4-fluoronaphthalen-1-yl)methylamino)cyclobutyl)hexanoic acid

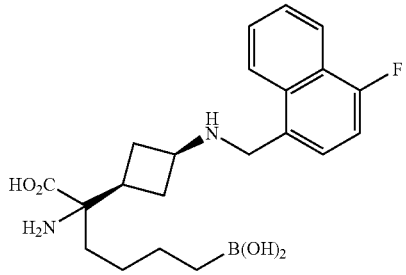 [SMILES: NC(CCCCB(O)O)(C(=O)O)[C@H]1C[C@@H](NCc2ccc(F)c3ccccc23)C1]

(S)-2-Amino-6-borono-2-((1s,3R)-3-((4-fluoronaphthalen-1-yl)methylamino)cyclobutyl)hexanoic acid was prepared in a manner analogous to that set forth in Example 1, except 4-fluoro-1-naphthaldehyde was used instead of 3-phenylpropanal in step 6. $^1$H NMR (D$_2$O) δ 8.26 (d, J=7.6, 1H), 8.09 (d, J=8.4 Hz, 1H), 7.82-7.51 (m, 2H), 7.64 (dd, J=8.0, 5.6 Hz, 2H), 7.30 (dd, J=10.4, 8.0 Hz, 1H), 4.64 (s, 2H), 3.83-3.74 (m, 1H), 2.61-2.35 (m, 4H), 2.07-1.94 (m, 1H), 1.92-1.80 (m, 1H), 1.68-1.57 (m, 1H), 1.49-1.13 (m, 4H), 0.78 (t, J=8.0 Hz, 2H). MS found for $C_{21}H_{28}BFN_2O_4$ m/z [403 (M+1)].

Example 11

Preparation of (S)-2-amino-6-borono-2-((1s,3R)-3-((5-fluoronaphthalen-1-yl)methylamino)cyclobutyl)hexanoic acid

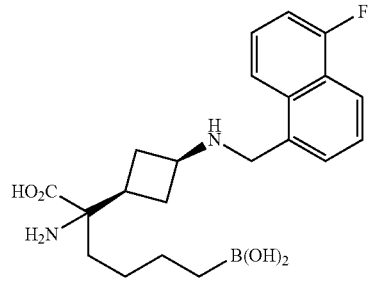 [SMILES: NC(CCCCB(O)O)(C(=O)O)[C@H]1C[C@@H](NCc2cccc3c(F)cccc23)C1]

(S)-2-Amino-6-borono-2-((1s,3R)-3-((5-fluoronaphthalen-1-yl)methylamino)cyclobutyl)hexanoic acid was prepared in a manner analogous to that set forth in Example 1, except 5-fluoro-1-naphthaldehyde was used instead of 3-phenylpropanal in step 6. $^1$H NMR (D$_2$O) δ 8.28 (d, J=8.4, 1H), 7.89 (d, J=8.8 Hz, 1H), 7.73 (dd, J=7.2, 1.2 Hz, 1H), 7.70-7.63 (m, 2H), 7.37 (dd, J=10.8, 7.2 Hz, 1H), 4.68 (s, 2H), 3.85-3.73 (m, 1H), 2.63-2.36 (m, 4H), 2.08-1.94 (m, 1H), 1.92-1.80 (m, 1H), 1.70-1.57 (m, 1H), 1.50-1.11 (m, 4H), 0.78 (t, J=7.6 Hz, 2H). MS found for $C_{21}H_{28}BFN_2O_4$ m/z [403 (M+1)].

Example 12

Preparation of (S)-2-amino-2-((1s,3R)-3-(anthracen-9-ylmethylamino)cyclobutyl)-6-boronohexanoic acid

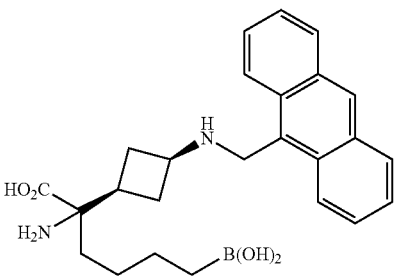 [SMILES: NC(CCCCB(O)O)(C(=O)O)[C@H]1C[C@@H](NCc2c3ccccc3cc3ccccc23)C1]

(S)-2-Amino-2-((1s,3R)-3-(anthracen-9-ylmethylamino) cyclobutyl)-6-boronohexanoic acid was prepared in a manner analogous to that set forth in Example 1, except anthracene-9-carbaldehyde was used instead of 3-phenylpropanal in step 6. $^1$H NMR (D$_2$O) δ 8.68 (m, 1H), 8.23 (d, J=8.8, 2H), 8.16 (d, J=8.8 Hz, 2H), 7.74 (m, 2H), 7.63 (m, 2H), 5.13 (s, 2H), 3.92-3.80 (m, 1H), 2.62-2.25 (m, 4H), 2.08-1.80 (m, 2H), 1.70-1.53 (m, 1H), 1.52-1.11 (m, 4H), 0.78 (t, J=8.0 Hz, 2H). MS found for $C_{25}H_{31}BN_2O_4$ m/z [435 (M+1)].

Example 13

Preparation of (S)-2-amino-6-borono-2-((1s,3R)-3-(2-morpholinobenzylamino)cyclobutyl)hexanoic acid

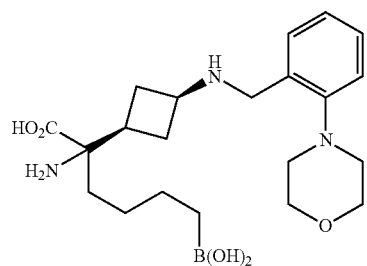 [SMILES: NC(CCCCB(O)O)(C(=O)O)[C@H]1C[C@@H](NCc2ccccc2N2CCOCC2)C1]

(S)-2-Amino-6-borono-2-((1s,3R)-3-(2-morpholinobenzylamino)cyclobutyl)hexanoic acid was prepared in a manner analogous to that set forth in Example 1, except 2-morpholinobenzaldehyde was used instead of 3-phenylpropanal in step 6. $^1$H NMR (D$_2$O) δ 7.40-7.24 (m, 4H), 4.47 (s, 2H), 3.98-3.89 (m, 1H), 3.77-3.67 (m, 1H), 3.67-3.56 (m, 1H), 3.42-3.25 (m, 4H), 3.12-3.00 (m, 1H), 2.64-2.34 (m, 4H), 2.05-1.80 (m, 2H), 1.74-1.50 (m, 2H), 1.50-1.14 (m, 4H), 0.80 (t, J=8.0 Hz, 2H). MS found for $C_{21}H_{34}BN_3O_5$ m/z [420 (M+1)].

Example 14

Preparation of (S)-2-amino-6-borono-2-((1R,3R)-3-(((S)-1,2,3,4-tetrahydroisoquinolin-3-yl)methylamino)cyclobutyl)hexanoic acid

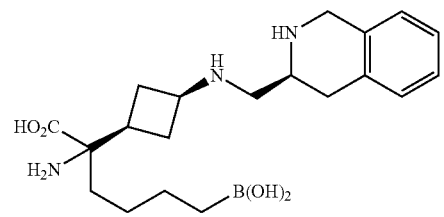 [SMILES: NC(CCCCB(O)O)(C(=O)O)[C@H]1C[C@@H](NC[C@@H]2Cc3ccccc3CN2)C1]

(S)-2-Amino-6-borono-2-((1R,3R)-3-(((S)-1,2,3,4-tetrahydroisoquinolin-3-yl)methylamino)cyclobutyl)hexanoic acid was prepared in a manner analogous to that set forth in Example 1, except (S)-tert-butyl 3-formyl-3,4-dihydroisoquinoline-2(1H)-carboxylate was used instead of 3-phenylpropanal in step 6. $^1$H NMR (D$_2$O) δ 7.55-7.49 (m, 1H), 7.41 (d, J=8.0 Hz, 1H), 7.28 (dt, J=1.2, 8.4 Hz, 1H), 4.26 (s, 2H), 3.96-3.88 (m, 4H), 3.75-3.65 (m, 1H), 3.03-2.97 (m, 4H), 2.57-2.38 (m, 4H), 2.07-1.80 (m, 2H), 1.75-1.56 (m, 1H), 1.50-1.13 (m, 4H), 0.79 (t, J=8.0 Hz, 2H). MS found for $C_{20}H_{32}BN_3O_4$ m/z[390 (M+1)].

Example 15

Preparation of (S)-2-amino-6-borono-2-((1s,3R)-3-((2,3-dihydrobenzofuran-5-yl)methylamino)cyclobutyl)hexanoic acid

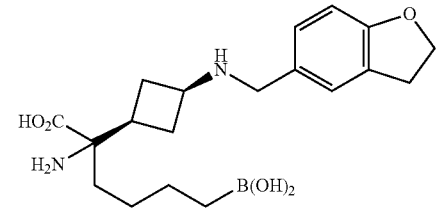 [SMILES: NC(CCCCB(O)O)(C(=O)O)[C@H]1C[C@@H](NCc2ccc3c(c2)CCO3)C1]

(S)-2-Amino-6-borono-2-((1s,3R)-3-((2,3-dihydrobenzofuran-5-yl)methylamino)cyclobutyl)hexanoic acid was prepared in a manner analogous to that set forth in Example 1, except 2,3-dihydrobenzofuran-5-carbaldehyde was used instead of 3-phenylpropanal in step 6. $^1$H NMR (D$_2$O) δ 7.33 (d, J=1.2 Hz, 1H), 7.21 (dd, J=8.4, 1.8 Hz, 1H), 6.87 (d, J=8.4 Hz, 1H), 4.63 (t, J=8.8 Hz, 2H), 4.08 (s, 2H), 3.71-3.58 (m, 1H), 3.25 (t, J=8.8 Hz, 2H), 2.60-2.34 (m, 4H), 2.05-1.80 (m, 2H), 1.71-1.55 (m, 1H), 1.50-1.13 (m, 4H), 0.79 (t, J=8.0 Hz, 2H). MS found for $C_{19}H_{29}BN_2O_5$ m/z [377 (M+1)].

Example 16

Preparation of (S)-2-amino-6-borono-2-((1s,3R)-3-((3',4'-dichlorobiphenyl-4-yl)methylamino)cyclobutyl)hexanoic acid

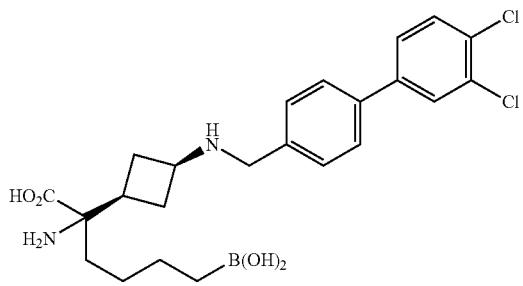 [SMILES: NC(CCCCB(O)O)(C(=O)O)[C@H]1C[C@@H](NCc2ccc(-c3ccc(Cl)c(Cl)c3)cc2)C1]

(S)-2-Amino-6-borono-2-((1s,3R)-3-((3',4'-dichlorobiphenyl-4-yl)methylamino)cyclobutyl)hexanoic acid was prepared in a manner analogous to that set forth in Example 1, except 3',4'-dichlorobiphenyl-3-carbaldehyde was used instead of 3-phenylpropanal in step 6. $^1$H NMR (D$_2$O) δ 7.75 (s, 1H), 7.67-7.59 (m, 2H), 7.57-7.42 (m, 4H), 4.13 (s, 2H), 3.63 (m, 1H), 2.60-2.25 (m, 4H), 2.01-1.75 (m, 2H), 1.66-1.53 (m, 1H), 1.40-1.04 (m, 4H), 0.70 (t, J=7.2 Hz, 2H). MS found for $C_{23}H_{29}BCl_2N_2O_4$ m/z [502 (M+Na)].

Example 17

Preparation of (S)-2-amino-6-borono-2-((1s,3R)-3-((4'-chlorobiphenyl-4-yl)methylamino)cyclobutyl)hexanoic acid

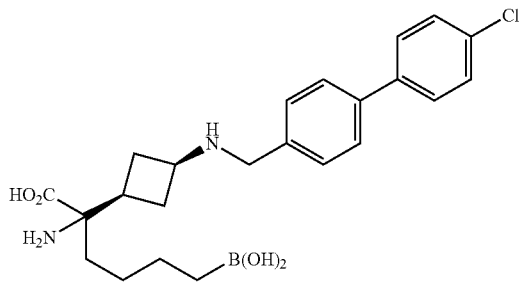 [SMILES: NC(CCCCB(O)O)(C(=O)O)[C@H]1C[C@@H](NCc2ccc(-c3ccc(Cl)cc3)cc2)C1]

(S)-2-amino-6-borono-2-((1s,3R)-3-((4'-chlorobiphenyl-4-yl)methylamino)cyclobutyl)hexanoic acid was prepared in a manner analogous to that set forth in Example 1, except 4'-chlorobiphenyl-3-carbaldehyde was used instead of 3-phenylpropanal in step 6. $^1$H NMR (D$_2$O) δ 7.67 (d, J=8.0, 2H), 7.60 (d, J=8.0 Hz, 2H), 7.44 (m, 4H), 4.13 (s, 2H), 3.64 (m, 1H), 2.58-2.26 (m, 4H), 2.02-1.78 (m, 2H), 1.67-1.55 (m, 1H), 1.42-1.07 (m, 4H), 0.71 (t, J=7.2 Hz, 2H). MS found for $C_{23}H_{30}BClN_2O_4$ m/z [445 (M+1)].

Example 18

Preparation of (S)-2-amino-6-borono-2-((1s,3R)-3-((4'-(trifluoromethyl)biphenyl-4-yl)methylamino)cyclobutyl)hexanoic acid

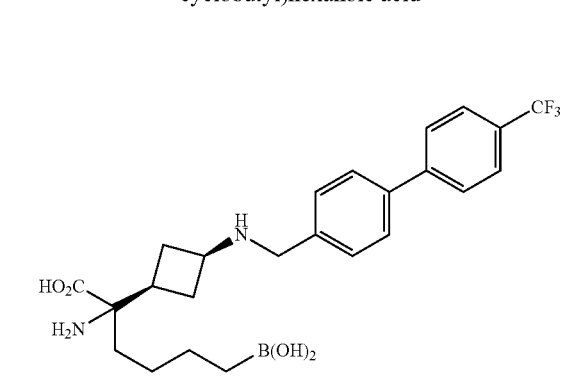

(S)-2-Amino-6-borono-2-((1s,3R)-3-((4'-(trifluoromethyl)biphenyl-4-yl)methylamino)cyclobutyl)hexanoic acid was prepared in a manner analogous to that set forth in Example 1, except 4'-(trifluoromethyl)biphenyl-3-carbaldehyde was used instead of 3-phenylpropanal in step 6. $^1$H NMR (D$_2$O) δ 7.84-7.71 (m, 6H), 7.51 (d, J=7.6 Hz, 2H), 4.15 (s, 2H), 3.65 (m, 1H), 2.56-2.59 (m, 4H), 2.02-1.73 (m, 2H), 1.67-1.53 (m, 1H), 1.44-1.08 (m, 4H), 0.71 (t, J=7.2 Hz, 2H). MS found for $C_{24}H_{30}BF_3N_2O_4$ m/z [479 (M+1)].

Example 19

Preparation of (S)-2-amino-6-borono-2-((1s,3R)-3-((4'-fluorobiphenyl-4-yl)methylamino)cyclobutyl)hexanoic acid

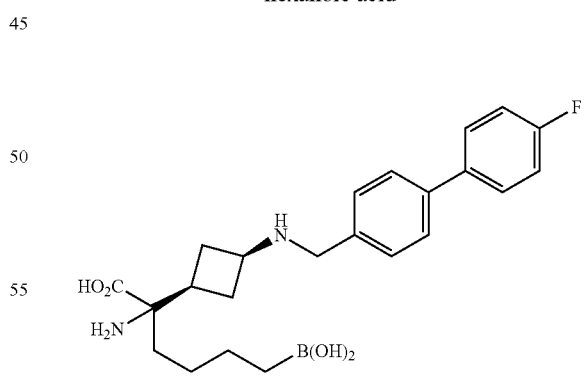

(S)-2-Amino-6-borono-2-((1s,3R)-3-((4'-fluorobiphenyl-4-yl)methylamino)cyclobutyl)hexanoic acid was prepared in a manner analogous to that set forth in Example 1, except 4'-fluorobiphenyl-3-carbaldehyde was used instead of 3-phenylpropanal in step 6. $^1$H NMR (D$_2$O) δ 7.70-7.60 (m, 4H), 7.46 (d, J=7.6 Hz, 2H), 7.18 (t, J=8.8 Hz, 2H), 7.44 (m, 4H), 4.13 (s, 2H), 3.64 (m, 1H), 2.59-2.25 (m, 4H), 2.00-1.76 (m, 2H), 1.68-1.54 (m, 1H), 1.42-1.05 (m, 4H), 0.71 (t, J=7.2 Hz, 2H). MS found for $C_{23}H_{30}BFN_2O_4$ m/z [429 (M+1)].

Example 20

Preparation of (S)-2-amino-6-borono-2-((1s,3R)-3-(4-hydroxybenzylamino)cyclobutyl)hexanoic acid

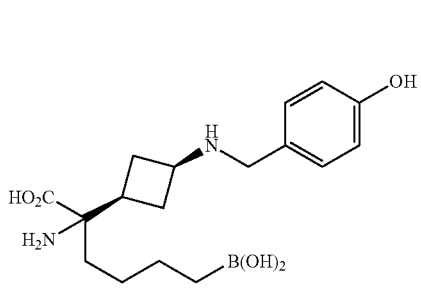 [SMILES: NC(CCCCB(O)O)(C(=O)O)[C@H]1C[C@@H](NCc2ccc(O)cc2)C1]

(S)-2-Amino-6-borono-2-((1s,3R)-3-(4-hydroxybenzylamino)cyclobutyl)hexanoic acid was prepared in a manner analogous to that set forth in Example 1, except 4-(benzyloxy)benzaldehyde was used instead of 3-phenylpropanal in step 6. $^1$H NMR (D$_2$O) δ 7.26 (d, J=7.2, 2H), 6.87 (d, J=7.2 Hz, 2H), 4.01 (s, 2H), 3.59 (m, 1H), 2.60-2.18 (m, 4H), 1.96-1.78 (m, 2H), 1.67-1.53 (m, 1H), 1.40-1.04 (m, 4H), 0.72 (m, 2H). MS found for $C_{17}H_{27}BN_2O_5$ m/z [351 (M+1)].

Example 21

Preparation of (S)-2-amino-6-borono-2-((1s,3R)-3-(4-(4-chlorophenoxy)benzylamino)cyclobutyl)hexanoic acid

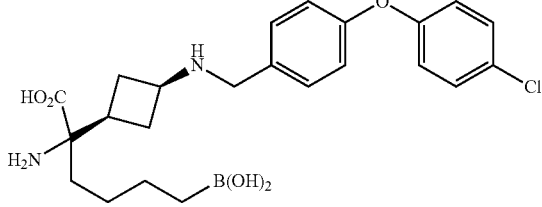

(S)-2-Amino-6-borono-2-((1s,3R)-3-(4-(4-chlorophenoxy)benzylamino)cyclobutyl)hexanoic acid was prepared in a manner analogous to that set forth in Example 1, except 4-(4-chlorophenoxy)benzaldehyde was used instead of 3-phenylpropanal in step 6. $^1$H NMR (D$_2$O) δ 7.37 (m, 4H), 7.09-6.97 (m, 4H), 4.07 (s, 2H), 3.64 (m, 1H), 2.56-2.20 (m, 4H), 2.00-1.70 (m, 2H), 1.66-1.52 (m, 1H), 1.43-1.01 (m, 4H), 0.72 (m, 2H). MS found for $C_{23}H_{30}BClN_2O_5$ m/z [461 (M+1)].

Example 22

Preparation of (S)-2-amino-6-borono-2-((1s,3R)-3-((4'-chlorobiphenyl-2-yl)methylamino)cyclobutyl)hexanoic acid

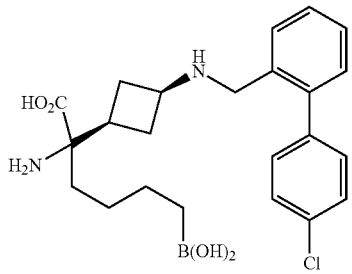 [SMILES: NC(CCCCB(O)O)(C(=O)O)[C@H]1C[C@@H](NCc2ccccc2-c2ccc(Cl)cc2)C1]

(S)-2-Amino-6-borono-2-((1s,3R)-3-((4'-chlorobiphenyl-2-yl)methylamino)cyclobutyl) hexanoic acid was prepared in a manner analogous to that set forth in Example 1, except 4'-chlorobiphenyl-2-carbaldehyde was used instead of 3-phenylpropanal in step 6. $^1$H NMR (D$_2$O) δ 7.52-7.41 (m, 5H), 7.39-7.28 (m, 3H), 4.12 (s, 2H), 3.38-3.27 (m, 1H), 2.40-2.28 (m, 1H), 2.16-1.91 (m, 3H), 1.79-1.47 (m, 3H), 1.40-1.01 (m, 4H), 0.71 (t, J=8.0 Hz, 2H). MS found for $C_{23}H_{30}BClN_2O_4$ m/z [445 (M+1)].

Example 23

Preparation of (S)-2-amino-6-borono-2-((1s,3R)-3-((6-phenylpyridin-3-yl)methylamino)cyclobutyl)hexanoic acid

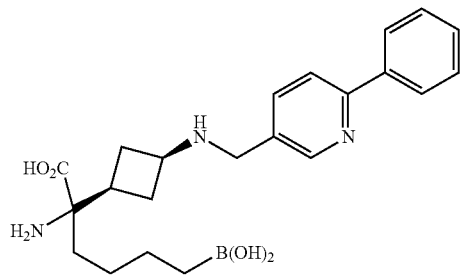 [SMILES: NC(CCCCB(O)O)(C(=O)O)[C@H]1C[C@@H](NCc2ccc(-c3ccccc3)nc2)C1]

(S)-2-Amino-6-borono-2-((1s,3R)-3-((6-phenylpyridin-3-yl)methylamino)cyclobutyl)hexanoic acid was prepared in a manner analogous to that set forth in Example 1, except 6-phenylnicotinaldehyde was used instead of 3-phenylpropanal in step 6. $^1$H NMR (D$_2$O) δ 8.82 (s, 1H), 8.58 (m, 1H), 8.29 (m, 1H), 7.85 (d, J=7.1 Hz, 2H), 7.70-7.58 (m, 3H), 4.38 (s, 2H), 3.77 (m, 1H), 2.62-2.38 (m, 4H), 2.07-1.80 (m, 2H), 1.68-1.56 (m, 1H), 1.42-1.09 (m, 4H), 0.72 (t, J=7.6 Hz, 2H). MS found for $C_{22}H_{30}BN_3O_4$ m/z [412 (M+1)].

Example 24

Preparation of (S)-2-((1s,3R)-3-((9H-fluoren-2-yl)methylamino)cyclobutyl)-2-amino-6-boronohexanoic acid

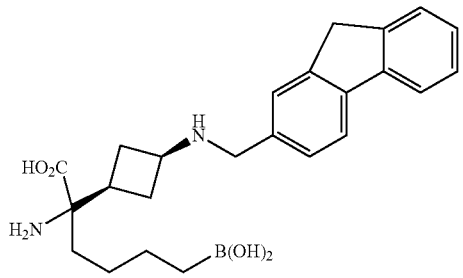 [SMILES: NC(CCCCB(O)O)(C(=O)O)[C@H]1C[C@@H](NCc2ccc3c(c2)Cc2ccccc2-3)C1]

(S)-2-((1s,3R)-3-((9H-Fluoren-2-yl)methylamino)cyclobutyl)-2-amino-6-boronohexanoic acid was prepared in a manner analogous to that set forth in Example 1, except 9H-fluorene-2-carbaldehyde was used instead of 3-phenylpropanal in step 6. $^1$H NMR (D$_2$O) δ 7.89-7.83 (m, 2H), 7.62-7.56 (m, 2H), 7.44-7.32 (m, 3H), 4.14 (s, 2H), 3.91 (s, 2H), 3.63 (m, 1H), 2.54-2.27 (m, 4H), 2.00-1.77 (m, 2H), 1.63-1.53 (m, 1H), 1.40-1.04 (m, 4H), 0.70 (t, J=7.6 Hz, 2H). MS found for $C_{24}H_{31}BN_2O_4$ m/z [423 (M+1)].

Example 25

Preparation of (S)-2-amino-6-borono-2-((1s,3R)-3-((4'-(trifluoromethyl)biphenyl-2-yl)methylamino)cyclobutyl)hexanoic acid

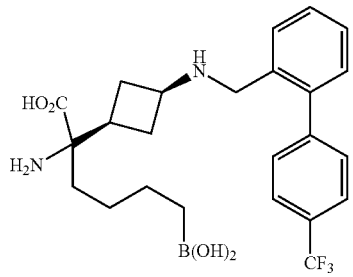 [SMILES: NC(CCCCB(O)O)(C(=O)O)[C@H]1C[C@@H](NCc2ccccc2-c2ccc(C(F)(F)F)cc2)C1]

(S)-2-Amino-6-borono-2-((1s,3R)-3-((4'-(trifluoromethyl)biphenyl-2-yl)methylamino)cyclobutyl)hexanoic acid was prepared in a manner analogous to that set forth in Example 1, except 4'-(trifluoromethyl)biphenyl-2-carbaldehyde was used instead of 3-phenylpropanal in step 6. $^1$H NMR (D$_2$O) δ 7.82 (d, J=8.1 Hz, 2H), 7.56-7.45 (m, 5H), 7.42-7.36 (m, 1H), 4.12 (s, 2H), 3.34-3.26 (m, 1H), 2.45-2.24 (m, 1H), 2.16-1.86 (m, 3H), 1.75-1.61 (m, 2H), 1.54-1.43 (m, 1H), 1.39-1.01 (m, 4H), 0.70 (t, J=8.0 Hz, 2H). MS found for $C_{24}H_{30}BF_3N_2O_4$ m/z[479 (M+1)].

Example 26

Preparation of (S)-2-amino-6-borono-2-((1s,3R)-3-(4-cyclohexylbenzylamino)cyclobutyl)hexanoic acid

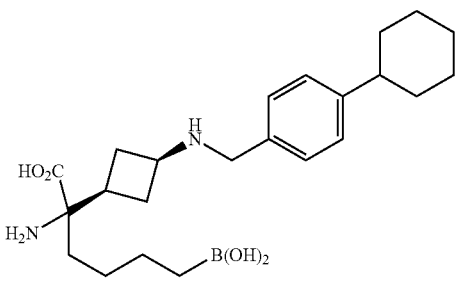 [SMILES: NC(CCCCB(O)O)(C(=O)O)[C@H]1C[C@@H](NCc2ccc(C3CCCCC3)cc2)C1]

(S)-2-Amino-6-borono-2-((1s,3R)-3-(4-cyclohexylbenzylamino)cyclobutyl) hexanoic acid was prepared in a manner analogous to that set forth in Example 1, except 4-cyclohexylbenzaldehyde was used instead of 3-phenylpropanal in step 6. $^1$H NMR (D$_2$O) δ 7.31 (s, 4H), 4.05 (s, 2H), 3.58 (m, 1H), 2.57-2.22 (m, 5H), 1.96-1.50 (m, 8H), 1.41-1.05 (m, 9H), 0.71 (t, J=7.8 Hz, 2H). MS found for $C_{23}H_{37}BN_2O_4$ m/z [417 (M+1)].

Example 27

Preparation of (S)-2-amino-6-borono-2-((1s,3R)-3-(dibenzylamino)cyclobutyl)hexanoic acid

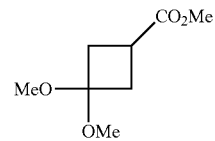 [SMILES: COC(=O)C1CC(OC)(OC)C1]

Step 1: Methyl 3,3-dimethoxycyclobutanecarboxylate

Using the method described in J. Org. Chem. (2006) 61, 2174-2178, 3-oxocyclobutanecarboxylic acid (11.4 g, 100 mmol) was dissolved in MeOH (133 mL) and treated with p-toluenesulfonic acid hydrate (0.38 g, 2.0 mmol). The mixture was heated 55° C. for 3 days, cooled to room temperature and concentrated in vacuo to ~⅓ volume. The resulting solution was diluted with H$_2$O, extracted with dichloromethane (3×), washed with saturated aqueous sodium chloride and concentrated in vacuo to give the crude product (15.2 g) which was used without further purification. R$_f$ 0.41 (20% ethyl acetate in heptane). $^1$H NMR (CDCl$_3$, 300 MHz) δ $^1$H-NMR: 2.50-2.30 (m, 4H); 2.89 (quint, J=8.6 Hz, 1H), 3.14 (s, 3H); 3.17 (s, 3H); 3.69 (s, 3H).

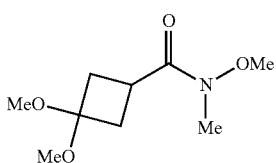 [SMILES: CON(C)C(=O)C1CC(OC)(OC)C1]

Step 2:
N,3,3-trimethoxy-N-methylcyclobutanecarboxamide

Methyl 3,3-dimethoxycyclobutanecarboxylate (11.65 g, 66.9 mmol) was dissolved in THF (134 mL) and treated with N,O-dimethylhydroxylamine hydrochloride (10.12 g, 103.7 mmol). The mixture was cooled to 0° C. and treated with isopropylmagnesium chloride (2 M solution in THF, 100.3 mL, 200.7 mmol) and stirred for 2 h. The reaction was quenched with saturated ammonium chloride solution (75 mL), diluted with ethyl acetate, washed with water and saturated aqueous sodium chloride, and concentrated in vacuo. The residue was chromatographed on silica gel eluting with 20-100% ethyl acetate in heptane to afford the desired product (9.16 g, 67%). $R_f$ 0.06 (20% ethyl acetate in heptane). $^1$H NMR (CDCl$_3$, 300 MHz) δ 3.61 (s, 3H), 3.20 (s, 3H), 3.19 (s, 3H), 3.15 (s, 3H), 2.39 (d, J=9.0 Hz, 4H). ESI MS found for C$_9$H$_{17}$NO$_4$ m/z [204.1 (M+1)].

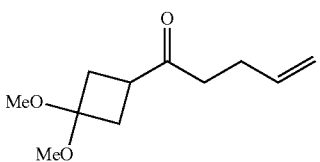

Step 3: 1-(3,3-dimethoxycyclobutyl)pent-4-en-1-one

N,3,3-trimethoxy-N-methylcyclobutanecarboxamide (12.19 g, 60.0 mmol) was dissolved in THF (130 mL), cooled to 0° C. and treated with 3-butenylmagnesium bromide (168 mL, 0.5 M/THF, 84 mmol). After stirring for 1.5 h at room temperature, the reaction was re-cooled to 0° C. and quenched with 1 N citric acid (30 mL), diluted with ethyl acetate, washed successively with water, saturated aqueous sodium chloride, dried over MgSO$_4$, and concentrated in vacuo. The residue was chromatographed on silica gel eluting with 5-40% ethyl acetate in heptane to afford the desired product 10.98 g (92%). $R_f$ 0.77 (50% ethyl acetate in heptane). $^1$H NMR (CDCl$_3$, 300 MHz) δ 5.87-5.72 (m, 1H), 5.06-4.95 (m, 2H), 3.17 (s, 3H), 3.13 (s, 3H), 3.06-2.88 (m, 1H), 2.54-2.48 (m, 2H), 2.38-2.28 (m, 6H).

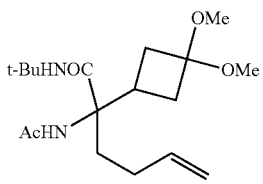

Step 4: 2-acetamido-N-tert-butyl-2-(3,3-dimethoxy-cyclobutyl)hex-5-enamide 1-(3,3-dimethoxycyclobutyl)pent-4-en-1-one (3.0, 15.1) was dissolved in 2,2,2-trifluoroethanol (7 mL). Ammonium acetate (4.66 g, 60.5 mmol) and tert-butyl isocyanide (3.40 mL, 30.3 mmol) were added and the reaction was stirred 3 days at room temperature. The reaction was diluted with ethyl acetate, washed successively with water, saturated aqueous sodium chloride, dried over MgSO$_4$, and concentrated in vacuo. The residue was chromatographed on silica gel eluting with 20-100% ethyl acetate in heptane to afford the desired product (4.04 g, 79%). $R_f$ 0.16 (50% ethyl acetate in heptane). $^1$H NMR (CDCl$_3$, 300 MHz) δ 7.10 (br s, 1H), 6.71 (br s, 1H), 5.83-5.69 (m, 1H), 5.03-4.91 (m, 2H), 3.14 (s, 6H), 2.91-2.72 (m, 2H), 2.39-2.24 (m, 2H), 2.13-1.79 (m, 7H), 1.53-1.33 (m, 10H). ESI MS found for C$_{18}$H$_{32}$N$_2$O$_4$ m/z [363.0 (M+Na$^+$)].

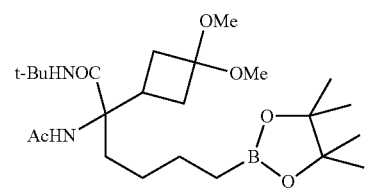

Step 5: 2-acetamido-N-tert-butyl-2-(3,3-dimethoxy-cyclobutyl)-6-(4,4,5,5-tetramethyl-1,3,2-dioxaborolan-2-yl)hexanamide 2-Acetamido-N-tert-butyl-2-(3,3-dimethoxycyclobutyl)hex-5-enamide (4.04 g, 11.87 mmol) was dissolved in dichloromethane (119 mL) and treated with [Ir(COD)Cl]$_2$ (239 mg, 0.356 mmol) and dppe (276 mg, 0.712 mmol). The reaction was stirred 15 minutes, then cooled to 0° C. and treated with pinacolborane (2.41 mL, 16.61 mmol). The reaction was stirred overnight at room temperature, then diluted with ethyl acetate, washed with saturated aqueous sodium chloride, dried over MgSO$_4$, and concentrated in vacuo. The residue was chromatographed on silica gel eluting with 18-100% ethyl acetate in heptane to afford the desired product (5.21 g, 94%). $R_f$ 0.29 (75% ethyl acetate in heptane). $^1$H NMR (CDCl$_3$, 300 MHz) δ 7.05 (br s, 1H), 6.75 (br s, 1H), 3.14 (s, 6H), 2.81-2.64 (m, 2H), 2.38-2.21 (m, 2H), 2.12-1.91 (m, 6H), 1.51-1.04 (m, 25H), 0.74 (t, J=8.0 Hz, 2H). ESI MS found for C$_{24}$H$_{45}$BN$_2$O$_6$ m/z [491.4 (M+Na$^+$)].

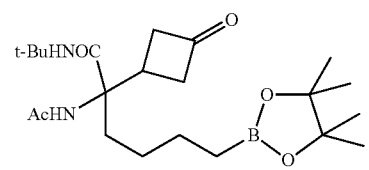

Step 6: 2-acetamido-N-tert-butyl-2-(3-oxocyclobutyl)-6-(4,4,5,5-tetramethyl-1,3,2-dioxaborolan-2-yl)hexanamide 2-Acetamido-N-tert-butyl-2-(3,3-dimethoxycyclobutyl)-6-(4,4,5,5-tetramethyl-1,3,2-dioxaborolan-2-yl)hexanamide (5.21 g, 11.10 mmol) was dissolved in acetone (110 mL) and treated with p-toluenesulfonic acid (106 mg, 0.56 mmol). The reaction was stirred overnight at room temperature, then diluted with benzene (500 mL) and heptane (250 mL), washed successively with water and saturated aqueous sodium chloride, dried over MgSO$_4$, and concentrated in vacuo. The residue was chromatographed on silica gel eluting with 50-75% ethyl acetate in heptane to afford the desired product (3.40 g, 73%). R$_f$ 0.31 (75% ethyl acetate in heptane). $^1$H NMR (CDCl$_3$, 300 MHz) δ 6.83 (br s, 1H), 5.84 (br s, 1H), 3.45-3.33 (m, 1H), 3.09-2.82 (m, 6H), 2.02 (s, 3H), 1.54-1.05 (m, 25H), 0.77 (t, J=7.4 Hz, 2H). ESI MS found for C$_{22}$H$_{39}$BN$_2$O$_5$ m/z [423.1 (M+1)].

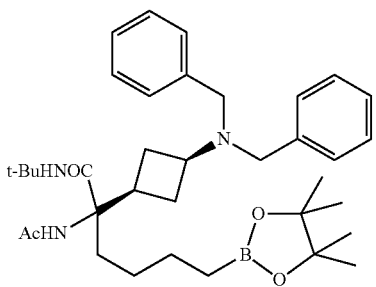

Step 7: (S)-2-acetamido-N-tert-butyl-2-((1s,3R)-3-(dibenzylamino)cyclobutyl)-6-(4,4,5,5-tetramethyl-1,3,2-dioxaborolan-2-yl)hexanamide 2-Acetamido-N-tert-butyl-2-(3-oxocyclobutyl)-6-(4,4,5, 5-tetramethyl-1,3,2-dioxaborolan-2-yl)hexanamide (211 mg, 0.50 mmol) was dissolved in ethyl acetate (1.4 mL) and treated with dibenzylamine (96 μL, 0.50 mmol). After stirring 5 minutes, NaBH(OAc)$_3$ (159 mg, 0.75 mmol) was added and the mixture was stirred overnight. The reaction was diluted with ethyl acetate, washed successively with saturated sodium bicarbonate solution, saturated aqueous sodium chloride, dried over MgSO$_4$, and concentrated in vacuo. The reside was chromatographed on silica gel eluting with 3-25% ethyl acetate in heptane to afford the crude product (209 mg) as a mixture of cis- and trans-isomers which was carried on without further purification. R$_f$ 0.45 (75% ethyl acetate in heptane). ESI MS found for C$_{36}$H$_{54}$BN$_3$O$_4$ m/z [604.5 (M+1)].

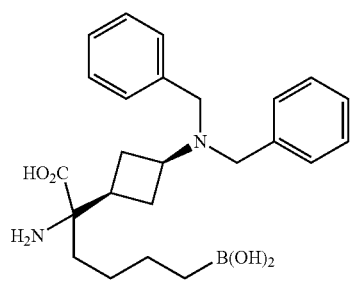

Step 8. (S)-2-amino-6-borono-2-((1s,3R)-3-(dibenzylamino)cyclobutyl)hexanoic acid 2-acetamido-N-tert-butyl-2-((1s,3s)-3-(dibenzylamino) cyclobutyl)-6-(4,4,5,5-tetramethyl-1,3,2-dioxaborolan-2-yl) hexanamide (209 mg, 0.347 mmol) was treated with 6 N HCl (3.6 mL) and heated to 100° C. overnight. The reaction was cooled to room temperature, diluted with H$_2$O, washed with dichloromethane (3×), and concentrated in vacuo. The residue was purified by preparative HPLC (10-100% CH$_3$CN/H$_2$O) to afford the desired product. $^1$H NMR (D$_2$O, 300 MHz) δ 7.41-7.23 (m, 10H), 4.15 (br s, 4H), 3.73-3.62 (m, 1H), 2.33-2.02 (m, 4H), 1.94-1.78 (m, 1H), 1.74-1.59 (m, 1H), 1.51-1.36 (m, 1H), 1.33-0.95 (m, 4H), 0.65 (t, J=7.2 Hz, 2H). ESI MS found for C$_{24}$H$_{33}$BN$_2$O$_4$ m/z [425.1 (M+1)].

Example 28

Preparation of (S)-2-amino-6-borono-2-((1r,3S)-3-(dibenzylamino)cyclobutyl)hexanoic acid

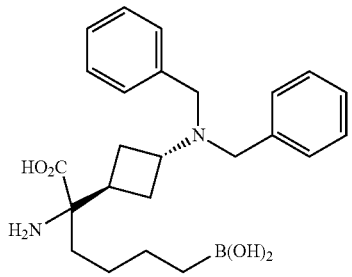

(S)-2-Amino-6-borono-2-((1r,3S)-3-(dibenzylamino)cyclobutyl)hexanoic acid was prepared in a manner analogous to that set forth in Example 27, except the trans-isomer was used from step 7. $^1$H NMR (D$_2$O, 300 MHz) δ 7.41-7.25 (m, 10H), 4.18 (br s, 4H), 3.88-3.76 (m, 1H), 2.66-2.54 (m, 1H), 2.45-2.17 (m, 4H), 1.86-1.67 (m, 1H), 1.57-1.42 (m, 1H), 1.37-1.01 (m, 4H), 0.66 (t, J=7.8 Hz, 2H). ESI MS found for C$_{24}$H$_{33}$BN$_2$O$_4$ m/z [425.1 (M+1)].

Example 29

Preparation of 2-amino-6-borono-2-((1s,3R)-3-(isoindolin-2-yl)cyclobutyl)hexanoic acid

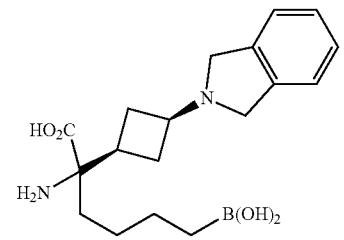 [SMILES: NC(CCCCB(O)O)(C(=O)O)[C@H]1C[C@@H](N2Cc3ccccc3C2)C1]

2-Amino-6-borono-2-((1s,3R)-3-(isoindolin-2-yl)cyclobutyl)hexanoic acid was prepared in a manner analogous to that set forth in Example 27 except that isoindoline was used instead of dibenzylamine in step 7. $^1$H NMR (D$_2$O, 300 MHz) δ 7.37-7.20 (m, 10H), 4.58-4.30 (m, 4H), 3.86-3.76 (m, 1H), 2.55-2.31 (m, 4H), 2.06-1.57 (m, 3H), 1.36-1.02 (m, 4H), 0.66 (t, 2H, J=6.9 Hz). ESI MS found for $C_{18}H_{27}BN_2O_4$ m/z [311.1 (M–2H$_2$O)].

Example 30

Preparation of 6-borono-2-(2-(isoindolin-2-yl)ethyl)-2-(methylamino)hexanoic acid

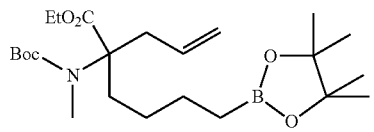 [SMILES: C=CCC(CCCCB1OC(C)(C)C(C)(C)O1)(C(=O)OCC)N(C)C(=O)OC(C)(C)C]

Step 1: Ethyl 2-allyl-2-(tert-butoxycarbonyl(methyl)amino)-6-(4,4,5,5-tetramethyl-1,3,2-dioxaborolan-2-yl)hexanoate Ethyl 2-allyl-2-(tert-butoxycarbonylamino)-6-(4,4,5,5-tetramethyl-1,3,2-dioxaborolan-2-yl)hexanoate (0.64 g, 1.50 mmol) was dissolved in THF (5 mL) and cooled to 0° C. NaHMDS (1 M solution in THF, 2.5 mL, 2.5 mmol) was added dropwise and the reaction was stirred for 20 min. Methyl iodide (0.47 mL, 7.5 mmol) was added and the reaction was warmed to room temperature and stirred overnight. The reaction was quenched with saturated NH$_4$Cl solution (5 mL), diluted with ethyl acetate, washed successively with saturated sodium bicarbonate solution and saturated aqueous sodium chloride, dried over MgSO$_4$, and concentrated in vacuo. The residue was chromatographed on silica gel eluting with 2-25% ethyl acetate in heptane to afford the desired product (0.518 g, 79%). R$_f$ 0.53 (30% ethyl acetate in heptane). $^1$H NMR (CDCl$_3$, 300 MHz) δ 5.78-5.62 (m, 1H), 5.15-5.03 (m, 2H), 4.12 (q, J=9.0 Hz, 2H), 2.90 (s, 3H), 2.89-2.81 (m, 1H), 2.58-2.51 (m, 1H), 1.94-1.83 (m, 1H), 1.76-1.66 (m, 1H), 1.54-1.08 (m, 29H), 0.77 (t, J=8.0 Hz, 2H). ESI MS found for $C_{23}H_{42}B_1N_1O_6$ m/z [440.2 (M+1)].

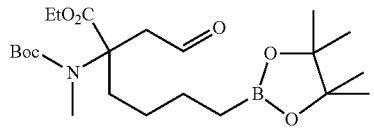

Step 2: Ethyl 2-(tert-butoxycarbonyl(methyl)amino)-2-(2-oxoethyl)-6-(4,4,5,5-tetramethyl-1,3,2-dioxaborolan-2-yl)hexanoate Ethyl 2-allyl-2-(tert-butoxycarbonyl(methyl)amino)-6-(4,4,5,5-tetramethyl-1,3,2-dioxaborolan-2-yl)hexanoate (0.518 g, 1.18 mmol) was dissolved in dichloromethane (60 mL) and cooled to –78° C. Ozone was bubbled through the solution until a blue color persisted. The reaction was flushed with nitrogen for 15 min, then treated with Ph$_3$P (0.928 g, 3.54 mmol), and stirred 2 hours at room temperature. The reaction was concentrated in vacuo and the residue was chromatographed on silica gel with 7-60% ethyl acetate in heptane to afford the desired product (0.375 g, 79%). R$_f$ 0.31 (30% ethyl acetate in heptane). $^1$H NMR (CDCl$_3$, 300 MHz) δ 9.42 (s, 1H), 4.17 (q, J=9.0 Hz, 2H), 3.21 (br d, J=15.0 Hz, 1H), 2.92 (s, 3H), 2.64 (br d, J=15.0 Hz, 1H), 1.87-1.79 (m, 2H), 1.46-1.09 (m, 28H), 0.77 (t, J=8.0 Hz, 2H). ESI MS found for $C_{22}H_{40}B_1N_1O_7$ m/z [442.2 (M+1)].

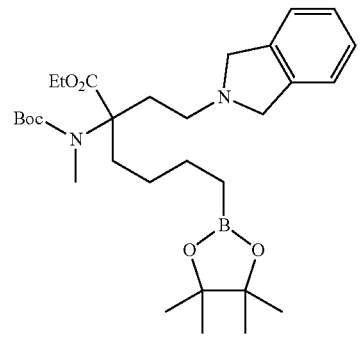 [SMILES: CCOC(=O)C(CCCCB1OC(C)(C)C(C)(C)O1)(CCN1Cc2ccccc2C1)N(C)C(=O)OC(C)(C)C]

Step 3: Ethyl 2-(tert-butoxycarbonyl(methyl)amino)-2-(2-(isoindolin-2-yl)ethyl)-6-(4,4,5,5-tetramethyl-1,3,2-dioxaborolan-2-yl)hexanoate Ethyl 2-(tert-butoxycarbonyl(methyl)amino)-2-(2-(isoindolin-2-yl)ethyl)-6-(4,4,5,5-tetramethyl-1,3,2-dioxaborolan-2-yl)hexanoate was prepared in accordance with the procedure of step 6 in Example 27 except that ethyl 2-(tert-butoxycarbonyl(methyl)amino)-2-(2-oxoethyl)-6-(4,4,5,5-tetramethyl-1,3,2-dioxaborolan-2-yl)hexanoate was used instead of 3-phenylpropanal and isoindoline was used instead of (R)-2-acetamido-2-((1s,3S)-3-aminocyclobutyl)-N-tert-butyl-6-(4,4,5,5-tetramethyl-1,3,2-dioxaborolan-2-yl)hexanamide hydrochloride. R$_f$ 0.32 (10% MeOH in dichloromethane). $^1$H NMR (CDCl$_3$, 300 MHz) δ 7.20-7.14 (m, 4H), 4.13 (q, J=8.0 Hz, 2H), 3.96 (br s, 4H), 3.00-2.88 (m, 4H), 2.75-2.60 (m, 2H), 2.41-2.31 (m, 1H), 2.15-1.95 (m, 2H), 1.87-1.74 (m, 2H), 1.49-1.08 (m, 26H), 0.79 (t, J=8.5 Hz, 2H). ESI MS found for $C_{30}H_{49}B_1N_2O_6$ m/z [545.6 (M+1)].

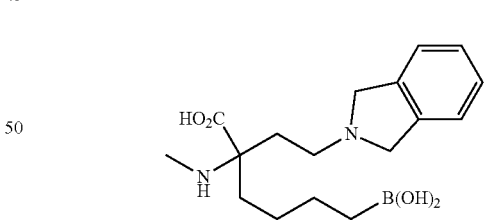

Step 4: 6-borono-2-(2-(isoindolin-2-yl)ethyl)-2-(methylamino)hexanoic acid 6-borono-2-(2-(isoindolin-2-yl)ethyl)-2-(methylamino)hexanoic acid was deprotected in a manner analogous to that set forth in Example 27, step 8. $^1$H NMR (D$_2$O, 400 MHz) δ 7.41-7.38 (m, 4H), 4.57 (br s, 4H), 3.47-3.43 (m, 1H), 3.33-3.28 (m, 1H), 2.69 (s, 3H), 2.33-2.24 (m, 2H), 1.96-1.83 (m, 2H), 1.50-1.42 (m, 2H), 1.36-1.30 (m, 1H), 1.25-1.19 (m, 1H), 0.82 (t, J=7.2 Hz, 2H). ESI MS found for $C_{17}H_{27}BN_2O_4$ m/z [335.2 (M+1)].

Example 31 (1799)

Preparation of 6-borono-2-(2-(5-chloro-3,4-dihydroisoquinolin-2(1H)-yl)ethyl)-2-(methylamino)hexanoic acid

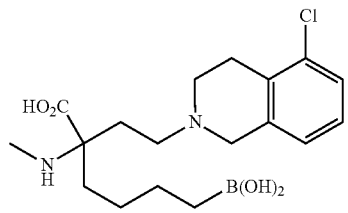 [SMILES: CNC(CCCCB(O)O)(CCN1CCc2c(Cl)cccc2C1)C(=O)O]

6-Borono-2-(2-(5-chloro-3,4-dihydroisoquinolin-2(1H)-yl)ethyl)-2-(methylamino)hexanoic acid was prepared in a manner analogous to that set forth in Example 30, except 5-chloro-1,2,3,4-tetrahydroisoquinoline was used as the amine in step 3. $^1$H NMR (D$_2$O, 500 MHz) δ 7.38 (d, J=8.0 Hz, 1H), 7.24 (dd, $J_1=J_2$=8.0 Hz, 1H), 7.10 (d, J=8.0 Hz, 1H), 4.53-4.48 (m, 1H), 4.32-4.26 (m, 1H), 3.81-3.75 (m, 1H), 3.42-3.35 (m, 1H), 3.34-3.21 (m, 2H), 3.20-3.12 (m, 1H), 3.11-3.01 (m, 1H), 2.57 (s, 3H), 1.92-1.75 (m, 5H), 1.75-1.65 (m, 1H), 1.40-1.34 (m, 2H), 1.31-1.18 (m, 1H), 1.16-1.06 (m, 1H), 0.70 (t, J=7.5 Hz, 2H). ESI MS found for $C_{19}H_{30}BClN_2O_4$ m/z [361.4 (M−2×18+1)]. Elemental Analysis for $C_{19}H_{30}BClN_2O_4$ 2HCl.2H$_2$O. Calc: C, 45.13; H, 7.18; N, 5.54. Found C, 45.18; H, 6.95; N, 5.62.

Example 32

Preparation of 6-borono-2-(2-(5-chloro-3,4-dihydroisoquinolin-2(1H)-yl)ethyl)-2-(methylamino)hexanoic acid

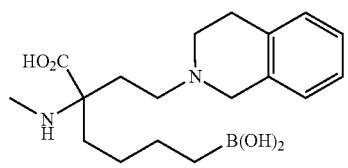 [SMILES: CNC(CCCCB(O)O)(CCN1CCc2ccccc2C1)C(=O)O]

6-Borono-2-(2-(5-chloro-3,4-dihydroisoquinolin-2(1H)-yl)ethyl)-2-(methylamino)hexanoic acid was prepared in a manner analogous to that set forth in Example 30, except 1,2,3,4-tetrahydroisoquinoline was used as the amine in step 3. $^1$H NMR (D$_2$O, 500 MHz) δ 7.30-71.8 (m, 3H), 7.12 (d, J=8.5 Hz, 1H), 4.57-4.48 (m, 1H), 4.33-4.26 (m, 1H), 3.80-3.70 (m, 1H), 3.51-3.35 (m, 2H), 3.31-3.22 (m, 1H), 3.21-3.10 (m, 1H), 3.10-3.02 (m, 1H), 2.60 (s, 3H), 2.41-2.26 (m, 2H), 1.92-1.77 (m, 2H), 1.40-1.32 (m, 2H), 1.30-1.19 (m, 1H), 1.19-1.07 (m, 1H), 0.70 (t, J=7.2 Hz, 2H). ESI MS found for $C_{18}H_{29}BN_2O_4$ m/z [313.5 (M−2×18+1)].

Example 33

Preparation of 6-borono-2-(methylamino)-2-(2-(4-methylpiperidin-1-yl)ethyl)hexanoic acid

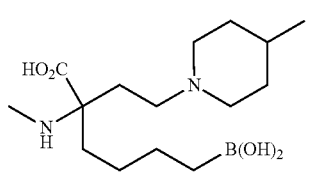

6-Borono-2-(methylamino)-2-(2-(4-methylpiperidin-1-yl)ethyl)hexanoic acid was prepared in a manner analogous to that set forth in Example 30, except 4-methylpiperidine was used as the amine in step 3. $^1$H NMR (D$_2$O, 500 MHz) δ 3.51-3.41 (m, 2H), 3.24-3.16 (m, 1H), 3.06-2.97 (m, 1H), 2.95-2.80 (m, 2H), 2.50 (s, 3H), 2.28-2.12 (m, 2H), 1.88-1.70 (m, 4H), 1.64-1.48 (m, 1H), 1.36-1.17 (m, 5H), 1.17-1.04 (m, 1H), 0.84 (d, J=8.2 Hz, 3H), 0.70 (t, J=7.2 Hz, 2H). ESI MS found for $C_{15}H_{31}BN_2O_4$ m/z [297.5 (M−18+1)]. Elemental Analysis for $C_{15}H_{31}BN_2O_4$ 2 HCl.⅓H$_2$O. Calc: C, 45.83; H, 8.63; N, 7.13. Found C, 45.77; H, 8.56; N, 7.10.

Example 34

Preparation of 6-borono-2-(2-(4,4-dimethylpiperidin-1-yl)ethyl)-2-(methylamino)hexanoic acid

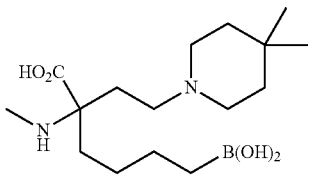

6-Borono-2-(2-(4,4-dimethylpiperidin-1-yl)ethyl)-2-(methylamino)hexanoic acid was prepared in a manner analogous to that set forth in Example 30, except 4,4-dimethylpiperidine was used as the amine in step 3. $^1$H NMR (D$_2$O, 500 MHz) δ 3.39-3.28 (m, 2H), 3.28-3.20 (m, 1H), 3.12-2.96 (m, 3H), 2.56 (s, 3H), 2.30-2.15 (m, 2H), 1.89-1.72 (m, 2H), 1.59-1.50 (m, 4H), 1.39-1.30 (m, 2H), 1.28-1.16 (m, 1H), 1.15-1.04 (m, 1H), 0.93 (s, 3H), 0.88 (s, 3H), 0.69 (t, J=7.5 Hz, 2H). ESI MS found for $C_{16}H_{33}BN_2O_4$ m/z [311.5 (M−18+1)].

Example 35

Preparation of 6-borono-2-(2-(3,4-dichlorobenzylamino)ethyl)-2-(methylamino)hexanoic acid

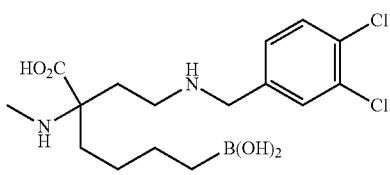 [SMILES: CNC(CCCCB(O)O)(CCNCc1ccc(Cl)c(Cl)c1)C(=O)O]

6-Borono-2-(2-(3,4-dichlorobenzylamino)ethyl)-2-(methylamino)hexanoic acid was prepared in a manner analogous to that set forth in Example 30, except (3,4-dichlorophenyl)methanamine was used as the amine in step 3. $^1$H NMR ($D_2O$, 500 MHz) δ 7.56 (s, 1H), 7.52 (d, J=8.5 Hz, 1H), 7.28 (d, J=8.5 Hz, 1H), 4.20 ($d_{AB}$, J=11.5 Hz, 1H), 4.10 ($d_{AB}$, J=11.5 Hz, 1H), 3.20-3.11 (m, 1H), 3.08-2.98 (m, 1H), 2.51 (s, 3H), 2.19-2.05 (m, 2H), 1.71-1.62 (m, 2H), 1.32-1.24 (m, 2H), 1.21-1.11 (m, 1H), 1.11-0.99 (m, 1H), 0.63 (t, J=7.2 Hz, 2H). ESI MS found for $C_{16}H_{25}BCl_2N_2O_4$ m/z [355.4/357.4 (M−2×18+1)].

Example 36

Preparation of 6-borono-2-(methylamino)-2-(2-(4-phenylpiperidin-1-yl)ethyl)hexanoic acid

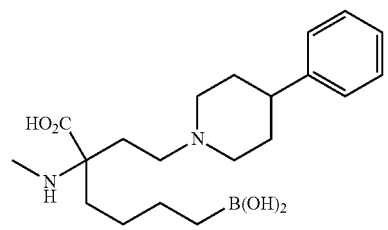 [SMILES: CNC(CCCCB(O)O)(CCN1CCC(c2ccccc2)CC1)C(=O)O]

6-Borono-2-(methylamino)-2-(2-(4-phenylpiperidin-1-yl)ethyl)hexanoic acid was prepared in a manner analogous to that set forth in Example 30, except 4-phenylpiperidine was used as the amine in step 3. $^1$H NMR ($D_2O$, 500 MHz) δ 7.30-7.24 (m, 2H), 7.22-7.16 (m, 3H), 3.62-3.51 (m, 2H), 3.30-3.20 (m, 1H), 3.12-2.96 (m, 3H), 2.86-2.74 (m, 1H), 2.55 (s, 3H), 2.31-2.12 (m, 2H), 2.09-1.97 (m, 2H), 1.88-1.72 (m, 4H), 1.39-1.28 (m, 2H), 1.28-1.14-1.03 (m, 1H), 0.66 (t, J=7.5 Hz, 2H). ESI MS found for $C_{20}H_{33}BN_2O_4$ m/z [341.5 (M−2×18+1)]. Elemental Analysis for $C_{20}H_{33}BN_2O_4$ 2 HCl.2H$_2$O. Calc: C, 49.50; H, 8.10; N, 5.77. Found C, 49.46; H, 7.88; N, 5.87.

Example 37

Preparation of 6-borono-2-(2-(4-(4-chlorophenyl)piperidin-1-yl)ethyl)-2-(methylamino)hexanoic acid

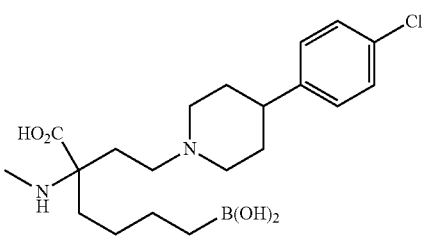

6-Borono-2-(2-(4-(4-chlorophenyl)piperidin-1-yl)ethyl)-2-(methylamino)hexanoic acid was prepared in a manner analogous to that set forth in Example 30, except 4-(4-chlorophenyl)piperidine was used as the amine in step 3. $^1$H NMR ($D_2O$, 500 MHz) δ 7.21 (d, J=8.5 Hz, 2H), 7.12 (d, J=8.5 Hz, 2H), 3.58-3.47 (m, 2H), 3.25-3.15 (m, 1H), 3.08-2.92 (m, 3H), 2.80-2.72 (m, 1H), 2.51 (s, 3H), 2.28-2.11 (m, 2H), 2.02-1.90 (m, 2H), 1.84-1.67 (m, 4H), 1.31-1.22 (m, 2H), 1.21-1.10 (m, 1H), 1.10-0.98 (m, 1H), 0.62 (t, J=7.5 Hz, 2H). ESI MS found for $C_{20}H_{32}BClN_2O_4$ m/z [375.3/377.5 (M−2×18+1)]. Elemental Analysis for $C_{20}H_{32}BClN_2O_4$ 2 HCl.2H$_2$O. Calc: C, 46.22; H, 7.37; N, 5.39. Found C, 46.46; H, 7.66; N, 5.50.

Example 38

Preparation of 2-amino-6-borono-2-(3-(pyrrolidin-1-yl)propyl)hexanoic acid

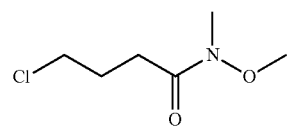

Step 1: 4-chloro-N-methoxy-N-methylbutanamide

While under argon, a solution of N,O-dimethylhydroxylamine hydrochloride (16.9 g, 0.173 mol) and triethylamine (53 mL, 0.381 mol) in dichloromethane (240 mL) was carefully treated with 4-chlorobutyryl chloride (20 g, 0.19 mol) over 40 minutes. After the addition was complete, the reaction mixture was stirred overnight at room temperature. The solid triethylamine hydrochloride was removed by filtration and the remaining solution was washed successively with aq 2 N HCl (×2), 1M $K_2CO_3$ and saturated aqueous sodium chloride. The organic layer was dried over MgSO$_4$, filtered and concentrated to give 4-chloro-N-methoxy-N-methylbutanamide (21.8 g) of crude yellow oil that was used in the next step without further purification. ESI MS found for $C_6H_{12}ClNO_2$ m/z [166.0/168.0 (M+1)].

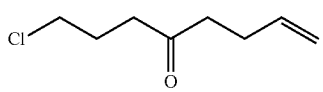

Step 2: 1-chlorooct-7-en-4-one

In a flame-dried flask, under an argon atmosphere, magnesium (7.8 g, 0.33 mol) and a small crystal of iodine in just enough THF to cover the magnesium was heated to a gentle reflux until the color had disappeared. Approximately 10% of a solution of 4-bromo-1-buten (32.5 mL, 0.321 mol) in THF (100 mL) was added all at once and reflux was continued until a brown coloration appeared. The remainder of the solution was added dropwise with continued reflux. After the addition was complete heating was maintained for 10 min, at which point almost all of the Mg had dissolved. The Grignard reagent solution was added to a second cooled (ice-bath) solution of 4-chloro-N-methoxy-N-methylbutanamide (21.3 g, 0.128 mol) in THF (200 mL). The resulting mixture was stirred for at room temperature for 2 h, poured into a mixture of ether and saturated aqueous ammonium chloride. The layers were separated and the aqueous phase was extracted with ether. The combined extracts were dried over $Mg_2SO_4$, filtered and concentrated under reduced pressure to give crude 1-chlorooct-7-en-4-one (17 g, 85%) as yellow liquid. $^1H$ NMR ($CDCl_3$, 500 MHz) δ 5.93-5.69 (m, 1H), 5.11-4.92 (m, 2H), 3.58 (t, J=6.5 Hz, 2H), 2.65-2.50 (m, 4H), 2.41-2.26 (m, 2H), 2.11-1.98 (qw, J=6.5 Hz, 2H).

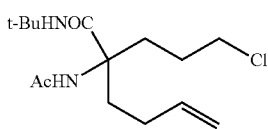

Step 3: 2-acetamido-N-tert-butyl-2-(3-chloropropyl)hex-5-enamide

A solution of 1-chlorooct-7-en-4-one (1 g, 6.22 mmol), t-butyl isonitrile (2.8 mL, 24.8 mmol) and ammonium acetate 2.8 g (37.3 mmol) in 2,2,2-trifluoroethanol (3 mL), was stirred at room temperature. Once the starting ketone was consumed the reaction was diluted with ethyl acetate, quenched with 2M HCl and extracted with ethyl acetate. The organic extract was washed successively with 2M HCl and saturated aqueous sodium chloride, dried over $MgSO_4$ and concentrated. Purification by column chromatography (ethyl acetate in hexane gave 2-acetamido-N-tert-butyl-2-(3-chloropropyl)hex-5-enamide as yellow oil 1.7 g (94%). ESI MS found for $C_{15}H_{27}ClN_2O_2$ m/z [303 (M+1), 325.3 (M+23)].

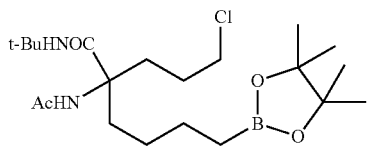

Step 4: 2-acetamido-N-tert-butyl-2-(3-chloropropyl)-6-(4,4,5,5-tetramethyl-1,3,2-dioxaborolan-2-yl)hexanamide While under argon, a cooled solution (ice-bath) of bis(1,5-dicyclooctadiene)diiridium(I)dichloride (100 mg, 3% mol), diphenylphosphinoethan (118 mg, 6% mol) and 4,4,5,5-tetramethyl-1,3,2-dioxaborolane (2.8 mL, 19.8 mmol) in dry dichloromethane (20 mL) was treated with a second solution of olefin (1.5 g, 4.95 mmol) in dry dichloromethane (20 mL). After 4 h the reaction was washed with water and saturated aqueous sodium chloride, dried over $MgSO_4$, concentrated and purified by flash chromatography (20-30% ethyl acetate in hexane to give 2-acetamido-N-tert-butyl-2-(3-chloropropyl)-6-(4,4,5,5-tetramethyl-1,3,2-dioxaborolan-2-yl)hexanamide as yellow oil (1.6 g, 76%). ESI MS found for $C_{21}H_{40}BClN_2O_4$ m/z [431.5 (M+1), 453.5 (M+23)].

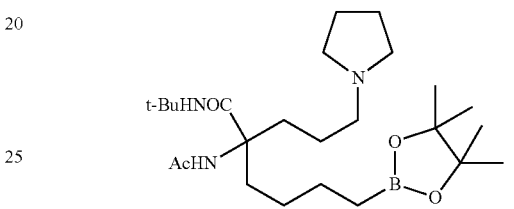

Step 5: 2-acetamido-N-tert-butyl-2-(3-(pyrrolidin-1-yl)propyl)-6-(4,4,5,5-tetramethyl-1,3,2-dioxaborolan-2-yl)hexanamide A solution of 2-acetamido-N-tert-butyl-2-(3-chloropropyl)-6-(4,4,5,5-tetramethyl-1,3,2-dioxaborolan-2-yl)hexanamide (0.39 g, 0.9 mmol) in acetonitrile was treated with NaI (10% mol) and pyrolidine (0.75 mL, 9 mmol). The mixture was warmed to 50° C. and stirred overnight. After cooling to room temperature, the reaction was diluted with water, extracted with dichloromethane, dried over $MgSO_4$, and concentrated to give crude 2-acetamido-N-tert-butyl-2-(3-(pyrrolidin-1-yl)propyl)-6-(4,4,5,5-tetramethyl-1,3,2-dioxaborolan-2-yl)hexanamide (0.31 g). This material was used in the next step without further purification. ESI MS found for $C_{25}H_{48}BN_3O_4$ m/z [466.6 (M+1)].

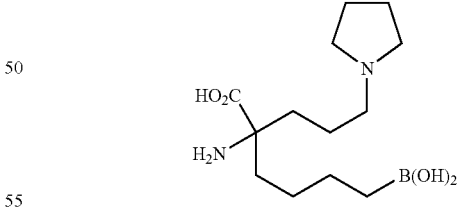

Step 6: 2-amino-6-borono-2-(3-(pyrrolidin-1-yl)propyl)hexanoic acid

A solution of 2-acetamido-N-tert-butyl-2-(3-(pyrrolidin-1-yl)propyl)-6-(4,4,5,5-tetramethyl-1,3,2-dioxaborolan-2-yl)hexanamide in 6 N HCl was heated to reflux overnight. After cooling to room temperature, the mixture was concentrated to dryness and purified by preparative HPLC (MeCN and water). $^1H$ NMR ($D_2O$, 500 MHz) δ 3.52-3.59 (m, 2H), 3.15-3.08 (m, 2H), 3.01-2.94 (m, 2H), 2.09-2.00 (m, 2H), 1.94-1.66 (m, 7H), 1.63-1.53 (m, 1H), 1.37-1.25 (m, 3H), 1.21-1.08 (m, 1H), 0.698 (t, J=7.5 Hz, 2H). ESI MS found for $C_{13}H_{27}BN_2O_4$ m/z [251 (M+1−2×$H_2O$)].

Example 39

Preparation of 2-amino-6-borono-2-(3-(isoindolin-2-yl)propyl)hexanoic acid

2-Amino-6-borono-2-(3-(isoindolin-2-yl)propyl)hexanoic acid was prepared in a manner analogous to that set fourth in Example 38 except isoindoline was used as the amine in step 5. $^1$H NMR ($D_2O$, 200 MHz) δ 7.37 (bs, 4H), 4.91-4.80 (m, 2H), 4.56-4.47 (m, 2H), 3.51-3.38 (m, 2H), 2.05-1.68 (m, 6H), 1.48-1.05 (m, 4H), 0.70 (t, J=7.2 Hz, 2H). ESI MS found for $C_{17}H_{27}BN_2O_4$ m/z [299.4 (M−2×18+1)].

Example 40

Preparation of 2-amino-6-borono-2-(3-(5-chloro-3,4-dihydroisoquinolin-2(1H)-yl)propyl)hexanoic acid 2-Amino-6-borono-2-(3-(5-chloro-3,4-dihydroisoquinolin-2(1H)-yl)propyl)hexanoic acid was prepared in a manner analogous to that set fourth in Example 38 except 5-chloro-1,2,3,4-tetrahydroisoquinoline was used as the amine in step 5. $^1$H NMR ($D_2O$, 500 MHz) δ 7.35 (d, J=8.0 Hz, 1H), 7.20 (dd, $J_1$=$J_2$=8.0 Hz, 1H), 7.06 (d, J=8.0 Hz, 1H), 4.54-4.47 (m, 1H), 4.31-4.25 (m, 1H), 3.82-3.74 (m, 1H), 3.41-3.32 (m, 1H), 3.32-3.20 (m, 2H), 3.18-2.99 (m, 2H), 2.00-1.83 (m, 4H), 1.83-1.69 (m, 2H), 0.70 (t, J=7.2 Hz, 2H). ESI MS found for $C_{18}H_{28}BClN_2O_4$ m/z [347.4/349.4 (M−2×18+1)].

Example 41

Preparation of 2-amino-6-borono-2-(3-(3,4-dihydroisoquinolin-2(1H)-yl)propyl)hexanoic acid 2-Amino-6-borono-2-(3-(3,4-dihydroisoquinolin-2(1H)-yl)propyl)hexanoic acid was prepared in a manner analogous to that set fourth in Example 38 except 1,2,3,4-tetrahydroisoquinoline was used as the amine in step 5. $^1$H NMR ($D_2O$, 500 MHz) δ 7.28-7.15 (m, 3H), 7.10 (d, J=8.5 Hz, 1H), 4.52-4.45 (m, 1H), 4.29-4.21 (m, 1H), 3.75-3.67 (m, 1H), 3.39-3.00 (m, 5H), 2.00-1.68 (m, 6H), 1.36-1.27 (m, 3H), 1.20-1.10 (m, 1H), 0.70 (t, J=7.2 Hz, 2H). ESI MS found for $C_{18}H_{29}BN_2O_4$ m/z [313.4 (M−2×18+1)].

Example 42

Preparation of 2-Amino-2-(1R,3S)-3-(biphen-4-ylmethylamino)-cyclopentyl)-6-borono hexanoic acid

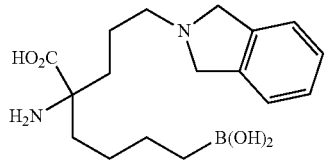 [SMILES: NC(CCCCB(O)O)(CCCN1Cc2ccccc2C1)C(=O)O]

Step 1: (1R,3S)-3-(biphenyl-4-ylmethylamino)cyclopentanecarboxylic acid

Biphenyl carboxaldehyde (2.82 g, 15.5 mmol) was added to a stirred solution of (1R,3S)-3-aminocyclopentanecarboxylic acid (2.0 g, 15.5 mmol) in anhydrous methanol (50 mL) and acetic acid (2 mL). After stirring at room temperature for 1 hour, sodium triacetoxyborohydride (6.57 g, 31 mmol) was added portion wise over 10 minutes and the reaction was stirred at room temperature for 4 hours, diluted with saturated aqueous sodium chloride, and extracted with ethyl acetate (3×30 mL). The combined organic phase was washed with saturated aqueous sodium chloride, dried over anhydrous magnesium sulfate, filtered and concentrated in vacuo to give crude (1R,3S)-3-(biphen-4-ylmethyl-amino)-cyclopentane carboxylic acid, which was used in the next step without further purification; m/z for $C_{19}H_{21}NO_2$ expected 295.2. found 318.1 (M+Na)$^+$, 296.3 (M+H)$^+$.

Step 2: (1R,3S)-3-((biphenyl-4-ylmethyl)(tert-butoxycarbonyl)amino)cyclopentane carboxylic acid To a solution of the crude (1R,3S)-3-(biphen-4-ylmethylamino)-cyclopentane carboxylic acid in ethyl acetate (25 mL) and saturated aqueous NaHCO3 solution (25 mL), was added Boc anhydride (6.76 g, 31 mmol), and the mixture was stirred overnight at room temperature. The reaction mixture was then acidified to pH 3-4 with 2N hydrochloric acid and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-60% ethyl acetate in heptane) gave (1R,3S)-3-{(Biphen-4-ylmethyl)-(tert-butoxycarbonyl)amino}-cyclopentane carboxylic acid as a white solid (1.96 g, 32%); $^1$H NMR (CDCl$_3$, 400 MHz) δ 7.61 (d, J=7.5 Hz, 2H), 7.56 (d, J=7.5 Hz, 2H), 7.45 (t, J=7.5 Hz, 2H), 7.36 (m, 1H), 7.28 (m, 2H), 4.46 (m, 3H), 2.80 (m, 1H), 2.16 (m, 1H), 1.84-2.06 (m, 4H), 1.75 (m, 1H), 1.44 (s, 9H); m/z for C$_{24}$H$_{29}$NO$_4$ expected 395.2. found 418.1 (M+Na)$^+$, 396.1 (M+H)$^+$.

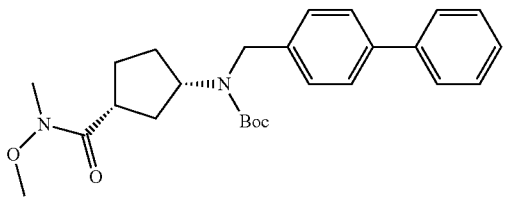 [SMILES: CON(C)C(=O)[C@@H]1CC[C@H](N(Cc2ccc(-c3ccccc3)cc2)C(=O)OC(C)(C)C)C1]

Step 3: tert-Butyl-biphen-4-ylmethyl-{(1S,3R)-3-(methoxy(methyl)carbamoyl)-cyclopentyl}-carbamate EDC (901 mg, 4.7 mmol) was added portion wise to a stirred solution of (1R,3S)-3-{(biphen-4-ylmethyl)-(tert-butoxycarbonyl)amino}-cyclopentane carboxylic acid (930 mg, 2.35 mmol), DMAP (10 mg), and N,O-dimethylhydroxylamine hydrochloride (459 mg, 4.7 mmol) in dichloromethane (15 mL). Triethylamine (1.31 mL, 9.4 mmol) was added drop wise, and the reaction mixture was stirred at room temperature overnight. The resulting solution was poured into water, and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 10-60% ethyl acetate in heptane) gave tert-Butyl-biphen-4-ylmethyl-{(1S,3R)-3-(methoxy(methyl)carbamoyl)-cyclopentyl}-carbamate (800 mg, 78%) as a colorless oil; $^1$H NMR (CDCl$_3$, 400 MHz) δ 7.61 (d, J=7.5 Hz, 2H), 7.54 (d, J=7.5 Hz, 2H), 7.45 (t, J=7.5 Hz, 2H), 7.35 (m, 1H), 7.30 (m, 2H), 4.72 (br, s, 1H), 4.49 (m, 2H), 3.68 (s, 3H), 3.19 (s, 3H), 3.10-3.20 (m, 1H), 2.10 (m, 1H), 1.64-2.01 (m, 5H), 1.41 (s, 9H).

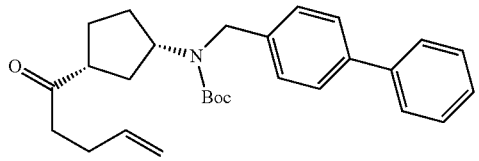 [SMILES: C=CCCC(=O)[C@@H]1CC[C@H](N(Cc2ccc(-c3ccccc3)cc2)C(=O)OC(C)(C)C)C1]

Step 4: tert-Butyl-biphen-4-ylmethyl-{(1S,3R)-3-pent-4-enoylcyclopentyl}-carbamate While under a nitrogen atmosphere, a solution of tert-Butyl-biphen-4-ylmethyl-{(1S,3R)-3-(methoxy(methyl)carbamoyl)-cyclopentyl}-carbamate (1.2 g, 2.74 mmol), in tetrahydrofuran (20 mL) was cooled to 0° C. and treated with 3-butenylmagnesiun bromide (0.5 M in THF, 13.7 mL, 6.85 mmol) in a drop wise manner. The solution was stirred for 1 hour at 0° C. then allowed to warm to room temperature overnight. The resulting solution was poured into water, acidified to pH 3-4 with 1 N hydrochloric acid, and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 0-30% ethyl acetate in heptane) gave tert-Butyl-biphen-4-ylmethyl-{(1S,3R)-3-pent-4-enoylcyclopentyl}-carbamate as a colorless oil (1.12 g, 94%); $^1$H NMR (CDCl$_3$, 400 MHz) δ 7.62 d, J=7.5 Hz, (2H), 7.56 (d, J=7.5 Hz, 2H), 7.46 (t, J=7.5 Hz, 2H), 7.36 (m, 1H), 7.28 (m, 2H), 5.80 (m, 1H), 5.01 (m, 2H), 4.48 m, (3H), 2.92 (m, 1H), 2.54 (m, 2H), 2.37 (m, 2H), 2.04 (m, 1H), 1.74-1.94 (m, 4H), 1.48-1.66 (m, 1H), 1.43 (s, 9H).

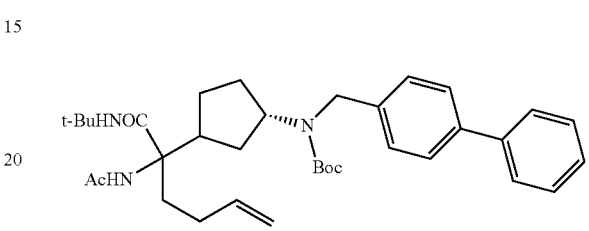

Step 5: tert-butyl-(1S,3S)-3-{(2-acetamido-1-(tert-butylamino)-1-oxo-hex-5-en-2-yl)cyclopentyl-biphen-4-ylmethyl}-carbamate and tert-butyl-(1S,3R)-3-{(2-acetamido-1-(tert-butylamino)-1-oxo-hex-5-en-2-yl)cyclopentyl-biphen-4-ylmethyl}-carbamate A solution of tert-Butyl-biphen-4-ylmethyl-{(1S,3R)-3-pent-4-enoylcyclopentyl}-carbamate (402 mg, 0.93 mmol) and ammonium acetate (716 mg, 9.3 mmol) in 2,2,2-trifluoroethanol (1 mL) was treated with tert-butyl isocyanide (387 mg, 0.53 mL, 4.65 mmol). After stirring at room temperature for 2 days, the reaction mixture was added to a separatory funnel, diluted with water (10 mL) and extracted with ethyl acetate (2×20 mL). The organic layer was washed with saturated aqueous sodium chloride, dried over MgSO$_4$, filtered and concentrated. Purification by flash column chromatography (silica gel, 10-60% ethyl acetate in heptane) gave tert-butyl-(1S,3S)-3-{(2-acetamido-1-(tert-butylamino)-1-oxo-hex-5-en-2-yl)cyclopentyl-biphen-4-ylmethyl}-carbamate as a colorless foam (120 mg, 22%); $^1$H NMR (CDCl$_3$, 400 MHz) δ 7.61 (d, J=7.5 Hz, 2H), 7.56 (d, J=7.5 Hz, 2H), 7.46 (t, J=7.5 Hz, 2H), 7.37 (m, 1H), 7.29 (m, 2H), 7.00 (br s, NH, 1H), 6.18 (br s, NH, 1H), 5.80 (m, 1H), 4.98 (m, 2H), 4.50 (d, J=16.5 Hz, 1H), 4.31 (d, J=16.5 Hz, 1H), 4.14 (m, 1H), 3.00 (m, 1H), 2.58 (m, 1H), 1.94-2.10 (m, 3H), 2.03 (s, 3H), 1.72-1.88 (m, 3H), 1.43 (s, 9H), 1.36 (s, 9H), 1.21-1.56 (m, 3H), and tert-butyl-(1S,3R)-3-{(2-acetamido-1-(tert-butylamino)-1-oxo-hex-5-en-2-yl)cyclopentyl-biphen-4-ylmethyl}-carbamate as a colorless foam (360 mg, 67%); $^1$H NMR (CDCl$_3$, 400 MHz) δ 7.60 (d, J=7.5 Hz, 2H), 7.56 (d, J=7.5 Hz, 2H), 7.46 (t, J=7.5 Hz, 2H), 7.36 (m, 1H), 7.27 (m (2 Ar—H+NH), 3H), 6.87 (d, J=11.5 Hz, NH, 1H), 5.79 (m, 1H), 4.98 (m, 2H), 4.45 (m, 2H), 4.25 (m, 1H), 3.04 (m, 1H), 2.75 (m, 1H), 2.02 (s, 3H), 1.76-2.00 (m, 3H), 1.52-1.72 (m, 3H), 1.44 (s, 9H), 1.35 (s, 9H), 1.21-1.56 (m, 3H).

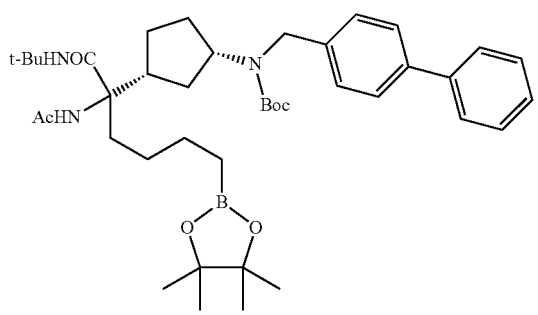

Step 6: tert-Butyl-(1S,3R)-3-{[2-acetamido-1-(tert-butylamino)-1-oxo-6-(4,4,5,5-tetramethyl-1,3,2-dioxaborolan-2-yl)-hexan-2-yl]cyclopentyl-biphen-4-ylmethyl}-carbamate A solution of tert-Butyl-(1S,3R)-3-{(2-acetamido-1-(tert-butylamino)-1-oxo-hex-5-en-2-yl)cyclopentyl-biphen-4-ylmethyl}-carbamate (360 mg, 0.63 mmol) in dichloromethane (10 mL), was treated with chloro-1,5-cyclooctadiene iridium (I) dimer (13 mg, 3 mol %) and 1,2-bis(diphenylphosphino) ethane (15 mg, 6 mol %). The solution was stirred at 0° C. for 30 minutes and then 4,4,5,5-tetramethyl-[1,3,2]dioxaborolane (0.091 mL, 9.9 mmol) was added drop wise, and the reaction was then stirred for 1 hr at 0° C. and then warmed overnight to room temperature. The reaction was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 30-70% ethyl acetate in heptane) gave tert-Butyl-(1S,3R)-3-{[2-acetamido-1-(tert-butylamino)-1-oxo-6-(4,4,5,5-tetramethyl-1,3,2-dioxaborolan-2-yl)-hexan-2-yl]cyclopentyl-biphen-4-ylmethyl}-carbamate as a colorless oil (319 mg, 72%); $^1$H NMR (CDCl$_3$, 400 MHz) δ 7.61 (d, J=7.5 Hz, 2H), 7.55 (d, J=7.5 Hz, 2H), 7.45 (t, J=7.5 Hz, 2H), 7.36 (m, 1H), 7.26 (m (2 Ar—H+NH), 3H), 6.85 (d, J=10.5 Hz, NH, 1H), 4.46 (m, 2H), 4.26 (m, 1H), 2.62-2.95 (m, 2H), 2.00 (s, 3H), 1.76-2.00 (m, 3H), 1.52-1.72 (m, 5H), 1.43 (s, 9H), 1.34 (s, 9H), 1.24 (s, 12H), 1.21-1.36 (m, 2H), 1.05 (m, 1H), 0.75 (t, J=7.5 Hz, 2H); m/z for C$_{41}$H$_{62}$BN$_3$O$_6$ expected 703.5. found 726.4 (M+Na)$^+$, 704.5 (M+H)$^+$, 648.4 (M+H–iBu)$^+$, 604.1 (M+H–Boc)$^+$.

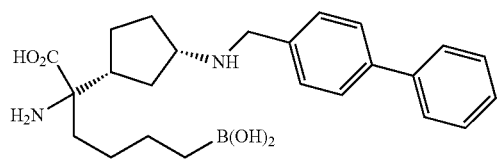

Step 7: 2-Amino-2-(1R,3S)-3-(biphen-4-ylmethylamino)-cyclopentyl)-6-boronohexanoic acid tert-Butyl-(1S,3R)-3-{[2-acetamido-1-(tert-butylamino)-1-oxo-6-(4,4,5,5-tetramethyl-1,3,2-dioxaborolan-2-yl)-hexan-2-yl]cyclopentyl-biphen-4-ylmethyl}-carbamate (310 mg) was suspended in 6N hydrochloric acid, and then heated, with stirring, to 170° C. for 30 minutes in a Biotage microwave reactor. After cooling to room temperature, the reaction mixture was transferred to a separatory funnel, diluted with deionized water (15 mL) and washed with dichloromethane (2×15 mL). The aqueous layer was concentrated to give an off-white solid that was purified by reverse phase HPLC (10-100% acetonitrile in water). The fractions containing product were acidified with 6N HCl and then concentrated to give 2-Amino-2-(1R,3S)-3-(biphen-4-ylmethylamino)-cyclopentyl)-6-boronohexanoic acid (78 mg) as its dihydrochloride salt. $^1$H NMR (D$_2$O, 400 MHz) δ 7.63 (d, J=7.5 Hz, 2H), 7.59 (d, J=7.5 Hz, 2H), 7.42 (m, 4H), 7.34 (m, 1H), 4.14 (m, 2H), 3.57 (sept, J=7.5 Hz, 1H), 2.61 (m, 1H), 2.00-2.41 (m, 3H), 1.48-1.94 (m, 5H), 1.30 (m, 3H), 1.11 (m, 1H), 0.66 (t, J=7.5 Hz, 2H); m/z for C$_{24}$H$_{33}$BN$_2$O$_4$ expected 424.3. found 425.2 (M+H)$^+$, 407.2 (M+H–H$_2$O)$^+$, 389.3 (M+H–2H$_2$O)$^+$.

Example 43

Preparation of 2-Amino-2-(1S,3S)-3-(biphen-4-ylmethylamino)-cyclopentyl)-6-boronohexanoic acid

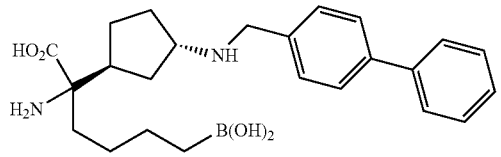 [SMILES: NC(CCCCB(O)O)(C(=O)O)[C@H]1CC[C@H](NCc2ccc(-c3ccccc3)cc2)C1]

2-Amino-2-(1S,3S)-3-(biphen-4-ylmethylamino)-cyclopentyl)-6-borono hexanoic acid was prepared in analogous fashion to its (1R,3S) diastereoisomer, from the minor product, tert-Butyl-(1S,3S)-3-{(2-acetamido-1-(tert-butylamino)-1-oxo-hex-5-en-2-yl)cyclopentyl-biphen-4-ylmethyl}-carbamate (Example 42), obtained from the earlier Ugi condensation reaction. The product was purified by reverse phase HPLC (10-100% acetonitrile in water). The fractions containing product were acidified with 6N HCl and then concentrated, to give 2-amino-2-(1S,3S)-3-(biphen-4-ylmethylamino)-cyclopentyl)-6-boronohexanoic acid (22 mg) as its dihydrochloride salt. $^1$H NMR (D$_2$O, 400 MHz) δ 7.67 (d, J=7.5 Hz, 2H), 7.63 (d, J=7.5 Hz, 2H), 7.45 (m, 4H), 7.36 (m, 1H), 4.19 (s, 2H), 3.63 (m, 1H), 2.42 (m, 1H), 2.34 (m, 1H), 2.12 (m, 1H), 1.92 (m, 1H), 1.76 (m, 4H), 1.24-1.46 (m, 4H), 1.13 (m, 1H), 0.69 (t, J=7.5 Hz, 2H); m/z for C$_{24}$H$_{33}$BN$_2$O$_4$ expected 424.3. found 425.1 (M+H)$^+$, 407.3 (M+H–H$_2$O)$^+$, 389.1 (M+H–2H$_2$O)$^+$.

Example 44

Preparation of 2-Amino-2-(1S,3R)-3-(biphen-4-ylmethylamino)-cyclopentyl)-6-boronohexanoic acid

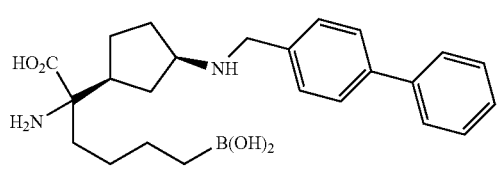 [SMILES: NC(CCCCB(O)O)(C(=O)O)[C@H]1CC[C@@H](NCc2ccc(-c3ccccc3)cc2)C1]

2-Amino-2-(1S,3R)-3-(biphen-4-ylmethylamino)-cyclopentyl)-6-boronohexanoic acid was prepared in identical fashion to 2-Amino-2-(1R,3S)-3-(biphen-4-ylmethylamino)-cyclopentyl)-6-boronohexanoic acid using the amino acid (1S,3R)-3-aminocyclopentane carboxylic acid as the initial starting material for the synthetic sequence outlined in Example 42. The title compound was isolated as its dihydrochloride salt (72 mg); $^1$H NMR (D$_2$O, 400 MHz) δ 7.66 (d, J=7.5 Hz, 2H), 7.62 (d, J=7.5 Hz, 2H), 7.45 (m, 4H), 7.37 (m, 1H), 4.19 (m, 2H), 3.61 (m, 1H), 2.61 (m, 1H), 2.05-2.46 (m, 3H), 1.50-1.96 (m, 5H), 1.32 (m, 3H), 1.14 (m, 1H), 0.69 (t, J=7.5 Hz, 2H); m/z for $C_{24}H_{33}BN_2O_4$ expected 424.3. found 425.3 (M+H)$^+$, 407.3 (M+H–H$_2$O)$^+$, 389.5 (M+H–2H$_2$O)$^+$.

Example 45

Preparation of 2-amino-6-borono-2-{(1R,5S)-8-(4-chlorobenzyl)-8-aza-bicycli[3.2.1]-octan-3-yl}-hexanoic acid

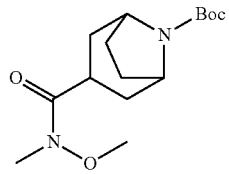 [SMILES: CON(C)C(=O)C1CC2CCC(C1)N2C(=O)OC(C)(C)C]

Step 1: tert-butyl 3-(methoxy(methyl)carbamoyl)-8-azabicyclo[3.2.1]octane-8-carboxylate EDC (2.99 g, 15.6 mmol) was added portion wise to a stirred solution of (1R,5S)-8-(tert-butoxycarbonyl)-8-azabicyclo[3.2.1]octane-3-carboxylic acid, (2.0 g, 7.8 mmol), DMAP (10 mg), and N,O-dimethylhydroxylamine hydrochloride (1.52 g, 15.6 mmol) in dichloromethane (20 mL). Triethylamine (4.37 mL, 31.33 mmol) was added dropwise, and the reaction mixture was stirred at room temperature overnight. The resulting solution was poured into water, and extracted with ethyl acetate (3×). The combined organic phase was washed with saturated aqueous sodium chloride, dried over anhydrous magnesium sulfate, filtered and concentrated in vacuo to give tert-butyl 3-(methoxy(methyl)carbamoyl)-8-azabicyclo[3.2.1]octane-8-carboxylate (1.7 g, 73%) as a colorless oil, which was used without further purification; m/z for $C_{15}H_{26}N_2O_4$ expected 298.2. found 321.3 (M+Na)$^+$, 299.3 (M+H)$^+$.

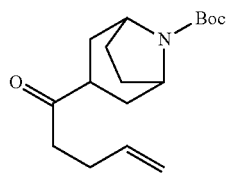 [SMILES: C=CCCC(=O)C1CC2CCC(C1)N2C(=O)OC(C)(C)C]

Step 2: tert-butyl 3-pent-4-enoyl-8-azabicyclo[3.2.1]octane-8-carboxylate

While under a nitrogen atmosphere, a solution of tert-butyl 3-(methoxy(methyl)carbamoyl)-8-azabicyclo[3.2.1]octane-8-carboxylate (1.7 g, 5.7 mmol), in tetrahydrofuran (25 mL) was cooled to 0° C. and treated with 3-butenylmagnesiun bromide (0.5 M in THF, 28.5 mL, 14.3 mmol) in a drop wise manner. The solution was stirred for 1 hour at 0° C. then allowed to warm to room temperature overnight. The resulting solution was poured into water, acidified to pH 3-4 with 1 N hydrochloric acid, and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 0-25% ethyl acetate in heptane) gave (1R,5S)-tert-Butyl-3-pent-4-enoyl-8-azabicyclo[3.2.1]-octane-8-carboxylic acid as a colorless oil (1.45 g, 87%); $^1$H NMR (CDCl$_3$, 400 MHz) δ 5.81 (m, 1H), 5.01 (m, 2H), 4.29 (br s, 2H), 2.83 (m, 1H), 2.53 (t, J=7.5 Hz, 1H), 2.32 (q, J=7 Hz, 2H), 2.03 (m, 2H), 1.83 (t, J=12.5 Hz, 2H), 1.60-1.71 (m, 5H) and 1.48 (s, 9H); m/z for $C_{17}H_{27}NO_3$ expected 293.2. found 316.3 (M+Na)$^+$, 294.3 (M+H)$^+$.

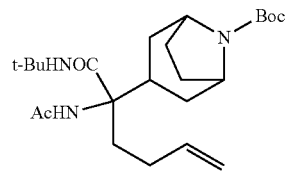

Step 3: (1R,5S)-tert-Butyl-3-(2-acetamido)-1-(tert-butylamino)-1-oxo-hex-5-en-2-yl)-8-azabicyclo[3.2.1]octane-8-carboxylic acid A solution (1R,5S)-tert-butyl-3-pent-4-enoyl-8-azabicyclo[3.2.1]-octane-8-carboxylic acid (1.45 g, 4.95 mmol) and ammonium acetate (3.82 g, 49.5 mmol) in 2,2,2-trifluoroethanol (4 mL) was treated with tert-butyl isocyanide (2.06 g, 2.60 mL, 24.75 mmol). After stirring at room temperature for 3 days, the reaction mixture was added to a separatory funnel, diluted with water (20 mL) and extracted with ethyl acetate (2×20 mL). The organic layer was washed with saturated aqueous sodium chloride, dried over MgSO$_4$, filtered and concentrated. Purification by flash column chromatography (silica gel, 10-60% ethyl acetate in heptane) gave (1R,5S)-tert-Butyl-3(2-acetamido)-1-(tert-butylamino)-1-oxo-hex-5-en-2-yl)-8-azabicyclo[3.2.1]octane-8-carboxylic acid as a colorless foam (1.91 g, 89%).; $^1$H NMR (CDCl$_3$, 400 MHz) δ 6.90 (s, NH, 1H), 5.79 (m, 1H), 5.59 (s, NH, 1H), 4.98 (m, 2H), 4.15 (m, 2H), 2.93 (m, 2H), 2.07 (m, 1H), 2.00 (s, 3H), 1.74-1.96 (m, 3H), 1.50-1.72 (m, 6H), 1.45 (s, 9H), 1.38 (s, 9H), 1.20-1.36 (m, 1H).

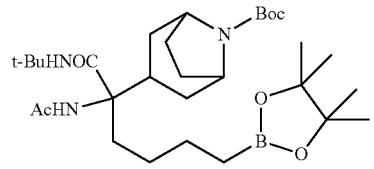

Step 4: (1R,5S)-tert-Butyl-3-{2-acetamido)-1-(tert-butylamino)-1-oxo-6-(4,4,5,5-tetramethyl-1,3,2-dioxaborolan-2-yl)-hexan-2-yl}-8-azabicyclo[3.2.1]octane-8-carboxylic acid A solution of (1R,5S)-tert-Butyl-3(2-acetamido)-1-(tert-butylamino)-1-oxo-hex-5-en-2-yl)-8-azabicyclo[3.2.1]octane-8-carboxylic acid (1.91 g, 4.4 mmol) in dichloromethane (30 mL), was treated with chloro-1,5-cyclooctadiene iridium(I) dimer (88 mg, 3 mol %) and 1,2- bis(diphenylphosphino)ethane (105 mg, 6 mol %). The solution was stirred at 0° C. for 30 minutes and then 4,4,5,5-tetramethyl-[1,3,2]dioxaborolane (0.96 mL, 6.6 mmol) was added drop wise, and the reaction was then stirred for 1 hr at 0° C. and then warmed overnight to room temperature. The reaction was poured into water and extracted with ethyl acetate (3×). The combined organic phase was washed with saturated aqueous sodium chloride, dried over anhydrous magnesium sulfate, filtered and concentrated in vacuo. Purification by flash column chromatography (silica gel, 30-70% ethyl acetate in heptane) gave (1R,5S)-tert-Butyl-3-{2-acetamido)-1-(tert-butylamino)-1-oxo-6-(4,4,5,5-tetramethyl-1,3,2-dioxaborolan-2-yl)-hexan-2-yl}-8-azabicyclo[3.2.1]-octane-8-carboxylic acid as a colorless oil (1.9 g, 77%); m/z for $C_{30}H_{54}BN_3O_6$ expected 563.4. found 586.2 $(M+Na)^+$, 564.2 $(M+H)^+$, 508.5 $(M+H-iBu)^+$,

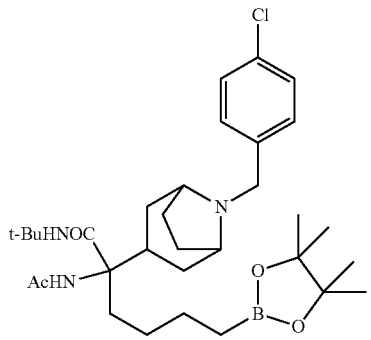

Step 6: 2-acetamido-N-tert-butyl-2-{(1R,5S)-8-(4-chlorobenzyl)-8-azabicyclo[3.2.1]octan-3-yl}-6-(4,4,5,5-tetramethyl-1,3,2-dioxaborolan-2-yl)-hexanamide A solution of 2-acetamido-2-{(1R,5S)-8-azabicyclo[3.2.1]octan-3-yl}-N-tert-butyl-6-(4,4,5,5-tetramethyl-1,3,2-dioxaborolan-2-yl)-hexanamide (170 mg, 0.37 mmol) and 4-chlorobenzaldehyde (104 mg, 0.74 mmol) and acetic acid (44 mg, 41 µL, 0.74 mmol) in 1,2-dichloroethane (1 mL) was stirred at room temperature for 30 minutes and then treated with sodium triacetoxyborohydride (196 mg, 0.93 mmol). After 24 hours, the reaction mixture was quenched with saturated aqueous sodium bicarbonate (10 mL), diluted with saturated aqueous sodium chloride (20 mL) and extracted with dichloromethane (3×20 mL). The combined organic phase was collected, dried over $MgSO_4$, filtered and concentrated to give 2-acetamido-N-tert-butyl-2-{(1R,5S)-8-(4-chlorobenzyl)-8-azabicyclo[3.2.1]octan-3-yl}-6-(4,4,5,5-tetramethyl-1,3,2-dioxaborolan-2-yl)-hexanamide as a pale yellow oil which was used immediately in the next step; m/z for $C_{32}H_{51}BClN_3O_4$ expected 587.4. found 589.7 $(M+H(^{37}Cl))^+$, 588.0 $(M+H(^{35}Cl))^+$,

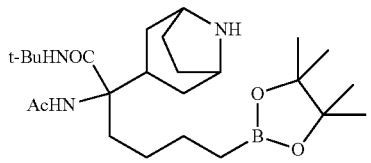

Step 5: 2-acetamido-2-{(1R,5S)-8-azabicyclo[3.2.1]octan-3-yl}-N-tert-butyl-6-(4,4,5,5-tetramethyl-1,3,2-dioxaborolan-2-yl)-hexanamide 4N Hydrogen Chloride in dioxane (0.94 ml, 3.76 mmol) was added to a stirred solution of (1R,5S)-tert-Butyl-3-{2-acetamido)-1-(tert-butylamino)-1-oxo-6-(4,4,5,5-tetramethyl-1,3,2-dioxaborolan-2-yl)-hexan-2-yl}-8-azabicyclo[3.2.1]octane-8-carboxylic acid (400 mg, 0.75 mmol) in dioxane (2 mL). The solution was stirred for 2 hrs at room temperature and then concentrated in vacuo to give a colorless foam. The foam was dissolved in a mixture of ethyl acetate (20 mL) and sat. NaHCO3 solution (20 mL) and stirred for 5 minutes. The phases were separated; the aq. phase was further extracted with ethyl acetate (3×10 mL). The combined organic phase was washed with saturated aqueous sodium chloride, dried over anhydrous magnesium sulfate, filtered and concentrated in vacuo to give 2-acetamido-2-{(1R,5S)-8-azabicyclo[3.2.1]octan-3-yl}-N-tert-butyl-6-(4,4,5,5-tetramethyl-1,3,2-dioxaborolan-2-yl)-hexanamide which was used without further purification (340 mg, 97%).; $^1$H NMR (CDCl$_3$, 400 MHz) δ 6.71 br s, NH, (1H), 5.71 (s, NH, 1H), 3.70 (m, 1H), 3.58 (m, 1H), 3.48 (br s, NH, 1H), 2.74 (t, J=7.5 Hz, 1H), 2.45 (m, 1H), 1.93 (s, 3H), 1.48-1.76 (m, 5H), 1.11-1.46 (m, 8H), 1.30 (s, 9H), 1.16 (s, 12H), 0.67 (t, J=7.5 Hz, 2H); m/z for $C_{25}H_{46}BN_3O_4$ expected 463.4. found 464.4 $(M+H)^+$,

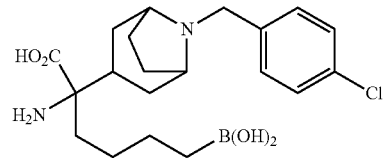 [SMILES: NC(CCCCB(O)O)(C(=O)O)C1CC2CCC(C1)N2Cc1ccc(Cl)cc1]

Step 7: 2-Amino-6-borono-2-{(1R,5S)-8-(4-chlorobenzyl)-8-aza-bicycli[3.2.1]-octan-3-yl}-hexanoic acid The solution of crude 2-acetamido-N-tert-butyl-2-{(1R,5S)-8-(4-chlorobenzyl)-8-aza-bicyclo[3.2.1]octan-3-yl}-6-(4,4,5,5-tetramethyl-1,3,2-dioxaborolan-2-yl)-hexanamide, obtained in the previous step, was suspended in 6N hydrochloric acid, and was then heated, with stirring, to 170° C. for 30 minutes in a Biotage microwave reactor. After cooling to room temperature, the reaction mixture was transferred to a reparatory funnel, diluted with deionized water (15 mL) and washed with dichloromethane (2×15 mL). The aqueous layer was concentrated to give an off-white solid that was purified by reverse phase HPLC (10-100% acetonitrile in water). The fractions containing product were acidified with 6N HCl and then concentrated to give 2-Amino-6-borono-2-{(1R,5S)-8-

(4-chlorobenzyl)-8-aza-bicycli[3.2.1]-octan-3-yl}-hexanoic acid (29 mg) as its dihydrochloride salt. $^1$H NMR (D$_2$O, 400 MHz) δ 7.45 (d, J=8 Hz, 2H), 7.41 (d, J=8 Hz, 2H), 4.11 (s, 2H), 3.98 (s, 2H), 2.35 (m, 3H), 1.90-2.05 (m, 4H), 1.62-1.82 (m, 4H), 1.33 (m, 3H), 1.12 (m, 1H) and 0.71 (t, J=7 Hz, 2H); m/z for C$_{20}$H$_{30}$BClN$_2$O$_4$ expected 408.2. found 409.2 (M+H)$^+$, 391.3 (M+H−H$_2$O)$^+$, 373.3 (M+H−2H$_2$O)$^+$.

Example 46

Preparation of 2-Amino-6-borono-2-{(1R,5S)-8-(3, 4-dichlorobenzyl)-8-aza-bicycli[3.2.1]-octan-3-yl}-hexanoic acid

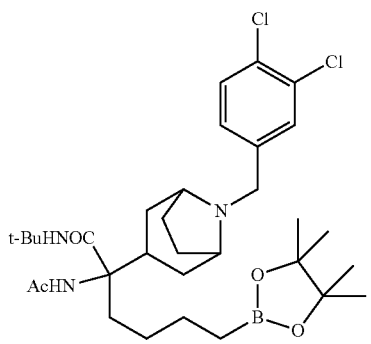

Step 1: 2-acetamido-N-tert-butyl-2-(8-(3,4-dichlorobenzyl)-8-azabicyclo[3.2.1]octan-3-yl)-6-(4,4,5,5-tetramethyl-1,3,2-dioxaborolan-2-yl)hexanamide A solution of 2-acetamido-2-{(1R,5S)-8-azabicyclo[3.2.1]octan-3-yl}-N-tert-butyl-6-(4,4,5,5-tetramethyl-1,3,2-dioxaborolan-2-yl)-hexanamide (170 mg, 0.37 mmol) and 3,4-dichlorobenzaldehyde (129 mg, 0.74 mmol) and acetic acid (44 mg, 41 µL, 0.74 mmol) in 1,2-dichloroethane (1 mL) was stirred at room temperature for 30 minutes then treated with sodium triacetoxyborohydride (196 mg, 0.93 mmol). After 24 hours, the reaction mixture was quenched with saturated aqueous sodium bicarbonate (10 mL), diluted with saturated aqueous sodium chloride (20 mL) and extracted with dichloromethane (3×20 mL). The combined organic phase was collected, dried over MgSO$_4$, filtered and concentrated to give 2-acetamido-N-tert-butyl-2-{(1R,5S)-8-(3,4-dichlorobenzyl)-8-azabicyclo[3.2.1]octan-3-yl}-6-(4,4,5,5-tetramethyl-1,3,2-dioxaborolan-2-yl)-hexanamide as a pale yellow oil which was used immediately in the next step; m/z for C$_{32}$H$_{50}$BCl$_2$N$_3$O$_4$ expected 621.3. found 644.5 (M+Na ($^{35}$Cl))$^+$, 622.1 (M+H($^{35}$Cl))$^+$,

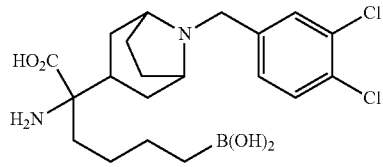 [SMILES: NC(CCCCB(O)O)(C(=O)O)C1CC2CCC(C1)N2Cc1ccc(Cl)c(Cl)c1]

Step 2: 2-Amino-6-borono-2-{(1R,5S)-8-(3,4-dichlorobenzyl)-8-aza-bicycli[3.2.1]-octan-3-yl}-hexanoic acid The solution of crude 2-acetamido-N-tert-butyl-2-{(1R, 5S)-8-(3,4-dichlorobenzyl)-8-aza-bicyclo[3.2.1]octan-3-yl}-6-(4,4,5,5-tetramethyl-1,3,2-dioxaborolan-2-yl)-hexanamide, obtained in the previous step, was suspended in 6N hydrochloric acid, and was then heated, with stirring, to 170° C. for 30 minutes in a Biotage microwave reactor. After cooling to room temperature, the reaction mixture was transferred to a separatory funnel, diluted with deionized water (15 mL) and washed with dichloromethane (2×15 mL). The aqueous layer was concentrated to give an off-white solid that was purified by reverse phase HPLC (10-100% acetonitrile in water). The fractions containing product were acidified with 6N HCl and then concentrated to give 2-Amino-6-borono-2-{(1R,5S)-8-(3,4-dichlorobenzyl)-8-aza-bicycli[3.2.1]-octan-3-yl}-hexanoic acid (28 mg) as its dihydrochloride salt. $^1$H NMR (D$_2$O, 400 MHz) δ 7.62 (d, J=2 Hz, 1H), 7.57 (d, J=8.5 Hz, 1H), 7.35 (dd, J$_1$=8.5 Hz, J$_1$=2 Hz, 1H), 4.11 (s, 2H), 3.99 (br s, 2H), 2.38 (m, 3H), 1.88-2.05 (m, 4H), 1.65-1.85 (m, 4H), 1.33 (m, 3H), 1.14 (m, 1H) and 0.71 (t, J=7 Hz, 2H); m/z for C$_{20}$H$_{29}$BCl$_2$N$_2$O$_4$ expected 442.2. found 443.2 (M+H)$^+$, 425.1 (M+H−H$_2$O)$^+$, 407.2 (M+H−2H$_2$O)$^+$.

Example 47

Preparation of (S)-2-amino-6-borono-2-((1s,3R)-3-(4-phenylcyclohexylamino)cyclobutyl)hexanoic acid (racemic)

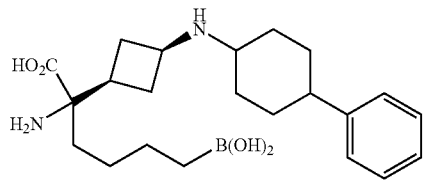 [SMILES: NC(CCCCB(O)O)(C(=O)O)[C@H]1C[C@@H](NC2CCC(c3ccccc3)CC2)C1]

(S)-2-amino-6-borono-2-((1s,3R)-3-(4-phenylcyclohexylamino)cyclobutyl) hexanoic acid was prepared in a manner analogous to that set fourth in example 1, except 4-phenylcyclohexanecarbaldehyde was used as the aldehyde in step 6. $^1$H NMR (D$_2$O) δ 7.46-7.10 (m, 5H), 3.74 (m, 1H), 3.42-3.07 (m, 1H), 2.76-2.26 (m, 5H), 2.14-1.96 (m, 2H), 1.96-1.60 (m, 8H), 1.60-1.43 (m, 1H), 1.43-1.24 (m, 3H), 1.24-1.03 (m, 1H), 0.72 (t, J=8.0 Hz, 2H). MS found for C$_{22}$H$_{35}$BN$_2$O$_4$ m/z [403 (M+1)].

Example 48

Preparation of (S)-2-amino-6-borono-2-((1s,3R)-3-((2-fluorobiphenyl-3-yl)methylamino)cyclobutyl) hexanoic acid (racemic)

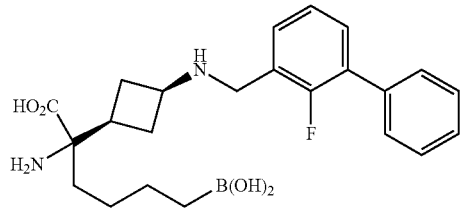

(S)-2-amino-6-borono-2-((1s,3R)-3-((2-fluorobiphenyl-3-yl)methylamino)cyclobutyl) hexanoic acid was prepared in a manner analogous to that set fourth in example 1, except 2-fluorobiphenyl-4-carbaldehyde was used as the aldehyde in step 6. $^1$H NMR (D$_2$O) δ 7.63-7.34 (m, 6H), 7.23-7.10 (m, 2H), 4.11 (s, 2H), 3.63 (m, 1H), 2.62-2.23 (m, 4H), 2.10-1.80 (m, 2H), 1.74-1.60 (m, 1H), 1.40-1.07 (m, 4H), 0.71 (m, 2H). MS found for C$_{23}$H$_{30}$BFN$_2$O$_4$ m/z [429 (M+1)].

Example 49

Preparation of (S)-2-amino-6-borono-2-((1s,3R)-3-((4'-chloro-3-fluorobiphenyl-4-yl)methylamino)cyclobutyl)hexanoic acid

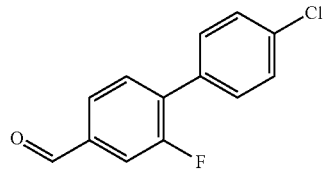 [SMILES: O=Cc1ccc(-c2ccc(Cl)cc2)c(F)c1]

Step 1: 4'-Chloro-2-fluoro-biphenyl-4-carbaldehyde

2-Fluoro-4-formylphenyl boronic acid (263 mg, 1.57 mmol) was added to the mixture of 1-chloro-4-iodobenzene (250 mg, 1.05 mmol), PdCl$_2$(PPh$_3$)$_2$ (36 mg, 0.5 mmol), and disodium carbonate (332 mg, 3.13 mmol) in a solution of water (1 mL) and dioxane (2 mL). The mixture was reacted at 130° C. for 22 min in a microwave reactor. After cooling, water was added, and the mixture was extracted with ethylacetate. The organic solvent was dried over Na$_2$SO$_4$, filtered, and concentrated. The residue was purified by column chromatography on silica gel, eluting with ethyl acetate in heptane to give the title compound (220 mg, 0.94 mmol, 90%) as a white solid. $^1$H NMR (D$_2$O) δ 10.02 (s, 1H), 7.75 (d, J=7.8 Hz, 1H), 7.67 (d, J=10.4 Hz, 1H), 7.60 (t, J=7.5 Hz, 1H), 7.53 (d, J=8.3 Hz, 2H), 7.46 (d, J=8.3 Hz, 2H).

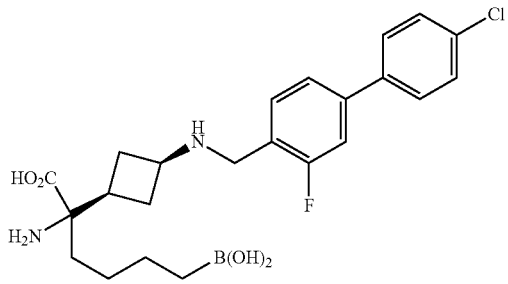 [SMILES: NC(CCCCB(O)O)(C(=O)O)[C@H]1C[C@@H](NCc2ccc(-c3ccc(Cl)cc3)cc2F)C1]

Step 2: (S)-2-amino-6-borono-2-((1s,3R)-3-((4'-chloro-3-fluorobiphenyl-4-yl)methylamino)cyclobutyl)hexanoic acid (S)-2-amino-6-borono-2-((1s,3R)-3-((4'-chloro-3-fluoro-biphenyl-4-yl)methylamino)cyclobutyl)hexanoic acid was prepared in a manner analogous to that set fourth in example 1, except 4'-Chloro-2-fluoro-biphenyl-4-carbaldehyde was used as the aldehyde in step 6. $^1$H NMR (D$_2$O) δ 7.50-7.29 (m, 7H), 4.14 (s, 2H), 3.64 (m, 1H), 2.61-2.22 (m, 4H), 1.98 (m, 1H), 1.90-1.77 (m, 1H), 1.64 (m, 1H), 1.37-1.21 (m, 3H), 1.18-1.04 (m, 1H), 0.67 (t, J=7.1 Hz, 2H). MS found for C$_{23}$H$_{29}$BClFN$_2$O$_4$ m/z [463 (M+1)].

Example 50

Preparation of (S)-2-amino-6-borono-2-((1s,3R)-3-((4'-chloro-2,3-difluorobiphenyl-4-yl)methylamino)cyclobutyl)hexanoic acid (racemic)

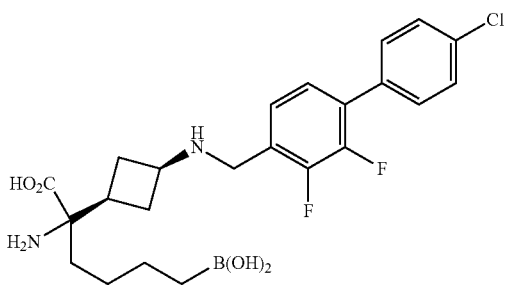 [SMILES: NC(CCCCB(O)O)(C(=O)O)[C@H]1C[C@@H](NCc2ccc(-c3ccc(Cl)cc3)c(F)c2F)C1]

(S)-2-amino-6-borono-2-((1s,3R)-3-((4'-chloro-2,3-difluorobiphenyl-4-yl)methylamino)cyclobutyl)hexanoic acid (racemic) was prepared in a manner analogous to that set fourth in example 1, except 4'-chloro-2,3-difluorobiphenyl-4-carbaldehyde was used as the aldehyde in step 6 and this was prepared using the method described in Example 49, Step 1. $^1$H NMR (D$_2$O) δ 7.46 (dd, J=20.0, 8.0 Hz, 4H), 7.25 (m, 2H), 4.22 (s, 2H), 3.68 (m, 1H), 2.64-2.26 (m, 4H), 2.00 (q, J=10.0 Hz, 1H), 1.87 (m, 1H), 1.66 (m, 1H), 1.41-1.22 (m, 3H), 1.20-1.06 (m, 1H), 0.70 (t, J=7.6 Hz, 2H). MS found for C$_{23}$H$_{28}$BClF$_2$N$_2$O$_4$ m/z [481 (M+1)].

Example 51

Preparation of (S)-2-amino-6-borono-2-((1s,3R)-3-((4'-chloro-2-fluorobiphenyl-4-yl)methylamino)cyclobutyl)hexanoic acid

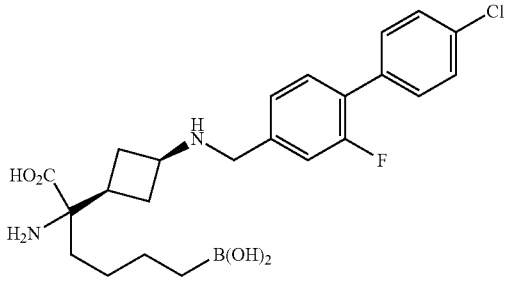 [SMILES: NC(CCCCB(O)O)(C(=O)O)[C@H]1C[C@@H](NCc2ccc(-c3ccc(Cl)cc3)c(F)c2)C1]

(S)-2-amino-6-borono-2-((1s,3R)-3-((4'-chloro-2-fluorobiphenyl-4-yl)methylamino)cyclobutyl)hexanoic acid (racemic) was prepared in a manner analogous to that set fourth in example 1, except 4'-chloro-2-fluorobiphenyl-4-carbaldehyde was used as the aldehyde in step 6 and this was prepared using the method described in Example 49, Step 1. $^1$H NMR (D$_2$O) δ 7.43-7.18 (m, 7H), 4.10 (s, 2H), 3.64 (m, 1H), 2.62-2.28 (m, 4H), 2.03 (q, J=10.0 Hz, 1H), 1.92-1.78 (m, 1H), 1.67 (d, J=12.0 Hz, 1H), 1.41-1.24 (m, 3H), 1.23-1.08 (m, 1H), 0.72 (t, J=8.0 Hz, 2H). MS found for $C_{23}H_{29}BClFN_2O_4$ m/z [463 (M+1)].

Example 52

Preparation of (S)-2-amino-6-borono-2-((1s,3R)-3-((2,2'-difluoro-5'-methylbiphenyl-4-yl)methylamino)cyclobutyl)hexanoic acid

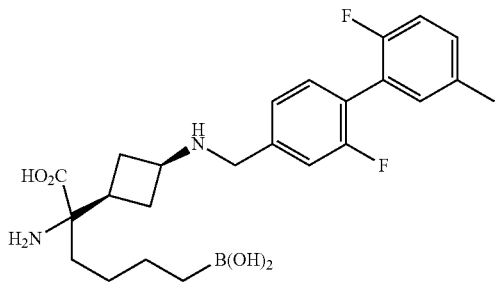 [SMILES: Cc1ccc(F)c(-c2ccc(CN[C@H]3C[C@@H](C(N)(CCCCB(O)O)C(=O)O)C3)cc2F)c1]

(S)-2-amino-6-borono-2-((1s,3R)-3-((2,2'-difluoro-5'-methylbiphenyl-4-yl)methylamino)cyclobutyl)hexanoic acid (racemic) was prepared in a manner analogous to that set fourth in example 1, except 2,2'-difluoro-5'-methylbiphenyl-4-carbaldehyde was used as the aldehyde in step 6 and this was prepared using the method described in Example 49, Step 1. $^1$H NMR (D$_2$O) δ 7.46 (d, J=8.0 Hz, 1H), 7.36-7.18 (m, 4H), 7.12 (d, J=9.3 Hz, 1H), 4.19 (s, 2H), 3.71 (m, 1H), 2.70-2.35 (m, 4H), 2.31 (s, 3H), 2.05 (q, J=10.0 Hz, 1H), 1.93 (m, 1H), 1.72 (m, 1H), 1.47-1.29 (m, 3H), 1.27-1.11 (m, 1H), 0.76 (t, J=7.1 Hz, 2H). MS found for $C_{24}H_{31}BF_2N_2O_4$ m/z [461 (M+1)].

Example 53

Preparation of (S)-2-amino-6-borono-2-((1s,3R)-3-((2,4'-difluorobiphenyl-4-yl)methylamino)cyclobutyl)hexanoic acid (racemic)

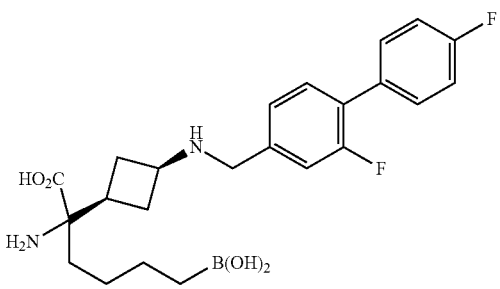 [SMILES: NC(CCCCB(O)O)(C(=O)O)[C@H]1C[C@@H](NCc2ccc(-c3ccc(F)cc3)c(F)c2)C1]

(S)-2-amino-6-borono-2-((1s,3R)-3-((2,4'-difluorobiphenyl-4-yl)methylamino)cyclobutyl)hexanoic acid (racemic) was prepared in a manner analogous to that set fourth in example 1, except 2,4'-difluorobiphenyl-4-carbaldehyde was used as the aldehyde in step 6 and this was prepared using the method described in Example 49, Step 1. $^1$H NMR (D$_2$O) δ 7.52-7.36 (m, 3H), 7.32-7.21 (m, 2H), 7.12 (d, J=8.0 Hz, 1H), 4.13 (s, 2H), 3.67 (qt, J=8.0 Hz, 1H), 2.67-2.29 (m, 4H), 2.05 (q, J=10.0 Hz, 1H), 1.96-1.83 (m, 1H), 1.71 (d, J=12.0 Hz, 1H), 1.44-1.26 (m, 3H), 1.26-1.08 (m, 1H), 0.73 (t, J=8.0 Hz, 2H). MS found for $C_{23}H_{29}BF_2N_2O_4$ m/z [447 (M+1)].

Example 54

Preparation of (S)-2-amino-6-borono-2-((1s,3R)-3-((2,2'-difluorobiphenyl-4-yl)methylamino)cyclobutyl)hexanoic acid (racemic)

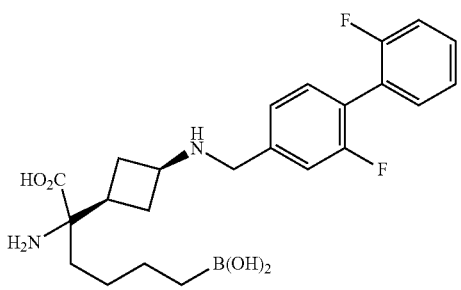 [SMILES: NC(CCCCB(O)O)(C(=O)O)[C@H]1C[C@@H](NCc2ccc(-c3ccccc3F)c(F)c2)C1]

(S)-2-amino-6-borono-2-((1s,3R)-3-((2,2'-difluorobiphenyl-4-yl)methylamino)cyclobutyl)hexanoic acid (racemic) was prepared in a manner analogous to that set fourth in example 1, except 2,2'-difluorobiphenyl-4-carbaldehyde was used as the aldehyde in step 6 and this was prepared using the method described in Example 49, Step 1. $^1$H NMR (D$_2$O) δ 7.53-7.38 (m, 3H), 7.36-7.19 (m, 4H), 4.18 (s, 2H), 3.70 (qt, J=8.0 Hz, 1H), 2.67-2.30 (m, 4H), 2.06 (q, J=10.0 Hz, 1H), 1.99-1.86 (m, 1H), 1.73 (t, J=12.0 Hz, 1H), 1.46-1.28 (m, 3H), 1.27-1.12 (m, 1H), 0.76 (t, J=8.0 Hz, 2H). MS found for $C_{23}H_{29}BF_2N_2O_4$ m/z [447 (M+1)].

Example 55

Preparation of (S)-2-amino-6-borono-2-((1s,3R)-3-((2,2',4'-trifluorobiphenyl-4-yl)methylamino)cyclobutyl)hexanoic acid

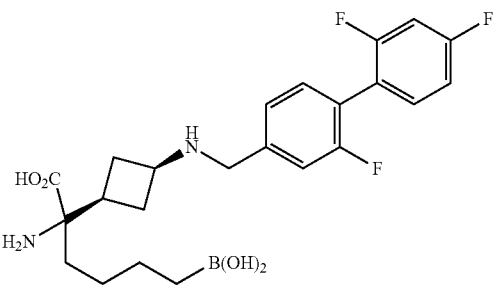 [SMILES: NC(CCCCB(O)O)(C(=O)O)[C@H]1C[C@@H](NCc2ccc(-c3ccc(F)cc3F)c(F)c2)C1]

(S)-2-amino-6-borono-2-((1s,3R)-3-((2,2',4'-trifluorobiphenyl-4-yl)methylamino)cyclobutyl)hexanoic acid (racemic) was prepared in a manner analogous to that set fourth in example 1, except 2,2',4'-trifluorobiphenyl-4-carbaldehyde was used as the aldehyde in step 6 and this was prepared using the method described in Example 49, Step 1. $^1$H NMR (D$_2$O) δ 7.49-7.23 (m, 4H), 7.07-6.96 (m, 2H), 4.18 (s, 2H), 3.70 (qt, J=8.0 Hz, 1H), 2.70-2.30 (m, 4H), 2.06 (q, J=10.0 Hz, 1H), 1.99-1.85 (m, 1H), 1.73 (t, J=12.0 Hz, 1H), 1.45-1.28 (m, 3H), 1.26-1.11 (m, 1H), 0.75 (t, J=8.0 Hz, 2H). MS found for $C_{23}H_{28}BF_3N_2O_4$ m/z [465 (M+1)].

Example 56

Preparation of (S)-2-amino-6-borono-2-((1s,3R)-3-(3-(4-(trifluoromethyl)phenyl)propylamino)cyclobutyl)hexanoic acid

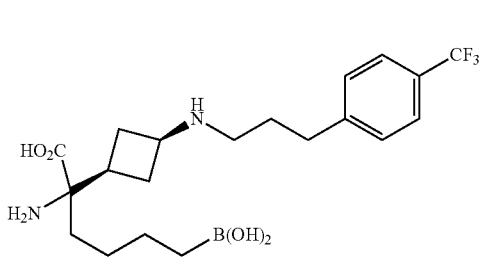 [SMILES: NC(CCCCB(O)O)(C(=O)O)[C@H]1C[C@@H](NCCCc2ccc(C(F)(F)F)cc2)C1]

(S)-2-Amino-6-borono-2-((1s,3R)-3-(3-(4-(trifluoromethyl)phenyl)propylamino)cyclobutyl)hexanoic acid was prepared in a manner analogous to that set fourth in example 1, except 3-(4-(trifluoromethyl)phenyl)propanal was used as the aldehyde in step 6. $^1$H NMR (D$_2$O, 300 MHz) δ 7.58 (d, J=7.7 Hz, 2H), 7.34 (d, J=7.9 Hz, 2H), 3.59-3.51 (m, 1H), 2.85 (t, J=7.6 Hz, 2H), 2.70 (t, J=7.4 Hz, 2H), 2.54-2.21 (m, 4H), 1.98-1.82 (m, 4H), 1.66-1.59 (m, 1H), 1.36-1.25 (m, 3H), 1.13-1.08 (m, 1H), 0.70 (t, J=7.0 Hz, 2H). ESI MS found for $C_{20}H_{30}BF_3N_2O_4$ m/z [431.4 (M+1)].

Example 57

Preparation of (S)-2-amino-2-((1s,3R)-3-(4-benzylbenzylamino)cyclobutyl)-6-boronohexanoic acid

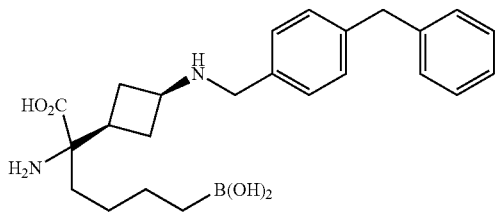 [SMILES: NC(CCCCB(O)O)(C(=O)O)[C@H]1C[C@@H](NCc2ccc(Cc3ccccc3)cc2)C1]

(S)-2-amino-2-((1s,3R)-3-(4-benzylbenzylamino)cyclobutyl)-6-boronohexanoic acid (racemic) was prepared in a manner analogous to that set fourth in example 1, except 4-benzylbenzaldehyde was used as the aldehyde in step 6. $^1$H NMR (D$_2$O) δ 7.40-7.23 (m, 9H), 4.11 (s, 2H), 4.02 (s, 2H), 3.66 (qt, J=8.0 Hz, 1H), 2.66-2.26 (m, 4H), 2.06-1.85 (m, 2H), 1.72 (t, J=12.0 Hz, 1H), 1.48-1.30 (m, 3H), 1.27-1.13 (m, 1H), 0.79 (t, J=7.8 Hz, 2H). MS found for $C_{24}H_{33}BN_2O_4$ m/z [425 (M+1)].

Example 58

Preparation of (S)-2-amino-6-borono-2-((1s,3R)-3-((4'-chloro-3,5-difluorobiphenyl-4-yl)methylamino)cyclobutyl)hexanoic acid

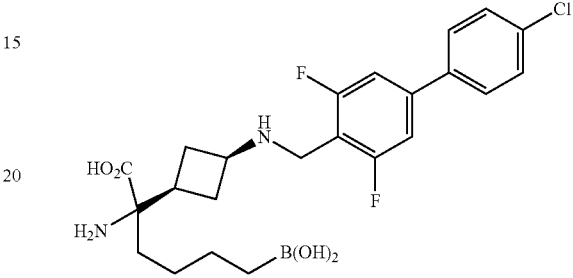

(S)-2-amino-6-borono-2-((1s,3R)-3-((4'-chloro-3,5-difluorobiphenyl-4-yl)methylamino)cyclobutyl)hexanoic acid (racemic) was prepared in a manner analogous to that set fourth in example 1, except 4'-chloro-3,5-difluorobiphenyl-4-carbaldehyde was used as the aldehyde in step 6 and this was prepared using the method described in Example 49, Step 1. $^1$H NMR (D$_2$O) δ 7.59 (d, J=7.7 Hz, 2H), 7.48 (d, J=7.7 Hz, 2H), 7.36 (s, 1H), 7.34 (s, 1H), 4.30 (s, 2H), 3.78 (qt, J=8.0 Hz, 1H), 2.73-2.34 (m, 4H), 2.08 (q, J=10.0 Hz, 1H), 2.01-1.88 (m, 1H), 1.81-1.68 (m, 1H), 1.49-1.31 (m, 3H), 1.29-1.14 (m, 1H), 0.78 (t, J=8.0 Hz, 2H). MS found for $C_{23}H_{28}BClF_2N_2O_4$ m/z[481 (M+1)].

Example 59

Preparation of 4-(4-(((1R,3s)-3-((S)-1-amino-5-borono-1-carboxypentyl)cyclobutylamino)methyl)piperidin-1-yl)benzoic acid

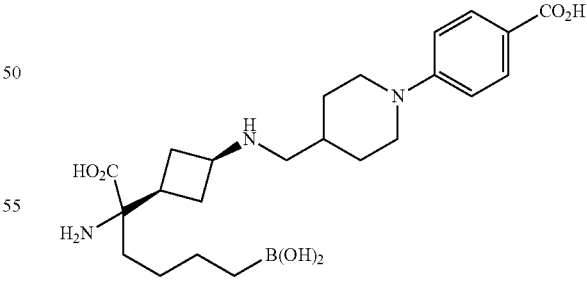

4-(4-(((1R,3s)-3-((S)-1-amino-5-borono-1-carboxypentyl)cyclobutylamino)methyl)piperidin-1-yl)benzoic acid (racemic) was prepared in a manner analogous to that set fourth in example 1, except 4-(4-formylpiperidin-1-yl)benzoic acid was used as the aldehyde in step 6. $^1$H NMR (D$_2$O) δ 8.21 (d, J=8.0 Hz, 2H), 7.74 (d, J=8.0 Hz, 2H), 3.89-3.80 (m, 2H), 3.78-3.66 (m, 3H), 3.04 (d, J=6.4 Hz, 2H), 2.72-2.36 (m, 4H), 2.34-2.18 (m, 3H), 2.15-2.04 (m, 1H), 2.04-1.92 (m, 1H), 1.91-1.71 (m, 3H), 1.51-1.32 (m, 3H), 1.29-1.16 (m, 1H), 0.78 (t, J=7.4 Hz, 2H). MS found for $C_{23}H_{36}BN_3O_6$ m/z[444 (M–H$_2$O+1)].

Example 60

Preparation of (S)-2-amino-6-borono-2-((1s,3R)-3-((1-(4-(trifluoromethyl)phenyl)piperidin-4-yl)methylamino)cyclobutyl)hexanoic acid

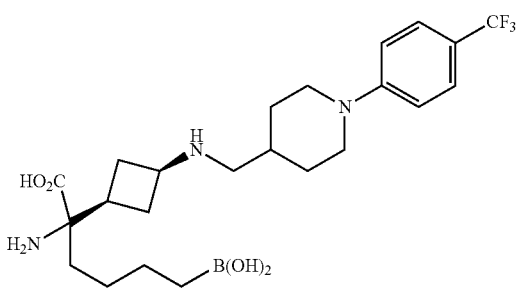 [SMILES: NC(CCCCB(O)O)(C(=O)O)[C@H]1C[C@@H](NCC2CCN(c3ccc(C(F)(F)F)cc3)CC2)C1]

(S)-2-amino-6-borono-2-((1s,3R)-3-((1-(4-(trifluoromethyl)phenyl)piperidin-4-yl)methylamino)cyclobutyl)hexanoic acid (racemic) was prepared in a manner analogous to that set fourth in example 1, except 1-(4-(trifluoromethyl)phenyl)piperidine-4-carbaldehyde was used as the aldehyde in step 6. $^1$H NMR (D$_2$O) δ 7.94 (d, J=8.3 Hz, 2H), 7.80 (d, J=8.3 Hz, 2H), 3.86-3.77 (m, 2H), 3.77-3.65 (m, 3H), 3.06 (d, J=6.4 Hz, 2H), 2.71-2.34 (m, 4H), 2.32-2.15 (m, 3H), 2.13-2.02 (m, 1H), 2.02-1.91 (m, 1H), 1.90-1.68 (m, 3H), 1.49-1.30 (m, 3H), 1.28-1.13 (m, 1H), 0.78 (t, J=7.4 Hz, 2H). MS found for $C_{23}H_{35}BF_3N_3O_4$ m/z[485 (M+1)].

Example 61

Preparation of 2-amino-2-(8-azabicyclo[3.2.1]octan-3-yl)-6-boronohexanoic acid

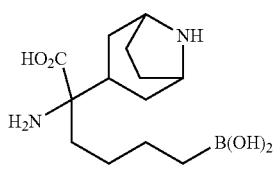 [SMILES: NC(CCCCB(O)O)(C(=O)O)C1CC2CCC(C1)N2]

2-Amino-2-(8-azabicyclo[3.2.1]octan-3-yl)-6-boronohexanoic acid was prepared in a manner analogous to that set fourth in example 45, except step 6 was eliminated. $^1$H NMR (D$_2$O, 400 MHz) δ 4.01 (s, 2H), 2.41-2.28 (m, 1H), 2.11-1.58 (m, 10H), 1.40-1.24 (m, 3H), 1.19-1.04 (m, 1H), 0.69 (t, J=6.4, 2H). MS found for $C_{13}H_{25}BN_2O_4$ m/z[285 (M+1)].

Example 62

Preparation of 2-amino-2-(8-benzyl-8-azabicyclo[3.2.1]octan-3-yl)-6-boronohexanoic acid

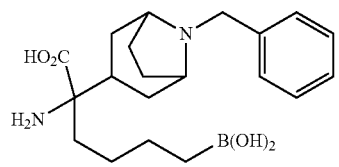 [SMILES: NC(CCCCB(O)O)(C(=O)O)C1CC2CCC(C1)N2Cc1ccccc1]

2-Amino-2-(8-benzyl-8-azabicyclo[3.2.1]octan-3-yl)-6-boronohexanoic acid was prepared in a manner analogous to that set fourth in example 45, except benzaldehyde was used as the aldehyde in step 6. $^1$H NMR (D$_2$O, 400 MHz) δ 7.51 (s, 5H), 4.19 (s, 2H), 4.05 (s, 2H), 2.55-2.35 (m, 3H), 2.13-1.65 (m, 8H), 1.49-1.30 (m, 3H), 1.28-1.10 (m, 1H), 0.77 (t, J=6.9, 2H). MS found for $C_{20}H_{31}BN_2O_4$ m/z[375 (M+1)].

Example 63

Preparation of 2-amino-6-borono-2-(8-(3,4-difluorobenzyl)-8-azabicyclo[3.2.1]octan-3-yl)hexanoic acid

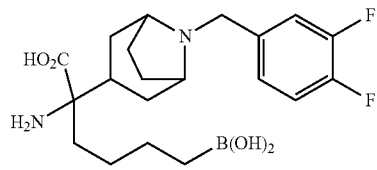

2-Amino-6-borono-2-(8-(3,4-difluorobenzyl)-8-azabicyclo[3.2.1]octan-3-yl)hexanoic acid was prepared in a manner analogous to that set fourth in example 45, except 3,4-difluorobenzaldehyde was used as the aldehyde in step 6. $^1$H NMR (D$_2$O, 400 MHz) δ 7.50-7.24 (m, 5H), 4.16 (s, 2H), 4.04 (s, 2H), 2.55-2.31 (m, 3H), 2.12-1.66 (m, 8H), 1.47-1.27 (m, 3H), 1.26-1.10 (m, 1H), 0.75 (t, J=6.9, 2H). MS found for $C_{20}H_{29}BF_2N_2O_4$ m/z[411 (M+1)].

Example 64

Preparation of 2-amino-6-borono-2-(8-(4-(trifluoromethoxy)benzyl)-8-azabicyclo[3.2.1]octan-3-yl)hexanoic acid

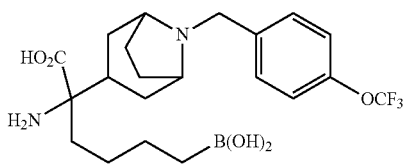 [SMILES: NC(CCCCB(O)O)(C(=O)O)C1CC2CCC(C1)N2Cc1ccc(OC(F)(F)F)cc1]

2-Amino-6-borono-2-(8-(4-(trifluoromethoxy)benzyl)-8-azabicyclo[3.2.1]octan-3-yl)hexanoic acid was prepared in a manner analogous to that set fourth in example 45, except 4-trifluoromethoxybenzaldehyde was used as the aldehyde in step 6. $^1$H NMR (D$_2$O, 400 MHz) δ 7.62 (d, J=7.9, 2H), 7.44 (d, J=7.9, 2H), 4.24 (s, 2H), 4.07 (s, 2H), 2.57-2.37 (m, 3H), 2.16-1.70 (m, 8H), 1.53-1.32 (m, 3H), 1.31-1.13 (m, 1H), 0.79 (t, J=7.0, 2H). MS found for C$_{21}$H$_{30}$BF$_3$N$_2$O$_5$ m/z[459 (M+1)].

Example 65

Preparation of (S)-2-amino-2-((1s,3R)-3-(2-(biphenyl-4-yl)ethylamino)cyclobutyl)-6-boronohexanoic acid

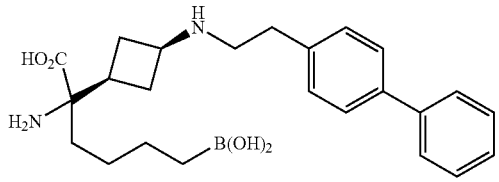 [SMILES: NC(CCCCB(O)O)(C(=O)O)[C@H]1C[C@@H](NCCc2ccc(-c3ccccc3)cc2)C1]

(S)-2-Amino-2-((1s,3R)-3-(2-(biphenyl-4-yl)ethylamino)cyclobutyl)-6-boronohexanoic acid was prepared in a manner analogous to that set fourth in example 27, except (S)-2-amino-6-borono-2-isopropylhexanoic acid was used as the amine in step 6. $^1$H NMR (D$_2$O, 300 MHz) δ 7.70-7.61 (m, 5H), 7.51-7.44 (m, 2H), 7.41-7.34 (m, 2H), 3.60-3.51 (m, 1H), 3.50-3.17 (m, 2H), 3.03-2.93 (m, 2H), 2.52-2.25 (m, 4H), 1.97-1.75 (m, 2H), 1.64-1.53 (m, 1H), 1.39-1.22 (m, 3H), 1.16-1.07 (m, 1H), 0.70 (t, J=7.2 Hz, 2H). ESI MS found for C$_{24}$H$_{33}$BN$_2$O$_4$ m/z [425.1 (M+1)].

Example 66

Preparation of (R)-2-amino-6-borono-2-(2-(2,3-dihydro-1H-inden-2-ylamino)ethyl)hexanoic acid

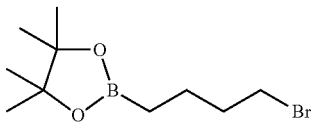

Step 1: 2-(4-bromobutyl)-4,4,5,5-tetramethyl-1,3,2-dioxaborolane

After gently warming until melted, 4-bromo-1-butylboronic acid catechol ester (112.2 g, 0.44 mol, 1.0 equiv), while under a stream of nitrogen, was added to a 3-necked 500 mL round-bottomed flask, diluted with freshly distilled THF (150 mL, 3.0 M) and treated with pinacol (104.0 g, 0.88 mol, 2 equiv) in one portion. After stirring for 16 h under a nitrogen atmosphere the resulting solution was concentrated. The crude product was diluted with heptane (500 mL) and cooled in an ice-water bath. After 1 h, the precipitated catechol was removed by filtration and the remaining solution was filtered through a short pad of silica gel (500 g) wetted with heptane. After eluting with solutions of 5% ethyl acetate in heptane (700 mL) and 10% ethyl acetate in heptane (700 mL), the filtrate was concentrated to give 2-(4-bromobutyl)-4,4,5,5-tetramethyl-1,3,2-dioxaborolane as a colorless oil (112.7 g, 97%). $^1$H NMR (CDCl$_3$, 300 MHz) δ 3.38 (t, J=6.6 Hz, 2H), 1.90-1.78 (m, 2H), 1.58-1.44 (m, 2H), 1.26 (s, 12H), 0.78 (t, J=7.5 Hz, 2H); ESI-LCMS m/z calcd for C$_{10}$H$_{20}$BBrO$_2$: expected 262.1. found 263.1 (M+H)$^+$.

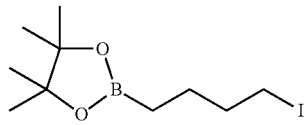

Step 2: 2-(4-iodobutyl)-4,4,5,5-tetramethyl-1,3,2-dioxaborolane

While under a nitrogen atmosphere, a solution of 2-(4-bromobutyl)-4,4,5,5-tetramethyl-1,3,2-dioxaborolane (46.2 g, 0.176 mol, 1.0 equiv) and sodium iodide (52.8 g, 0.35 mol, 2 equiv) in acetone (176 mL, 1.0 M) was heated to 50° C. for 4 h. After cooling to room temperature the solution was concentrated under reduced pressure. The resulting residue was diluted with heptane (200 mL) and filtered through a short pad of silica gel (300 g) wetted with heptane. After eluting with a solution of 10% ethyl acetate in heptane (500 mL) the filtrate was concentrated to give 2-(4-iodobutyl)-4,4,5,5-tetramethyl-1,3,2-dioxaborolane as a colorless oil (53.5 g, 98%). $^1$H NMR (CDCl$_3$, 300 MHz) δ 3.18 (t, J=7.2 Hz, 2H), 1.90-1.78 (m, 2H), 1.58-1.44 (m, 2H), 1.24 (s, 12H), 0.79 (t, J=7.5 Hz, 2H); ESI-LCMS m/z calcd for C$_{10}$H$_{20}$BIO$_2$: expected 310.1. found 311.1 (M+H)$^+$.

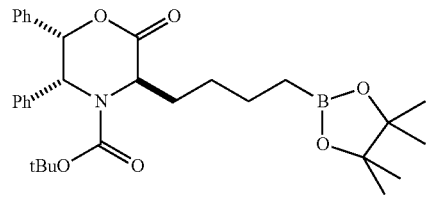 [SMILES: CC(C)(C)OC(=O)N1[C@H](CCCCB2OC(C)(C)C(C)(C)O2)C(=O)O[C@@H](c2ccccc2)[C@H]1c1ccccc1]

Step 3: (3R,5R,6S)-tert-butyl 2-oxo-5,6-diphenyl-3-(4-(4,4,5,5-tetramethyl-1,3,2-dioxaborolan-2-yl)butyl)morpholine-4-carboxylate A solution of (2S,3R)-tert-butyl 6-oxo-2,3-diphenylmorpholine-4-carboxylate (4.69 g, 13.27 mmol) and 2-(4-iodobutyl)-4,4,5,5-tetramethyl-1,3,2-dioxaborolane (d 1.38, 5.96 mL, 8.23 g, 26.5 mmol, 2 equiv) in THF (66 mL, 0.2 M) and HMPA (6.6 mL) was cooled to −78° C. and treated with sodium bis(trimethylsilyl)amide (14.6 mL, 1.0 M, 1.1 equiv) drop wise over 5 min and stirred for 1 h. After warming to room temperature and stirring for an additional 2 h, the solution was cooled to 0° C. and quenched with 0.5 N HC (2-3 equiv). The resulting solution was diluted with heptane and washed successively with water and saturated aqueous NaCl, dried over MgSO$_4$, filtered and concentrated. Purification by MPLC (1-60% ethyl acetate in heptane over 6 CV) gave (3R,5R,6S)-tert-butyl 2-oxo-5,6-diphenyl-3-(4-(4,4,5,5-tetramethyl-1,3,2-dioxaborolan-2-yl)butyl)morpholine-4-carboxylate as a white solid (6.66 g, 94%); ESI-LCMS m/z calcd for C$_{31}$H$_{42}$BNO$_2$: expected 535.3. found 536.4 (M+H)$^+$.

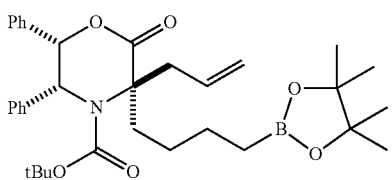 [SMILES: C=CC[C@]1(CCCCB2OC(C)(C)C(C)(C)O2)C(=O)O[C@@H](c2ccccc2)[C@@H](c2ccccc2)N1C(=O)OC(C)(C)C]

Step 4: (3R,5R,6S)-tert-butyl 3-allyl-2-oxo-5,6-diphenyl-3-(4-(4,4,5,5-tetramethyl-1,3,2-dioxaborolan-2-yl)butyl)morpholine-4-carboxylate A solution of (3R,5R,6S)-tert-butyl 2-oxo-5,6-diphenyl-3-(4-(4,4,5,5-tetramethyl-1,3,2-dioxaborolan-2-yl)butyl)morpholine-4-carboxylate (5.00 g, 9.34 mmol) and TMEDA (10 mL, 65 mmol, 7 equiv) in THF (51 mL, 0.2 M) was cooled to −78° C. and treated with allyl iodide (17 mL, 187 mmol, 20 equiv) and potassium bis(trimethylsilyl)amide (47 mL, 0.9 M in THF, 46.7 mmol, 5 equiv) drop wise and stirred for 30 min. Once the addition was complete, the cooling bath was removed and the mixture was stirred over night. Once complete by TLC, the reaction mixture was quenched with 0.5 N HCl (5-10 equiv), diluted with heptane and washed successively with water and saturated aqueous NaCl, dried over MgSO$_4$, filtered and concentrated. Purification by MPLC (1-60% ethyl acetate in heptane over 6 CV) gave (3R,5R,6S)-tert-butyl 3-allyl-2-oxo-5,6-diphenyl-3-(4-(4,4,5,5-tetramethyl-1,3,2-dioxaborolan-2-yl)butyl)morpholine-4-carboxylate as colorless oil (5.2 g, 96%). R$_f$ 0.55 (30% ethyl acetate in heptane); $^1$H NMR (CDCl$_3$, 300 MHz) δ 7.39-7.14 (m, 10H), 7.10 (dd, J$_1$=5.4 Hz, J$_2$=1.8 Hz, 1H), 6.08 (d, J=5.4 Hz, 1H), 5.95-5.80 (m, 1H), 5.27-5.17 (m, 2H), 3.30-3.15 (m, 1H), 2.89-2.76 (m, 1H), 2.20-2.07 (m, 2H), 1.54 (s, 9H), 1.35-1.21 (m, 4H), 1.78 (s, 12H), 0.46 (t, J=8.4 Hz, 2H); ESI-LCMS m/z calcd for C$_{34}$H$_{46}$BNO$_6$: expected 575.3. found 574.3 (M+H)$^+$.

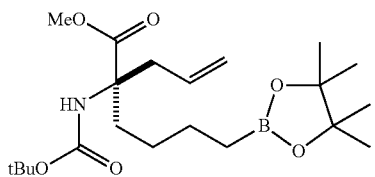 [SMILES: C=CC[C@@](CCCCB1OC(C)(C)C(C)(C)O1)(NC(=O)OC(C)(C)C)C(=O)OC]

Step 5: (R)-methyl 2-allyl-2-(tert-butoxycarbonylamino)-6-(4,4,5,5-tetramethyl-1,3,2-dioxaborolan-2-yl)hexanoate A three-necked RBF equipped with nitrogen inlet tube and dry ice condenser was charged with (3R,5R,6S)-tert-butyl 3-allyl-2-oxo-5,6-diphenyl-3-(4-(4,4,5,5-tetramethyl-1,3,2-dioxaborolan-2-yl)butyl)morpholine-4-carboxylate (4.60 g, 8.00 mmol) and THF (10 mL). After cooling the condenser to −78° C. and the flask to −45° C. (CO$_2$ (s), CH$_3$CN), ammonia (80 mL) was condensed into the flask. Once complete, lithium metal (0.55 g, 80 mmol, small pieces) was carefully added over 10 min. After stirring an additional 40 min, the reaction mixture was carefully quenched with NH$_4$Cl (s) until the solution became clear. The bath was removed and the ammonia was allowed to evaporate over night. The resulting residue was diluted with ethyl acetate and washed successively with 0.5 N HCl and saturated aqueous NaCl, dried over MgSO$_4$, filtered and concentrated. The crude product was dissolved in 50% methanol in toluene (80 mL, 0.1 M) and treated with TMSCHN$_2$ (2.0 M in hexanes) until the pale yellow color persisted. With TLC indicating the reaction complete, the excess TMSCHN$_2$ was quenched with acetic acid until the solution became clear. The solution was concentrated, diluted with ethyl acetate and washed successively with saturated aqueous NaHCO$_3$ and saturated aqueous NaCl, dried over MgSO$_4$, filtered and concentrated. Purification by MPLC (1-60% ethyl acetate in heptane over 6 CV) gave (R)-methyl 2-allyl-2-(tert-butoxycarbonylamino)-6-(4,4,5,5-tetramethyl-1,3,2-dioxaborolan-2-yl)hexanoate as colorless oil (1.9 g, 58%). R$_f$ 0.46 (30% ethyl acetate in heptane); $^1$H NMR (CDCl$_3$, 300 MHz) δ 5.70-5.52 (m, 1H), 5.49-5.36 (m, 1H), 5.05 (dd, J$_1$=13.8 Hz, J$_2$=1.2 Hz, 1H), 3.73 (s, 3H), 3.09-2.96 (m, 1H), 2.50 (dd, J$_1$=13.8 Hz, J$_2$=7.8 Hz, 1H), 2.29-2.10 (m, 1H), 1.78-1.65 (m, 1H), 1.43 (s, 9H), 1.42-1.26 (m, 4H), 1.23 (s, 12H), 0.74 (t, J=7.5 Hz, 2H); ESI-LCMS m/z calcd for C$_{21}$H$_{38}$BNO$_6$: expected 411.3. found 412.3 (M+H)$^+$.

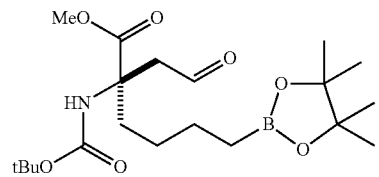 [SMILES: COC(=O)[C@](CC=O)(CCCCB1OC(C)(C)C(C)(C)O1)NC(=O)OC(C)(C)C]

Step 6: (R)-methyl 2-(tert-butoxycarbonylamino)-2-(2-oxoethyl)-6-(4,4,5,5-tetramethyl-1,3,2-dioxaborolan-2-yl)hexanoate A solution of (R)-methyl 2-allyl-2-(tert-butoxycarbonylamino)-6-(4,4,5,5-tetramethyl-1,3,2-dioxaborolan-2-yl)hexanoate (1.90 g, 4.62 mmol) in dichloromethane (90 mL, 0.05 M) was cooled to −78° C. and treated with ozone until a pale blue-gray color appeared. After TLC indicated the absence of starting material, the ozone inlet tube was replaced with nitrogen and nitrogen was bubbled through the solution for 20 min to remove any excess ozone. Triphenylphosphine (3.6 g, 13.8 mmol, 3 equiv) was added in one portion, the cooling bath was removed and the mixture was stirred for 4 h. The solution was concentrated and purified by MPLC (1-50% ethyl acetate in heptane over 6 CV) gave (R)-methyl 2-(tert-butoxycarbonylamino)-2-(2-oxoethyl)-6-(4,4,5,5-tetramethyl-1,3,2-dioxaborolan-2-yl)hexanoate as a colorless oil (1.28 g, 67%). R$_f$ 0.55 (30% ethyl acetate in heptane); $^1$H NMR (CDCl$_3$, 300 MHz) δ 9.66 (s, 1H), 5.62 (br s, 1H), 3.75 (s, 3H), 3.60 (br d, J=17.4 Hz, 1H), 2.95 (d, J=17.4 Hz, 1H), 2.30-2.15 (m, 1H), 1.70-1.54 (m, 1H), 1.40 (s, 9H), 1.39-1.24 (m, 4H), 0.74 (t, J=7.8 Hz, 2H); ESI-LCMS m/z calcd for C$_{20}$H$_{36}$BNO$_7$: expected 413.3. found 414.3 (M+H)$^+$.

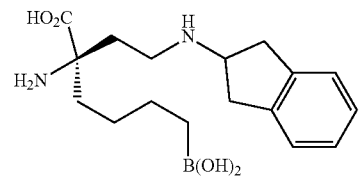 [SMILES: N[C@](CCCCB(O)O)(CCNC1Cc2ccccc2C1)C(=O)O]

Step 7: (R)-2-amino-6-borono-2-(2-(2,3-dihydro-1H-inden-2-ylamino)ethyl)hexanoic acid The final two steps in the synthesis of (R)-2-amino-6-borono-2-(2-(2,3-dihydro-1H-inden-2-ylamino)ethyl)hexanoic acid were prepared in a manner analogous to that set fourth in example 1, steps 6 and 7. $^1$H NMR (D$_2$O) δ 7.37-7.20 (m, 4H), 4.20-4.08 (m, 2H), 3.47-2.90 (m, 6H), 2.41-2.09 (m, 2H), 2.02-1.75 (m, 2H), 1.50-1.13 (m, 4H), 0.78 (m, 2H). MS found for C$_{17}$H$_{27}$BN$_2$O$_4$ m/z[317 (M-H$_2$O+1)].

Example 67

Preparation of (R)-2-amino-6-borono-2-(2-(ethyl(2-hydroxyethyl)amino)ethyl)hexanoic acid

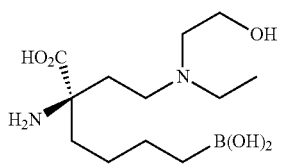 [SMILES: CCN(CCO)CC[C@](N)(CCCCB(O)O)C(=O)O]

(R)-2-amino-6-borono-2-(2-(ethyl(2-hydroxyethyl)amino)ethyl)hexanoic acid was prepared in a manner analogous to that set fourth in example 66, except 2-(ethylamino)ethanol was used as the amine in step 7. $^1$H NMR (D$_2$O) δ 3.95-3.80 (m, 2H), 3.65-3.15 (m, 6H), 2.39-2.24 (m, 2H), 2.01-1.78 (m, 2H), 1.45-1.32 (m, 3H), 1.32-1.15 (m, 4H), 0.75 (m, 2H). MS found for C$_{12}$H$_{27}$BN$_2$O$_4$ m/z[273 (M-H$_2$O+1)].

Example 68

Preparation of (R)-2-amino-6-borono-2-(2-(diethylamino)ethyl)hexanoic acid

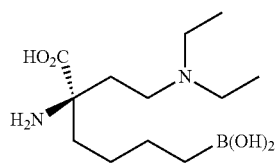 [SMILES: CCN(CC)CC[C@](N)(CCCCB(O)O)C(=O)O]

(R)-2-amino-6-borono-2-(2-(diethylamino)ethyl)hexanoic acid was prepared in a manner analogous to that set fourth in example 66, except diethylamine was used as the amine in step 7. $^1$H NMR (D$_2$O) δ 3.42-3.29 (m, 1H), 3.28-3.07 (m, 5H), 2.36-2.21 (m, 2H), 2.04-1.80 (m, 2H), 1.45-1.30 (m, 3H), 1.29-1.14 (m, 7H), 0.74 (t, J=6.0 Hz, 2H). MS found for C$_{12}$H$_{27}$BN$_2$O$_4$ m/z[257 (M-H$_2$O+1)].

Example 69

Preparation of (R)-2-amino-6-borono-2-(2-(methyl(propyl)amino)ethyl)hexanoic acid

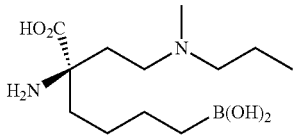 [SMILES: CCCN(C)CC[C@](N)(CCCCB(O)O)C(=O)O]

(R)-2-amino-6-borono-2-(2-(diethylamino)ethyl)hexanoic acid was prepared in a manner analogous to that set fourth in example 66, except methylpropylamine was used as the amine in step 7. $^1$H NMR (D$_2$O) δ 3.53-3.03 (m, 4H), 2.87 (s, 3H), 2.43-2.25 (m, 2H), 2.06-1.82 (m, 2H), 1.81-1.62 (m, 2H), 1.48-1.33 (m, 3H), 1.33-1.15 (m, 1H), 0.95 (t, J=7.0 Hz, 3H), 0.79 (m, 2H). MS found for C$_{12}$H$_{27}$BN$_2$O$_4$ m/z[257 (M-H$_2$O+1)].

Example 70

Preparation of (R)-2-amino-6-borono-2-(2-(isopropylamino)ethyl)hexanoic acid

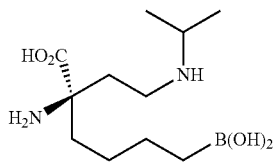 [SMILES: CC(C)NCC[C@](N)(CCCCB(O)O)C(=O)O]

(R)-2-amino-6-borono-2-(2-(isopropylamino)ethyl)hexanoic acid was prepared in a manner analogous to that set fourth in example 66, except isopropylamine was used as the amine in step 7. $^1$H NMR (D$_2$O) δ 3.54-3.37 (m, 2H), 3.34-3.15 (m, 2H), 3.15-3.00 (m, 2H), 2.25 (m, 2H), 2.04-1.81 (m, 2H), 1.49-1.35 (m, 3H), 1.35-1.20 (m, 7H), 0.79 (m, 2H). MS found for C$_{11}$H$_{25}$BN$_2$O$_4$ m/z[243 (M-H$_2$O+1)].

Example 71

Preparation of (R)-2-amino-6-borono-2-(2-(isobutylamino)ethyl)hexanoic acid

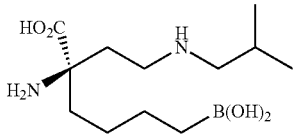 [SMILES: CC(C)CNCC[C@](N)(CCCCB(O)O)C(=O)O]

(R)-2-Amino-6-borono-2-(2-(isobutylamino)ethyl)hexanoic acid was prepared in a manner analogous to that set fourth in example 66, except isobutylamine was used as the amine in step 7. $^1$H NMR (D$_2$O) δ 3.65-3.46 (m, 1H), 3.35-2.99 (m, 2H), 2.96-2.86 (m, 1H), 2.51-2.02 (m, 2H), 2.06-

1.76 (m, 3H), 1.50-1.16 (m, 4H), 1.05-0.93 (m, 3H), 0.92-0.69 (m, 5H). MS found for $C_{12}H_{27}BN_2O_4$ m/z[275 (M+1)].

Example 72

Preparation of (R)-2-amino-6-borono-2-(2-(isoindolin-2-yl)ethyl)hexanoic acid

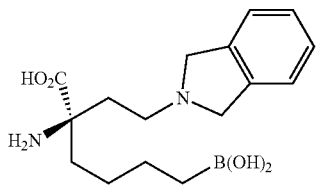 [SMILES: N[C@](CCCCB(O)O)(CCN1Cc2ccccc2C1)C(=O)O]

(R)-2-Amino-6-borono-2-(2-(isoindolin-2-yl)ethyl)hexanoic acid was prepared in a manner analogous to that set fourth in example 66, except isoindoline was used as the amine in step 7. $^1$H NMR (D$_2$O) δ 7.34 (s, 4H), 4.94-4.80 (m, 2H), 4.55-4.42 (m, 2H), 3.71-3.59 (m, 1H), 3.54-3.38 (m, 1H), 2.35 (t, J=7.8 Hz, 2H), 2.00-1.75 (m, 2H), 1.42-1.08 (m, 4H), 0.71 (m, 2H). MS found for $C_{16}H_{25}BN_2O_4$ m/z[321 (M+1)].

Example 73

Preparation of 2-amino-2-(3-amino-3-(4-chlorophenyl)cyclobutyl)-6-boronohexanoic acid

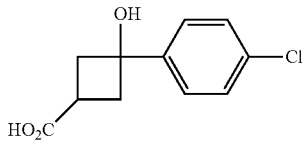

Step 1:
3-(4-chlorophenyl)-3-hydroxycyclobutanecarboxylic acid

While under argon, isopropylmagnesium chloride lithium chloride complex (1.3 M solution in THF, 160 mL, 0.208 mol) was added dropwise over 15 minutes to a solution of p-chloroiodobenzene (54.3 g, 0.227 mol) in 100 mL of dry THF at −78° C. After 1 h, 3-oxocyclobutanecarboxylic acid (7.42 g, 0.065 mol) in 40 mL of dry THF was added and the reaction mixture was allowed to warm to room temperature and stir overnight. The reaction was quenched with 1 M HCl to pH-3, and stirred 2 h. Diethyl ether was added, the solution was stirred vigorously and the phases separated. The product was leached from organic layer with 1 M NaOH, reacidified to pH-3 with 6 M HCl and extracted with diethyl ether (2×). The combined organic layers were dried over MgSO$_4$ filtered and concentrated to give the crude product as an off-white solid. Recrystallization from diethyl ether and n-heptane afforded the subject compound as a white solid 4.03 g (27.3%). $^1$H NMR (DMSO-d$_6$, 600 MHz) δ 12.25 (bs, 1H), 7.58 (d, J=8.7 Hz, 2H), 7.45 (d, J=8.7 Hz, 2H), 5.86 (bs, 1H), 2.74-2.80 (m, 1H), 2.62-2.65 (m, 2H), 2.53-2.57 (m, 2H). ESI MS found for $C_{11}H_{11}ClO_3$ m/z [225.1/227.1 (M−1)].

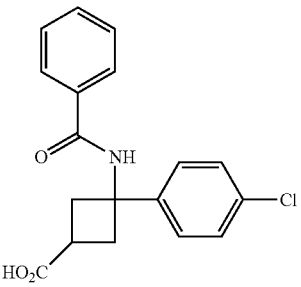 [SMILES: O=C(NC1(c2ccc(Cl)cc2)CC(C(=O)O)C1)c1ccccc1]

Step 2: 3-benzamido-3-(4-chlorophenyl)cyclobutanecarboxylic acid

A solution of 3-(4-chlorophenyl)-3-hydroxycyclobutanecarboxylic acid (4 g, 0.0176 mol) and benzonitrile (8.66 mL, 0.0847 mol) in water (4.4 mL, 0.245 mol) was treated with bismuth triflate (2.32 g, 0.0035 mol) and heated to 100° C. for 16 h. After cooling to 0° C., the reaction was quenched with 1 M HCl to pH~, dichloromethane was added, the solution was stirred vigorously and the phases were separated. The product was leached from organic layer with 1 M NaOH. This aqueous solution was acidified with to pH-3 with 6 M HCl and extracted two times with diethyl ether. The combined organic layers were dried over MgSO$_4$, filtered and concentrated to give a light brown residue. This crude product was dissolved in diethyl ether, and diluted with n-heptane to precipitate the product. It was filtrated, washed with n-heptane and dried at 45° C. to give the product as a white crystalline solid (1.65 g, 29%). $^1$H NMR (DMSO-d$_6$, 600 MHz) δ 12.25 (bs, 1H), 9.16 (s, 1H), 7.82 (d, J=7.2 Hz, 2H), 7.50-7.53 (m, 3H), 7.43-7.45 (m, 2H), 7.38 (d, J=8.7 Hz, 2H), 2.94-3.00 (m, 1H), 2.72-2.78 (m, 4H). ESI MS found for $C_{18}H_{16}ClNO_3$ m/z [352.3/354, 3 (M+Na$^+$), 330.4/332.4 (M+1), 328.2/330.2 (M−1)].

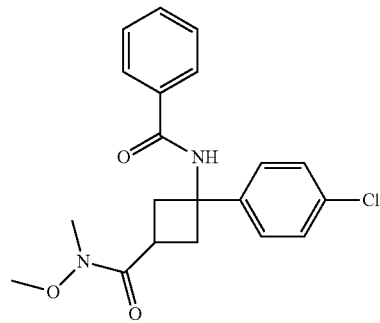 [SMILES: CON(C)C(=O)C1CC(NC(=O)c2ccccc2)(c2ccc(Cl)cc2)C1]

Step 3: N-(1-(4-chlorophenyl)-3-(methoxy(methyl)carbamoyl)cyclobutyl)benzamide

A solution of 3-benzamido-3-(4-chlorophenyl)cyclobutanecarboxylic acid (1.16 g, 3.52 mmol), diisopropylethylamine (1.57 mL, 9.14 mmol) and N,O-dimethylhydroxylamine hydrochloride (0.446 g, 4.572 mmol) in dichloromethane (45 mL) was treated with HATU (1.61 g, 4.22 mmol). After stirring overnight, the solution was diluted with dichloromethane (50 mL), washed successively with 1 M HCl (3×), 5% aqueous NaHCO$_3$ and saturated aqueous sodium chloride. The organic phase dried over MgSO$_4$, filtered and concentrated to give a colorless gum. Crystallization from diethyl ether gave the subject compound as a white crystalline solid (1.13 g 86%). $^1$H NMR (CDCl$_3$, 600 MHz) δ 7.79 (d, J=7.5 Hz, 2H), 7.49-7.52 (m, 3H), 7.42-7.45 (m, 2H), 7.35 (d, J=8.5 Hz, 2H), 7.08 (bs, 1H), 3.68 (s, 3H), 3.43-3.47 (m, 1H), 3.22 (s, 3H), 2.98-3.01 (m, 2H), 2.87-2.91 (m, 2H). ESI MS found for C$_{20}$H$_{21}$ClN$_2$O$_3$ m/z [395.4/397.3 (M+NO), 373.3/375.3 (M+1), 371.3/373.3 (M−1)].

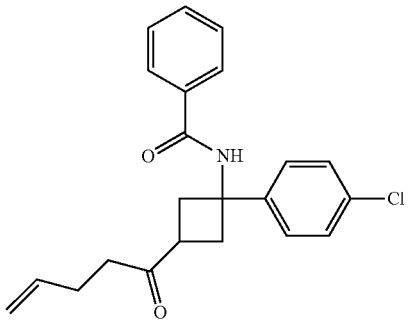 [SMILES: C=CCCC(=O)C1CC(NC(=O)c2ccccc2)(c2ccc(Cl)cc2)C1]

Step 4: N-(1-(4-chlorophenyl)-3-pent-4-enoylcyclobutyl)benzamide

Magnesium powder (1.05 g, 42.0 mmol) was placed into a round-bottomed flask with a small piece of iodine. Dry THF was added to cover the magnesium and the solution was heated to a gentle reflux for 30 minutes. While refluxing, a second solution of 4-bromo-1-buten (4.72 mL, 42.0 mmol) in dry THF (5 mL) was added. After 12 min, the mixture was cooled to room temperature and added to a solution of N-(1-(4-chlorophenyl)-3-(methoxy(methyl)carbamoyl)cyclobutyl)benzamide (1.12 g, 3.0 mmol) in dry THF (30 mL). After 2 h, the reaction was quenched with saturated aqueous NH$_4$Cl. 1M HCl was added to pH-3 and the solution was extracted with diethyl ether (×2). The combined organic layers were washed successively with 1M HCl, water and saturated aqueous sodium chloride, dried over MgSO$_4$, filtered and concentrated to give the crude product that was used to the next step without further purification. $^1$H NMR (CDCl$_3$, 600 MHz) δ 7.76 (d, J=7.2 Hz, 2H), 7.47-7.50 (m, 1H), 7.46 (d, J=8.7 Hz, 2H), 7.40-7.43 (m, 2H), 7.33 (d, J=8.7 Hz, 2H), 6.77 (s, 1H), 5.72-5.80 (m, 1H), 4.92-5.01 (m, 2H), 3.16-3.22 (m, 1H), 2.90-2.94 (m, 2H), 2.82-2.86 (m, 2H), 2.54 (t, J=7.3 Hz, 2H), 2.30-2.35 (m, 2H). ESI MS found for C$_{22}$H$_{22}$ClNO$_2$ m/z [368.4/370.4 (M+1)].

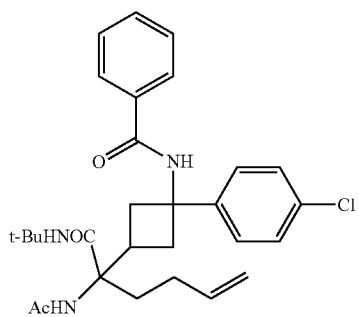

Step 5: N-(3-(2-acetamido-1-(tert-butylamino)-1-oxohex-5-en-2-yl)-1-(4-chlorophenyl)cyclobutyl)benzamide A suspension of N-(1-(4-chlorophenyl)-3-pent-4-enoylcyclobutyl)benzamide (1.21 g, 3.0 mmol), ammonium acetate (2.08 g, 27.0 mmol) in 2,2,2-trifluoroethanol (12 mL) was treated with tert-butylisocyanate (2 mL, 18.0 mmol). After stirring for three days at room temperature, the reaction was quenched with 1M HCl (5 mL) and diluted with ethyl acetate (15 mL). After vigorous stirring for 1 h, the phases were separated and the organic layer was washed successively with 1 M HCl, water and saturated aqueous sodium chloride. The solution was dried over MgSO$_4$, filtered and concentrated to give the crude product as a mixture of diastereomers (1.77 g). It was used to the next step without further purification. ESI MS found for C$_{29}$H$_{36}$ClN$_3$O$_3$ m/z [510.7/512.7 (M+1), 508.7/509.9 (M−1)].

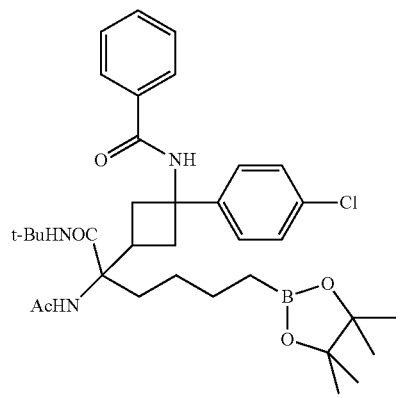

Step 6: N-(3-(2-acetamido-1-(tert-butylamino)-1-oxo-6-(4,4,5,5-tetramethyl-1,3,2-dioxaborolan-2-yl)hexan-2-yl)-1-(4-chlorophenyl)cyclobutyl)benzamide While under argon, a solution of bis(1,5-dicyclooctadiene)diiridium(I)dichloride (58 mg, 0.086 mmol) and diphenylphosphinoethane (68 mg, 0.172 mmol) in dichloromethane (10 mL) was cooled to 0° C., and charged with 4,4,5,5-tetramethyl-1,3,2-dioxaborolane (1.66 mL, 11.44 mmol). After stirring for 15 min, a solution of N-(3-(2-acetamido-1-(tert-butylamino)-1-oxohex-5-en-2-yl)-1-(4-chlorophenyl)cyclobutyl)benzamide (1.46 g, −2.8 mmol) in dichloromethane (35 mL) was added in one portion and the resulting solution was allowed to slowly warm to room temperature. After stirring for 16 h dichloromethane (40 mL) added and the organic layer was washed with water and saturated aqueous sodium chloride. The resulting solution was dried over MgSO$_4$, filtered and concentrated to give the crude product as a mixture of diastereomers. Purification by flash column chromatography (20-80% ethyl acetate in heptane) gave two products. The more lipophilic isomer was isolated and used in the next step (590 mg, 0.924 mmol). $^1$H NMR (CDCl$_3$, 600 MHz) δ 8.65 (s, 1H), 7.97 (s, 1H), 7.67 (d, J=7.2 Hz, 2H), 7.49-7.53 (m, 3H), 7.40-7.43 (m, 4H), 6.17 (s, 1H), 3.37-3.42 (m, 1H), 3.30-3.34 (m, 1H), 2.72-2.80 (m, 2H), 2.39-2.51 (m, 2H), 2.31 (s, 3), 1.66-1.72 (m, 2H), 1.30 (s, 9H), 1.19 (s, 12H), 1.10-1.17 (m, 2H), 0.83-8.89 (m, 1H), 0.72 (t, J=7.8 Hz, 2H). ESI MS found for C$_{35}$H$_{49}$BClN$_3$O$_5$ m/z [638.7/640.8 (M+1), 636.7/638.9 (M−1)]

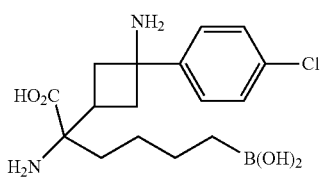

Step 7: 2-amino-2-(3-amino-3-(4-chlorophenyl)cyclobutyl)-6-boronohexanoic acid

A solution of N-(3-(2-acetamido-1-(tert-butylamino)-1-oxo-6-(4,4,5,5-tetramethyl-1,3,2-dioxaborolan-2-yl)hexan-2-yl)-1-(4-chlorophenyl)cyclobutyl)benzamide 555 mg (0.870 mmol) in 6M HCl was heated to a gentle reflux. After stirring for 16 h, the pale-yellow solution was cooled to room temperature and purified by preparative HPLC followed by treatment with 6 M HCl and concentrating gave the subject compound as a white solid. (38 mg, Yield 10%). $^1$H NMR (D$_2$O, 600 MHz) δ 7.31-7.40 (m, 2H), 7.20-7.29 (m, 2H), 1.62-3.08 (m, 7H), 1.24-1.35 (m, 3H), 1.06-1.21 (m, 1H), 0.63-0.69 (m, 1H). ESI MS found for C$_{16}$H$_{24}$BClN$_2$O$_4$ m/z [338.4/340.4 (M+1−NH$_3$), 320.4/322.4 (M+1−NH$_3$—H$_2$O), 336.3/338.3 (M−1−NH$_3$), 318.3/320.3 (M−1−NH$_3$—H$_2$O)].

Example 74

Preparation of 2-amino-2-(3-amino-3-(4-chlorobenzyl)cyclobutyl)-6-boronohexanoic acid

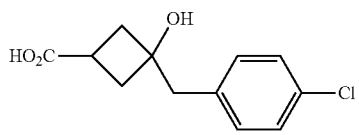 [SMILES: O=C(O)C1CC(O)(Cc2ccc(Cl)cc2)C1]

Step 1:
3-(4-chlorobenzyl)-3-hydroxycyclobutanecarboxylic acid

In a dry flask, under argon, magnesium (1.7 g, 70.11 mmol), a crystal of I$_2$ and just enough Et$_2$O to cover the magnesium was heated to reflux until the purple color dissipated (ca. 10 min.). Approximately 10% of a solution of 4-chlorobenzyl chloride (11.3 g, 70.11 mmol) in Et$_2$O (20 mL) was added all at once and reflux was continued until the solution became brown. While maintaining a gentle reflux, the remainder of the 4-chlorobenzyl chloride solution was slowly added. After the addition was complete, heating was continued for 0.5 h. The solution was cooled to room temperature and added to a solution of 3-oxocyclobutanecarboxylic acid (2 g, 17.53 mmol) in THF (30 mL) pre-cooled to 0° C. Once the addition was complete, the resulting solution was allowed to warm to room temperature with continued stirring for 16 h. The reaction mixture was then poured into a solution of ether and 1 M HCl. The layers were separated and the aqueous phase was extracted with ether (3×). The combined extracts were concentrated, dissolved in 1 M NaOH and washed with ether. The aqueous phase was re-acidified with 2 M HCl and extracted with Et$_2$O, dried over MgSO$_4$ and concentrated to give the subject compound as a white solid (2.5 g, 59%) of white solid. $^1$H NMR (CDCl$_3$, 500 MHz) δ 7.44 (d, J=8.24 Hz, 2H), 7.35 (d, J=8.24 Hz, 2H), 3.02 (s, 2H), 2.90-2.84 (m, 1H), 2.66-2.62 (m, 2H), 2.47-2.42 (m, 2H). ESI MS found for C$_{12}$H$_{13}$ClO$_3$ m/z [239.1 (M−1)].

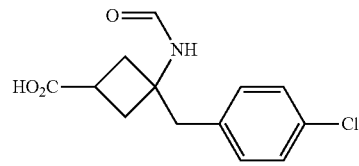 [SMILES: O=CNC1(Cc2ccc(Cl)cc2)CC(C(=O)O)C1]

Step 2: 3-(4-chlorobenzyl)-3-formamidocyclobutanecarboxylic acid

A solution of 3-(4-chlorobenzyl)-3-hydroxycyclobutanecarboxylic acid (1 g, 4.17 mmol) in TFA (17.5 mL) was charged with KCN (813 mg, 12.5 mmol), cooled to 0° C. and treated with H$_2$SO$_4$ (3.5 mL) dropwise. The cooling bath was removed and stirring was continued for 1.5 h. Once the reaction was complete, the mixture was re-cooled to 0° C. diluted with water, and extracted with diethyl ether. The organic layer was washed successively with 1M NaOH and saturated aqueous sodium chloride. The solution was dried over MgSO$_4$, filtered and concentrated. Purification by flash column chromatography (gradient 1-20% methanol in dichloromethane) afforded the subject compound (500 mg, 45% yield). $^1$H NMR (DMSO-d6, 600 MHz) δ 12.15 (bs, 1H), 8.38 (s, 1H), 7.88 (d, J=1.13 Hz, 1H), 7.36-7.32 (m, 4H), 2.94-2.89 (m, 1H), 2.57-2.53 (m, 1H), 2.36-2.32 (m, 1H), 2.26-2.22 (m, 1H), 2.03-1.96 (m, 1H), 1.95-1.88 (m, 2H). ESI MS found for C$_{13}$H$_{14}$ClNO$_3$ m/z [266.1 (M−1)].

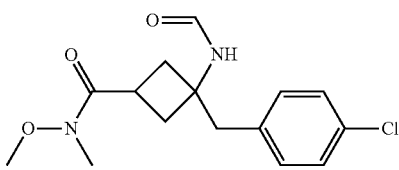 [SMILES: CON(C)C(=O)C1CC(Cc2ccc(Cl)cc2)(NC=O)C1]

Step 3: 3-(4-chlorobenzyl)-3-formamido-N-methoxy-N-methylcyclobutanecarboxamide

A solution of 3-(4-chlorobenzyl)-3-formamidocyclobutanecarboxylic acid (1.3 g, 4.87 mmol), DIPEA (2.17 mL, 12.6 mmol), O,N-dimethylhydroxylamine hydrochloride (617 mg, 6.33 mmol) in dichloromethane (20 mL) was treated with HATU (2.2 g, 5.84 mmol) and stirred at room temperature for 16 h. The solution was diluted with dichloromethane (20 mL), washed successively with 1 M HCl (2×), 5% aqueous NaHCO$_3$ and saturated aqueous sodium chloride, dried over MgSO$_4$, filtered and concentrated. The crude product was purified by column chromatography (gradient 0.5-1.0% methanol in dichloromethane) to give the subject compound (0.5 g, 33.3%). ESI MS found for C$_{15}$H$_{19}$ClN$_2$O$_3$ m/z [211.4 (M+1), 233.4 (M+Na$^+$)].

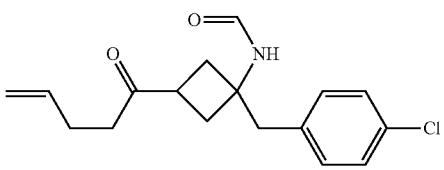 [SMILES: C=CCCC(=O)C1CC(Cc2ccc(Cl)cc2)(NC=O)C1]

Step 4: N-(1-(4-chlorobenzyl)-3-pent-4-enoylcyclobutyl)formamide

Magnesium powder (0.548 g, 22.6 mmol) was placed into a round-bottomed flask with a small piece of iodine. Dry THF was added to cover the magnesium and the solution was heated to a gentle reflux until the color had dissipated (approximately 30 minutes). While refluxing, a second solution of 4-bromo-1-buten (2.3 mL, 22.6 mmol) in dry THF (5 mL) was added. After 12 min, the mixture was cooled 0° C. and added to a solution of 3-(4-chlorobenzyl)-3-formamido-N-methoxy-N-methylcyclobutanecarboxamide (0.5 g, 1.61 mmol) in dry THF (30 mL). After 2 h, the reaction was allowed to warm to room temperature and stir overnight. The reaction was quenched with saturated aqueous NH$_4$Cl and extracted with diethyl ether (×2). The combined organic layers were washed successively with 1M HCl, water and saturated aqueous sodium chloride, dried over MgSO$_4$, filtered and concentrated to give the crude product (0.48 g) that was used to the next step without further purification. ESI MS found for C$_{17}$H$_{20}$ClNO$_2$ m/z [306.3 (M+1), 328.3 (M+Na$^+$), 304.5 (M−1)].

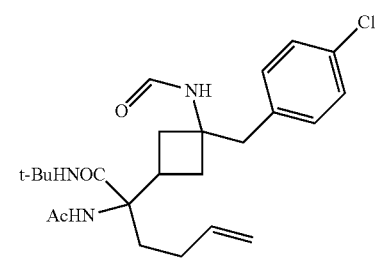

Step 5: 2-acetamido-N-tert-butyl-2-(3-(4-chlorobenzyl)-3-formamidocyclobutyl)hex-5-enamide A solution of N-(1-(4-chlorobenzyl)-3-pent-4-enoylcyclobutyl)formamide (0.5 g, 1.64 mmol) and ammonium acetate (1.14 g, 9.84 mmol) in 2,2,2-trifluoroethanol (4 mL). was treated with tert-butyl isocyanide (1.1 mL, 9.84 mmol) and stirred at room temperature for 3 days. Once complete, the solution was diluted with ethyl acetate (15 mL) and quenched with 2M HCl (10 mL). After stirring vigorously for 1 h, the phases were separated and the organic layer was washed with water and saturated aqueous sodium chloride, dried over MgSO$_4$, filtered and concentrated. Purification by column chromatography (gradient 25-75% ethyl acetate in heptane) afforded the subject compound as a colorless oil (330, mg, 45% yield). ESI MS found for C$_{24}$H$_{34}$ClN$_3$O$_3$ m/z [448.6 (M+1), 470.6 (M+Na$^+$), 446.3 (M−1)].

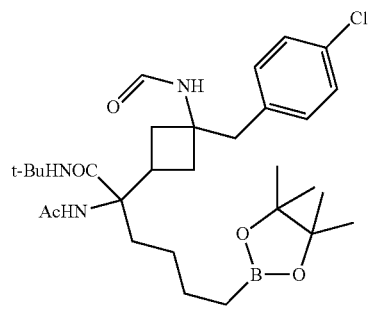

Step 6: 2-acetamido-N-tert-butyl-2-(3-(4-chlorobenzyl)-3-formamidocyclobutyl)-6-(4,4,5,5-tetramethyl-1,3,2-dioxaborolan-2-yl)hexanamide While under argon, bis(1,5-dicyclooctadiene)diiridium(I) dichloride (15 mg, 0.022 mmol) and diphenylphosphinoethan (18 mg, 0.044 mmol) in dichloromethane (3 mL) was cooled to 0° C. and treated with 4,4,5,5-tetramethyl-1,3,2-dioxaborolane (0.430 mL, 2.95 mmol). After 30 min, a solution of 2-acetamido-N-tert-butyl-2-(3-(4-chlorobenzyl)-3-formamidocyclobutyl)hex-5-enamide (330 mg, 0.738 mmol) in dichloromethane (10 mL) was added and the cooling bath was removed. After 16 h, the solution was diluted with dichloromethane (20 mL) and washed with water and saturated aqueous sodium chloride. The organic layer was dried over MgSO$_4$, filtered and concentrated to give the crude product (420 mg, 99%), which was used in the next step without further purification. ESI MS found for C$_{30}$H$_{47}$BClN$_3$O$_5$ m/z [576.8 (M+1), 574.7 (M−1)].

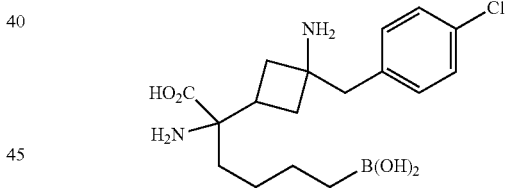

Step 7: 2-amino-2-(3-amino-3-(4-chlorobenzyl)cyclobutyl)-6-boronohexanoic acid

A solution of 2-acetamido-N-tert-butyl-2-(3-(4-chlorobenzyl)-3-formamidocyclobutyl)-6-(4,4,5,5-tetramethyl-1,3,2-dioxaborolan-2-yl)hexanamide (140 mg) in 6M HCl was heated to a gentle reflux for 16 h. After cooling to room temperature, the solution was washed with ether and concentrated to dryness. The resulting residue was dissolved in water and adjusted to pH~1 3 with 1M NaOH and washed with ether. The aqueous layer was adjusted to pH~3 with 6 M HCl and concentrated to dryness. Methanol was added, and the resulting white solid (NaCl) was filtered off. The filtrate was concentrated and purified on preparative HPLC to give the subject compound as a white solid (10 mg, 9.3%). $^1$H NMR (D$_2$O, 600 MHz) δ 7.47-7.34 (m, 4H), 2.66-2.34 (m, 2H), 2.25-2.16 (m, 1H), 2.05-1.82 (m, 3H), 1.80-1.61 (m, 1H), 1.40-1.20 (m, 3H), 1.17-1.04 (m, 1H), 0.8-0.63 (m, 2H). ESI MS found for $C_{17}H_{26}BClN_2O_4$ m/z [369.4 (M+1), 391.5 (M+Na+), 367.5 (M−1)].

Example 75

Preparation of (S)-2-((1s,3R)-3-aminocyclobutyl)-6-borono-2-(methylamino)hexanoic acid

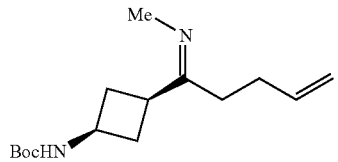 [SMILES: C=CCC/C(=N/C)[C@H]1C[C@@H](NC(=O)OC(C)(C)C)C1]

Step 1: tert-butyl (1s,3s)-3-((Z)-1-(methylimino) pent-4-enyl)cyclobutylcarbamate Tert-butyl (1s,3s)-3-pent-4-enoylcyclobutylcarbamate (199 mg, 0.79 mmol) was dissolved in a 2 M solution of MeNH$_2$ in THF (2 mL, 5.0 mmol) and treated with 3 angstrom molecular sieves (1.5 g). The mixture was allowed to stand overnight at room temperature, then decanted from the sieves and concentrated in vacuo to afford the desired product which was used without further purification. $^1$H NMR (CDCl$_3$, 400 MHz) δ 5.87-5.76 (m, 1H), 5.10-4.96 (m, 2H), 4.77-4.64 (m, 1H), 4.15-4.02 (m, 1H), 3.20 (s, 3H), 2.80-2.65 (m, 1H), 2.62-2.44 (m, 2H), 2.41-2.13 (m, 4H), 2.00-1.89 (m, 2H), 1.45 (s, 9H).

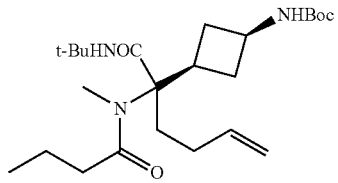

Step 2: tert-butyl (1R,3s)-3-((S)-1-(tert-butylamino)-2-(N-methylbutyramido)-1-oxohex-5-en-2-yl)cyclobutylcarbamate A solution of crude tert-butyl (1s,3s)-3-(1-(methylimino) pent-4-enyl)cyclobutylcarbamate and butyric acid (0.182 mL, 1.98 mmol) in 2,2,2-trifluoroethanol (1 mL) was treated with tert-butyl isocyanide (0.270 mL, 2.37 mmol) and the stirred 3 days at room temperature. The reaction was diluted with ethyl acetate, washed water, saturated aqueous sodium chloride, dried over MgSO$_4$, and concentrated. The residue was chromatographed on silica gel eluting with 35% ethyl acetate in heptane to afford the desired product (83 mg, 24% for two steps). $^1$H NMR (CDCl$_3$, 400 MHz) δ 5.87-5.71 (m, 1H), 5.32 (br s, 1H), 5.09-4.93 (m, 2H), 4.60 (br s, 1H), 3.92 (br s, 1H), 3.00 (s, 3H), 2.59-2.28 (m, 6H), 2.11-1.80 (m, 6H), 1.75-1.50 (m, 4H), 1.45 (s, 9H), 1.37 (s, 9H). ESI MS found for $C_{24}H_{43}N_3O_4$ m/z [438.3 (M+1)].

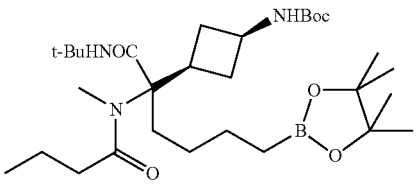

Step 3: tert-butyl (1R,3s)-3-((S)-1-(tert-butylamino)-2-(N-methylbutyramido)-1-oxo-6-(4,4,5,5-tetramethyl-1,3,2-dioxaborolan-2-yl)hexan-2-yl)cyclobutylcarbamate A solution of tert-butyl (1R,3s)-3-((S)-1-(tert-butylamino)-2-(N-methylbutyramido)-1-oxohex-5-en-2-yl)cyclobutylcarbamate (83 mg, 0.19 mmol) and dppe (7.8 mg, 0.020 mmol) was in dichloromethane (2 mL) and treated with [Ir(COD)Cl]$_2$ (6.4 mg, 0.010 mmol). After stirring 15 minutes, the solution was cooled to 0° C. and charged with pinacolborane (0.041 mL, 0.29 mmol). The reaction was stirred overnight at room temperature, then diluted with ethyl acetate, washed with saturated aqueous sodium chloride, dried over MgSO$_4$ and concentrated. The residue was chromatographed on silica gel eluting with 10-80% ethyl acetate in heptane to afford the desired product (90 mg, 84%). $^1$H NMR (CDCl$_3$, 400 MHz) δ 4.63 (br s, 1H), 3.90 (br s, 1H), 2.98 (s, 3H), 2.59-2.49 (m, 1H), 2.44-2.25 (m, 6H), 2.09-1.61 (m, 12H), 1.45 (s, 9H), 1.37 (s, 9H), 1.26 (s, 12H), 0.79 (t, J=7.3 Hz, 2H). ESI MS found for $C_{30}H_{56}BN_3O_6$ m/z [566.6 (M+1)].

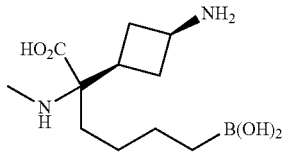 [SMILES: CNC(CCCCB(O)O)(C(=O)O)[C@H]1C[C@@H](N)C1]

Step 4: (S)-2-((1s,3R)-3-aminocyclobutyl)-6-borono-2-(methylamino)hexanoic acid tert-Butyl (1R,3s)-3-((S)-1-(tert-butylamino)-2-(N-methylbutyramido)-1-oxo-6-(4,4,5,5-tetramethyl-1,3,2-dioxaborolan-2-yl)hexan-2-yl)cyclobutylcarbamate (90 mg, 0.16 mmol) was treated with 6 N HCl (3.6 mL) and heated to 170° C. for 25 minutes in a microwave reactor. The reaction was cooled to room temperature, diluted with H$_2$O, washed dichlormethane (3×), and concentrated. The residue was purified by preparative HPLC (10-100% CH$_3$CN/H$_2$O) to afford the desired product. $^1$H NMR (D$_2$O, 400 MHz) δ 3.73-3.63 (m, 1H), 2.59 (s, 3H), 2.53-2.36 (m, 3H), 2.05-1.64 (m, 4H), 1.47-1.21 (m, 3H), 1.20-1.08 (m, 1H), 0.78 (t, J=7.3 Hz, 2H). ESI MS found for $C_{11}H_{23}BN_2O_4$ m/z [259.4 (M+1)].

Methods and Uses

The inventive compounds are useful for inhibiting the expression or activity of arginase I, arginase II or a combination of these enzymes. The enzymes of the arginase family play an important role in regulating the physiological levels of the L-arginine, a precursor of the signaling molecule nitric oxide (nitric oxide (NO)), as well as in regulating levels of L-omithine, a precursor of certain polyamines that are important physiological signal transducers.

More specifically, the invention provides methods and uses for inhibiting arginase I, arginase II, or a combination thereof in a cell, comprising contacting the cell with at least one compound according to the present invention, or a composition thereof as described herein. In some embodiments, the invention provides a method for the treatment or prevention of a disease or condition associated with expression or activity of arginase I, arginase II, or a combination thereof in a subject.

For instance, the disease or condition is selected from the group consisting of cardiovascular disorders, gastrointestinal disorders, sexual disorders, pulmonary disorders, immune disorders, infection, autoimmune disorders, pulmonary disorders, and hemolytic disorders.

According to one embodiment, the inventive compounds are candidate therapeutics useful for treating cardiovascular disorders, such as diseases or conditions selected from the group consisting of hypertension, including systemic hypertension, pulmonary arterial hypertension (PAH), pulmonary arterial hypertension in high altitude, ischemia reperfusion (IR) injury, myocardial infarction, atherosclerosis.

Exemplary sexual disorders that can be treated using the inventive compounds are disease or conditions selected from the group consisting of Peyronie's Disease and erectile dysfunction (ED).

In one embodiment an arginase inhibitor in accordance with the present invention is suitable for treating a pulmonary disorder selected from the group consisting of chemically-induced lung fibrosis, idiopathic pulmonary fibrosis, cystic fibrosis, chronic obstructive pulmonary disease (COPD and asthma.

Compounds in accordance with the present invention are also useful at treating gastrointestinal disorders, such as diseases or conditions selected from the group consisting of gastrointestinal motility disorders, gastric cancers, inflammatory bowel disease, Crohn's disease, ulcerative colitis, and gastric ulcers.

The transport of organs, such as liver, kidney and heart increases the risk of ischemic reperfusion injury (IR). The inventive compounds are useful in protecting transported organs from IR during transport.

According to an embodiment of the present invention, the inventive compounds are useful for treating autoimmune disorders. Exemplary diseases or conditions include without limitation encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

Arginase inhibitors in accordance with the present invention are also useful for treating immune disorders, such as a disease or condition selected from the group consisting of myeloid-derived suppressor cell (MDSC) mediated T-cell dysfunction, human immunodeficiency virus (HIV), autoimmune encephalomyelitis, and ABO mismatch transfusion reaction.

In one embodiment, the inventive compounds are useful as candidate therapeutics for treating a subject suffering from hemolytic disorders. Exemplary diseases or conditions include without limitation sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

Other exemplary disease conditions for which compounds described herein are candidate therapeutics are inflammation, psoriasis, leishmaniasis, neurodegenerative diseases, wound healing, hepatitis B virus (HBV), H. pylori infections, fibrotic diseases, arthritis, candidiasis, periodontal disease, keloids, adenotonsilar disease, African sleeping sickness, and Chagas' disease.

Advantageously, compounds in accordance with the present invention are especially useful at treating diseases or conditions selected from the group consisting of pulmonary arterial hypertension (PAH), erectile dysfunction (ED), hypertension, myocardial infarction, atherosclerosis, renal disease, asthma, inflammation, psoriasis, immune response, T-cell dysfunction, such as myeloid-derived suppressor cell (MDSC) mediated T-cell dysfunction, leishmaniasis, ischemia reperfusion injury, sickle cell disease, neurodegenerative diseases, wound healing, human immunodeficiency virus (HIV), hepatitis B virus (HBV), H. pylori infections, and fibrotic diseases such as cystic fibrosis. In addition, the compounds described herein are useful in the protection of organs, such as during organ transport.

In some embodiments, the subject receiving treatment is a mammal. For instance, the methods and uses described herein are suitable for medical use in humans. Alternatively, the methods and uses are also suitable in a veterinary context, wherein the subject includes but is not limited to a dog, cat, horse, cow, sheep, lamb and reptile.

More specific descriptions of diseases and conditions follow below.

Erectile Dysfunction

The observation that there are differences in the activity of arginase in the penis of young mice versus older mice led to the conclusion that arginase may play a role in erectile dysfunction (ED). In this context, Champion et. al., (Am. J. Physiol. Heart Circ. Physiol. 292:340-351, (2006) and Biochem. and Biophys. Research Communications, 283:923-27, (2001)), observed an increase of mRNA expression levels and arginase protein in aged mice along with a reduction in the activity of constitutively active NOS.

Nitric oxide is implicated in nonadrenergic, noncholinergic neurotransmission that leads to smooth-muscle relaxation in the corpus cavernosum enabling penile erection (New England Journal of Medicine, 326, (1992)), Hence, erectile dysfunction can often be treated by elevating penile tissue nitric oxide (NO) levels. Such an elevation in tissue nitric oxide (NO) levels can be achieved by inhibiting arginase activity in penile tissue of aged subjects. Stated differently, arginase has been postulated to deplete the pool of free L-arginine available to NOS in cells which results in lower levels of nitric oxide (NO) and erectile dysfunction. See, Christianson et. al., (Acc. Chem. Res., 38:191-201, (2005)), and (Nature Structural Biol., 6(11):1043-1047, (1999)) Inhibitors of arginase, therefore, can play a role in the treatment of erectile dysfunction.

Pulmonary Hypertension

It has been proposed that alterations in arginine metabolism are involved in the pathogenesis of pulmonary hypertension (Xu et al., FASEB J., 18:1746-48, 2004). The proposition is based in part on the finding that arginase II expression and arginase activity are significantly elevated in pulmonary artery endothelial cells derived from lung explants of patients with class I pulmonary hypertension.

Additionally, secondary pulmonary hypertension is emerging as one of the leading causes of mortality and morbidity in patients suffering from hemolytic anemias, such as thalassemia and sickle cell disease. The underlying cause for secondary pulmonary hypertension is impaired nitric oxide bioavailability due to release of arginase following hemolysis which decreases the pool of free arinine that is required for nitric oxide (NO) synthesis. Accordingly, inhibition of arginase activity can provide a potential therapeutic avenue for treating pulmonary hypertension.

Hypertension

Xu, W. et al., FASEB 2004, 14, 1746-8 proposed a fundamental role of arginase II in blood pressure regulation. In this context, high levels of vascular arginase are correlated to concomitant reduction of vascular nitric oxide (NO) in hypertensive animals. For instance, up-regulation of arginase activity precedes a rise in blood pressure in rats that were genetically predisposed to hypertension (i.e., spontaneously hypertensive rats), but administration of the anti-hypertensive agent hydralazine lowered blood pressure with a decrease in the expression levels of vascular arginase, thereby indicating a strong correlation between the arginase activity and blood pressure (Berthelot et al. Life Sciences, 80:1128-34, (2008). Similar administration of the known arginase inhibitor $N^\omega$-hydroxy-nor-L-arginine (nor-NOHA) lowered blood pressure and improved the vascular response of resistance vessels to blood flow and pressure in spontaneously hypertensive animals, thereby highlighting inhibitors of arginase as candidate therapeutics for treating hypertension (Demougeot et al., (J. Hypertension, 26:1110-18, (2008).

Arginase also plays a role in reflex cutaneous hypertension by lowering the cellular levels of nitric oxide (NO). Nitric oxide causes vasodilation and levels of nitric oxide (NO) are normally elevated or lowered to maintain blood pressure at physiologically acceptable levels. Kenny et al., (J. of Physiology 581 (2007) 863-872), hypothesized that reflex vasodilation in hypertensive subjects can attenuate arginase inhibition, thereby implicating a role for arginase inhibitors for the treatment of hypertension.

Asthma

Arginase activity is also associated with airway hyperresponsiveness in asthma. For example, arginase I is upregulated in human asthmatics and in mice suffering from acute and chronic asthma, whilst levels of arginase II and NOS isoforms remain unchanged (Scott et al., Am. J. Physiol. Lung Cell Mol. Physiol. 296:911-920 (2009)). Furthermore, methacholine induced responsiveness of the central airways in the murine chronic model attenuated upon the administration of the arginase inhibitor S-(2-boronoethyl)-L-cysteine. The similarity between expression profiles of ARG I in humans and in mice having chronic asthma indicates that compounds capable of inhibiting arginase activity are candidate therapeutics for treating asthma.

Other lines of evidence reveal further correlations between increased activity of arginase in asthmatic lung tissue and disease progression, such as an upregulation for genes related to the metabolism of cationic amino acids, including arginase I and II in mice having asthma (Rothenberg et al., (J. Clin. Invest., 111:1863-74 (2003), and Meurs et. al., (Expert Opin. Investig Drugs, 14(10:12211231, (2005)).

Further, levels of all amino acids are lower in the plasma of asthmatics, but the levels of arginine are significantly lower in plasma compared to that of a normal subject (Morris et al., (Am. J. Respir. Crit Care Med., 170:148-154, (2004)). Thus, arginase activity is significantly increased in the plasma from an asthmatic, in which elevated levels of arginase activity may contribute to the lower bioavailability of plasma arginine that creates an nitric oxide (NO) deficiency, which is responsible for promoting hyperreactive airways in asthmatics.

Inflammation

Arginase activity also is associated with autoimmune inflammation (Chen et al., Immunology, 110:141-148, (2003)). The authors identified upregulation in the expression levels of the ARG I gene in murine spinal cells from animals undergoing experimental autoimmune encephalomyelitis (EAE). Administration of the arginase inhibitor amino-6-boronohexanoic acid (ABH), however, resulted in the animals developing a much milder form of EAE than in control animals. These results implicate inhibitors of arginase in a therapeutic role for treating autoimmune encephalomyelitis.

Moreover, Horowitz et al., (American J. Physiol Gastrointestinal Liver Physiol., 292:G1323-36, (2007)), suggest a role for arginase enzymes in vascular pathophysiology. For example, these authors indicate a loss of nitric oxide (NO) production in chronically inflamed gut blood vessels in patients suffering from irritable bowel disease (IBD), Crohn's disease and ulcerative colitis. The loss in nitric oxide (NO) production correlated with an upregulation of arginase expression and activity that reduced levels of arginine preventing nitric oxide synthase (NOS), from synthesizing nitric oxide (NO) Inhibitors of arginase activity, therefore, may be candidate therapeutics for treating vascular pathophysiology.

Ischaemia Reperfusion

Arginase inhibition is also suggested to play a cardioprotective role during ischaemia reperfusion. More specifically, inhibition of arginase protects against myocardial infarction by a mechanism that may be dependent on NOS activity and the consequent bioavailability of nitric oxide (NO) (Pernow et al., (Cardiovascular Research, 85:147-154 (2010)).

Myocardial Infarction and Artherosclerosis

Arginase I polymorphism is associated with myocardial infarction along with an increased risk of developing carotid artery intima media thickness that is considered to be a reliable indicator of arthrosclerosis as well as of other coronary arterial diseases (Brousseau et al., (J. Med Genetics, 44:526-531, (2007)). Increased arginase activity elevates levels of ornithine that is biochemically involved in promoting the formation of the matrix and cellular components of artherosclerotic plaque. Id. Thus, arginase inhibitors may serve as candidate therapeutics for treating artherosclerosis. Berkowitz et al., (Circ. Res. 102, 102, (2008), p. 923-932), implicated a role for ARGII in the formation of plaque and artherosclerosis. Oxidation of LDLP that accompanies plaque formation increases arginase activity and lower nitric oxide (NO) levels in endothelial cells. In particular, levels of ARGII are elevated in artherosclerotic mice, indicating a role for inhibitors of arginase as candidate therapeutics for treating artherosclerosis.

Additionally, studies by Ming et. al., (Current Hypertension Reports., 54:54-59, (2006)), indicate that an upregulation of arginase rather than endothelial nitric oxide (NO) dysfunction plays an important role in cardiovascular disorders, including artherosclerosis. That arginase is involved in cardiovascular diseases is further supported by the observation ARGI and ARGII activity is upregulated in cardiac myocytes which in turn negatively impacts NOS activity and myocardial contractility. (See, Margulies et. al., Am. J. Physiol. Heart Circ. Physiol., 290:1756-62, (2006)).

Immune Response

The arginine/nitric oxide (NO) pathway may also play a role in immune response, such as after organ transplants. For instance, it was postulated that reperfusion of an orthotopic liver transplant graft caused a significant increase in ornithine levels due to upregulation of arginase activity in the graft (Tsikas et al., (Nitric oxide, 20:61-67, (2009)). The elevated levels of hydrolytic and proteolytic enzymes in the graft may result in a less favorable outcome for the grafted organ. Thus, inhibiting the arginase enzymes may present an alternate therapeutic avenue for improving the outcome of a transplant.

Psoriasis

Arginase has been implicated to play a role in the pathogenesis of psoriasis. For example, ARG I is highly expressed in hyperproliferative psoriasis, and in fact, it is responsible for down regulation of nitric oxide (NO) an inhibitor of cell proliferation, by competing for the common substrate L-arginine as postulated by D. Bruch-Gerharz et al. *American Journal of Pathology* 162(1) (2003) 203-211. More recent work by Abeyakirthi et al. (British J. Dermatology, (2010)), and Berkowitz et al, (WO/2007/005620) support the finding of low nitric oxide (NO) levels in psoriatic keratinocytes. Abeyakirthi et al, found that psoriatic keratinocytes were poorly differentiated and hyperproliferative. The poor differentiation was postulated to result from low levels of nitric oxide (NO), not because of poor expression of NOS, but rather the over expression of arginase that competes with NOS for substrate L-arginine. Thus, inhibition of arginase may provide therapeutic relief from psoriasis.

Wound Healing

Under normal physiological conditions, nitric oxide (NO) plays an important role in promoting wound healing. For example, Hulst et al., (Nitric Oxide, 21:175-183, (2009)), studied the role of ARGI and ARG II in wound healing. Immediately following injury, it is desirable to elevate tissue levels of nitric oxide (NO) so as to promote angiogenesis and cell proliferation that are important for healing Inhibitors of arginase may therefore find use as therapeutics to treat wounds because such compounds would elevate tissue levels of nitric oxide (NO). Further support for the use of arginase inhibitors as candidate therapeutics for treating wounds was provided by South et al. (Experimental Dermatology, 29:664-668 (2004)), who found a 5-fold increase in arginase I in chronic wounds such as skin erosions and blisters.

Cystic Fibrosis

Cystic fibrosis (CF) is a multisystem disorder caused by mutations of the cystic fibrosis transmembrane conductance regulator (CFTR) gene. The common symptoms of CF are persistent pulmonary infection, difficulty in breathing, pancreatic insufficiency, and elevated sweat chloride levels. CF can be fatal if untreated, with pulmonary diseases, resulting from mucus build-up and decreased mucociliary clearance, being the leading cause of morbidity and mortality.

It has been asserted that patients with cystic fibrosis (CF) have increased plasma and sputum arginase activity, with an accompanying decrease in the levels of plasma 1-arginine (H. Grasemann et al., *Am. J. Respir. Crit. Care Med.* 172(12) (2005) 1523-1528. The increased arginase activity, however, results in lower physiological levels of nitric oxide (NO) that can cause airway obstruction decreased pulmonary function in patients suffering from cystic fibrosis (CF).

Impaired electrical field induced-stimulation of smooth muscle relaxation in the airway of a mouse model of CF and the administration of 1-arginine and NO reversed this effect as proposed by M. Mhanna et al. *Am. J. Respir. Cell Mol. Biol.* 24(5) (200)1 621-626. Graesmann et al., found a positive correlation exists between pulmonary function and exhaled NO and NO metabolite concentrations in the sputum of CF patients (Grasemann, H; Michler, E; Wallot, M; Ratjen, F., *Pediatr Pulmonol.* 1997, 24, 173-7).

Taken together, theses results indicate that increased Arginase activity in CF contributes to the NO deficiency and pulmonary obstruction in CF by limiting the availability of 1-arginine to NOS. Thus, inhibitors of arginase activity are candidate therapeutics for treating cystic fibrosis (CF)

Organ Protection

Another therapeutic avenue for compounds in accordance with the present invention is protecting organs during transport from donor to a site where they will be transplanted into a recipient. Ischemic reperfusion injury (IR) due to exposure of the transplant organs to a period of warm ischemia (time from donor until flushed with preservation media), and cold ischemia (hypothermic preservation) is frequently observed in patients undergoing transplant surgery. Ischemic reperfusion injury (IR) and accompanying primary graft dysfunction and/or acute or chronic rejection results due to alteration in the cellular activity of the L-Arginine/NO pathway.

It was proposed that Arginase 1 and arginase 2 are released from apoptotic endothelial cells and kidney cells within the first 24 hours of organ removal from the body. To counteract the released arginase, L-Arginine is added to preservation media. Results with canine kidney transplants indicate that addition of L-arginine reduced the incidence and severity of ischemia, resulted in post-transplant with lower MDA levels at 1 hour, and lowered BUN & Serum creatinine levels during the first 72 hrs. See Erkasap, S; Ates, E., *Nephrol Dial Transplant.* 2000, 15, 1224-7.

Similar results were observed for canine lung grafts over a 24 hour period when lungs were preserved in the University of Wisconsin solution supplemented with L-Arginine. Yen et al., observed that the addition of L-arginine to the preservation medium increased pulmonary endothelial protection and lowered the incidence of ischemia when compared to a control that is preserved in medium that does not contain L-arginine (Chu, Y; Wu, Y. C.; Chou, Y. C.; Chueh, H. Y, Liu H P, Chu J J, Lin P J., *J Heart Lung Transplant.* 2004, 23, 592-8).

Koch et al. stated that improved myocardial contractility and relaxation in heart muscle of rats following transplantation when hearts were preserved in HTK solution having L-Arginine and N-alpha-acetyl-histidine (Koch A, Radovits T, Loganathan S, Sack F U, Karck M, Szabó G B., *Transplant Proc.* 2009, 41, 2592-4).

Addition of an arginase inhibitor, therefore, can be a candidate therapeutic for preventing and/or reducing the incidence and risk of ischemic reperfusion injury by a synergistically increasing the organ protective effect of the preservation media. Given the low number of available organs that are suitable for transplant and the loss and injury of organs due to the onset of ischemia, arginase inhibitors in accordance with the present invention can find use as therapeutics for preserving organs, increasing organ availability by reducing the amount of ischemic reperfusion injury during organ transport.

Leishmaniasis

Leishmaniasis is caused by a protozoan and manifests as cutaneous leishmaniasis (i.e., skin infection causing hypopigmented nodules) and visceral lieshmaniasis (more severe affecting internal organs). Arginase it postulated to play a role in disease progression since the parasite relies on arginase for the synthesis of cellular polyamines that are essential for pathogenesis Inhibition of arginase, therefore, would reduce cellular parasitic burden and promote increased nitric oxide (NO) levels enhancing parasitic clearance. See Liew F Y et al. *Eur J Immunol* 21 (1991) 2489, Iniesta V et al. *Parasite Immunol.* 24 (2002) 113-118, and Kane M M et al. *J. Immunol.* 166 (2001) 1141-1147. Compounds according to the present invention, therefore can be used as therapeutics for treating liesmaniasis.

Myeloid Derived Suppressor Cells (MDSC)

MDSC's are potent immune modulators that limit immune responses through several pathways, such as, L-arginine depletion via arginase 1 release into the microenvironment (Rodriguez 2009 Cancer Res), MHC restricted suppression (Nagaraj S, Gupta K, Pisarev V, Kinarsky L, Sherman S, Kang L, Herber D L, Schneck J, Gabrilovich D I., *Nat Med.* 2007, 13, 828-35), induction of T regulatory cells (Serafini P, Mgebroff S, Noonan K, Borrello I., *Cancer Res.* 2008, 68, 5439-49), and production of IL10 (Rodrigues J C, Gonzalez G C, Zhang L, Ibrahim G, Kelly J J, Gustafson M P, Lin Y, Dietz A B, Forsyth P A, Yong V W, Parney I F., *Neuro Oncol.* 2010, 12, 351-65) (Sinha P, Clements V K, Bunt S K, Albelda S M, Ostrand-Rosenberg S., *J Immunol.* 2007, 179, 977-83), for instance.

It is postulated that tumor development is accompanied by an increase in the number of MDSC's both peripherally and infiltrated within tumors. See Almand B, Clark J I, Nikitina E, van Beynen J, English N R, Knight S C, Carbone D P, Gabrilovich D I., *J Immunol.* 2001, 166, 678-89 and Gabrilovich D., *Nat Rev Immunol.* 2004, 4, 941-52. Treatment of tumor bearing mice with established chemotherapeutics such as gemcitabine and 5-Fluorouracil eliminates MDSC immunesuppression and results in delayed tumor growth. See Le H K, Graham L, Cha E, Morales J K, Manjili M H, Bear H D., *Int Immunopharmacol.* 2009, 9, 900-9 and Vincent J, Mignot G, Chalmin F, Ladoire S, Bruchard M, Chevriaux A, Martin F, Apetoh L, Rae C, Ghiringhelli F., *Cancer Res.* 2010, 70, 3052-61, respectively. Moreover, inhibition of arginase 1 enhanced antitumor immunity by reducing MDSC function. Thus, inhibitors of arginase, such as compounds in accordance with the present invention reduce or delay tumor growth and can be used in combination with established anti-cancer agents in the treatment of cancer.

Helicobacter pylori (*H. pylori*)

Helicobacter pylori (*H. pylori*) is a Gram-negative bacterium that colonizes the human gastric mucosa. Bacterial colonization can lead to acute or chronic gastritis and is highly associated with peptic ulcer disease and stomach cancer. The observation that the addition of L-arginine to co-culture of *H. pylori* and macrophages increased nitric oxide (NO) mediated killing of the *H. pylori* (Chaturvedi R, Asim M, Lewis N D, Algood H M, Cover T L, Kim P Y, Wilson K T., *Infect Immun.* 2007, 75, 4305-15), supports the hypothesis that bacterial arginase competes with macrophage arginase for free arginine that is required for nitric oxide (NO) synthesis. See Gobert A P, McGee D J, Akhtar M, Mendz G L, Newton J C, Cheng Y, Mobley H L, Wilson K T., *Proc Natl Acad Sci USA.* 2001, 98, 13844-9. L-arginine is required for T-cell activation and for the rapid clearance of bacteria from infected cells. By depleting the pools of free L-arginine in vivo, *H. pyroli* reduces arginine-induced CD3zeta expression on T-cells and prevents T-cell activation and proliferation. See Zabaleta J, McGee D J, Zea A H, Hernandez C P, Rodriguez P C, Sierra R A, Correa P, Ochoa A C., *J Immunol.* 2004, 173, 586-93.

The inhibition of bacterial arginase using the known inhibitor NOHA, however, reestablished CD3 expression on T-cells and (Zabaleta J 2004), and enhanced production of NO by macrophages, thus, promoting macrophage mediated clearance of bacteria from infected cells. See Chaturvedi R, Asim M, Lewis N D, Algood H M, Cover T L, Kim P Y, Wilson K T., *Infect Immun.* 2007, 75, 4305-15.

Furthermore, Lewis et al., have suggested a role for arginase II in *H. pyroli* infection. For example, these authors indicate that argII−/− primary macrophages incubated with *H. pylori* extracts showed enhanced NO production and correspondingly an increased (~15%) NO-mediated killing of bacterial cells (Lewis N D, Asim M, Barry D P, Singh K, de Sablet T, Boucher J L, Gobert A P, Chaturvedi R, Wilson K T., *J Immunol.* 2010, 184, 2572-82) Inhibitors of arginase activity, therefore, may be candidate therapeutics for treating vascular pathophysiology Inhibitors of arginase activity, therefore, may be candidate therapeutics for treating *H. pyroli* infections and for treating gastric ulcers, peptic ulcers and cancer.

Sickle Cell Disease (SCD)

Sickle-cell disease (SCD), or sickle-cell anaemia, or drepanocytosis, is a genetic blood disorder, characterized by red blood cells that assume an abnormal, rigid, sickle shape. Sickling decreases the cells' flexibility and increases the risk of complications. An increase in the concentration of reactive oxygen species (ROS) in circulation causes adherence of blood cells and consumption of NO that results in poor vasodilation or the inability of blood vessels to vasodilate. The inability to vasodilate along with the increased adherence of blood cells in SCD results in vaso occlusive crisis and pain.

Low levels of plasma L-arginine are normally detected in patients with SCD (Morris C R, Kato G J, Poljakovic M, Wang X, Blackwelder W C, Sachdev V, Hazen S L, Vichinsky E P, Morris S M Jr, Gladwin M T., *JAMA.* 2005, 294, 81-90) According to these authors, lysis of red blood cells (RBC's) in patients suffering from SCD causes the release of arginase and a subsequent lowering of physiological L-Arginine levels. This sequence of biological events lowers physiological concentrations of nitric oxide (NO), a signaling molecule that plays a role in vasodilation. Other biological events also limit NO bioavailabilty. These include, for example, the uncoupling of nitric oxide synthase (NOS), and the subsequent decrease in physiological NO levels, as well as the reaction of superoxide ($O^{-2}$) reactive oxygen species with NO to sequester the latter as $ONOO^-$.

Based on theses observations, inhibitors of arginase, especially arginase I inhibitors are being proposed by the present inventors as candidate therapeutics for patients with sickle cell disease. As stated above, SCD causes the uncoupling of eNOS due to low physiological levels L-arginine Inhibition of arginase present in the blood circulation, however, may address this problem by increasing the physiological levels L-arginine, the substrate of endothelial nitric oxide synthase (eNOS). This sequence of events, importantly, are proposed by the present inventors to enhance endothelial function and relieve vasoconstriction associated with SCD.

Human Immunodeficiency Virus (HIV)

HIV is caused by virus that infects CD4+ helper T cells and causes severe lymphopaenia that predisposes the infected individuals to opportunistic infection. Although, anti-retroviral therapy (ART) is extensively used to combat HIV infection, the wide spread use of anti-retroviral drugs has resulted in the generation of resistant strains of HIV.

A correlation exists between the activity of arginase in patients suffering from HIV and the severity of HIV disease. That is increased arginase activity has been correlated to increased viral titres in HIV patients. These patients also show decrease serum arginine levels as well as decreased levels of CD4+/CD8+ cells.

Taken together, these observations suggest a role for arginase inhibitors, such as compounds according to Formulae I or II as candidate therapeutics in the treatment of HIV infection.

Chronic Hepatitis B Virus (HBV)

Chronic hepatitis B infection is a viral disease that is transmitted by contact with infected body fluids. Chronic HBV infections are characterized by inflammation of the liver and jaundice and if left untreated can cause cirrhosis of the liver that can progresses to form hepatocellular carcinomas. Antiviral drugs currently used, however, have low efficacy against chronic HBV infections. Serum and liver homogenates of patients with chronic HBV infections show reduced levels of arginine and increased arginase activity. For infected patients moreover, the increased arginase activity is correlated to an impaired cytotoxic T-lymphocytes (CTL) response with reduced IL-2 production and CD3z expression.

Replenishing serum arginine to physiologically acceptable levels, however, reconstituted CD3z and IL-2 expression, implicating a role for arginase inhibitors as potential therapeutics in the treatment of chronic HBV infections.

Routes of Administration and Dosing Regimen

Despite ample evidence associating arginase inhibition with therapies of various diseases and conditions, only a limited number of compounds are known that are capable of inhibiting arginase activity. The present invention therefore provides compounds and their pharmaceutical compositions that are useful in treating a subject suffering from such a disease or condition, as more generally set forth above.

The compound of the invention can be formulated as described hereinabove and is suitable for administration in a therapeutically effective amount to the subject in any number of ways. The therapeutically effective amount of an inventive compound can depend upon the amounts and types of excipients used, the amounts and specific types of active ingredients in a dosage form, and the route by which the compound is to be administered to patients. However, typical dosage forms of the invention comprise a compound, or a pharmaceutically acceptable salt, solvate, hydrate, isomer, or prodrug thereof.

Typical dosage levels for a compound of the invention generally range from about 0.001 to about 100 mg per kg of the patient's body weight per day which can be administered in single or multiple doses. An exemplary dosage is about 0.01 to about 25 mg/kg per day or about 0.05 to about 10 mg/kg per day. In other embodiments, the dosage level is from about 0.01 to about 25 mg/kg per day, about 0.05 to about 10 mg/kg per day, or about 0.1 to about 5 mg/kg per day.

A dose typically ranges from about 0.1 mg to about 2000 mg per day, given as a single once-a-day dose or, alternatively, as divided doses throughout the day, optionally taken with food. In one embodiment, the daily dose is administered twice daily in equally divided doses. A daily dose range can be from about 5 mg to about 500 mg per day, such as, for example, between about 10 mg and about 300 mg per day. In managing the patient, the therapy can be initiated at a lower dose, perhaps from about 1 mg to about 25 mg, and increased if necessary up to from about 200 mg to about 2000 mg per day as either a single dose or divided doses, depending on the patient's global response.

Depending on the disease to be treated and the subject's condition, a pharmaceutically acceptable composition of the inventive compounds may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration. The compounds can be formulated, alone or together, in suitable dosage unit formulations containing conventional non-toxic pharmaceutically acceptable carriers, adjuvants and vehicles, as described above, that are appropriate for each route of administration. The invention also contemplates administration of the compounds of the invention in a depot formulation, in which the active ingredient is released over a defined time period.

Inhibition of Arginase

The inventive compounds inhibit human arginase I (ARG I) and arginase II (ARG II) as evidenced by an ex vivo assay set forth by a published protocol (Baggio et al. *J. Pharmacol. Exp. Ther.* 1999, 290, 1409-1416). The assay established the concentration of inhibitor that is required to reduce arginase activity by 50% ($IC_{50}$).

Assay Protocol

Inhibition of arginase I (ARG I) and arginase II (ARG II) by the inventive compounds is followed spectrophotometrically at 530 nm. The compound to be tested is dissolved in DMSO at an initial concentration 50-fold greater than its final concentration in the cuvette. 10 µl of the stock solution is diluted in 90 µl of the assay buffer that comprises 0.1M sodium phosphate buffer containing 130 mM NaCl, pH 7.4, to which is added ovalbumin (OVA) at a concentration of 1 mg/ml. Solutions of arginase I and II are prepared in 100 mM sodium phosphate buffer, pH 7.4 containing 1 mg/ml of OVA to give an arginase stock solution at a final concentration of 100 ng/ml.

To each well of a 96-well microtiter plate is add 40 µl of enzyme, 10 µl of an inventive compound and 10 µl of enzyme substrate (L-arginine+ manganese sulfate). For wells that are used as positive controls, only the enzyme and its substrate are added, while wells used as negative controls contain only manganese sulfate.

After incubating the microtiter plate at 37° C. for 60 minutes, 150 µl of a urea reagent obtained by combining equal proportions (1:1) of reagents A and B is added to each well of the microtiter plate to stop the reaction. The urea reagent is made just before use by combining Reagent A (10 mM o-phthaldialdehyde, and 0.4% polyoxyethylene (23) lauryl ether (w/v) in 1.8 M sulfuric acid) with Reagent B (1.3 mM primaquine diphosphate, 0.4% polyoxyethylene (23) lauryl ether (w/v), 130 mM boric acid in 3.6 M sulfuric acid). After quenching the reaction mixture, the microtiter plate is allowed to stand for an additional 10 minutes at room temperature to allow color development. The inhibition of arginase is computed by measuring the optical density (OD) of the reaction mixture at 530 nm and normalizing the OD value to percent inhibition observed in the control. The normalized OD is then used to generate a dose-response curve by plotting the normalized OD values against log [concentration] and using regression analysis to compute the $IC_{50}$ values.

Table 3 below ranks the potency of inventive compounds on a scale from 1 through 5, that is, the most potent compounds are designated as 1 and the least potent compounds are designated as 5. Thus, a potency value of 1 refers to inventive compounds with $IC_{50}$ values in the range from 0.1 nM to 25 nM; a potency value of 2 refers to inventive compounds with $IC_{50}$ values in the range from 26 nM to 100 nM; compounds having a potency value of 3 exhibit $IC_{50}$ values in the range from 101 nM to 500 nM; inventive compounds with $IC_{50}$ values in the range from 501 nM to 1500 nM are assigned a potency value of 4, and compounds with $IC_{50}$ values above 1501 nM are assigned a potency value of 5.

Table 3 also provides CHOK cell based $IC_{50}$ values for illustrative arginase inhibitors. $IC_{50}$ values were determined by measuring the production of urea in CHOK cells stably transfected with human-Arginase-1.

Briefly, CHOK cells were stably transfected with human-arginase-1. To determiner the $IC_{50}$ values for compounds in accordance with the present invention, parental CHOK cells and arginase-1 stably transfected cells were plated in a 96 well plate. Cells were plated using 200 µl of complete growth medium and incubated overnight at 37° C.

Media from each of the wells containing cells was first removed and growth media supplemented with arginine at a concentration of 5 mM was added to each well. The test compounds were dissolved in PBS buffer to the desired concentration and added to appropriate wells. The plate was then incubated at 37° C. for 24 hours. After 24 hours the plates were spun down at 3000 RPM for 5 min and 50 µl of the media were transferred to a new plate.

An aqueous solution of o-phthaldehyde, Brij, sulfuric acid, primaquine diphosphate and boric acid was added to each well and the plate was incubated for 10-15 minutes. The urea concentration in each well was determined by measuring the optical density at 520-530 nanometers using a standard curve.

The $IC_{50}$ values were calculated by measuring urea production at various concentrations of the inventive arginase inhibitors after subtracting the value related to the concentration of urea in control wells.

TABLE 3

| Ex. # | Structure | Potency (ARG I)[a] | Potency (ARG II)[a] | CHOK Cell[b] |
|---|---|---|---|---|
| 1 | 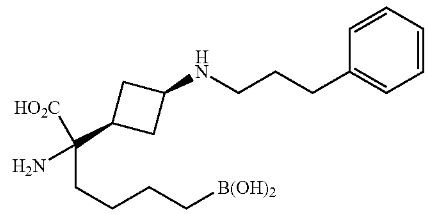 [SMILES: NC(CCCCB(O)O)(C(=O)O)[C@H]1C[C@@H](NCCCc2ccccc2)C1] | 1 | 2 | nd |
| 2 | 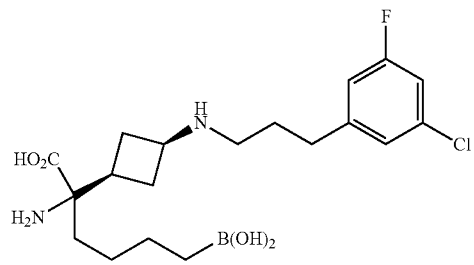 [SMILES: NC(CCCCB(O)O)(C(=O)O)[C@H]1C[C@@H](NCCCc2cc(F)cc(Cl)c2)C1] | 2 | 1 | nd |
| 3 | 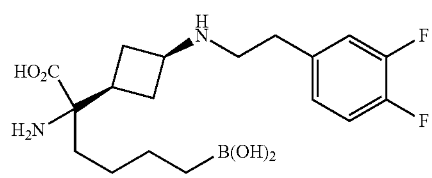 [SMILES: NC(CCCCB(O)O)(C(=O)O)[C@H]1C[C@@H](NCCc2ccc(F)c(F)c2)C1] | 2 | 2 | nd |
| 4 | 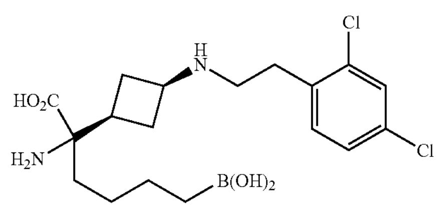 [SMILES: NC(CCCCB(O)O)(C(=O)O)[C@H]1C[C@@H](NCCc2ccc(Cl)cc2Cl)C1] | 2 | 2 | nd |
| 5 | 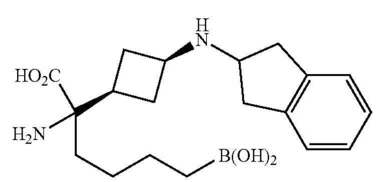 [SMILES: NC(CCCCB(O)O)(C(=O)O)[C@H]1C[C@@H](NC2Cc3ccccc3C2)C1] | 1 | 2 | 1 |
| 6 | 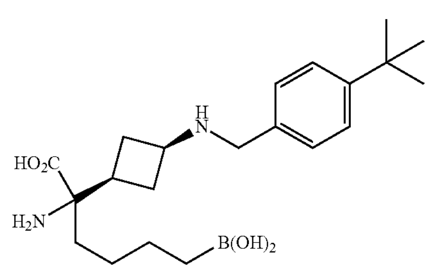 [SMILES: CC(C)(C)c1ccc(CN[C@H]2C[C@@H](C(N)(CCCCB(O)O)C(=O)O)C2)cc1] | 2 | 2 | 2 |

TABLE 3-continued

| Ex. # | Structure | Potency (ARG I)[a] | Potency (ARG II)[a] | CHOK Cell[b] |
|---|---|---|---|---|
| 7 | (structure) | 2 | 2 | nd |
| 8 | (structure) | 1 | 1 | 1 |
| 9 | (structure) | 1 | 1 | 2 |
| 10 | (structure) | 1 | 1 | 1 |
| 11 | (structure) | 1 | 2 | 1 |
| 12 | (structure) | 2 | 1 | 2 |

TABLE 3-continued

| Ex. # | Structure | Potency (ARG I)[a] | Potency (ARG II)[a] | CHOK Cell[b] |
|---|---|---|---|---|
| 13 | 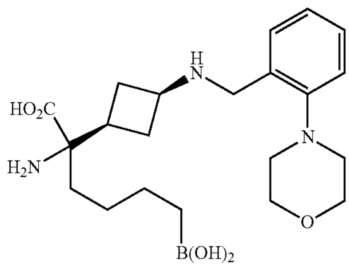 [SMILES: NC(CCCCB(O)O)(C(=O)O)[C@H]1C[C@@H](NCc2ccccc2N2CCOCC2)C1] | 2 | 2 | 2 |
| 14 | 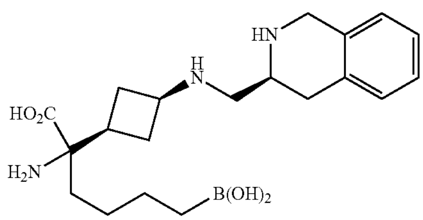 [SMILES: NC(CCCCB(O)O)(C(=O)O)[C@H]1C[C@@H](NC[C@@H]2Cc3ccccc3CN2)C1] | 2 | 2 | nd |
| 15 | 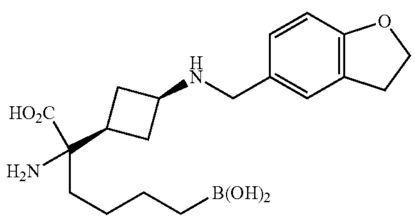 [SMILES: NC(CCCCB(O)O)(C(=O)O)[C@H]1C[C@@H](NCc2ccc3c(c2)CCO3)C1] | 2 | 2 | 1 |
| 16 | 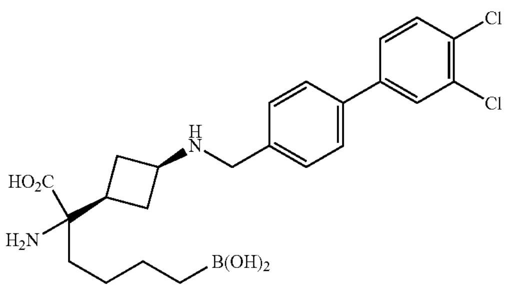 [SMILES: NC(CCCCB(O)O)(C(=O)O)[C@H]1C[C@@H](NCc2ccc(-c3ccc(Cl)c(Cl)c3)cc2)C1] | 1 | 1 | 1 |
| 17 | 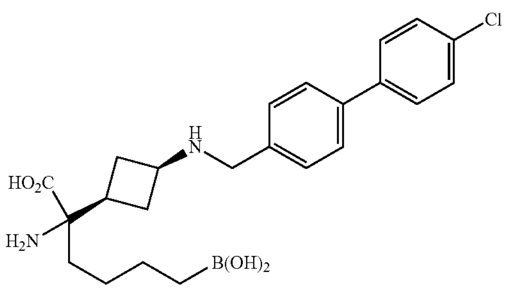 [SMILES: NC(CCCCB(O)O)(C(=O)O)[C@H]1C[C@@H](NCc2ccc(-c3ccc(Cl)cc3)cc2)C1] | 1 | 1 | 1 |
| 18 | 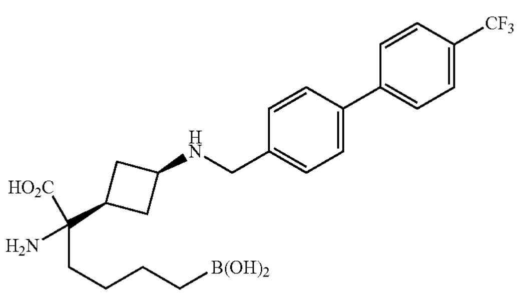 [SMILES: NC(CCCCB(O)O)(C(=O)O)[C@H]1C[C@@H](NCc2ccc(-c3ccc(C(F)(F)F)cc3)cc2)C1] | 1 | 1 | 1 |

TABLE 3-continued
| Ex. # | Structure | Potency (ARG I)[a] | Potency (ARG II)[a] | CHOK Cell[b] |
|---|---|---|---|---|
| 19 | 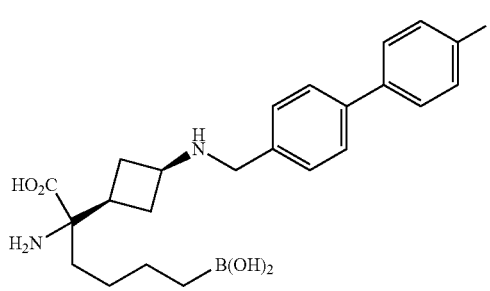 | 1 | 2 | 2 |
| 20 | 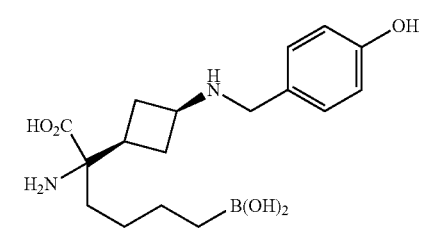 [SMILES: NC(CCCCB(O)O)(C(=O)O)[C@H]1C[C@@H](NCc2ccc(O)cc2)C1] | 2 | 2 | nd |
| 21 | 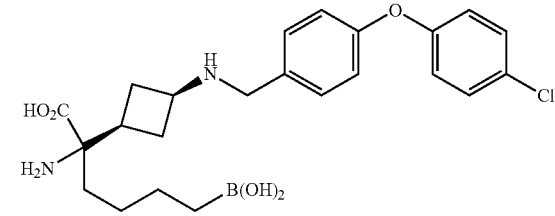 [SMILES: NC(CCCCB(O)O)(C(=O)O)[C@H]1C[C@@H](NCc2ccc(Oc3ccc(Cl)cc3)cc2)C1] | 1 | 1 | 2 |
| 22 | 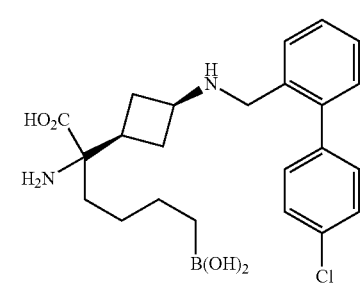 [SMILES: NC(CCCCB(O)O)(C(=O)O)[C@H]1C[C@@H](NCc2ccccc2-c2ccc(Cl)cc2)C1] | 2 | 2 | 2 |
| 23 | 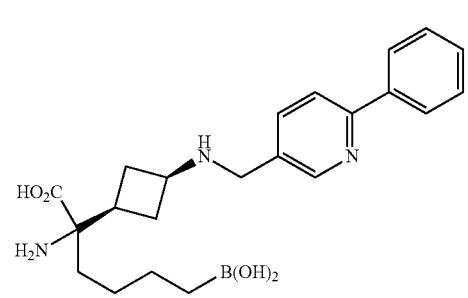 [SMILES: NC(CCCCB(O)O)(C(=O)O)[C@H]1C[C@@H](NCc2ccc(-c3ccccc3)nc2)C1] | 2 | 1 | 1 |

… TABLE 3-continued

| Ex. # | Structure | Potency (ARG I)[a] | Potency (ARG II)[a] | CHOK Cell[b] |
|---|---|---|---|---|
| 24 | 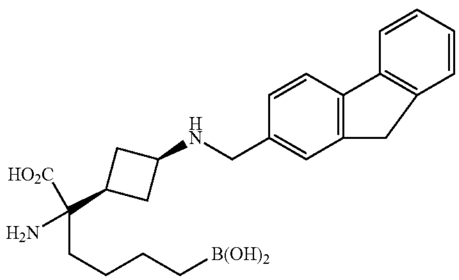 [SMILES: NC(CCCCB(O)O)(C(=O)O)[C@H]1C[C@@H](NCc2ccc3c(c2)Cc2ccccc2-3)C1] | 1 | 1 | 2 |
| 25 | 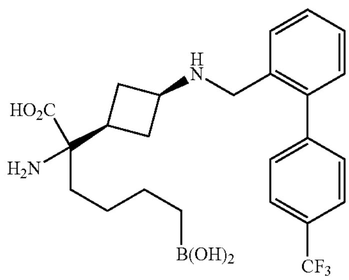 [SMILES: NC(CCCCB(O)O)(C(=O)O)[C@H]1C[C@@H](NCc2ccccc2-c2ccc(C(F)(F)F)cc2)C1] | 2 | 2 | 2 |
| 26 | 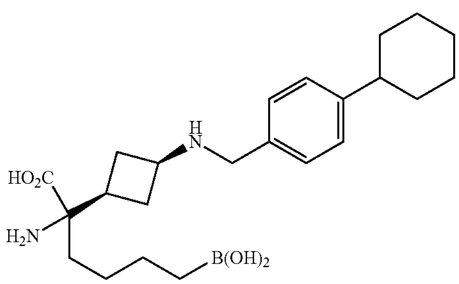 [SMILES: NC(CCCCB(O)O)(C(=O)O)[C@H]1C[C@@H](NCc2ccc(C3CCCCC3)cc2)C1] | 1 | 2 | 2 |
| 27 | 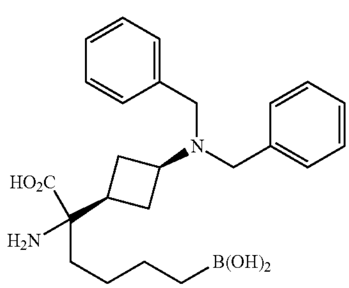 [SMILES: NC(CCCCB(O)O)(C(=O)O)[C@H]1C[C@@H](N(Cc2ccccc2)Cc2ccccc2)C1] | 3 | 4 | 2 |
| 28 | 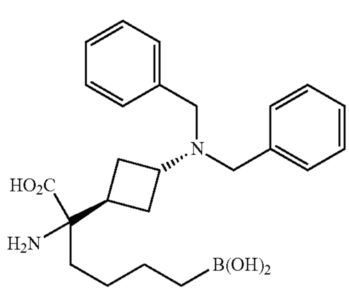 | 5 | 5 | nd |

TABLE 3-continued

| Ex. # | Structure | Potency (ARG I)a | Potency (ARG II)a | CHOK Cellb |
|---|---|---|---|---|
| 29 | 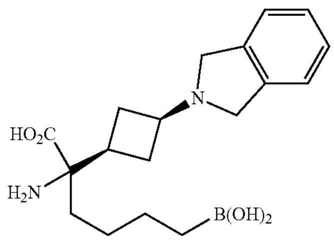 [SMILES: NC(CCCCB(O)O)(C(=O)O)[C@H]1C[C@@H](N2Cc3ccccc3C2)C1] | 3 | 3 | nd |
| 30 | 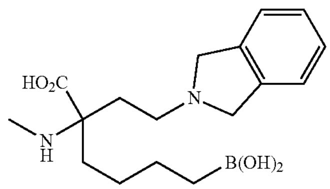 [SMILES: CNC(CCCCB(O)O)(CCN1Cc2ccccc2C1)C(=O)O] | 3 | 3 | 1 |
| 31 | 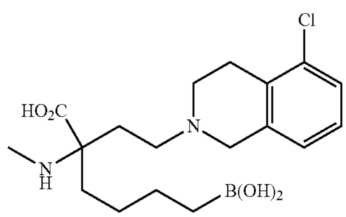 [SMILES: CNC(CCCCB(O)O)(CCN1CCc2c(Cl)cccc2C1)C(=O)O] | 3 | 3 | nd |
| 32 | 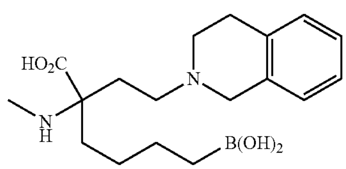 [SMILES: CNC(CCCCB(O)O)(CCN1CCc2ccccc2C1)C(=O)O] | 3 | 3 | nd |
| 33 | 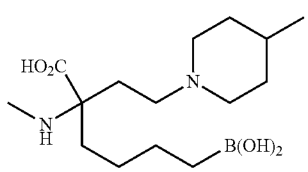 | 3 | 3 | 2 |
| 34 | 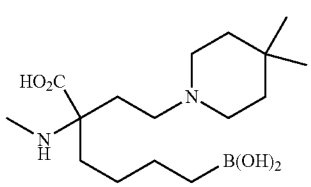 | 3 | 3 | nd |
| 35 | 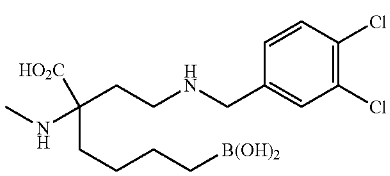 [SMILES: CNC(CCCCB(O)O)(CCNCc1ccc(Cl)c(Cl)c1)C(=O)O] | 3 | 3 | 2 |

TABLE 3-continued

| Ex. # | Structure | Potency (ARG I)[a] | Potency (ARG II)[a] | CHOK Cell[b] |
|---|---|---|---|---|
| 36 | 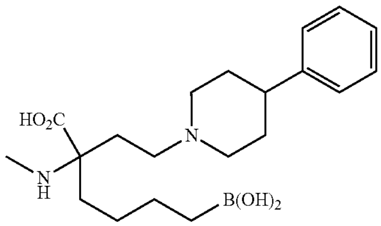 [SMILES: CNC(CCCCB(O)O)(CCN1CCC(c2ccccc2)CC1)C(=O)O] | 3 | 3 | 1 |
| 37 | 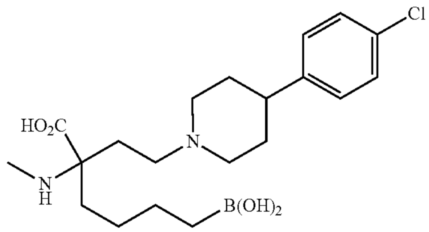 [SMILES: CNC(CCCCB(O)O)(CCN1CCC(c2ccc(Cl)cc2)CC1)C(=O)O] | 3 | 3 | nd |
| 38 | 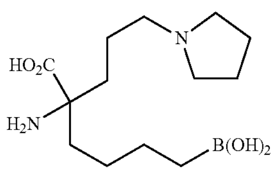 [SMILES: NC(CCCCB(O)O)(CCCN1CCCC1)C(=O)O] | 3 | 3 | nd |
| 39 | 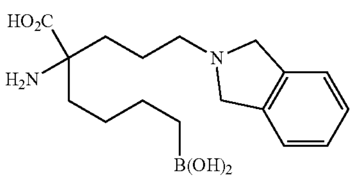 [SMILES: NC(CCCCB(O)O)(CCCN1Cc2ccccc2C1)C(=O)O] | 2 | 3 | 1 |
| 40 | 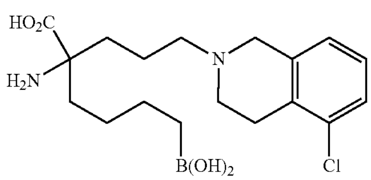 [SMILES: NC(CCCCB(O)O)(CCCN1CCc2c(Cl)cccc2C1)C(=O)O] | 2 | 3 | 1 |
| 41 | 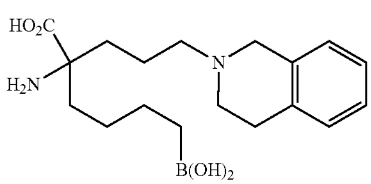 [SMILES: NC(CCCCB(O)O)(CCCN1CCc2ccccc2C1)C(=O)O] | 3 | 3 | 1 |
| 42 | 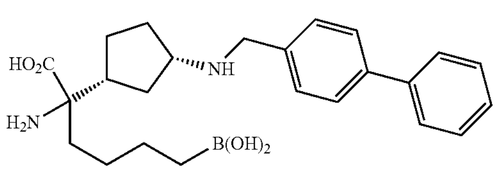 [SMILES: NC(CCCCB(O)O)(C(=O)O)[C@@H]1CC[C@H](NCc2ccc(-c3ccccc3)cc2)C1] | 2 | 2 | nd |
| 43 | 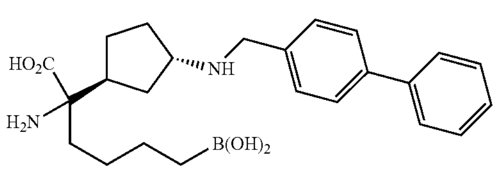 [SMILES: NC(CCCCB(O)O)(C(=O)O)[C@H]1CC[C@H](NCc2ccc(-c3ccccc3)cc2)C1] | 2 | 2 | 2 |

TABLE 3-continued

| Ex. # | Structure | Potency (ARG I)[a] | Potency (ARG II)[a] | CHOK Cell[b] |
|---|---|---|---|---|
| 44 | 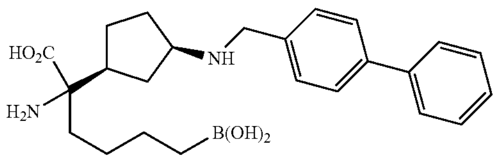 [SMILES: NC(CCCCB(O)O)(C(=O)O)[C@H]1CC[C@@H](NCc2ccc(-c3ccccc3)cc2)C1] | 2 | 2 | 2 |
| 45 | 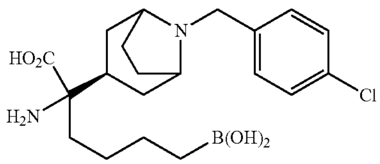 | 1 | 2 | 1 |
| 46 | 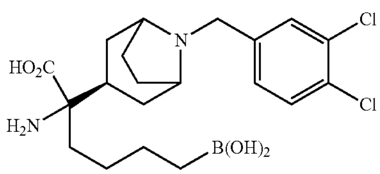 | 1 | 1 | 1 |
| 47 | 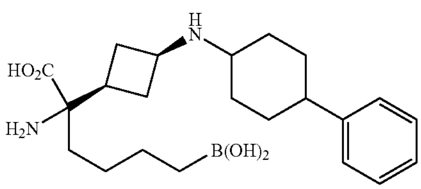 [SMILES: NC(CCCCB(O)O)(C(=O)O)[C@H]1C[C@@H](NC2CCC(c3ccccc3)CC2)C1] | 2 | 1 | 2 |
| 48 | 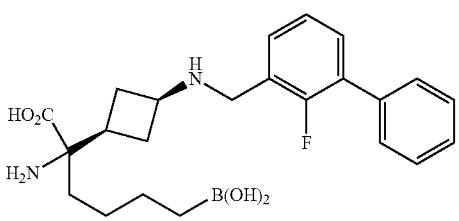 [SMILES: NC(CCCCB(O)O)(C(=O)O)[C@H]1C[C@@H](NCc2cccc(-c3ccccc3)c2F)C1] | 2 | 1 | 2 |
| 49 | 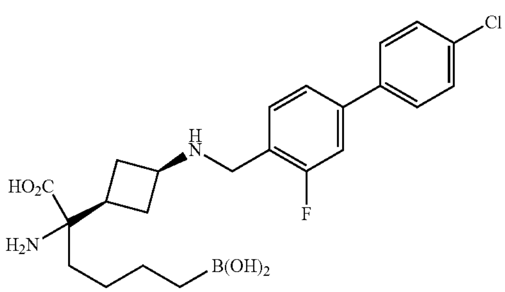 [SMILES: NC(CCCCB(O)O)(C(=O)O)[C@H]1C[C@@H](NCc2ccc(-c3ccc(Cl)cc3)cc2F)C1] | 1 | 1 | 1 |
| 50 | 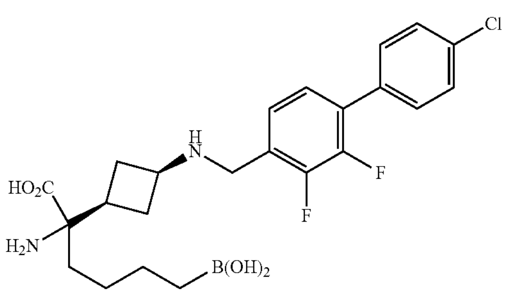 [SMILES: NC(CCCCB(O)O)(C(=O)O)[C@H]1C[C@@H](NCc2ccc(-c3ccc(Cl)cc3)c(F)c2F)C1] | 1 | 2 | 1 |

TABLE 3-continued

| Ex. # | Structure | Potency (ARG I)[a] | Potency (ARG II)[a] | CHOK Cell[b] |
|---|---|---|---|---|
| 51 | 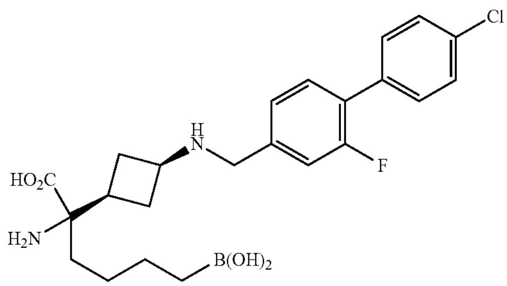 [SMILES: NC(CCCCB(O)O)(C(=O)O)[C@H]1C[C@@H](NCc2ccc(-c3ccc(Cl)cc3)c(F)c2)C1] | 2 | 1 | 2 |
| 52 | 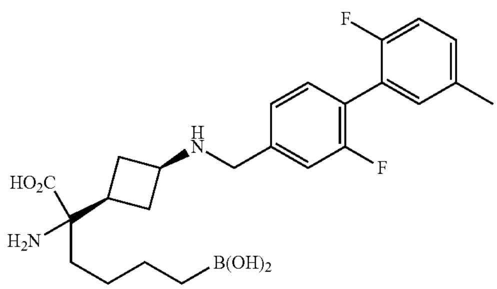 [SMILES: Cc1ccc(F)c(-c2ccc(CN[C@H]3C[C@@H](C(N)(CCCCB(O)O)C(=O)O)C3)cc2F)c1] | 1 | 1 | 1 |
| 53 | 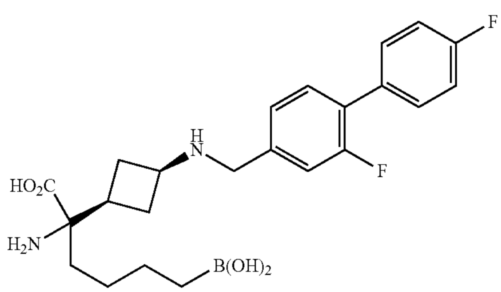 [SMILES: NC(CCCCB(O)O)(C(=O)O)[C@H]1C[C@@H](NCc2ccc(-c3ccc(F)cc3)c(F)c2)C1] | 1 | 2 | 2 |
| 54 | 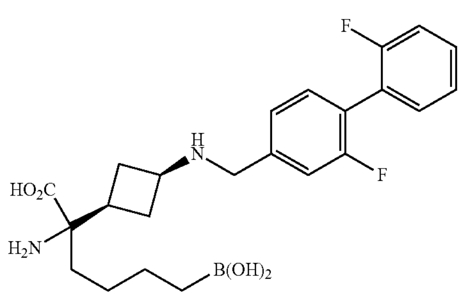 [SMILES: NC(CCCCB(O)O)(C(=O)O)[C@H]1C[C@@H](NCc2ccc(-c3ccccc3F)c(F)c2)C1] | 2 | 2 | 2 |
| 55 | 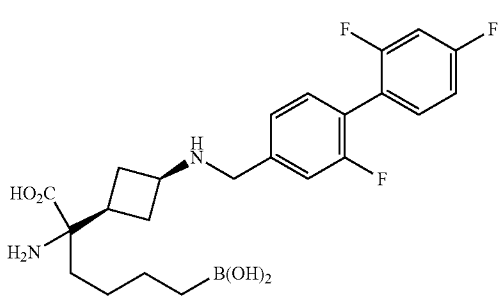 [SMILES: NC(CCCCB(O)O)(C(=O)O)[C@H]1C[C@@H](NCc2ccc(-c3ccc(F)cc3F)c(F)c2)C1] | 2 | 2 | 2 |

TABLE 3-continued

| Ex. # | Structure | Potency (ARG I)[a] | Potency (ARG II)[a] | CHOK Cell[b] |
|---|---|---|---|---|
| 56 | 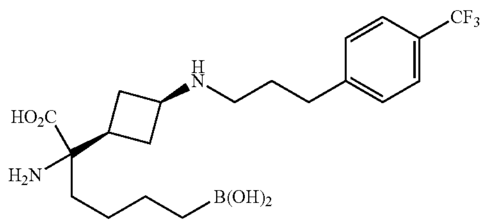 [SMILES: NC(CCCCB(O)O)(C(=O)O)[C@H]1C[C@@H](NCCCc2ccc(C(F)(F)F)cc2)C1] | 1 | 2 | 2 |
| 57 | 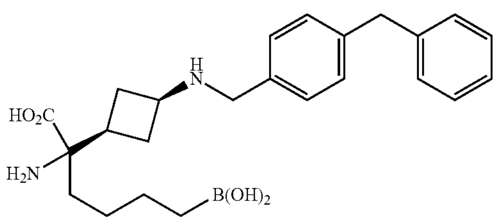 [SMILES: NC(CCCCB(O)O)(C(=O)O)[C@H]1C[C@@H](NCc2ccc(Cc3ccccc3)cc2)C1] | 2 | 2 | 2 |
| 58 | 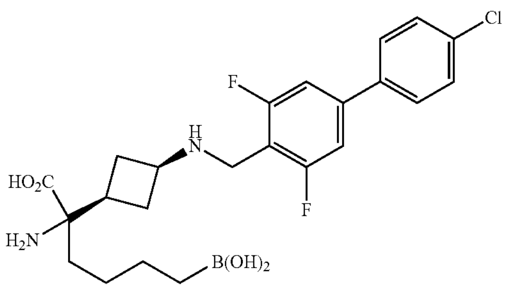 [SMILES: NC(CCCCB(O)O)(C(=O)O)[C@H]1C[C@@H](NCc2c(F)cc(-c3ccc(Cl)cc3)cc2F)C1] | 2 | 2 | 1 |
| 59 | 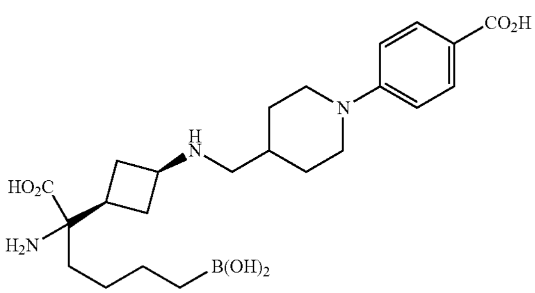 [SMILES: NC(CCCCB(O)O)(C(=O)O)[C@H]1C[C@@H](NCC2CCN(c3ccc(C(=O)O)cc3)CC2)C1] | 2 | 2 | nd |
| 60 | 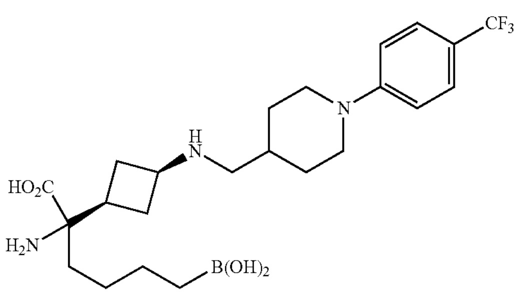 [SMILES: NC(CCCCB(O)O)(C(=O)O)[C@H]1C[C@@H](NCC2CCN(c3ccc(C(F)(F)F)cc3)CC2)C1] | 1 | 2 | 2 |
| 61 | 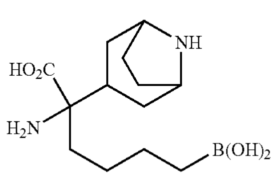 [SMILES: NC(CCCCB(O)O)(C(=O)O)C1CC2CCC(C1)N2] | 2 | 2 | 1 |

TABLE 3-continued

| Ex. # | Structure | Potency (ARG I)[a] | Potency (ARG II)[a] | CHOK Cell[b] |
|---|---|---|---|---|
| 62 | [structure: azabicyclic N-benzyl, with HO$_2$C, H$_2$N, B(OH)$_2$ chain] | 1 | 2 | 1 |
| 63 | [structure: azabicyclic N-(3,4-difluorobenzyl), with HO$_2$C, H$_2$N, B(OH)$_2$ chain] | 1 | 2 | 1 |
| 64 | [structure: azabicyclic N-(4-OCF$_3$-benzyl), with HO$_2$C, H$_2$N, B(OH)$_2$ chain] | 2 | 2 | 2 |
| 65 | [structure: cyclobutyl NH linked to biphenyl ethyl, with HO$_2$C, H$_2$N, B(OH)$_2$ chain] | 2 | 1 | nd |
| 66 | [structure: indanyl-NH, with HO$_2$C, H$_2$N, B(OH)$_2$ chain] | 3 | 3 | nd |
| 67 | [structure: N(ethyl)(2-hydroxyethyl), with HO$_2$C, H$_2$N, B(OH)$_2$ chain] | 4 | 3 | 1 |
| 68 | [structure: N,N-diethyl, with HO$_2$C, H$_2$N, B(OH)$_2$ chain] | 3 | 3 | 1 |
| 69 | [structure: N-methyl-N-propyl, with HO$_2$C, H$_2$N, B(OH)$_2$ chain] | 3 | 3 | nd |
| 70 | [structure: NH-isopropyl, with HO$_2$C, H$_2$N, B(OH)$_2$ chain] | 2 | 3 | nd |

TABLE 3-continued

| Ex. # | Structure | Potency (ARG I)[a] | Potency (ARG II)[a] | CHOK Cell[b] |
|---|---|---|---|---|
| 71 | 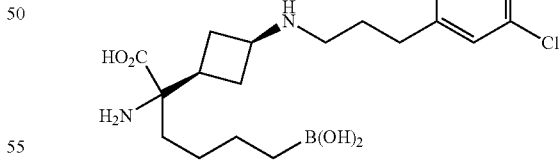 | 3 | 3 | nd |
| 72 | 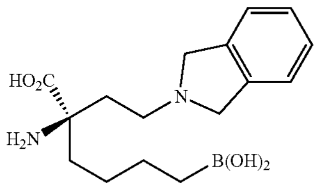 [SMILES: N[C@](CCCCB(O)O)(CCN1Cc2ccccc2C1)C(=O)O] | 3 | 4 | nd |
| 73 | 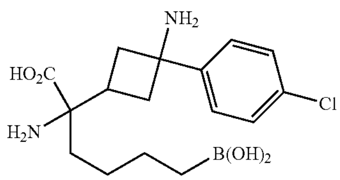 [SMILES: NC1(c2ccc(Cl)cc2)CC(C(N)(CCCCB(O)O)C(=O)O)C1] | 4 | 3 | nd |
| 74 | 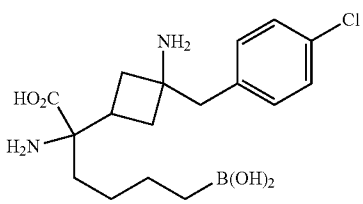 [SMILES: NC1(Cc2ccc(Cl)cc2)CC(C(N)(CCCCB(O)O)C(=O)O)C1] | 3 | 3 | nd |
| 75 | 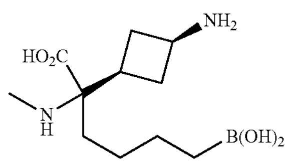 [SMILES: CNC(CCCCB(O)O)(C(=O)O)[C@H]1C[C@@H](N)C1] | 3 | 3 | nd |

[a]Order of Potency (highest-lowest): 1 = 0.1 nM → 25 nM; 2 = 26 nM → 100 nM; 3 = 101 nM → 500 nM; 4 = 501 nM → 1500 nM; and 5 = 1501 nM → greater;
[b]Order of Potency (highest-lowest): CHOK Cell: −1 = 1 μM → 25 μM; 2 = 26 μM → 100 μM; and "nd" = not determined.

The foregoing examples are intended illustrate certain embodiments of the invention, which is defined in full below by the claims. In addition, all publications cited herein are incorporated by reference as if fully set forth herein.

We claim:

1. A compound that is selected from the following table:

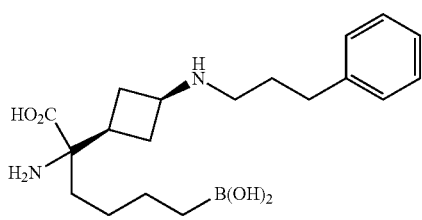 [SMILES: NC(CCCCB(O)O)(C(=O)O)[C@H]1C[C@@H](NCCCc2ccccc2)C1]

-continued

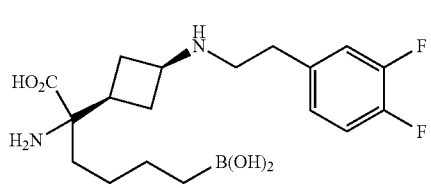 [SMILES: NC(CCCCB(O)O)(C(=O)O)[C@H]1C[C@@H](NCCc2ccc(F)c(F)c2)C1]

157
-continued
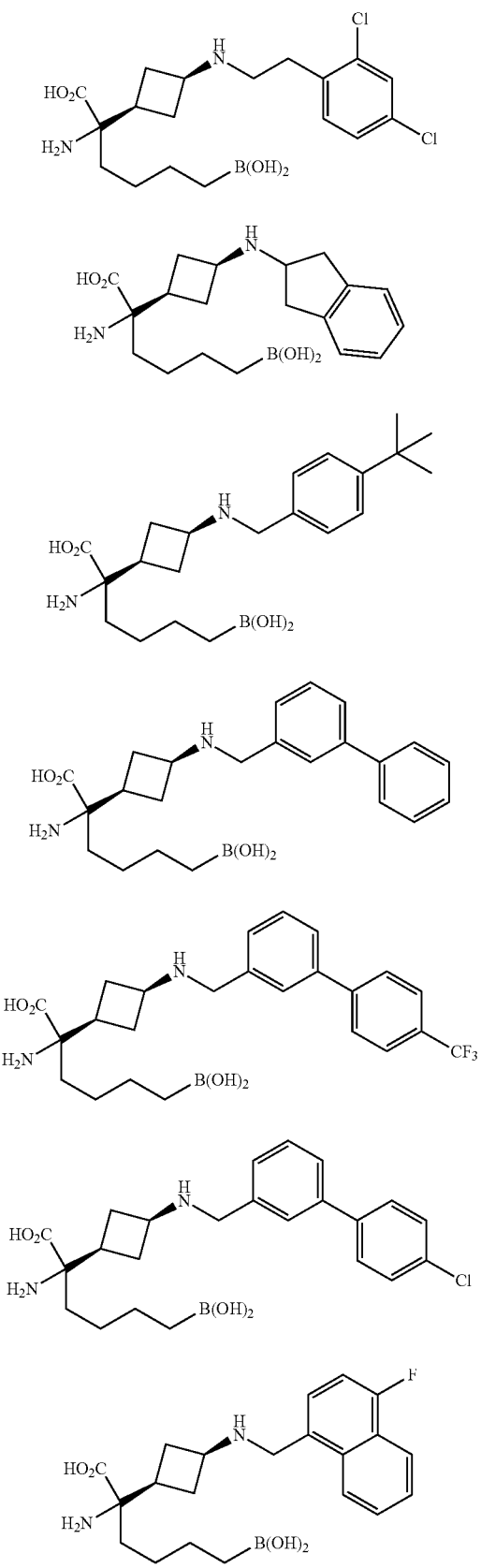
158
-continued
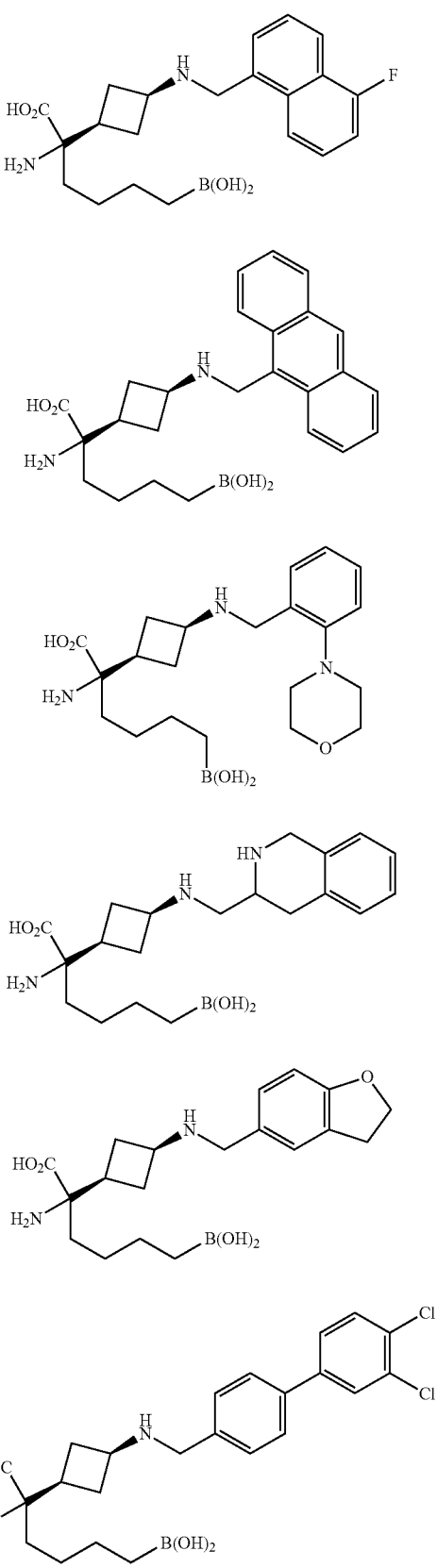

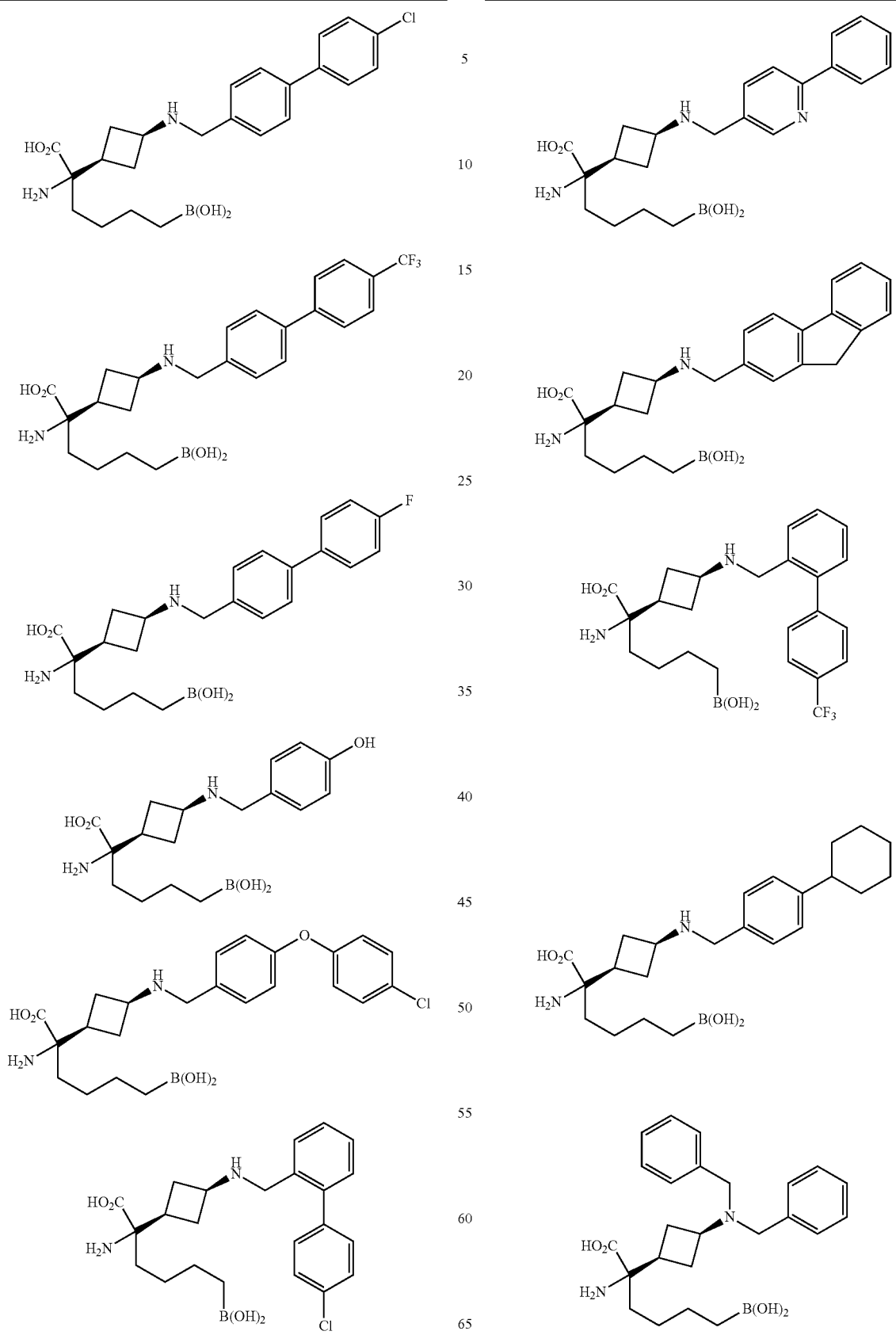

161
-continued
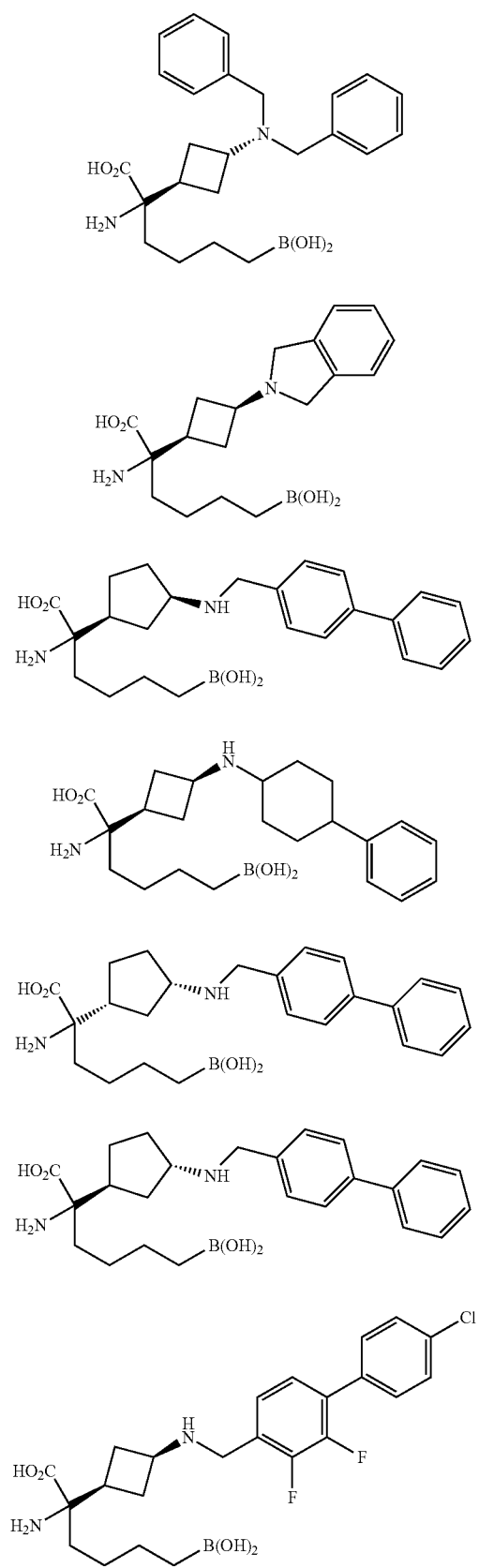
162
-continued
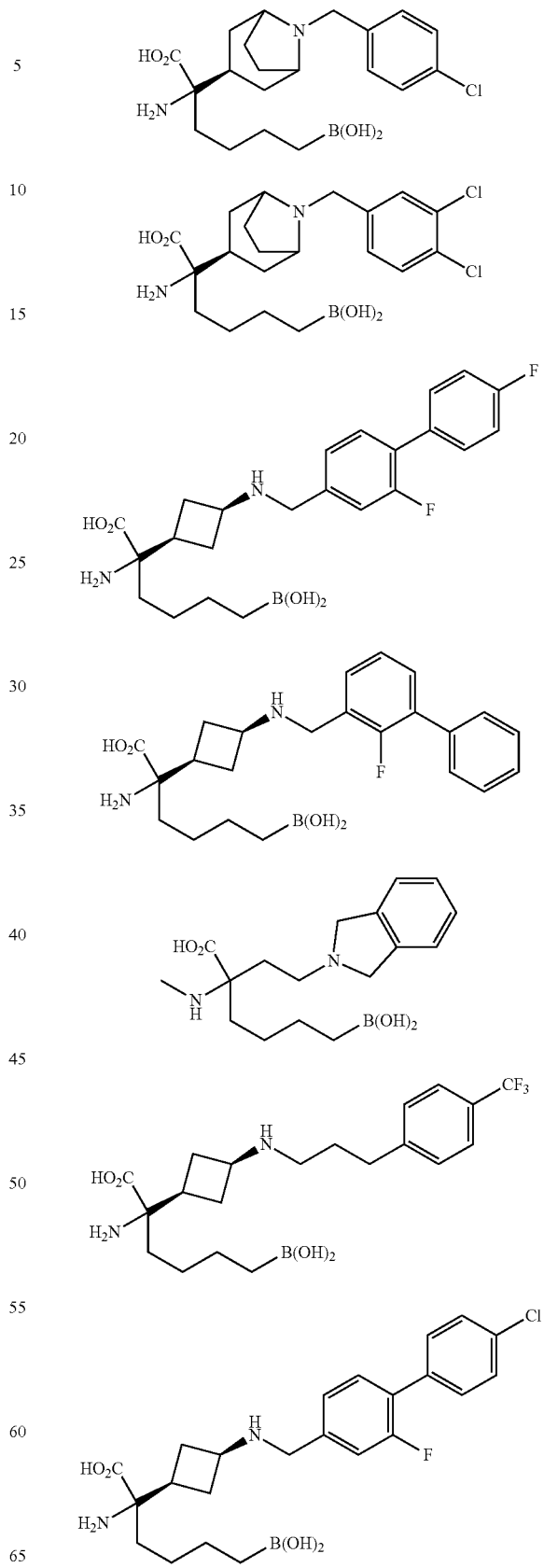

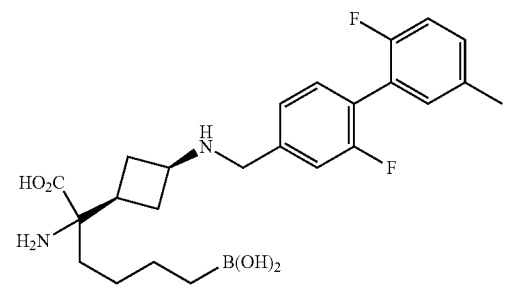
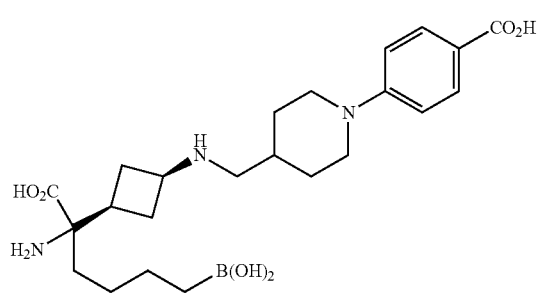 [SMILES: NC(CCCCB(O)O)(C(=O)O)[C@H]1C[C@@H](NCC2CCN(c3ccc(C(=O)O)cc3)CC2)C1]
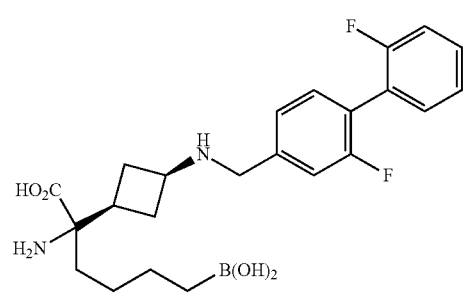 [SMILES: NC(CCCCB(O)O)(C(=O)O)[C@H]1C[C@@H](NCc2ccc(-c3ccccc3F)c(F)c2)C1]
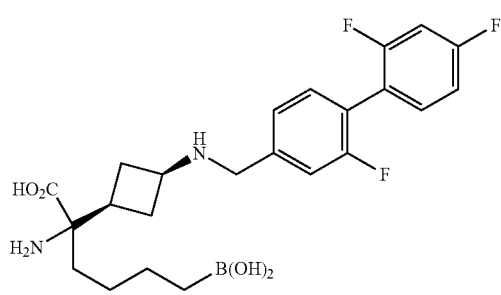 [SMILES: NC(CCCCB(O)O)(C(=O)O)[C@H]1C[C@@H](NCc2ccc(-c3ccc(F)cc3F)c(F)c2)C1]
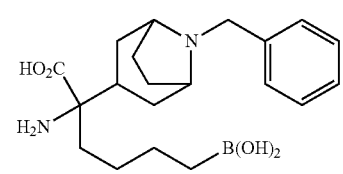 [SMILES: NC(CCCCB(O)O)(C(=O)O)C1CC2CCC(C1)N2Cc1ccccc1]
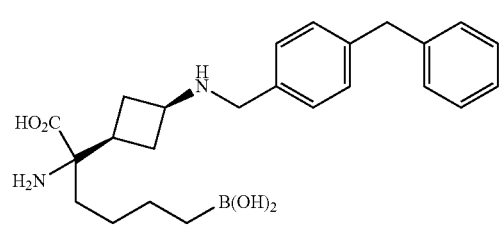 [SMILES: NC(CCCCB(O)O)(C(=O)O)[C@H]1C[C@@H](NCc2ccc(Cc3ccccc3)cc2)C1]
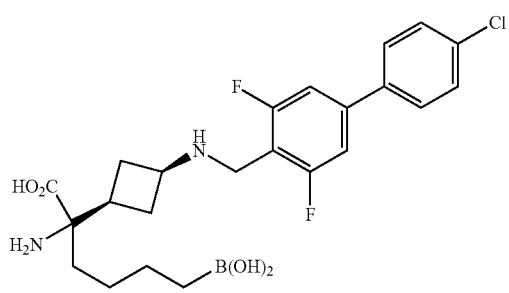
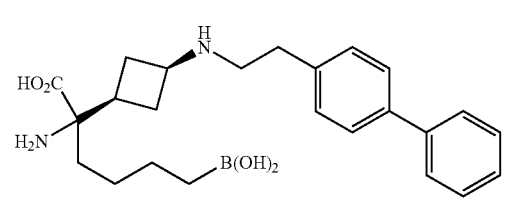 [SMILES: NC(CCCCB(O)O)(C(=O)O)[C@H]1C[C@@H](NCCc2ccc(-c3ccccc3)cc2)C1]
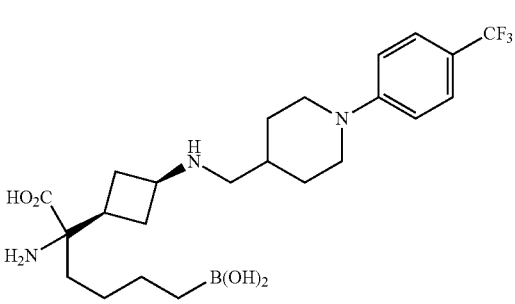
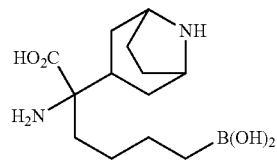
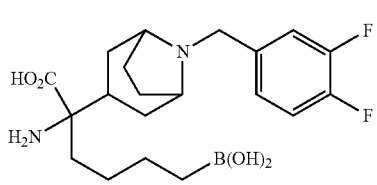 [SMILES: NC(CCCCB(O)O)(C(=O)O)C1CC2CCC(C1)N2Cc1ccc(F)c(F)c1]
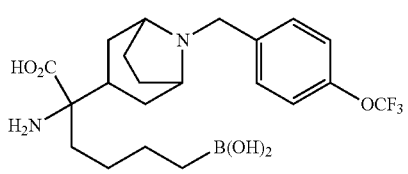 [SMILES: NC(CCCCB(O)O)(C(=O)O)C1CC2CCC(C1)N2Cc1ccc(OC(F)(F)F)cc1]
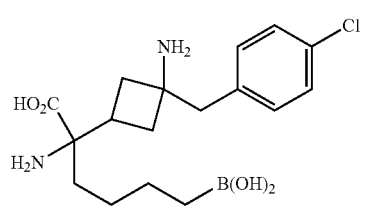 [SMILES: NC1(Cc2ccc(Cl)cc2)CC(C(N)(CCCCB(O)O)C(=O)O)C1]

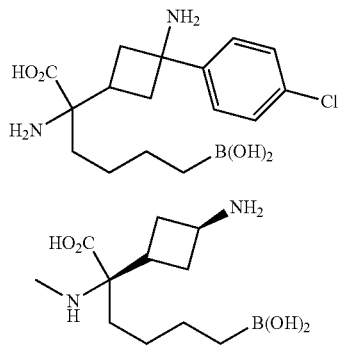

or a pharmaceutically acceptable salt or stereoisomer thereof.

2. A pharmaceutical composition comprising:
(i) at least one compound according to claim 1, or a pharmaceutically acceptable salt or stereoisomer thereof; and
(ii) a pharmaceutically acceptable carrier.

3. A method for inhibiting arginase I, arginase II, or a combination thereof in a cell, comprising contacting the cell with at least one compound according to claim 1, or a pharmaceutically acceptable salt or stereoisomer thereof.

4. A method for the treatment of a disease or condition associated with over-expression or elevated activity of arginase I, arginase II, or a combination thereof in a subject, comprising administering to the subject a therapeutically effective amount of at least one compound according to claim 1, or a pharmaceutically acceptable salt or stereoisomer thereof.

5. The method according to claim 4, wherein the disease or condition is selected from cardiovascular disorders, sexual disorders, wound healing, gastrointestinal disorders, immune disorders, infections, pulmonary disorders and hemolytic disorders.

6. The method according to claim 5, wherein the disease or condition is cardiovascular disorder selected from systemic hypertension, pulmonary arterial hypertension (PAH), ischemia reperfusion (IR) injury, myocardial infarction, and atherosclerosis.

7. The method according to claim 6, wherein the disease or condition is pulmonary arterial hypertension (PAH).

8. The method according to claim 6, wherein the disease or condition is myocardial infarction or atherosclerosis.

9. The method according to claim 5, wherein the disease or condition is a pulmonary disorder selected from chemically-induced lung fibrosis, idiopathic pulmonary fibrosis, cystic fibrosis, chronic obstructive pulmonary disease (COPD), and asthma.

10. The method according to claim 5, wherein the disease or condition is an autoimmune disorder selected from encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

11. The method according to claim 5, wherein the disease or condition is an immune disorder selected from myeloid-derived suppressor cell (MDSC) mediated T-cell dysfunction, human immunodeficiency virus (HIV), autoimmune encephalomyelitis, and ABO mismatch transfusion reaction.

12. The method according to claim 11, wherein the disease or condition is myeloid-derived suppressor cell (MDSC) mediated T-cell dysfunction.

13. The method according to claim 5, wherein the disease or condition is a hemolytic disorder selected from sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

14. The method according to claim 5, wherein the disease or condition is a gastrointestinal disorder selected from gastrointestinal motility disorders, gastric cancers, inflammatory bowel disease, Crohn's disease, ulcerative colitis, and gastric ulcers.

15. The method according to claim 5, wherein the disease or condition is a sexual disorder selected from Peyronie's Disease and erectile dysfunction.

16. The method according to claim 6, wherein the disease or condition is ischemia reperfusion (IR) injury selected from liver IR, kidney IR, and myocardial IR.

17. The method according to claim 4, wherein the disease or condition is selected from renal disease inflammation, psoriasis, leishmaniasis, neurodegenerative diseases, wound healing, human immunodeficiency virus (HIV), hepatitis B virus (HBV), H. pylori infections, fibrotic disorders, arthritis, candidiasis, periodontal disease, keloids, adenotonsilar disease, African sleeping sickness and Chagas' disease.

18. The method according to claim 17, wherein the disease or condition is wound healing selected from infected and uninfected wound healing.

19. The method according to claim 4, wherein the subject is a mammal selected from human, dog, cat, horse, sheep, and lamb.

20. The method according to claim 4, wherein the disease or condition is selected from systemic hypertension, pulmonary arterial hypertension (PAH), pulmonary arterial hypertension in high altitude, ischemia reperfusion (IR) injury, and atherosclerosis.

21. The method according to claim 4, wherein the disease or condition is gastric cancer.

22. The method according to claim 5, wherein the immune disorder is an autoimmune disorder.

* * * * *

UNITED STATES PATENT AND TRADEMARK OFFICE
CERTIFICATE OF CORRECTION

PATENT NO. : 9,266,908 B2  
APPLICATION NO. : 14/352554  
DATED : February 23, 2016  
INVENTOR(S) : Michael Van Zandt et al.

Page 1 of 1

It is certified that error appears in the above-identified patent and that said Letters Patent is hereby corrected as shown below:

In The Claims

Column 158, between lines 36 and 44, delete the following structure:

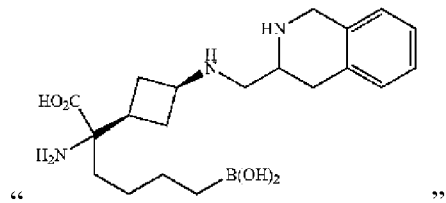

" "

and replace with the following structure:

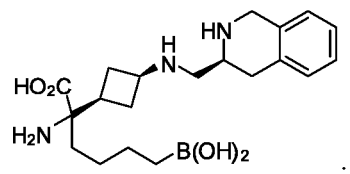

Column 162, between lines 38 and 45, delete the following structure:

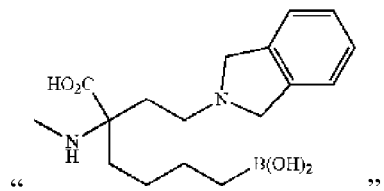

" "

and replace with the following structure:

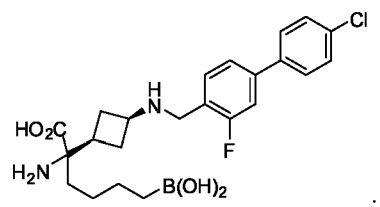

Signed and Sealed this  
Twenty-first Day of June, 2016

Michelle K. Lee  
*Director of the United States Patent and Trademark Office*